(12) United States Patent
Bensi et al.

(10) Patent No.: US 8,039,005 B2
(45) Date of Patent: Oct. 18, 2011

(54) MUTANT FORMS OF STREPTOLYSIN O

(75) Inventors: Giuliano Bensi, Siena (IT);
Immaculada Margarit Y Ros, Siena (IT); Emiliano Chiarot, Siena (IT);
Guido Grandi, Siena (IT); Maria Scarselli, Siena (IT)

(73) Assignee: Novartis AG, Basel (CH)

( * ) Notice: Subject to any disclaimer, the term of this patent is extended or adjusted under 35 U.S.C. 154(b) by 0 days.

(21) Appl. No.: 12/711,869

(22) Filed: Feb. 24, 2010

(65) Prior Publication Data

US 2010/0158935 A1   Jun. 24, 2010

Related U.S. Application Data

(63) Continuation of application No. 12/339,365, filed on Dec. 19, 2008, now Pat. No. 7,731,978.

(60) Provisional application No. 61/016,193, filed on Dec. 21, 2007, provisional application No. 61/088,381, filed on Aug. 13, 2008.

(51) Int. Cl.
*A61K 39/09* (2006.01)
*A61K 39/02* (2006.01)
*C07K 14/00* (2006.01)
*C12P 21/04* (2006.01)
*C07H 21/04* (2006.01)

(52) U.S. Cl. .............. 424/244.1; 424/184.1; 424/194.1; 530/350; 435/69.7

(58) Field of Classification Search .................. None
See application file for complete search history.

(56) References Cited

U.S. PATENT DOCUMENTS

| | | | |
|---|---|---|---|
| 4,454,121 A | 6/1984 | Beachey |
| 5,098,827 A | 3/1992 | Boyle et al. |
| 5,354,846 A | 10/1994 | Kehoe |
| 5,378,620 A | 1/1995 | Adams et al. |
| 5,391,712 A | 2/1995 | Adams |
| 5,445,820 A | 8/1995 | Seidel et al. |
| 5,523,205 A | 6/1996 | Cossart |
| 5,585,098 A | 12/1996 | Coleman |
| 5,700,648 A | 12/1997 | Kehoe |
| 5,821,088 A | 10/1998 | Darzins et al. |
| 5,846,547 A | 12/1998 | Cleary |
| 5,968,763 A | 10/1999 | Fischetti et al. |
| 6,174,528 B1 | 1/2001 | Cooper et al. |
| 6,372,222 B1 | 4/2002 | Michon et al. |
| 6,406,883 B1 | 6/2002 | Lutticken et al. |
| 6,420,152 B1 | 7/2002 | Adams et al. |
| 6,426,074 B1 | 7/2002 | Michel et al. |
| 6,579,711 B1 | 6/2003 | Gaier et al. |
| 6,635,623 B1 | 10/2003 | Hoogeveen et al. |
| 6,669,703 B2 | 12/2003 | Shue |
| 6,737,521 B1 | 5/2004 | Fischetti et al. |
| 6,747,437 B2 | 6/2004 | Chiu |
| 6,777,547 B1 | 8/2004 | Podbielski |
| 6,833,356 B1 | 12/2004 | Koenig et al. |
| 6,936,252 B2 | 8/2005 | Gilbert et al. |
| 7,033,765 B1 | 4/2006 | Dime et al. |
| 7,041,814 B1 | 5/2006 | Weinstock et al. |
| 7,098,182 B2 | 8/2006 | Le Page et al. |
| 7,101,692 B2 | 9/2006 | Schneewind et al. |
| 7,128,918 B1 | 10/2006 | Hamel et al. |
| 7,128,919 B2 | 10/2006 | Adderson et al. |
| 7,169,902 B2 | 1/2007 | Podbielski |
| 7,247,308 B2 | 7/2007 | Martin et al. |
| 7,348,006 B2 | 3/2008 | Contorni et al. |
| 7,407,664 B2 | 8/2008 | Beall et al. |
| 7,438,912 B2 | 10/2008 | Meinke et al. |
| 7,485,710 B2 | 2/2009 | Reinscheid et al. |
| 2002/0025516 A1 | 2/2002 | Black et al. |
| 2002/0045737 A1 | 4/2002 | Choi et al. |
| 2002/0061569 A1 | 5/2002 | Haselbeck et al. |
| 2002/0086023 A1 | 7/2002 | Dale |
| 2003/0035805 A1 | 2/2003 | Michel et al. |
| 2003/0109690 A1 | 6/2003 | Ruben et al. |
| 2003/0157122 A1 | 8/2003 | Dale |
| 2003/0171337 A1 | 9/2003 | Aylward et al. |
| 2004/0029129 A1 | 2/2004 | Wang et al. |
| 2004/0101536 A1 | 5/2004 | Teti et al. |
| 2004/0219639 A1 | 11/2004 | Potter et al. |
| 2004/0236072 A1 | 11/2004 | Olmsted et al. |
| 2005/0019345 A1 | 1/2005 | Podbielski |
| 2005/0020813 A1 | 1/2005 | Masignani et al. |
| 2005/0181388 A1 | 8/2005 | Edwards et al. |
| 2005/0214918 A1 | 9/2005 | Edwards et al. |
| 2005/0288866 A1 | 12/2005 | Sachdeva |
| 2006/0039922 A1 | 2/2006 | Mizzen et al. |
| 2006/0041961 A1 | 2/2006 | Abad et al. |
| 2006/0073530 A1 | 4/2006 | Schneewind et al. |
| 2006/0115479 A1 | 6/2006 | Reinscheid et al. |
| 2006/0160121 A1 | 7/2006 | Mounts et al. |

(Continued)

FOREIGN PATENT DOCUMENTS

| | | |
|---|---|---|
| EP | 0369825 | 5/1990 |
| EP | 0613947 | 1/1994 |
| EP | 555438 | 1/1997 |
| EP | 555439 | 10/1997 |
| EP | 1770171 | 4/2007 |
| GB | 2233977 | 1/1991 |
| WO | WO9006951 | 6/1990 |
| WO | WO9305155 | 3/1993 |
| WO | WO9305156 | 3/1993 |
| WO | WO9801561 | 1/1998 |

(Continued)

OTHER PUBLICATIONS

Abbas et al., *Cellular and Molecular Immunology*, 4th ed., Chapter 15, pp. 360-362, 2000.

(Continued)

*Primary Examiner* — Gary Nickol
*Assistant Examiner* — Padma Baskar
(74) *Attorney, Agent, or Firm* — Banner & Witcoff, Ltd.

(57) ABSTRACT

Forms of GAS25 (streptolysin O) which are not toxic but which still maintain the ability to induce protection against *S. pyogenes* are useful in vaccine compositions to induce protection against *S. pyogenes*.

7 Claims, 26 Drawing Sheets

| U.S. PATENT DOCUMENTS | | | |
|---|---|---|---|
| 2006/0165716 | A1 | 7/2006 | Telford et al. |
| 2006/0194751 | A1 | 8/2006 | Meinke et al. |
| 2006/0210579 | A1 | 9/2006 | Telford et al. |
| 2006/0210580 | A1 | 9/2006 | Telford et al. |
| 2006/0210581 | A1 | 9/2006 | Telford et al. |
| 2006/0210582 | A1 | 9/2006 | Telford et al. |
| 2006/0258849 | A1 | 11/2006 | Telford et al. |
| 2006/0269541 | A1 | 11/2006 | Meinke et al. |
| 2006/0275315 | A1 | 12/2006 | Telford et al. |
| 2007/0036828 | A1 | 2/2007 | Rappuoli et al. |
| 2007/0053924 | A1 | 3/2007 | Tettelin et al. |
| 2007/0065464 | A1 | 3/2007 | Grandi et al. |
| 2007/0098737 | A1 | 5/2007 | Dale |
| 2007/0116712 | A1 | 5/2007 | Hamel et al. |
| 2007/0128210 | A1 | 6/2007 | Olmsted et al. |
| 2007/0128211 | A1 | 6/2007 | Olmsted et al. |
| 2007/0128229 | A1 | 6/2007 | Olmsted et al. |
| 2007/0141635 | A1 | 6/2007 | James |
| 2008/0038268 | A1 | 2/2008 | Martin et al. |
| 2008/0220010 | A1 | 9/2008 | Telford et al. |
| 2009/0022753 | A1 | 1/2009 | Olmsted et al. |

FOREIGN PATENT DOCUMENTS

| WO | WO9818931 | 5/1998 |
|---|---|---|
| WO | WO9819689 | 5/1998 |
| WO | WO9823631 | 6/1998 |
| WO | WO9803677 | 8/1998 |
| WO | WO9913084 | 3/1999 |
| WO | WO9916882 | 4/1999 |
| WO | WO9926969 | 6/1999 |
| WO | WO9942588 | 8/1999 |
| WO | WO 99/49049 | 9/1999 |
| WO | WO9954457 | 10/1999 |
| WO | WO0006736 | 2/2000 |
| WO | WO0006737 | 2/2000 |
| WO | WO0023456 | 4/2000 |
| WO | WO0062804 | 10/2000 |
| WO | WO0078787 | 12/2000 |
| WO | WO0132882 | 5/2001 |
| WO | WO0212294 | 2/2002 |
| WO | WO0234771 | 5/2002 |
| WO | WO02075507 | 9/2002 |
| WO | WO02077183 | 10/2002 |
| WO | WO02092818 | 11/2002 |
| WO | WO03068813 | 8/2003 |
| WO | WO03087353 | 10/2003 |
| WO | WO03093306 | 11/2003 |
| WO | WO2004018646 | 3/2004 |
| WO | WO2004035618 | 3/2004 |
| WO | WO2004041157 | 5/2004 |
| WO | WO2004078907 | 9/2004 |
| WO | WO2004099242 | 11/2004 |
| WO | WO2005013666 | 2/2005 |
| WO | WO2005028618 | 3/2005 |
| WO | WO2005032582 | 4/2005 |
| WO | WO2005076010 | 8/2005 |
| WO | WO2005108419 | 11/2005 |
| WO | WO2006035311 | 4/2006 |
| WO | WO2006042027 | 4/2006 |
| WO | WO2006069200 | 6/2006 |
| WO | WO2006/078318 | 7/2006 |
| WO | WO2006078318 | 7/2006 |
| WO | WO2006082527 | 8/2006 |
| WO | WO2006082530 | 8/2006 |
| WO | WO2006130328 | 12/2006 |
| WO | WO2007018563 | 2/2007 |
| WO | WO2007039319 | 4/2007 |
| WO | WO2007052168 | 5/2007 |
| WO | WO 2007/144647 | 12/2007 |
| WO | WO2008020335 | 2/2008 |
| WO | WO2008108830 | 9/2008 |
| WO | WO2008003515 | 10/2008 |

OTHER PUBLICATIONS

Amara et al., "Molecular detection of methionine in rat brain using specific antibodies," Neurosci. Lett. 185, 147-50, Feb. 13, 1995.

Areschoug et al., "Group B streptococcal surface proteins as targets for protective antibodies: identification of two novel proteins in strains of serotype V.," Inf. Immun. 67(12), 6350-57, Dec. 1999.

Banks et al., "Progress toward characterization of the Group A Streptococcus metagenome: Complete genome sequence of a macrolide-resistant serotype M6 strain," J. Infectious Diseases 190, 727-38, Aug. 15, 2004.

Barnett & Scott, "Differential recognition of surface proteins in Streptococcus pyogenes by two sortase gene homologs," J. Bacteriol. 184, 2181-91, 2002.

Barnett et al., "A Novel Sortase, SrtC2, from Streptococcus pyogenes Anchors a Surface Protein Containing a QVPTGV Motif to the Cell Wall," Journal of Bacteriology, vol. 186, No. 17, pp. 5865-5875, Sep. 2004.

Beckmann et al., "Identification of Novel Adhesins from Group B Streptococci by Use of Phage Display Reveals that C5a Peptidase Mediates Fibronectin Binding," Inf. Immun. 70, 2869-76, Jun. 2002.

Bessen et al., "Genomic Localization of a T Serotype Locus to a Recombinatorial Zone Ending Extracellular Matrix-Binding Proteins in Streptococcus pyogenes," Infection and Immunity, vol. 70, No. 3, pp. 1159-1167, Mar. 2002.

Black et al: "Streptococcus pneumoniae polypeptide coding region"; Genbank Accession No. AAV42990, Nov. 9, 1998.

Blackburn et al., "The end of the (DNA) line," Nature Structural Biology 7, 847-49, Oct. 2000.

Bork et al., "Powers and pitfalls in sequence analysis: the 70% hurdle," Genome Research 10, 398-400, 2000.

Borovec et al., "Synthesis and assembly of hepatitis A virus-specific proteins in BS-C-1 cells," J. Virol. 67, 3095-301, Jun. 1993.

Bowie et al., "Deciphering the message in protein sequences: tolerance to amino acid substitution," Science 257, 1306-10, 1990.

Brodeur et al., "Identification of group B streptococcal Sip protein, which elicits cross-protective immunity," Inf. Immun. 68(10), 5610-8, Oct. 2000.

Burgess et al., "Possible dissociation of the heparin-binding and mitogenic activities of heparin-binding (acidic fibroblast) growth factor-1 from its receptor-binding activities by site-directed mutagenesis of a single lysine residue," J. Cell Biol. 111, 2129-38, 1990.

Chung et al., "chlorosome protein," NCBI Accession No. 2115394F, Jul. 10, 1992.

Clancy et al., "Cloning and Characterization of a Novel Macrolide Efflux Gene, mreA, from Streptococcus agalactiae," Antimicrobial Agents and Chemotherapy 41, 2719-23, 1997.

Collins et al., "Mutation of the principal sigma factor causes loss of virulence in a strain of the Mycobacterium tuberculosis complex," Proc. Natl. Acad. Sci. USA 92, 8036-40, 1995.

Dale et al., "New Protective Antigen of Gorup A Streptococci," J. Clin. Invest. 103, 1261-68, May 1999.

Dale et al., "Recombinant, octavalent group A streptococcal M protein vaccine," Vaccine 14, 944-48, 1996.

Dale, "Group A Streptococcal Vaccines," Infectious Disease Clinics of North America 13, 227-43, Mar. 1999.

Dale, "Multivalent group A streptococcal vaccine designed to optimize the immunogenicity of six tandem M protein fragments," Vaccine 17, 193-200, 1999.

Database EMBL, Accession No. AAX13129, Enterococcus faecalis genome contig SEQ ID No. 192, Mar. 19, 1999.

Database EPO Proteins, EBI Accession No. AX605513, "Sequence 3442 from WO0209818," Feb. 17, 2003.

Database Geneseq, "Group B Streptococcus protein sequence SEQ ID No. 49," EBI Accession No. GSP:AAY91320, May 30, 2000.

Database Geneseq, "Streptococcus agalactiae protein, SEQ ID 2382," EBI Accession No. GSP:ADV81242, Feb. 24, 2005.

Database Geneseq, "Fibrinogen-binding polypeptide, SEQ ID No. 17," EBI Accession No. GSP: ADS93952, Dec. 2, 2004; revised in 2007.

Database Geneseq, EBI Accession No. GSP: ABP30134, "Streptococcus polypeptide SEQ ID No. 9444," Jul. 2, 2002.

Database Geneseq, EBI Accession No. GSP: ABP27285, "Streptococcus polypeptide SEQ ID No. 3746," Jul. 2, 2002; revised in 2007.

Database Genseq, "Protein encoded by Prokaryotic essential gene #319788," Accession No. ABU46451, Jun. 13, 2003.
Database JPO Proteins, "Nucleic acid and protein originating in group B *Streptococcus*," EBI Accession No. JPOP:BD629260, Jul. 17, 2003.
Database Swissprot[Online] Oct. 1, 2002, accession No. EBI, Database accession No. Q9PGX9, Hypothetical protein XF0167.
Database UniProt [Online] Mar. 1, 2003, "Cell wall surface anchor family protein," retrieved from EBI accession No. UNIPROT: Q8DYR5, Database accession No. Q8DYR5, 87.2% identity with SEQ ID No. 20906.
Database UniProt [Online], Nov. 22, 2005, "Cell wall surface anchor family protein," retrieved from EBI accession No. UNIPROT: Q3D2D6; 100% identity with SEQ ID No. 20906; abstract.
De Boever et al., "*Enterococcus faecalis* conjugative plasmid pAM373. Complete nucleotide sequence and genetic analyses of sec phermone response," Mol. Microbiol. 37, 1327-41, 2000.
Dittmer et al., "Treatment of infectious diseases with immunostimulatory oligodeoxynucleotides containing CpG motifs," Curr. Opinion Microbiol. 6, 472-77, Oct. 2003.
Duez, "*Enterococcus hirae* mraR, pbp3s, mraY, murD, murG, ftsQ and ftsA genes, mraW, yllC and ftsZ partial genes," GENBANK Accesion No. Y13922, Apr. 18, 2005.
Ellis, *Vaccines*, Chapter 29, Plotkin et al., eds., W.B. Saunders Company (Philadelphia), pp. 568-575, 1988.
Examination Report for NZ 560966, Mar. 4, 2009, 2 pages.
Ferretti et al., "Complete genome sequence of an M1 strain of *Streptococcus pyogenes*," Proc. Natl. Acad. Sci. USA 98, 4658-63, Apr. 10, 2001.
Ferretti et al., "Putative surface exclusion protein," GENBANK Accession No. Q9A1H3, Oct. 31, 2006.
Ferretti et al: "*Streptococcus pyogenes* M1 Gas strain SF370, Section 87 of 167 of the complete genome" Database Accession No. AE006558.
Glaser et al., "Genome sequence of *Streptococcus agalactiae*, a pathogen causing invasive neonatal disease," Mol. Moicrobiol. 45, 1499-1513, 2002.
Grandi & Zagursky, "The impact of genomics in vaccine discovery: achievements and lessons," Expert. Rev. Vaccines 3, 621-23, 2004.
Grandi, "Genomics and Proteomics in Reverse Vaccines," in *Microbial Proteomics: Functional Biology of Whole Organisms*, Humphery-Smith & Hecker, eds., John Wiley & Sons, chapter 20, 2006.
Greenspan et al., "Defining epitopes: It's not as easy as it seems," Nature Biotechnol. 7, 936-37, 1999.
Gutekunst et al., "Analysis of RogB-Controlled Virulence Mechanisms and Gene Expression in *Streptococcus agalactiae*," *Inf. Immun.* 71, 5056-64, Sep. 2003.
Gutierrez et al., "insertional Mutagenesis and Recovery of Interrupted Genes of *Streptococcus* mutans by Using Transposon Tn917: Preliminary Characterization of Mutants Displaying Acid Sensitivity and Nutritional Requirements," J. Bacteriol. 178, 4166-75, Jul. 1996.
Guttierez et al., "*Streptococcus* mutans ProX (pouABC) gene, partial cds; YlxM (ylxM) gene, complete cds; Ffh (ffh) gene, complete cds, alternatively spliced; SatC (satC) and SatD (satD) gene, complete cds; and SatE (satE) gene, partical cds," GENBANK Accession No. U88582, Apr. 3, 2001.
Guzman et al., "Protective immune response against *Streptococcus pyogenes* in mice after intranasal vaccination with the fibronectin-binding protein Sfbl," J. Infectious Disease 179, 901-06, 1999.
Holmes, "PSMA specific antibodies and their diagnostic and therapeutic use," Exp. Opin. Invest. Drugs 10, 511-10, 2001.
Hong, "unnamed protein product [*Streptococcus pyogenes*]," NCBI Accession No. BAB1603, one page, Oct. 3, 2000.
Horvath et al., "Toward the development of a synthetic group a streptococcal vaccine of high purity and broad protective coverage," J Med Chem. Jul. 29, 2004;47(16):4100-4.
Hughs et al., "Identification of Major Outer surface Proteins of *Streptococcus agalactiae*," *Inf. Immun.* 70,1254-59, Mar. 2002.
International Preliminary Examination Report for PCT/GB01/04789 (published as WO 02/34771) dated Feb. 17, 2003.
International Preliminary Examination Report for PCT/GB2003/001882 (published as WO 03/093306) dated Aug. 18, 2004.
International Preliminary Examination Report for PCT/IB2005/036009 (published as WO 06/042027) dated Apr. 11, 2007.
International Preliminary Examination Report for PCT/US2003/029167 (published as WO 04/041157) dated Mar. 5, 2005.
International Preliminary Examination Report for PCT/US2004/024868 (published as WO 05/032582) dated Feb. 6, 2006.
International Preliminary Examination Report for PCT/US2004/030032 (published as WO 05/028618) dated Mar. 16, 2006.
International Search Report for PCT/GB01/04789 (published as WO 02/34771) dated Aug. 27, 2002.
International Search Report for PCT/GB2003/001882 (published as WO 03/093306) dated Nov. 14, 2002.
International Search Report for PCT/IB2005/036009 (published as WO 06/042027) dated Jun. 20, 2006.
International Search Report for PCT/US05/046491 dated Jun. 26, 2007 (published as WO 2006/069200).
International Search Report for PCT/US2003/029167 (published as WO 04/041157) dated Aug. 2, 2004.
International Search Report for PCT/US2004/024868 (published as WO 05/032582) dated Oct. 28, 2005.
International Search Report for PCT/US2004/030032 (published as WO 05/028618) dated Dec. 6, 2005.
International Search Report for PCT/US2005/027239 (published as WO 06/078318) dated Aug. 25, 2008.
International Search Report for PCT/US2007/022838 (published as WO 08/108830) dated Oct. 9, 2008.
Jobling et al., "Analysis of structure and function of the B subunit of cholera toxin by the use of site-directed mutagenesis," Mol. Microbiol. 5, 1755-67, 1991.
Kalman et al., "Comparative genomes of Chlamydia pneumoniae and C. trachomatis," Nature Genetics 21, 385-89, Apr. 1999.
Kehoe et al., "Nucleotide Sequence of the Streptolysin O (SLO) Gene: Structural Homologies between SLO and Other Membrane-Damaging, Thiol-Activated Toxins," Inf. Immun. 55, 3228-32, Dec. 1987.
Koch et al., "Complexity and expression patterns of the desmosomal adherins," Proc. Natl. Acad. Sci. USA 89, 353-57, Jan. 1992.
Kunst et al., "The complete genome sequence of the Gram positive bacterium *Bacillus subtilis*," NCBI Accession No. CAB14964, Nov. 20, 1997.
Lachenauer et al., "A protective surface protein from the Type V Group B *Streptococcus* shares N-terminal sequence homology with the Alpha C Protein," Inf. Immun. 64, 4255-60, Oct. 1996.
Larsson et al., "Protection against experimental infection with group B *Streptococcus* by immunization with a bivalent protein vaccine," *Vaccine* 17, 454-58, 1999.
Lauer et al., "Genome Analysis Reveals Pili in Group B *Streptococcus*," Science 309, 105, Jul. 1, 2005.
Lazar et al., "Transforming growth factor alpha: mutation of aspartic acid 47 and leucine 48 results in different biological activities," Mol. Cell. Biol. 8, 1247-52, 1988.
Le Page et al., *Streptococcus agalactiae* sequence 217 from WO 01/32882, GENBANK Accession No. AX134653, May 29, 2001.
Lei et al., "Identification and immunogenicity of group A *Streptococcus* culture supernatant proteins," Inf. Immunity 68, 6807-18, 2000.
Lewis, "Riddle of Biofilm Resistance," *Antimicrobial Agents and Chemotherapy*, vol. 45, No. 4, pp. 999-1007, Apr. 2001.
Lindahl et al., "Surface proteins of *Streptococcus agalactiae* and related proteins in other bacterial pathogens," Clinical Microbiol. Rev. 18(1), 102-07, Jan. 2005.
Madoff et al., "Maternal Immunization of Mice with Group B Streptococcal Type III Polysaccharide-Beta C Protein Conjugate Elicits Protective Antibody to Multiple Serotypes," J. Clinical Invest. 94, 286-92, 1994.
Maione et al., "Identification of a Universal Group B *Streptococcus* Vaccine by Multiple Genome Screen," *Science* 309, 148-50, Jul. 1, 2005.
McMillan et al., "Identification and assessment of new vaccine candidates for group A streptococcal infections," *Vaccine* 22, 2783-90, 2004.
McMillan et al., "Prospecting for new group A streptococcal vaccine candidates," *Indian J. Med. Res. 119*, 121-25, May 2004.

Meehan & Owen, "Sequence 1 from Patent WO9801561," GENBANK Accession No. A68631, May 6, 1999.

Meinke et al., "*S. pyogenes* hyperimmune system reactive antigen Spy0269," EBI Accession No. ADR83896, Dec. 2, 2004; revised Jun. 15, 2007.

Michel et al: "Cloned alpha and beta C-protein antigens of group B *Streptococci* elicit protective immunity"; Infection and Immunity; vol. 59, No. 6, Jun. 1991; pp. 2023-2028.

Molling et al., "Naked DNA for vaccine or therapy," J. Mol. Med. 75, 242-46, 1997.

Mora et al., "Group A *Streptococcus* produce pilus-like structures containing protective antigens and Lancefield T antigens," Proc. Natl. Acad. Sci. USA 102, 15641-46, Oct. 25, 2005.

Musser, "The Next Chapter in Reverse Vaccinology," Nat. Biotechnol. 24, 157-58, 2006.

Nakagawa et al., "Genome sequence of an M3 strain of *Streptococcus pyogenes* reveals a large-scale genomic rearrangement in invasive strains and new insights into phage evolution," *Genome Res.* 13, 1042-55, Jun. 2003.

Nakata et al., "MsmR, a specific positive regulator of the *Streptococcus pyogenes* FCT pathogenicity region and cytolysin-mediated translocation system genes," Mol. Microbiol. 57, 786-803, 2005.

Navarre et al., "Surface Proteins of Gram-Positive Bacteria and Mechanisms of Their Targeting to the Cell Wall Envelope," *Microbiology and Molecular Biology Reviews*, vol. 63, No. 1, pp. 174-229, Mar. 1999.

NCBI News, table on p. 4, "Microbial Genomes Available for BLAST Search," Jul. 1998.

Olive et al., "Protection of mice from group A streptococcal infection by intranasal immunization with a peptide vaccine that contains a conserved M protein B cell epitope and lacks a T cell autoepitope," Vaccine 20, 2816-25, 2002.

Orefici et al., "Possible virulence marker for *Streptococcus agalactiae* (Lancefiled Group B)," J. Clin. Microbiol. Infectious Diseases 7, 302-05, 1988.

Paoletti et al., "Neonatal mouse protection against infection with multiple group B *streptococcal* (GBS) serotypes by maternal immunization with a tetravalent GBS polysaccharide-tetanus toxoid conjugate vaccine," Inf. Immun. 62, 3236-43, 1994.

Paoletti, "Surface structure of group B *streptoccoccus* important in human immunity," in *Gram Positive Pathogens*, Fischetti et al., eds., Chapter 14, pp. 137-153, 2000.

Pournaras et al., "Pheromone responses and high-level aminoglycoside resistance of conjugative plasmids of *Enterococcus faecalis* from Greece," J. Antimicrobial Chemotherapy 46, 1013-16, 2000.

Pritzlaff et al., "Genetic basis for the beta-haemolytic cytolitic activity of group B *Streptococcus*," Mol. Microbiol. 39, 236-48, 2001.

Pritzlaff et al., "*Streptococcus agalactiae* cyl gene cluster, partial sequence," GENBANK Accession No. AF157015, Feb. 8, 2001.

Proft et al., "Identification and Characterization of Novel Superantigens from *Streptococcus pyogenes*," J. Exp. Med. 189, 89-101, Jan. 4, 1999.

Pucci et al., "*Enterococcus faecalis* strain A24836 cell wall/cell division gene cluster, yllB, yllc, yllD, pbpC, mraY, murD, murG, divlB, ftsA and fitsZ genes, complete cds," GENBANK Accession No. U94707, Sep. 10, 1997.

Quinn, "The response of rheumatic and non-rheumatic children to streptolysin O concentrate," J. Clin. Invest. 36, 793-802, Jun. 1957.

Ramachandran et al., "Two Distinct Genotypes of *prtF2*, Encoding a Fibronectin Binding Protein, and Evolution of the Gene Family in *Streptococcus pyogenes*," *Journal of Bacteriology*, vol. 186, No. 22, pp. 7601-7609, Nov. 2004.

Rodewald et al., "Neonatal mouse model of group b streptococcal infection," J. Infectious Diseases 166, 635-39, 1992.

Rodriguez-Ortega et al., "Characterization and identification of vaccine candidate proteins through analysis of the group A *Streptococcus* surface proteome," Nature Biotechnol. 24, 191-97, 2006.

Roitt et al., Structure of Antigens, *Immunology*, 4th ed., Mosby, London, pp. 7.7 and 7.8, 1998.

Rosini et al., "Identification of novel genomic islands coding for antigenic pilus-like structures in *Streptococcus agalactiae*," Mol. Microbial. 61, 126-41, 2006.

Rudenko et al., "Selection for activation of a new variant surface glycoprotein gene expression site in *Trypanosoma brucei* can result in deletion of the old one," Mol. Biochem. Parisitol. 95, 97-109, 1998; NCBI Accession No. CAD21770.

Rudinger et al., "Characteristics of the amino acids as components of a peptide hormone sequence," in *Peptide Hormones*, Parsons, ed., University Park Press, Jun. 1976, pp. 1-7.

Schneewind et al., "Sequence and Structural Characteristics of the Trypsin-Resistant T6 Surface Protein of Group A *Streptococci*," *Journal of Bacteriology*, vol. 172, No. 6, pp. 3310-3317, Jun. 1990.

Schneewind, "Structure of the Cell Wall anchor of Surface Proteins in *Staphylococcus aureus*," Science 268, 103-06, Apr. 7, 1995.

Segura et al., "*Streptococcus suis* and group B *Streptococcus* differ in their interactions with murine macrophages," FEMS Immunol. Med. Microbiol. 21, 189-95, 1998.

Seizen, "Multi-domain, cell envelope proteases of lactiv acid bacteria," Antonie von Leeuwenhoek 76, 139-55, 1999.

Simpson et al., "Xylella fastidiosa 9a5c, section 136 of 229 of the complete genome," GENBANK Accession No. AE003990, Jun. 4, 2004.

Smoot et al., "Genome sequence and comparative microarray analysis of serotype M18 group A *Streptococcus* strains associated with acute rheumatic fever outbreaks," Proc. Natl. Acad. Sci. USA 99, 4668-73, Apr. 2, 2002.

Spellerberg et al., "*Streptococcus agalactiae* cyl gene cluster, complete sequence," GENBANK Accession No. AF093787, Jul. 31, 2000.

Spellerberg et al: "Identification of genetic determinants for the hemolytic activity of *Streptococcus agalactiae* by ISSI transposition"; J. Bacteriol.; vol. 181, No. 10, May 1999; pp. 3212-3219.

Stalhammar-Carlemalm et al: "The R28 Protein of *Streptococcus pyogenes* is related to several group B streptococcal surface proteins, confer protective immunity and promotes binding to human epithelial cells"; Mol. Microbiol. Jul. 1, 1999, pp. 208-219.

Stephenson et al., "The Fap1 fimbrial adhesin is a glycoprotein: antibodies specific for the glycan moiety block the adhesion of *Streptococcus parasanguis* in an in vitro tooth model," Mol. Microbiol. 43, 147-57, 2002.

Su et al., "Identification of a Xenopus cDNA that prevents mitotic catastrophe in the fission yeast *Schizosaccharomyces pombe*," Gene 145, 155-56, 1994.

Supplementary Search report for EP 03799822 (corresponding to WO 04/041157) dated Jan. 21, 2008.

Surovov & Ferretti, "Physical and Genetic Chromosomal Map of an M Type 1 Strain of *Streptococcus pyogenes*," J. Bacteriol. 178, 5546-49, Sep. 1996.

Takami et al., "Two component sensor histidine kinase involved in phosphate regulation," NCBI Accession No. NP_244022.1, Sep. 10, 2001.

Telford et al., Sequence 7466 from WO 02/34771, EBI Accession No. CQ650509, Feb. 2, 2004; modified May 31, 2006.

Telford et al., "*Streptococcus* polypeptide SEQ ID No. 9188" of WO 02/34771, EBI Accession No. ABP300006, Jul. 2, 2002; revised Jun. 15, 1007.

Tettelin et al., "Complete genome sequence and comparative genomic analysis of an emerging human pathogen, serotype V *Streptococcus agalactiae*," Proc. Natl. Acad. Sci. USA 99, 12391-96, Sep. 17, 2002.

Tettelin et al., "Complete genome sequence of a virulent isolate of *Streptococcus pneumoniae*," Science 293, 498-506, 2001.

Tettelin et al., Database EMBL, Accession No. AE014193, *Streptococcus agalactiae* 2603V/R section 3 of 100 of the complete genome, Sep. 2, 2002.

Tettelin et al., Swiss-Prot Accession No. Q3DV91 for *Streptococcus agalactiae* strain 18R21, Nov. 22, 2005.

Tighe et al., "Gene vaccination: plasmid DNA is more than just a blueprint," Immunology Today 19, 89-97, Feb. 1998.

Todd, "Antigenic Streptococcal Hemolysin," J. Exp. Med. 55, 267-80, 1932.

Ton-That & Schneewind, "Assembly of pili on the surface of *Corynebacterium diphtheriae*," Mol. Microbiol. 50, 1429-38, 2003.

Ton-That et al., "Sortases and pilin elements involved in pilus assembly of *Corynebacterium diphtheriae*," Mol. Microbiol. 53, 251-61, 2004.

UniProt Accession No. A7CNQ7, Jul. 5, 2004.

UniProt Accession No. Q5XEL1, Nov. 23, 2004.

UniProt Accession No. Q8P318, Oct. 1, 2002.

Vallet et al., "The chaperone/usher pathways of *Pseudomonas aeruginosa*: Identification of fimbrial gene clusters (cup) and their involvement in biofilm formation," *PNAS*, vol. 98, No. 12, pp. 6911-6916, Jun. 2001.

Wang et al., "Protein encoded by prokaryotic essential gene #31978," EBI Accession No. ABU46451, Jun. 19, 2003; revised Jun. 15, 2007.

Watnick et al., "Steps in the development of a *Vibrio cholerae* El Tor biofilm," *Molecular Microbiology*, vol. 34, No. 3, pp. 586-595, 1999.

Wessels et al., "Stimulation of protective antibodies against type 1a and 1b group B *Streptococci* by a type 1a polysaccharide-tetanus toxoid conjugate vaccine," Inf. Immun. 61, 4760-66, 1993.

Woodson et al., "Analysis of a ribose transport operon from *Bacillus subtilis*," Microbiology 140, 1829-38, 1994.

Zhong et al., "Hypothetical protein of *Arabidopsis thaliana*," NCBI Accession No. AAD29767, May 11, 1999.

International Search Report and Written Opinion for PCT/IB2008/003725 mailed Jun. 12, 2009.

Palmer et al., "Assembly mechanism of the oligomeric streptolysin O pore: the early membrane lesion is lined by a free edge of the lipid membrane and is extended gradually during oligomerization," EMBO Journal 17, 1598-1605, 1998.

Pinkney et al., "The Thiol-Activated Toxin Streptolysin O Does Not Require a Thiol Group for Cytolytic Activity," Infection and Immunity 57, 2553-58, Aug. 1989.

SDS Page analysis of total proteins extracts

A. SLO P427L-W535F *tag-less* clone
B. SLO P427L-C530G *tag-less* clone
C. SLO P427L-C530G-W535F *tag-less* clone
N. Non induced culture
Molecular weight markers (97-66-45-30-20.1-14, SDS Page analysis of total proteins extracts A. SLO Wild Type *his-tagged* clone
B. SLO W535F *his-tagged* clone
C. SLO W535F-D482N *his-tagged* clone
D. SLO C530G *his-tagged* clone
E. SLO P427L *his-tagged* clone
F. SLO delta Ala 248 *his-tagged* clone
N. Non induced culture
Molecular weight markers (97-66-45-30-20.1-14,4)
Black arrow indicates SLO protein band in extracts from mutants and wild type clones

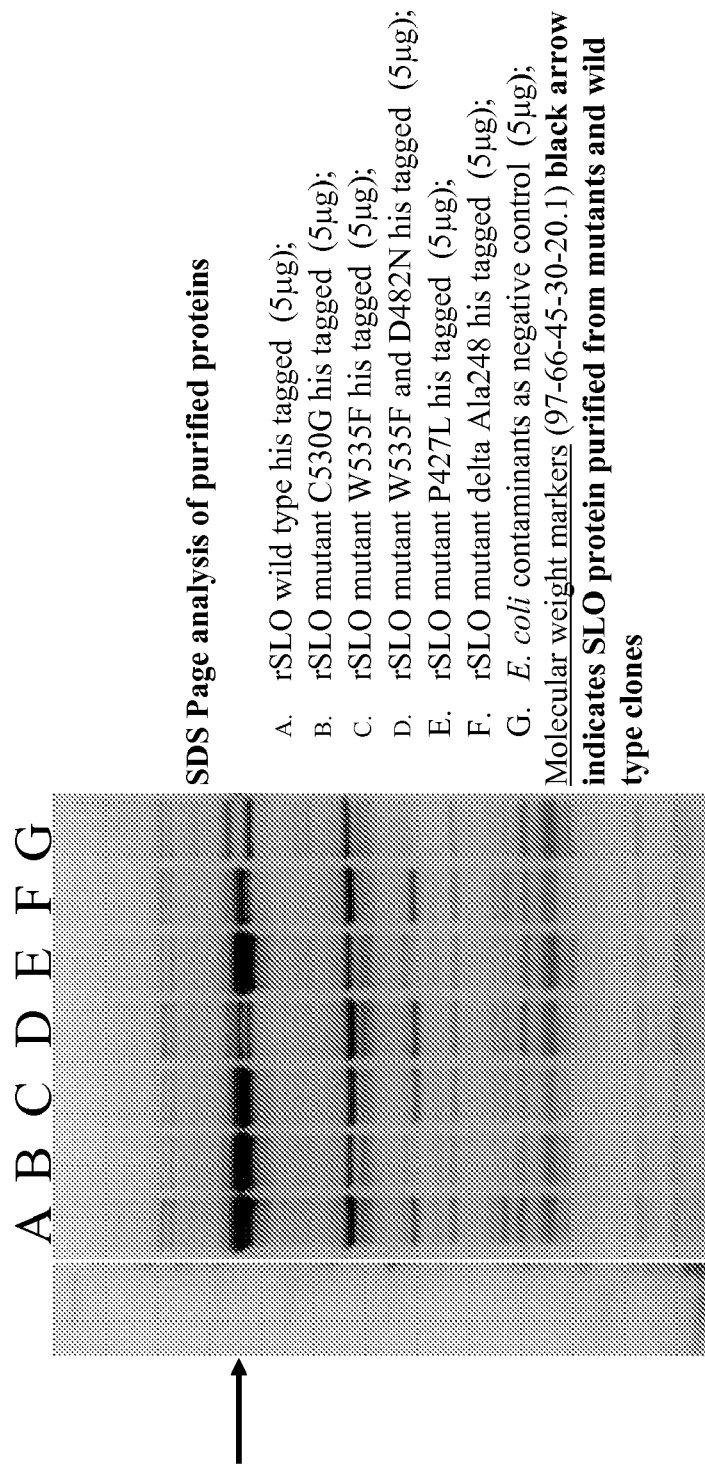

FIGURE 10

SDS Page analysis of purified proteins

A. rSLO wild type his tagged (5μg);
B. rSLO mutant C530G his tagged (5μg);
C. rSLO mutant W535F his tagged (5μg);
D. rSLO mutant W535F and D482N his tagged (5μg);
E. rSLO mutant P427L his tagged (5μg);
F. rSLO mutant delta Ala248 his tagged (5μg);
G. E. coli contaminants as negative control (5μg);

Molecular weight markers (97-66-45-30-20.1) black arrow indicates SLO protein purified from mutants and wild type clones

```
GAS25_M4     (301) EFTVSAKLPNNPALVFAKGVFFKELGRKVGNEALPLFSNVAYGKIYFV
                   351                                              400
GAS25_SF370  (351) KLPTSSKSNDVEAAFSAALKGTDVKTNGKYSDILENSSPTAVVLGGDAAE
GAS25_M12_2096 (351) KLPTSSKSNDVEAAFSAALKGTDVKTNGKYSDILENSSPTAVVLGGDAAE
GAS25_M12_9429 (351) KLPTSSKSNDVEAAFSAALKGTDVKTNGKYSDILENSSPTAVVLGGDAAE
GAS25_M1_5005 (351) KLPTSSKSNDVEAAFSAALKGTDVKTNGKYSDILENSSPTAVVLGGDAAE
GAS25_M2     (351) KLPTSSKSNDVEAAFSAALKGTDVKTNGKYSDILENSSPTAVVLGGDAAE
GAS25_M28    (351) KLPTSSKSNDVEAAFSAALKGTDVKTNGKYSDILENSSPTAVVLGGDAAE
GAS25_M6     (351) KLPTSSKSNDVEAAFSAALKGTDVKTNGKYSDILENSSPTAVVLGGDAAE
GAS25_M18    (351) KLPTSSKSNDVEAAFSAALKGTDVKTNGKYSDILENSSPTAVVLGGDAAE
GAS25_M5     (351) KLPTSSKSNDVEAAFSAALKGTDVKTNGKYSDILENSSPTAVVLGGDAAE
GAS25_M3     (351) KLPTSSKSNDVEAAFSAALKGTDVKTNGKYSDILENSSPTAVVLGGDAAE
GAS25_M3_SSI (351) KLPTSSKSNDVEAAFSAALKGTDVKTNGKYSDILENSSPTAVVLGGDAAE
GAS25_M4     (351) KLPTSSKSNDVEAAFSAALKGTDVKTNGKYSDILENSSPTAVVLGGDAAE
                   401                                              450
GAS25_SF370  (401) HNKVVTKDFDVTRNVIKDNATFSRNPAYPISYTSVFLKNNKIAGVNNR
GAS25_M12_2096 (401) HNKVVTKDFDVTRNVIKDNATFSRNPAYPISYTSVFLKNNKIAGVNNR
GAS25_M12_9429 (401) HNKVVTKDFDVTRNVIKDNATFSRNPAYPISYTSVFLKNNKIAGVNNR
GAS25_M1_5005 (401) HNKVVTKDFDVTRNVIKDNATFSRNPAYPISYTSVFLKNNKIAGVNNR
GAS25_M2     (401) HNKVVTKDFDVTRNVIKDNATFSRNPAYPISYTSVFLKNNKIAGVNNR
GAS25_M28    (401) HNKVVTKDFDVTRNVIKDNATFSRNPAYPISYTSVFLKNNKIAGVNNR
GAS25_M6     (401) HNKVVTKDFDVTRNVIKDNATFSRNPAYPISYTSVFLKNNKIAGVNNR
GAS25_M18    (401) HNKVVTKDFDVTRNVIKDNATFSRNPAYPISYTSVFLKNNKIAGVNNR
GAS25_M5     (401) HNKVVTKDFDVTRNVIKDNATFSRNPAYPISYTSVFLKNNKIAGVNNR
GAS25_M3     (401) HNKVVTKDFDVTRNVIKDNATFSRNPAYPISYTSVFLKNNKIAGVNNR
GAS25_M3_SSI (401) HNKVVTKDFDVTRNVIKDNATFSRNPAYPISYTSVFLKNNKIAGVNNR
GAS25_M4     (401) HNKVVTKDFDVTRNVIKDNATFSRNPAYPISYTSVFLKNNKIAGVNNR
                   451                                              500
GAS25_SF370  (451) EYVETTSTEYTSCKINLSHRGAYVAQYEILWDEINYDDKGKSVITKRWD
GAS25_M12_2096 (451) EYVETTSTEYTSCKINLSHRGAYVAQYEILWDEINYDDKGKSVITKRWD
GAS25_M12_9429 (451) EYVETTSTEYTSCKINLSHRGAYVAQYEILWDEINYDDKGKSVITKRWD
GAS25_M1_5005 (451) EYVETTSTEYTSCKINLSHRGAYVAQYEILWDEINYDDKGKSVITKRWD
GAS25_M2     (451) EYVETTSTEYTSCKINLSHRGAYVAQYEILWDEINYDDKGKSVITKRWD
GAS25_M28    (451) EYVETTSTEYTSCKINLSHRGAYVAQYEILWDEINYDDKGKSVITKRWD
GAS25_M6     (451) EYVETTSTEYTSCKINLSHRGAYVAQYEILWDEINYDDKGKSVITKRWD
GAS25_M18    (451) EYVETTSTEYTSCKINLSHRGAYVAQYEILWDEINYDDKGKSVITKRWD
GAS25_M5     (451) EYVETTSTEYTSCKINLSHRGAYVAQYEILWDEINYDDKGKSVITKRWD
GAS25_M3     (451) EYVETTSTEYTSCKINLSHRGAYVAQYEILWDEINYDDKGKSVITKRWD
GAS25_M3_SSI (451) EYVETTSTEYTSCKINLSHRGAYVAQYEILWDEINYDDKGKSVITKRWD
GAS25_M4     (451) EYVETTSTEYTSCKINLSHRGAYVAQYEILWDEINYDDKGKSVITKRWD
                   501                                              550
GAS25_SF370  (501) KNWNSKISPESVIPLGANSRNIRIMAKECTGLAWEWRKVTDERDVKLS
GAS25_M12_2096 (501) KNWNSKISPESVIPLGANSRNIRIMAKECTGLAWEWRKVTDERDVKLS
GAS25_M12_9429 (501) KNWNSKISPESVIPLGANSRNIRIMAKECTGLAWEWRKVTDERDVKLS
GAS25_M1_5005 (501) KNWNSKISPESVIPLGANSRNIRIMAKECTGLAWEWRKVTDERDVKLS
GAS25_M2     (501) KNWNSKISPESVIPLGANSRNIRIMAKECTGLAWEWRKVTDERDVKLS
GAS25_M28    (501) KNWNSKISPESVIPLGANSRNIRIMAKECTGLAWEWRKVTDERDVKLS
```

FIG. 23, cont.

```
    GAS25_M6   (501) NNWYSKTSPPSVIPLGANSKNIRTMASECIGLAWEAWRKVTDEPLVKLS
    GAS25_M18  (501) NNWYSKTSPPSVIPLGANSKNIRTMASECIGLAWEAWRKVTDEPLVKLS
    GAS25_M5   (501) NNWYSKTSPPSVIPLGANSKNIRTMASECIGLAWEAWRKVTDEPLVKLS
    GAS25_M3   (501) NNWYSKTSPPSVIPLGANSKNIRTMASECIGLAWEAWRKVTDEPLVKLS
  GAS25_M3_SSI (501) NNWYSKTSPPSVIPLGANSKNIRTMASECIGLAWEAWRKVTDEPLVKLS
    GAS25_M4   (501) NNWYSKTSPPSVIPLGANSKNIRTMASECIGLAWEAWRKVTDEKDVKLS
                     551                 572
    GAS25_SF370  (551) KEINVNLSGSTLSPYGSTYK-
    GAS25_M12_2096 (551) KEINVNLSGSTLSPYGSTYK-
    GAS25_M12_9429 (551) KEINVNLSGSTLSPYGSTYK-
    GAS25_M1_5005  (551) KEINVNLSGSTLSPYGSTYK-
    GAS25_M2    (551) KEINVNLSGSTLSPYGSTYK-
    GAS25_M28   (551) KEINVNLSGSTLSPYGSTYK-
    GAS25_M6    (551) KEINVNLSGSTLSPYGSTYK-
    GAS25_M18   (551) KEINVNLSGSTLSPYGSTYK-
    GAS25_M5    (551) KEINVNLSGSTLSPYGSTYK-
    GAS25_M3    (551) KEINVNLSGSTLSPYGSTYK-
  GAS25_M3_SSI  (551) KEINVNLSGSTLSPYGSTYK-
    GAS25_M4    (551) KEINVNLSGSTLSPYGSTYK-
```

Consensus positions: 99.8%
Identity positions: 97.7%

FIG. 24

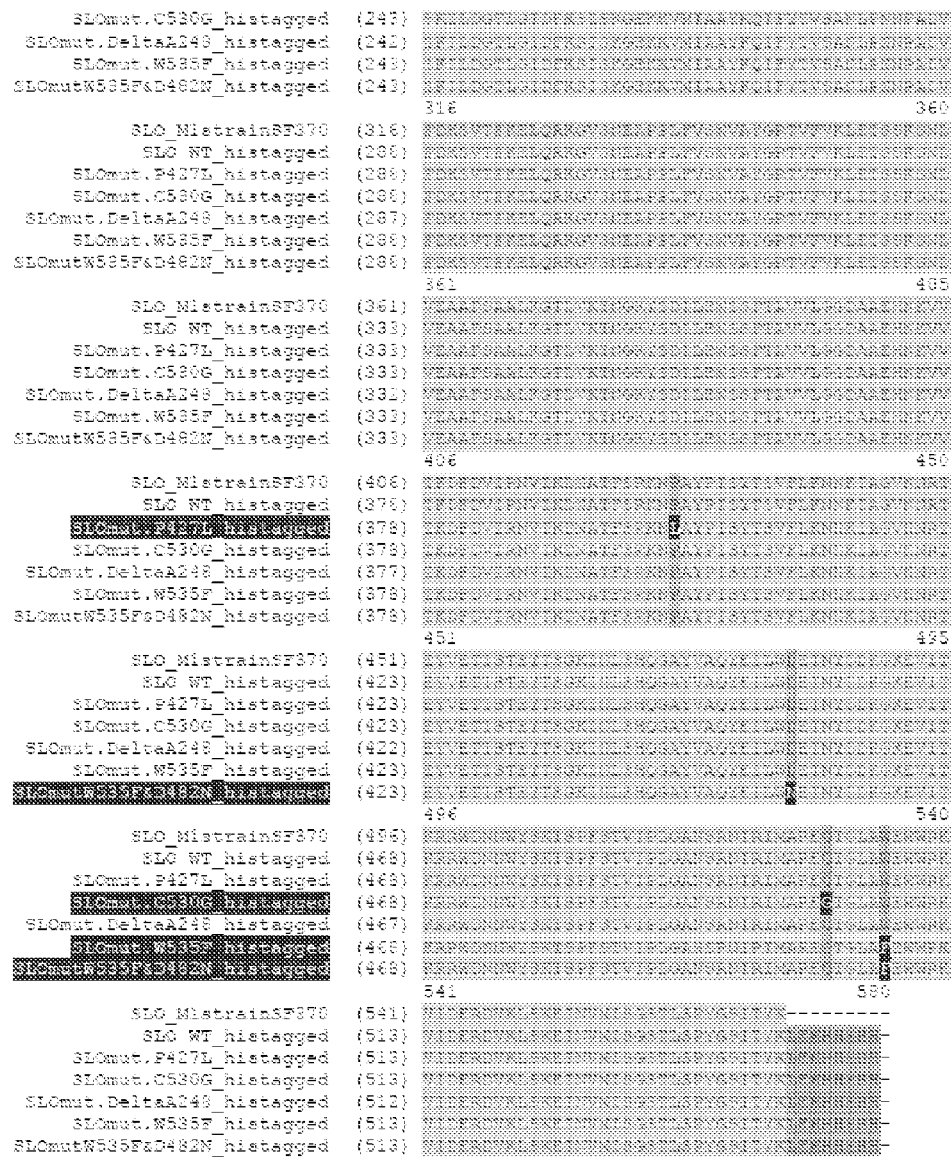
FIG. 24, cont.

MUTANT FORMS OF STREPTOLYSIN O

This application is a continuation of Ser. No. 12/339,365 filed on Dec. 19, 2008, now U.S. Pat. No. 7,731,978, which claims the benefit of Ser. No. 61/016,193 filed on Dec. 21, 2007 and Ser. No. 61/088,381 filed on Aug. 13, 2008. The complete contents of each of these applications are incorporated herein by reference.

This application incorporates by reference the contents of a 156 kb text file named "52564_sequencelisting.txt," created on Feb. 24, 2010, which is the sequence listing for this application.

FIELD OF THE INVENTION

The invention relates to the fields of immunology and vaccinology.

BACKGROUND OF THE INVENTION

Streptolysin O (SLO; GAS25) is one of the most important virulence factors of the human pathogen *Streptococcus pyogenes* (GAS). Because of its capacity to invoke an early and strong immune response in humans, it is routinely used as a diagnostic marker of GAS infection.

SLO belongs to the family of the highly homologous thiol-activated cytolysins (TACYs), which exert their cytolytic activity through interaction with cholesterol on the cell membrane, self-oligomerization, and formation of pores. Furthermore, their capacity to activate directly the classical complement pathway by binding to the Fc region of human IgG may result in direct complement-mediated attack on host cells. TACYs can also interfere with host defense and immune cell function by means of the induction of cytokines and inflammatory mediators.

Some TACYs can passively and actively protect laboratory animals. See *FEMS Lett.* 182, 197-205, 2000. However, the use of these toxins as vaccine candidates has been hampered by their complex pattern of harmful side effects. There is, therefore, a need in the art for SLO proteins which are not toxic.

BRIEF DESCRIPTION OF THE FIGURES

FIG. 8. Photomicrographs of SDS-PAGE analysis of total tag-less proteins in cell extracts.

FIG. 10. Photomicrograph of SDS-PAGE analysis of purified His-tagged proteins.

FIG. 11. Photomicrographs of SDS-PAGE analysis of purified tag-less proteins.

Figure 23:
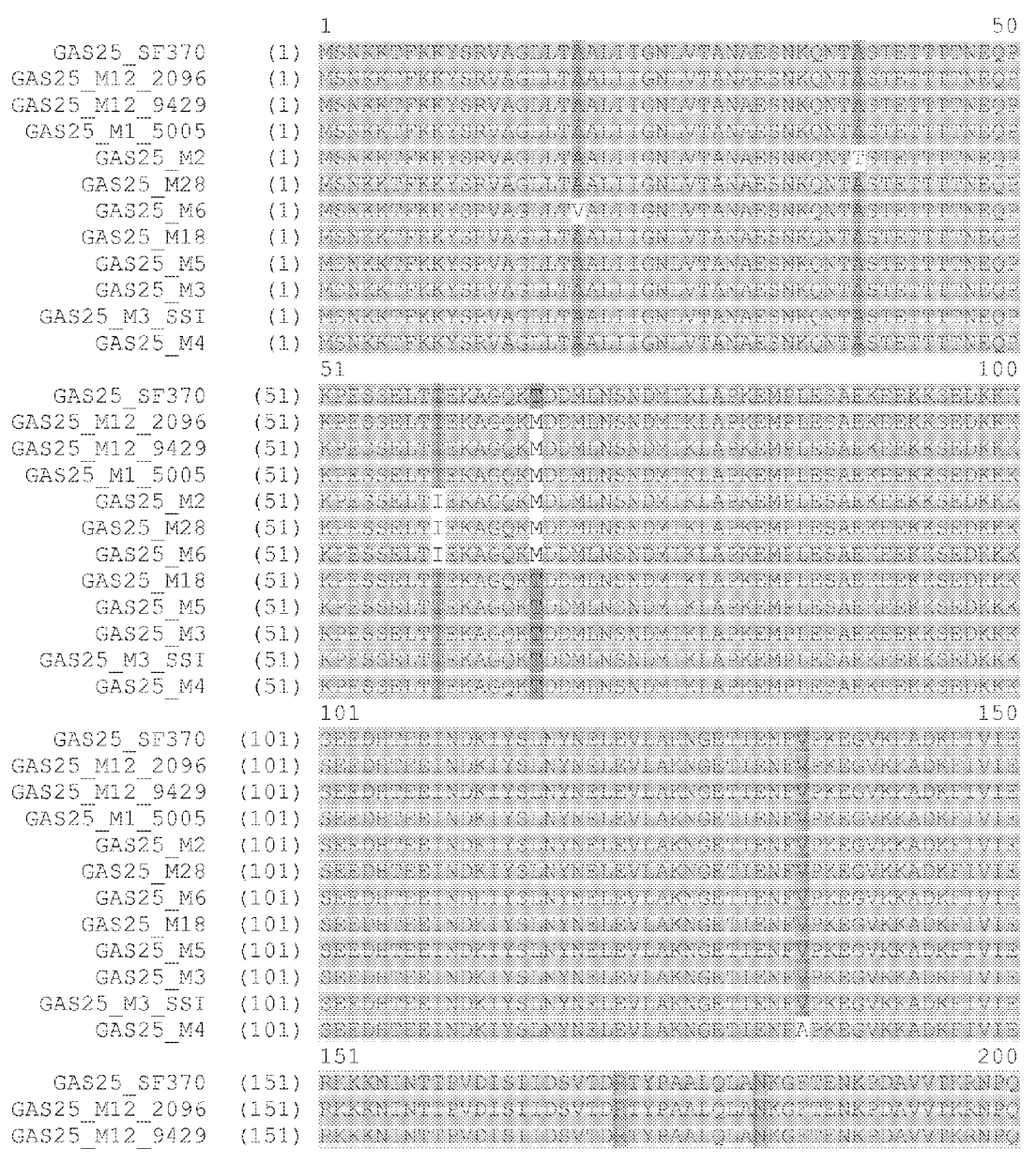
Figure 23:
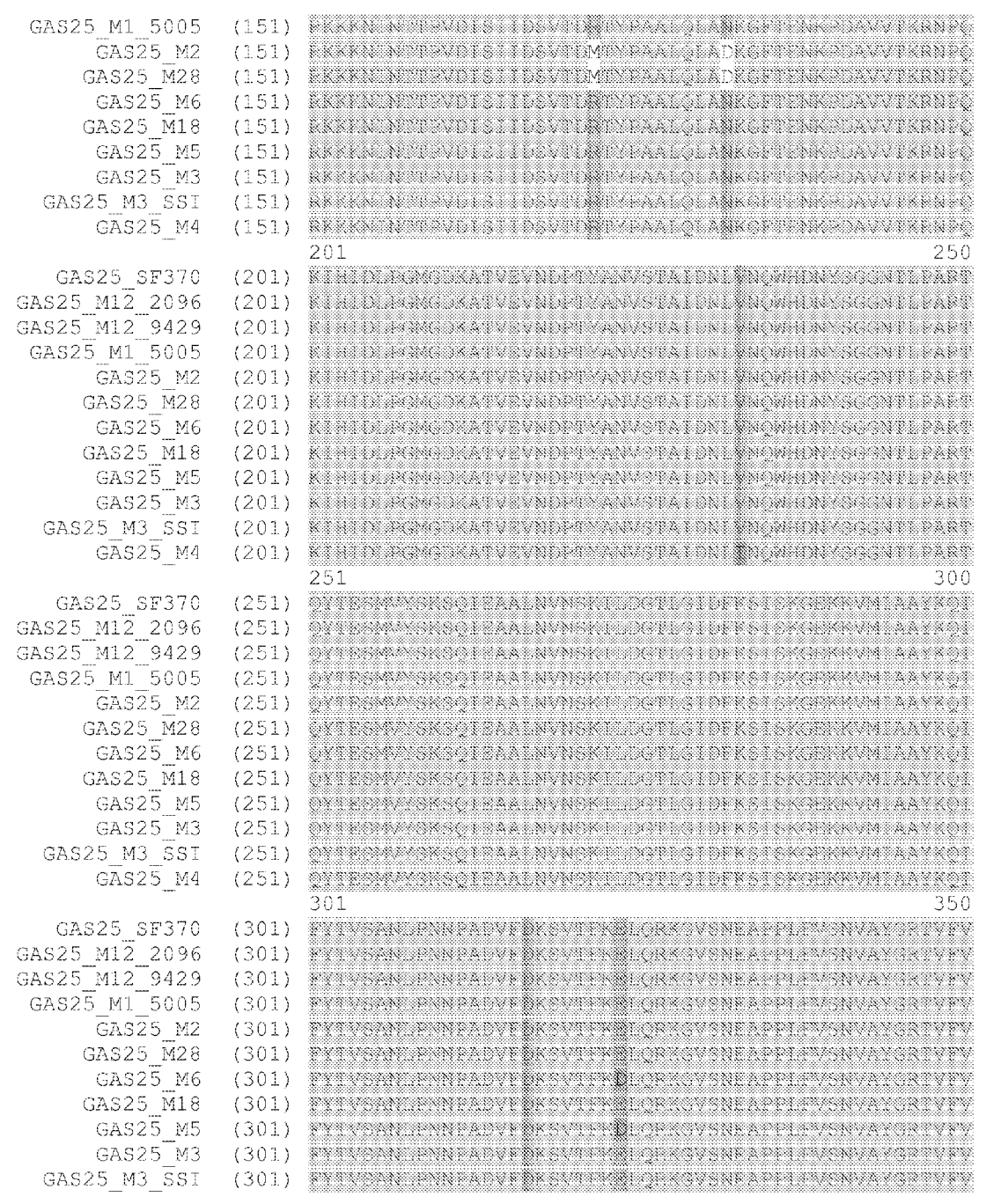

FIG. 23. Alignment of SLO proteins. M1_SF370, SEQ ID NO:1; M12__2096, SEQ ID NO:2; M12__9429, SEQ ID NO:3; M1__5005, SEQ ID NO:4; M2, SEQ ID NO:5; M28, SEQ ID NO:6; M6, SEQ ID NO:7; M18, SEQ ID NO:8; M5, SEQ ID NO:9; M3, SEQ ID NO:10; M3_SSI, SEQ ID NO:11; and M4, SEQ ID NO:12.

Figure 24:
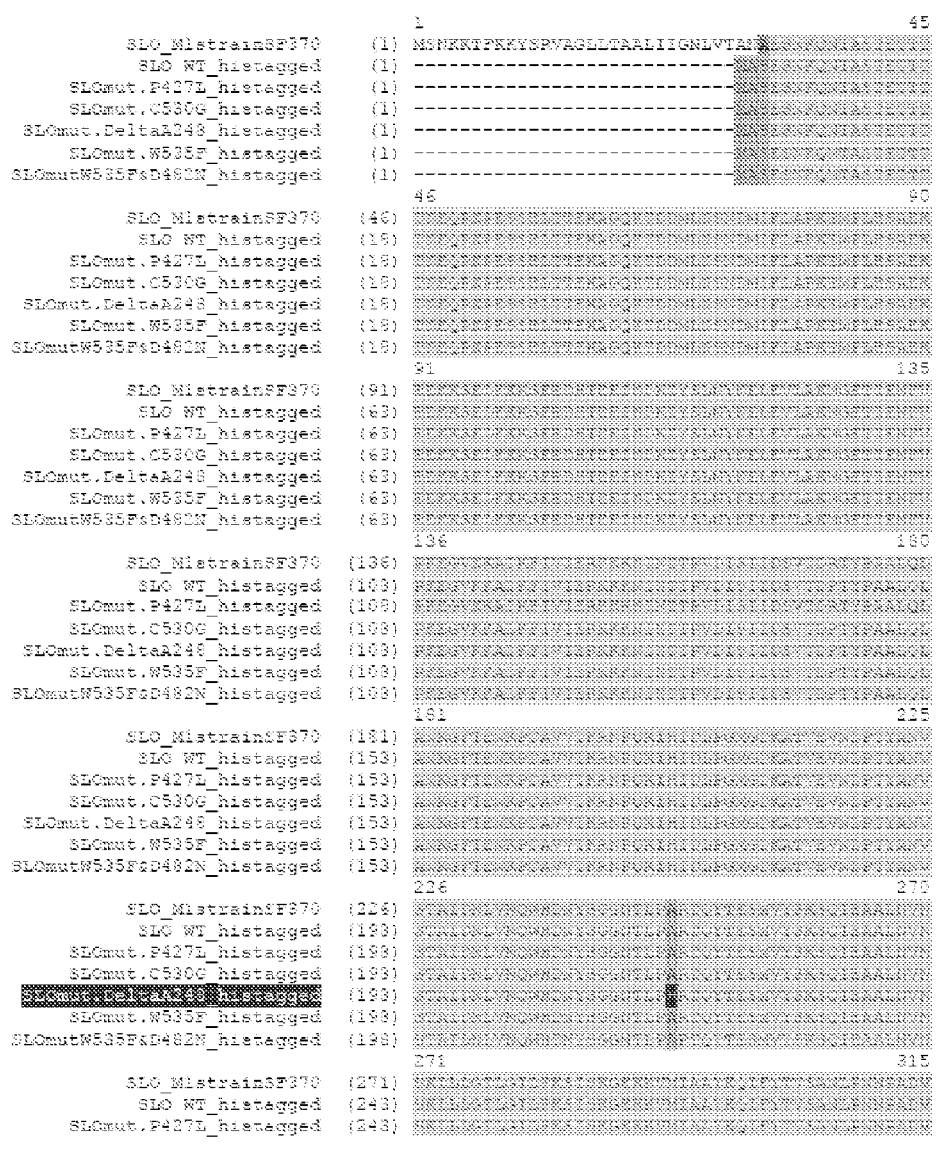

FIG. 24. Alignment of wild-type SLO and His-tagged SLO mutants. SLO_M1strainSF370, SEQ ID NO:13; SLO WT_histagged, SEQ ID NO:14; SLOmut.P427L_histagged, SEQ ID NO:15; SLOmut.C530G_histagged, SEQ ID NO:16; SLOmut.DeltaA248_histagged, SEQ ID NO:17; SLOmut.W535F_histagged, SEQ ID NO:18; and SLOmutW535F&D482N_histagged, SEQ ID NO:19.

DETAILED DESCRIPTION OF THE INVENTION

Figure 1:
FIG. 1. Three-dimensional computer model of SLO. Prolines are represented as space-filled. Pro427 is colored in white.

The invention provides mutants of streptolysin O (SLO; GAS25) which are non-toxic but which still maintain the ability to induce protection against *S. pyogenes*. Mutant forms of SLO are useful, inter alia, in vaccine compositions, to induce protection against *S. pyogenes*.

Mutant SLO Proteins

Mutant forms of SLO according to the invention have at least 50% less hemolytic activity than wild-type SLO (e.g., 50, 55, 60, 65, 70, 75, 80, 85, 90, 95, 96, 97, 98, 99, or 100%) relative to wild-type SLO as determined by a hemolytic assay but are immunogenic, e.g., they confer protection against GAS lethal challenge in a mouse model (e.g., see Example 7). SLO mutants of the invention include SLO mutants P427L (SEQ ID NO:20), W535F (SEQ ID NO:21), C530G (SEQ ID NO:22), ΔA248 (SEQ ID NO:23), W535F+D482N (SEQ ID NO:24), P427L+W535F (SEQ ID NO:25), P427L+C530G (SEQ ID NO:26), and P427L+C530G+W535F (SEQ ID NO:27). The invention also includes His-tagged versions of these mutants. Examples are shown in FIG. 24.

SLO mutants of the invention include those with an amino acid alteration (i.e., a substitution, deletion, or insertion) at one or more of amino acids P427, W535, C530, A248, and D482 numbered according to the wild-type SLO sequence shown in SEQ ID NO:1. FIG. 23 provides an alignment of wild-type GAS25 sequences from different M types.

SLO mutants of the invention include single, double, or triple amino acid alterations ("single mutants," "double mutants," "triple mutants") at positions P427, W535, C530, A248, and/or D482. Thus, SLO mutants can comprise the following:

i. P427L (SEQ ID NO:20), P427R, P427N, P427C, P427Q, P427E, P427G, P427H, P427I, P427L, P427K, P427M, P427F, P427A, P427S, P427T, P427W, P427Y, or P427V;

ii. W535F (SEQ ID NO:21), W535R, W535N, W535D, W535C, W535Q, W535E, W535G, W535I, W535L, W535K, W535M, W535A, W535P, W535S, W535T, W535Y, or W535V;

iii. C530G (SEQ ID NO:22), C530R, C530N, C530D, C530S, C530Q, C530E, C530A, C530H, C530I, C530L, C530K, C530M, C530F, C530P, C530T, C530W, C530Y, or C530V;

iv. D482L, D482R, D482N, D482C, D482Q, D482E, D482G, D482H, D482I, D482L, D482K, D482M, D482F, D482A, D482S, D482T, D482W, D482Y, or D482V;

v. A248L, A248R, A248N, A248C, A248Q, A248E, A248G, A248H, A248I, A248L, A248K, A248M, A248F, A248S, A248T, A248W, A248Y, or A248V vi. ΔP427; or ΔW535; or ΔC530; or ΔD482; or ΔA248 (SEQ ID NO:23); and vii. combinations thereof, such as W535F+D482N (SEQ ID NO:24), P427L+W535F (SEQ ID NO:25), P427L+C530G (SEQ ID NO:26), and P427L+C530G+W535F (SEQ ID NO:27).

Double mutants of the invention include P427L+W535F (SEQ ID NO25), P427L+C530G (SEQ ID NO:26), P427L+A248L, P427L+D482L, W535F+C530G, W535F+A248L, W535F+D482L, C530G+A248L, and A248L+D482L. Triple mutants include P427L+C530G+A248L, P427L+C530G+D482L, P427L+A248L+D482L, P427L+C530G+W535F (SEQ ID NO:27), W535F+C530G+A248L, W535F+C530G+D482L, W535F+A248L+D482L, and C530G+A248L+D482L.

Mutant SLO proteins of the invention also include fusion polypeptides which comprise a mutant SLO protein as disclosed above and another GAS antigen. GAS antigens are disclosed, e.g., in WO 02/34771 and include, but are not limited to, GAS39 (spy0266; gi-15674446), GAS40 (spy0269; gi-15674449), GAS42 (spy0287; gi-15674461), GAS45 (M5005 spy0249; gi-71910063), GAS57 (spy0416; gi-15674549), GAS58 (spy0430; gi-15674556), GAS84 (spy1274; gi-15675229), GAS95 (spt1733; gi-15675582), GAS117 (spy0448; gi-15674571), GAS130 (spy0591; gi-15674677), GAS137 (spy0652; gi-15674720), GAS159 (spy1105; gi-15675088), GAS193 (spy2025; gi-15675802), GAS202 (spy1309; gi-15675258), GAS217 (spy0925; gi-15674945), GAS236 (spy1126; gi-15675106), GAS253 (spy1524; gi-15675423), GAS277 (spy1939; gi-15675742), GAS294 (spy1173; gi-15675145), GAS309 (spy0124; gi-15674341), GAS366 (spy1525; gi-15675424), GAS372 (spy1625; gi-15675501), GAS384 (spy1874; gi-15675693), GAS389 (spy1981; gi-15675772), GAS504 (spy1751; gi-15675600), GAS509 (spy1618; gi-15675496), GAS290 (spy1959; gi-15675757), GAS511 (spy1743; gi-15675592), GAS527 (spy1204; gi-15675169), GAS529 (spy1280; gi-15675233), and GAS533 (spy1877; gi-15675696). Further GAS antigens include, but are not limited to GAS68 (Spy0163; gi13621456), GAS84 (Spy1274; gi13622398), GAS88 (Spy1361; gi13622470), GAS89 (Spy1390; gi13622493), GAS98 (Spy1882; gi13622916), GAS99 (Spy1979; gi13622993), GAS102 (Spy2016, gi13623025), GAS146 (Spy0763; gi13621942), GAS195 (Spy2043; gi13623043), GAS561 (Spy1134; gi13622269), GAS179 (Spy1718, gi13622773) and GAS681 (spy1152; gi1362228).

Nucleic Acid Molecules Encoding Mutant SLO Proteins

The invention includes nucleic acid molecules which encode mutant SLO proteins. The invention also includes nucleic acid molecules comprising nucleotide sequences having at least 50% sequence identity to such molecules. Depending on the particular sequence, the degree of sequence identity is preferably greater than 50% (e.g., 60%, 70%, 75%, 80%, 85%, 90%, 91%, 92%, 93%, 94%, 95%, 96%, 97%, 98%, 99% or more). Identity between nucleotide sequences is preferably determined by the Smith-Waterman homology search algorithm as implemented in the MPSRCH program (Oxford Molecular), using an affine gap search with parameters gap open penalty=12 and gap extension penalty=1.

The invention also provides nucleic acid molecules which can hybridize to these molecules. Hybridization reactions can be performed under conditions of different "stringency." Conditions which increase stringency of a hybridization reaction are widely known and published in the art. See, e.g., page 7.52 of Sambrook et al., Molecular Cloning: A Laboratory Manual, 1989. Examples of relevant conditions include (in order of increasing stringency): incubation temperatures of 25° C., 37° C., 50° C., 55° C., and 68° C.; buffer concentrations of 10×SSC, 6×SSC, 1×SSC, and 0.1×SSC (where SSC is 0.15 M NaCl and 15 mM citrate buffer) and their equivalents using other buffer systems; formamide concentrations of 0%, 25%, 50%, and 75%; incubation times from 5 minutes to 24 hours; 1, 2, or more washing steps; wash incubation times of 1, 2, or 15 minutes; and wash solutions of 6×SSC, 1×SSC, 0.1×SSC, or de-ionized water. Hybridization techniques and their optimization are well known in the art. See, e.g., Sambrook, 1989; Ausubel et al., eds., Short Protocols in Molecular Biology, 4th ed., 1999; U.S. Pat. No. 5,707,829; Ausubel et al., eds., Current Protocols in Molecular Biology, Supplement 30, 1987.

In some embodiments, nucleic acid molecules of the invention hybridize to a target under low stringency conditions; in other embodiments, nucleic acid molecules of the invention hybridize under intermediate stringency conditions; in preferred embodiments, nucleic acid molecules of the invention hybridize under high stringency conditions. An example of a low stringency hybridization condition is 50° C. and 10×SSC.

An example of an intermediate stringency hybridization condition is 55° C. and 1×SSC. An example of a high stringency hybridization condition is 68° C. and 0.1×SSC.

Production of Mutant SLO Proteins

Recombinant Production

The redundancy of the genetic code is well-known. Thus, any nucleic acid molecule (polynucleotide) which encodes wild-type SLO protein or a SLO mutant protein of the invention can be used to produce that protein recombinantly. Examples of nucleotide sequences which encode wild-type SLO, SLO mutant P427L, W535F, C530G, ΔA248, W535F+D482N, P427L+W535F, P427L+C530G, and P427L+C530G+W535F are provided in the sequence listing (see also SEQ ID NOS:28, 29, 30, 31, 32, 33, 34, 35, and 36, respectively. Nucleic acid molecules encoding wild-type SLO also can be isolated from the appropriate *S. pyogenes* bacterium using standard nucleic acid purification techniques or can be synthesized using an amplification technique, such as the polymerase chain reaction (PCR), or by using an automatic synthesizer. See Caruthers et al., Nucl. Acids Res. Symp. Ser. 215 223, 1980; Horn et al. Nucl. Acids Res. Symp. Ser. 225 232, 1980; Hunkapiller et al., Nature 310, 105-11, 1984; Grantham et al., Nucleic Acids Res. 9, r43-r74, 1981.

cDNA molecules can be made with standard molecular biology techniques, using mRNA as a template. cDNA molecules can thereafter be replicated using molecular biology techniques well known in the art. An amplification technique, such as PCR, can be used to obtain additional copies of polynucleotides of the invention, using either genomic DNA or cDNA as a template.

If desired, polynucleotides can be engineered using methods generally known in the art to alter antigen-encoding sequences for a variety of reasons, including but not limited to, alterations which modify the cloning, processing, and/or expression of the polypeptide or mRNA product. DNA shuffling by random fragmentation and PCR reassembly of gene fragments and synthetic oligonucleotides can be used to engineer the nucleotide sequences. For example, site directed mutagenesis can be used to insert new restriction sites, alter glycosylation patterns, change codon preference, produce splice variants, introduce mutations, and so forth.

Sequence modifications, such as the addition of a purification tag sequence or codon optimization, can be used to facilitate expression. For example, the N-terminal leader sequence may be replaced with a sequence encoding for a tag protein such as polyhistidine ("HIS") or glutathione S-transferase ("GST"). Such tag proteins may be used to facilitate purification, detection, and stability of the expressed protein. Codons preferred by a particular prokaryotic or eukaryotic host can be selected to increase the rate of protein expression or to produce an RNA transcript having desirable properties, such as a half life which is longer than that of a transcript generated from the naturally occurring sequence. These methods are well known in the art and are further described in WO05/032582.

Expression Vectors

A nucleic acid molecule which encodes a mutant SLO protein can be inserted into an expression vector which contains the necessary elements for the transcription and translation of the inserted coding sequence. Methods which are well known to those skilled in the art can be used to construct expression vectors containing coding sequences and appropriate transcriptional and translational control elements. These methods include in vitro recombinant DNA techniques, synthetic techniques, and in vivo genetic recombination.

Host Cells

Host cells for producing mutant SLO proteins can be prokaryotic or eukaryotic. *E. coli* is a preferred host cell, but other suitable hosts include *Lactococcus lactis, Lactococcus cremoris, Bacillus subtilis, Vibrio cholerae, Salmonella typhi, Salmonella typhimurium, Neisseria lactamica, Neisseria cinerea, Mycobacteria* (e.g., *M. tuberculosis*), yeasts, baculovirus, mammalian cells, etc.

A host cell strain can be chosen for its ability to modulate the expression of the inserted sequences or to process the expressed polypeptide in the desired fashion. Such modifications of the polypeptide include, but are not limited to, acetylation, carboxylation, glycosylation, phosphorylation, lipidation, and acylation. Post translational processing which cleaves a "prepro" form of the polypeptide also can be used to facilitate correct insertion, folding and/or function. Different host cells which have specific cellular machinery and characteristic mechanisms for post translational activities are available from the American Type Culture Collection (ATCC; 10801 University Boulevard, Manassas, Va. 20110-2209) and can be chosen to ensure the correct modification and processing of a foreign protein. See WO 01/98340.

Expression constructs can be introduced into host cells using well-established techniques which include, but are not limited to, transferrin-polycation-mediated DNA transfer, transfection with naked or encapsulated nucleic acids, liposome-mediated cellular fusion, intracellular transportation of DNA-coated latex beads, protoplast fusion, viral infection, electroporation, "gene gun" methods, and DEAE- or calcium phosphate-mediated transfection.

Host cells transformed with expression vectors can be cultured under conditions suitable for the expression and recovery of the protein from cell culture. The protein produced by a transformed cell can be secreted or contained intracellularly depending on the nucleotide sequence and/or the expression vector used. Those of skill in the art understand that expression vectors can be designed to contain signal sequences which direct secretion of soluble antigens through a prokaryotic or eukaryotic cell membrane.

Purification

Signal export sequences can be included in a recombinantly produced mutant SLO protein so that the antigen can be purified from cell culture medium using known methods. Alternatively, recombinantly produced mutant SLO proteins of the invention can be isolated from engineered host cells and separated from other components in the cell, such as proteins, carbohydrates, or lipids, using methods well-known in the art. Such methods include, but are not limited to, size exclusion chromatography, ammonium sulfate fractionation, ion exchange chromatography, affinity chromatography, and preparative gel electrophoresis. A preparation of purified mutant SLO proteins is at least 80% pure; preferably, the preparations are 90%, 95%, or 99% pure. Purity of the preparations can be assessed by any means known in the art, such as SDS-polyacrylamide gel electrophoresis. Where appropriate, mutant SLO proteins can be solubilized, for example, with urea.

Chemical Synthesis

Mutant SLO proteins can be synthesized, for example, using solid phase techniques. See, e.g., Merrifield, J. Am. Chem. Soc. 85, 2149 54, 1963; Roberge et al., Science 269, 202 04, 1995. Protein synthesis can be performed using manual techniques or by automation. Automated synthesis can be achieved, for example, using Applied Biosystems 431A Peptide Synthesizer (Perkin Elmer). Optionally, fragments of a mutant SLO protein can be separately synthesized and combined using chemical methods to produce a full-length molecule.

Antibodies

The invention provides antibodies which bind specifically to a mutant SLO protein of the invention but which do not bind wild-type SLO protein. The term "antibody" includes intact immunoglobulin molecules, as well as fragments thereof which are capable of binding an antigen. These include hybrid (chimeric) antibody molecules (e.g., Winter et al., Nature 349, 293-99, 1991; U.S. Pat. No. 4,816,567); $F(ab')_2$ and F(ab) fragments and Fv molecules; non-covalent heterodimers (e.g., Inbar et al., *Proc. Natl. Acad. Sci. U.S.A.* 69, 2659-62, 1972; Ehrlich et al., *Biochem* 19, 4091-96, 1980); single-chain Fv molecules (sFv) (e.g., Huston et al., *Proc. Natl. Acad. Sci. U.S.A.* 85, 5897-83, 1988); dimeric and trimeric antibody fragment constructs; minibodies (e.g., Pack et al., *Biochem* 31, 1579-84, 1992; Cumber et al., *J. Immunology* 149B, 120-26, 1992); humanized antibody molecules (e.g., Riechmann et al., *Nature* 332, 323-27, 1988; Verhoeyan et al., *Science* 239, 1534-36, 1988; and U.K. Patent Publication No. GB 2,276,169, published 21 Sep. 1994); and any functional fragments obtained from such molecules, as well as antibodies obtained through non-conventional processes such as phage display. Preferably, the antibodies are monoclonal antibodies. Methods of obtaining monoclonal antibodies are well known in the art.

Typically, at least 6, 7, 8, 10, or 12 contiguous amino acids are required to form an epitope. However, epitopes which involve non-contiguous amino acids may require more, e.g., at least 15, 25, or 50 amino acids. Various immunoassays (e.g., Western blots, ELISAs, radioimmunoassays, immunohistochemical assays, immunoprecipitations, or other immunochemical assays known in the art) can be used to identify antibodies having the desired specificity. Numerous protocols for competitive binding or immunoradiometric assays are well known in the art. Such immunoassays typically involve the measurement of complex formation between an immunogen and an antibody which specifically binds to the immunogen. A preparation of antibodies which specifically bind to a mutant SLO protein typically provides a detection signal at least 5-, 10-, or 20-fold higher than a detection signal provided with other proteins when used in an immunochemical assay and does not provide a detectable signal if contacted with wild-type SLO protein. Preferably, the antibodies do not detect other proteins in immunochemical assays and can immunoprecipitate the particular antigen from solution.

Generation of Antibodies

Mutant SLO proteins or non-SLO polypeptide antigens (described below) can be used to immunize a mammal, such as a mouse, rat, rabbit, guinea pig, monkey, or human, to produce polyclonal antibodies. If desired, an antigen can be conjugated to a carrier protein, such as bovine serum albumin, thyroglobulin, and keyhole limpet hemocyanin. Depending on the host species, various adjuvants can be used to increase the immunological response. Such adjuvants include, but are not limited to, Freund's adjuvant, mineral gels (e.g., aluminum hydroxide), and surface active substances (e.g. lysolecithin, pluronic polyols, polyanions, peptides, oil emulsions, keyhole limpet hemocyanin, and dinitrophenol). Among adjuvants used in humans, BCG (bacilli Calmette-Guerin) and *Corynebacterium parvum* are especially useful.

Monoclonal antibodies which specifically bind to an antigen can be prepared using any technique which provides for the production of antibody molecules by continuous cell lines in culture. These techniques include, but are not limited to, the hybridoma technique, the human B cell hybridoma technique, and the EBV hybridoma technique (Kohler et al., *Nature* 256, 495 497, 1985; Kozbor et al., *J. Immunol. Methods* 81, 3142, 1985; Cote et al., *Proc. Natl. Acad. Sci.* 80, 2026 2030, 1983; Cole et al., *Mol. Cell. Biol.* 62, 109 120, 1984).

In addition, techniques developed for the production of "chimeric antibodies," the splicing of mouse antibody genes to human antibody genes to obtain a molecule with appropriate antigen specificity and biological activity, can be used (Morrison et al., *Proc. Natl. Acad. Sci.* 81, 68516855, 1984; Neuberger et al., *Nature* 312, 604 608, 1984; Takeda et al., *Nature* 314, 452 454, 1985). Monoclonal and other antibodies also can be "humanized" to prevent a patient from mounting an immune response against the antibody when it is used therapeutically. Such antibodies may be sufficiently similar in sequence to human antibodies to be used directly in therapy or may require alteration of a few key residues. Sequence differences between rodent antibodies and human sequences can be minimized by replacing residues which differ from those in the human sequences by site directed mutagenesis of individual residues or by grating of entire complementarity determining regions.

Alternatively, humanized antibodies can be produced using recombinant methods, as described below. Antibodies which specifically bind to a particular antigen can contain antigen binding sites which are either partially or fully humanized, as disclosed in U.S. Pat. No. 5,565,332.

Alternatively, techniques described for the production of single chain antibodies can be adapted using methods known in the art to produce single chain antibodies which specifically bind to a particular antigen. Antibodies with related specificity, but of distinct idiotypic composition, can be generated by chain shuffling from random combinatorial immunoglobin libraries (Burton, *Proc. Natl. Acad. Sci.* 88, 11120 23, 1991).

Single-chain antibodies also can be constructed using a DNA amplification method, such as PCR, using hybridoma cDNA as a template (Thirion et al., 1996, *Eur. J. Cancer Prev.* 5, 507-11). Single-chain antibodies can be mono- or bispecific, and can be bivalent or tetravalent. Construction of tetravalent, bispecific single-chain antibodies is taught, for example, in Coloma & Morrison, *Nat. Biotechnol.* 15, 159-63, 1997. Construction of bivalent, bispecific single-chain antibodies is taught in Mallender & Voss, *J. Biol. Chem.* 269, 199-206, 1994.

A nucleotide sequence encoding a single-chain antibody can be constructed using manual or automated nucleotide synthesis, cloned into an expression construct using standard recombinant DNA methods, and introduced into a cell to express the coding sequence, as described below. Alternatively, single-chain antibodies can be produced directly using, for example, filamentous phage technology (Verhaar et al., *Int. J. Cancer* 61, 497-501, 1995; Nicholls et al., *J. Immunol. Meth.* 165, 81-91, 1993).

Antibodies which specifically bind to a particular antigen also can be produced by inducing in vivo production in the lymphocyte population or by screening immunoglobulin libraries or panels of highly specific binding reagents as disclosed in the literature (Orlandi et al., *Proc. Natl. Acad. Sci.* 86, 3833 3837, 1989; Winter et al., *Nature* 349, 293 299, 1991).

Chimeric antibodies can be constructed as disclosed in WO 93/03151. Binding proteins which are derived from immunoglobulins and which are multivalent and multispecific, such as the "diabodies" described in WO 94/13804, also can be prepared.

Antibodies can be purified by methods well known in the art. For example, antibodies can be affinity purified by passage over a column to which the relevant antigen is bound. The bound antibodies can then be eluted from the column using a buffer with a high salt concentration.

Pharmaceutical Compositions

The invention also provides compositions for use as medicaments (e.g., as immunogenic compositions or vaccines). Compositions of the invention are useful for preventing and/or treating disease caused as a result of *S. pyogenes* infection and comprise at least one active agent, which can be a polypeptide, a nucleic acid molecule, or an antibody. Said disease may be, for example, bacteremia, meningitis, puerperal fever, scarlet fever, erysipelas, pharyngitis, impetigo, necrotizing fasciitis, myositis or toxic shock syndrome.

Compositions containing mutant SLO proteins are preferably immunogenic compositions, and are more preferably vaccine compositions. The pH of such compositions preferably is between 6 and 8, preferably about 7. The pH can be maintained by the use of a buffer. The composition can be sterile and/or pyrogen free. The composition can be isotonic with respect to humans.

Vaccines according to the invention may be used either prophylactically or therapeutically, but will typically be prophylactic. Accordingly, the invention includes a method for the therapeutic or prophylactic treatment of a *Streptococcus pyogenes* infection. The animal is preferably a mammal, most preferably a human. The methods involve administering to the animal a therapeutic or prophylactic amount of the immunogenic compositions of the invention.

Some compositions of the invention comprise a polypeptide mutant SLO protein as described herein. Other compositions of the invention comprise a nucleic acid molecule which encodes the mutant SLO protein(s) and, optionally, other antigens which can be included in the composition (see below). See, e.g., Robinson & Tones (1997) Seminars in Immunology 9:271-283; Donnelly et al. (1997) Ann. Rev Immunol 15:617-648; Scott-Taylor & Dalgleish (2000) Expert Opin Investig Drugs 9:471-480; Apostolopoulos & Plebanski (2000) Curr Opin Mol Ther 2:441-447; Ilan (1999) Curr Opin Mol Ther 1:116-120; Dubensky et al. (2000) Mol Med 6:723-732; Robinson & Pertmer (2000) Adv Virus Res 55:1-74; Donnelly et al. (2000) Am J Respir Crit. Care Med 162 (4 Pt 2):S190-193; Davis (1999) Mt. Sinai J. Med. 66:84-90. Typically the nucleic acid molecule is a DNA molecule, e.g., in the form of a plasmid.

In some embodiments, compositions of the invention can include one or more additional active agents. Such agents include, but are not limited to, (a) another mutant SLO protein of the invention, (b) a polypeptide antigen which is useful in a pediatric vaccine, (c) a polypeptide antigen which is useful in a vaccine for elderly or immunocompromised individuals, (d) a nucleic acid molecule encoding (a)-(c), and an antibody which specifically binds to (a)-(c).

Additional Antigens

Compositions of the invention may be administered in conjunction with one or more additional antigens for use in therapeutic or prophylactic methods of the present invention. Suitable antigens include those listed below. Additionally, the compositions of the present invention may be used to treat or prevent infections caused by any of the below-listed pathogens. In addition to combination with the antigens described below, the compositions of the invention may also be combined with an adjuvant as described herein.

Antigens for use with the invention include, but are not limited to, one or more of the following antigens set forth below, or antigens derived from one or more of the pathogens set forth below:

A. Bacterial Antigens

Bacterial antigens suitable for use in the invention include proteins, polysaccharides, lipopolysaccharides, and outer membrane vesicles which may be isolated, purified or derived from a bacteria. In addition, bacterial antigens may include bacterial lysates and inactivated bacteria formulations. Bacteria antigens may be produced by recombinant expression. Bacterial antigens preferably include epitopes which are exposed on the surface of the bacteria during at least one stage of its life cycle. Bacterial antigens are preferably conserved across multiple serotypes. Bacterial antigens include antigens derived from one or more of the bacteria set forth below as well as the specific antigens examples identified below.

*Neisseria meningitides*: Meningitides antigens may include proteins (such as those identified in References 1-7), saccharides (including a polysaccharide, oligosaccharide or lipopolysaccharide), or outer-membrane vesicles (References 8, 9, 10, 11) purified or derived from *N. meningitides* serogroup such as A, C, W135, Y, and/or B. *Meningitides* protein antigens may be selected from adhesions, autotransporters, toxins, Fe acquisition proteins, and membrane associated proteins (preferably integral outer membrane protein).

*Streptococcus pneumoniae*: *Streptococcus pneumoniae* antigens may include a saccharide (including a polysaccharide or an oligosaccharide) and/or protein from *Streptococcus pneumoniae*. Saccharide antigens may be selected from serotypes 1, 2, 3, 4, 5, 6B, 7F, 8, 9N, 9V, 10A, 11A, 12F, 14, 15B, 17F, 18C, 19A, 19F, 20, 22F, 23F, and 33F. Protein antigens may be selected from a protein identified in WO 98/18931, WO 98/18930, U.S. Pat. No. 6,699,703, U.S. Pat. No. 6,800, 744, WO 97/43303, and WO 97/37026. *Streptococcus pneumoniae* proteins may be selected from the Poly Histidine Triad family (PhtX), the Choline Binding Protein family (CbpX), CbpX truncates, LytX family, LytX truncates, CbpX truncate-LytX truncate chimeric proteins, pneumolysin (Ply), PspA, PsaA, Sp128, Sp101, Sp130, Sp125 or Sp133.

*Streptococcus pyogenes* (Group A *Streptococcus*): Group A *Streptococcus* antigens may include a protein identified in WO 02/34771 or WO 2005/032582 (including, but not limited to, GAS39 (spy0266; gi-15674446), GAS40 (spy0269; gi-15674449), GAS42 (spy0287; gi-15674461), GAS45 (M5005_spy0249; gi-71910063), GAS57 (spy0416; gi-15674549), GAS58 (spy0430; gi-15674556), GAS84 (spy1274; gi-15675229), GAS95 (spt1733; gi-15675582), GAS117 (spy0448; gi-15674571), GAS130 (spy0591; gi-15674677), GAS137 (spy0652; gi-15674720), GAS159 (spy1105; gi-15675088), GAS193 (spy2025; gi-15675802), GAS202 (spy1309; gi-15675258), GAS217 (spy0925; gi-15674945), GAS236 (spy1126; gi-15675106), GAS253 (spy1524; gi-15675423), GAS277 (spy1939; gi-15675742), GAS294 (spy1173; gi-15675145), GAS309 (spy0124; gi-15674341), GAS366 (spy1525; gi-15675424), GAS372 (spy1625; gi-15675501), GAS384 (spy1874; gi-15675693), GAS389 (spy1981; gi-15675772), GAS504 (spy1751; gi-15675600), GAS509 (spy1618; gi-15675496), GAS290 (spy1959; gi-15675757), GAS511 (spy1743; gi-15675592), GAS527 (spy1204; gi-15675169), GAS529 (spy1280; gi-15675233), and GAS533 (spy1877; gi-15675696)), fusions of fragments of GAS M proteins (including those described in WO 02/094851, and Dale, Vaccine (1999) 17:193-200, and Dale, Vaccine 14(10): 944-948), fibronectin binding protein (Sfb1), Streptococcal heme-associated protein (Shp), and Streptolysin S (SagA). Further GAS antigens include GAS68 (Spy0163; gi13621456), GAS84 (Spy1274; gi13622398), GAS88 (Spy1361; gi13622470), GAS89 (Spy1390; gi13622493), GAS98 (Spy1882; gi13622916), GAS99 (Spy1979; gi13622993), GAS102 (Spy2016, gi13623025), GAS146 (Spy0763; gi13621942), GAS195 (Spy2043; gi13623043), GAS561 (Spy1134; gi13622269), GAS179 (Spy1718, gi13622773) and GAS681 (spy1152; gi1362228).

*Moraxella catarrhalis*: *Moraxella* antigens include antigens identified in WO 02/18595 and WO 99/58562, outer membrane protein antigens (HMW-OMP), C-antigen, and/or LPS.

*Bordetella pertussis*: Pertussis antigens include petussis holotoxin (PT) and filamentous haemagglutinin (FHA) from *B. pertussis*, optionally also combination with pertactin and/or agglutinogens 2 and 3 antigen.

*Staphylococcus aureus*: *Staphylococcus aureus* antigens include *S. aureus* type 5 and 8 capsular polysaccharides optionally conjugated to nontoxic recombinant *Pseudomonas aeruginosa* exotoxin A, such as StaphVAX™, or antigens derived from surface proteins, invasins (leukocidin, kinases, hyaluronidase), surface factors that inhibit phagocytic engulfment (capsule, Protein A), carotenoids, catalase production, Protein A, coagulase, clotting factor, and/or membrane-damaging toxins (optionally detoxified) that lyse eukaryotic cell membranes (hemolysins, leukotoxin, leukocidin).

*Staphylococcus epidermis*: *S. epidermidis* antigens include slime-associated antigen (SAA).

*Clostridium tetani* (Tetanus): Tetanus antigens include tetanus toxoid (TT), preferably used as a carrier protein in conjunction/conjugated with the compositions of the present invention.

*Cornynebacterium diphtheriae* (Diphtheria): Diphtheria antigens include diphtheria toxin, preferably detoxified, such as CRM197. Additionally antigens capable of modulating, inhibiting or associated with ADP ribosylation are contemplated for combination/co-administration/conjugation with the compositions of the present invention. The diphtheria toxoids may be used as carrier proteins.

*Haemophilus influenzae B* (Hib): Hib antigens include a Hib saccharide antigen.

*Pseudomonas aeruginosa*: *Pseudomonas* antigens include endotoxin A, Wzz protein, *P. aeruginosa* LPS, more particularly LPS isolated from PAO1 (O5 serotype), and/or Outer Membrane Proteins, including Outer Membrane Proteins F (OprF) (Infect Immun. 2001 May; 69(5): 3510-3515).

*Legionella pneumophila*. Bacterial antigens may be derived from *Legionella pneumophila*.

*Streptococcus agalactiae* (Group B *Streptococcus*): Group B *Streptococcus* antigens include a protein or saccharide antigen identified in WO 02/34771, WO 03/093306, WO 04/041157, or WO 2005/002619 (including proteins GBS 80, GBS 104, GBS 276 and GBS 322, and including saccharide antigens derived from serotypes 1a, 1b, Ia/c, II, III, IV, V, VI, VII and VIII).

*Neiserria gonorrhoeae*: Gonorrhoeae antigens include Por (or porin) protein, such as PorB (see Zhu et al., Vaccine (2004) 22:660-669), a transferring binding protein, such as TbpA and TbpB (See Price et al., Infection and Immunity (2004) 71(1):277-283), a opacity protein (such as Opa), a reduction-modifiable protein (Rmp), and outer membrane vesicle (OMV) preparations (see Plante et al., J Infectious Disease (2000) 182:848-855), also see e.g. WO99/24578, WO99/36544, WO99/57280, WO02/079243).

*Chlamydia trachomatis*: *Chlamydia trachomatis* antigens include antigens derived from serotypes A, B, Ba and C (agents of trachoma, a cause of blindness), serotypes L1, L2 & L3 (associated with *Lymphogranuloma venereum*), and serotypes, D-K. *Chlamydia trachomas* antigens may also include an antigen identified in WO 00/37494, WO 03/049762, WO 03/068811, or WO 05/002619, including PepA (CT045), LcrE (CT089), ArtJ (CT381), DnaK (CT396), CT398, OmpH-like (CT242), L7/L12 (CT316), OmcA (CT444), AtosS (CT467), CT547, Eno (CT587), HrtA (CT823), and MurG (CT761).

*Treponema pallidum* (Syphilis): Syphilis antigens include TmpA antigen.

*Haemophilus ducreyi* (causing chancroid): Ducreyi antigens include outer membrane protein (DsrA).

*Enterococcus faecalis* or *Enterococcus faecium*: Antigens include a trisaccharide repeat or other *Enterococcus* derived antigens provided in U.S. Pat. No. 6,756,361.

*Helicobacter pylori*: *H. pylori* antigens include Cag, Vac, Nap, HopX, HopY and/or urease antigen.

*Staphylococcus saprophyticus*: Antigens include the 160 kDa hemagglutinin of *S. saprophyticus* antigen.

*Yersinia enterocolitica* antigens include LPS (Infect Immun. 2002 August; 70(8): 4414).

*E. coli*: *E. coli* antigens may be derived from enterotoxigenic *E. coli* (ETEC), enteroaggregative *E. coli* (EAggEC), diffusely adhering *E. coli* (DAEC), enteropathogenic *E. coli* (EPEC), and/or enterohemorrhagic *E. coli* (EHEC).

*Bacillus anthracis* (anthrax): *B. anthracis* antigens are optionally detoxified and may be selected from A-components (lethal factor (LF) and edema factor (EF)), both of which can share a common B-component known as protective antigen (PA).

*Yersinia pestis* (plague): Plague antigens include F1 capsular antigen (Infect Immun. 2003 January; 71(1)): 374-383, LPS (Infect Immun. 1999 October; 67(10): 5395), *Yersinia pestis* V antigen (Infect Immun. 1997 November; 65(11): 4476-4482).

*Mycobacterium tuberculosis*: Tuberculosis antigens include lipoproteins, LPS, BCG antigens, a fusion protein of antigen 85B (Ag85B) and/or ESAT-6 optionally formulated in cationic lipid vesicles (Infect Immun. 2004 October; 72(10): 6148), *Mycobacterium tuberculosis* (Mtb) isocitrate dehydrogenase associated antigens (Proc Natl Acad Sci U S A. 2004 Aug. 24; 101(34): 12652), and/or MPT51 antigens (Infect Immun. 2004 July; 72(7): 3829).

*Rickettsia*: Antigens include outer membrane proteins, including the outer membrane protein A and/or B (OmpB) (Biochim Biophys Acta. 2004 Nov. 1; 1702(2):145), LPS, and surface protein antigen (SPA) (J. Autoimmun. 1989 June; 2 Supp1:81).

*Listeria monocytogenes*. Bacterial antigens may be derived from *Listeria monocytogenes*.

*Chlamydia pneumoniae*: Antigens include those identified in WO 02/02606.

*Vibrio cholerae*: Antigens include proteinase antigens, LPS, particularly lipopolysaccharides of *Vibrio cholerae* II, O1 Inaba O-specific polysaccharides, *V. cholera* O139, antigens of IEM108 vaccine (Infect Immun. 2003 October; 71(10):5498-504), and/or Zonula occludens toxin (Zot).

*Salmonella typhi* (typhoid fever): Antigens include capsular polysaccharides preferably conjugates (Vi, i.e. vax-TyVi).

*Borrelia burgdorferi* (Lyme disease): Antigens include lipoproteins (such as OspA, OspB, Osp C and Osp D), other surface proteins such as OspE-related proteins (Erps), decorin-binding proteins (such as DbpA), and antigenically variable VI proteins, such as antigens associated with P39 and P13 (an integral membrane protein, Infect Immun. 2001 May;

69(5): 3323-3334), VlsE Antigenic Variation Protein (J Clin Microbiol. 1999 December; 37(12): 3997).

*Porphyromonas gingivalis*: Antigens include *P. gingivalis* outer membrane protein (OMP).

*Klebsiella*: Antigens include an OMP, including OMP A, or a polysaccharide optionally conjugated to tetanus toxoid.

Further bacterial antigens of the invention may be capsular antigens, polysaccharide antigens or protein antigens of any of the above. Further bacterial antigens may also include an outer membrane vesicle (OMV) preparation. Additionally, antigens include live, attenuated, and/or purified versions of any of the aforementioned bacteria. The antigens of the present invention may be derived from gram-negative or gram-positive bacteria. The antigens of the present invention may be derived from aerobic or anaerobic bacteria.

Additionally, any of the above bacterial-derived saccharides (polysaccharides, LPS, LOS or oligosaccharides) can be conjugated to another agent or antigen, such as a carrier protein (for example CRM197). Such conjugation may be direct conjugation effected by reductive amination of carbonyl moieties on the saccharide to amino groups on the protein, as provided in U.S. Pat. No. 5,360,897 and Can J Biochem Cell Biol. 1984 May; 62(5):270-5. Alternatively, the saccharides can be conjugated through a linker, such as, with succinamide or other linkages provided in Bioconjugate Techniques, 1996 and CRC, Chemistry of Protein Conjugation and Cross-Linking, 1993.

B. Viral Antigens

Viral antigens suitable for use in the invention include inactivated (or killed) virus, attenuated virus, split virus formulations, purified subunit formulations, viral proteins which may be isolated, purified or derived from a virus, and Virus Like Particles (VLPs). Viral antigens may be derived from viruses propagated on cell culture or other substrate. Alternatively, viral antigens may be expressed recombinantly. Viral antigens preferably include epitopes which are exposed on the surface of the virus during at least one stage of its life cycle. Viral antigens are preferably conserved across multiple serotypes or isolates. Viral antigens include antigens derived from one or more of the viruses set forth below as well as the specific antigens examples identified below.

Orthomyxovirus: Viral antigens may be derived from an Orthomyxovirus, such as Influenza A, B and C. Orthomyxovirus antigens may be selected from one or more of the viral proteins, including hemagglutinin (HA), neuraminidase (NA), nucleoprotein (NP), matrix protein (M1), membrane protein (M2), one or more of the transcriptase components (PB1, PB2 and PA). Preferred antigens include HA and NA.

Influenza antigens may be derived from interpandemic (annual) flu strains. Alternatively influenza antigens may be derived from strains with the potential to cause pandemic a pandemic outbreak (i.e., influenza strains with new haemagglutinin compared to the haemagglutinin in currently circulating strains, or influenza strains which are pathogenic in avian subjects and have the potential to be transmitted horizontally in the human population, or influenza strains which are pathogenic to humans).

Paramyxoviridae viruses: Viral antigens may be derived from Paramyxoviridae viruses, such as Pneumoviruses (RSV), Paramyxoviruses (PIV) and Morbilliviruses (Measles).

Pneumovirus: Viral antigens may be derived from a Pneumovirus, such as Respiratory syncytial virus (RSV), Bovine respiratory syncytial virus, Pneumonia virus of mice, and Turkey rhinotracheitis virus. Preferably, the Pneumovirus is RSV. Pneumovirus antigens may be selected from one or more of the following proteins, including surface proteins Fusion (F), Glycoprotein (G) and Small Hydrophobic protein (SH), matrix proteins M and M2, nucleocapsid proteins N, P and L and nonstructural proteins NS1 and NS2. Preferred Pneumovirus antigens include F, G and M. See e.g., J Gen Virol. 2004 November; 85(Pt 11):3229). Pneumovirus antigens may also be formulated in or derived from chimeric viruses. For example, chimeric RSV/PIV viruses may comprise components of both RSV and PIV.

Paramyxovirus: Viral antigens may be derived from a Paramyxovirus, such as Parainfluenza virus types 1-4 (PIV), Mumps, Sendai viruses, Simian virus 5, Bovine parainfluenza virus and Newcastle disease virus. Preferably, the Paramyxovirus is PIV or Mumps. Paramyxovirus antigens may be selected from one or more of the following proteins: Hemagglutinin-Neuraminidase (HN), Fusion proteins F1 and F2, Nucleoprotein (NP), Phosphoprotein (P), Large protein (L), and Matrix protein (M). Preferred Paramyxovirus proteins include HN, F1 and F2. Paramyxovirus antigens may also be formulated in or derived from chimeric viruses. For example, chimeric RSV/PIV viruses may comprise components of both RSV and PIV. Commercially available mumps vaccines include live attenuated mumps virus, in either a monovalent form or in combination with measles and rubella vaccines (MMR).

Morbillivirus: Viral antigens may be derived from a Morbillivirus, such as Measles. Morbillivirus antigens may be selected from one or more of the following proteins: hemagglutinin (H), Glycoprotein (G), Fusion factor (F), Large protein (L), Nucleoprotein (NP), Polymerase phosphoprotein (P), and Matrix (M). Commercially available measles vaccines include live attenuated measles virus, typically in combination with mumps and rubella (MMR).

Picornavirus: Viral antigens may be derived from Picornaviruses, such as Enteroviruses, Rhinoviruses, Heparnavirus, Cardioviruses and Aphthoviruses. Antigens derived from Enteroviruses, such as Poliovirus are preferred.

Enterovirus: Viral antigens may be derived from an Enterovirus, such as Poliovirus types 1, 2 or 3, Coxsackie A virus types 1 to 22 and 24, Coxsackie B virus types 1 to 6, Echovirus (ECHO) virus) types 1 to 9, 11 to 27 and 29 to 34 and Enterovirus 68 to 71. Preferably, the Enterovirus is poliovirus. Enterovirus antigens are preferably selected from one or more of the following Capsid proteins VP1, VP2, VP3 and VP4. Commercially available polio vaccines include Inactivated Polio Vaccine (IPV) and Oral poliovirus vaccine (OPV).

Heparnavirus: Viral antigens may be derived from an Heparnavirus, such as Hepatitis A virus (HAV). Commercially available HAV vaccines include inactivated HAV vaccine.

Togavirus: Viral antigens may be derived from a Togavirus, such as a Rubivirus, an Alphavirus, or an Arterivirus. Antigens derived from Rubivirus, such as Rubella virus, are preferred. Togavirus antigens may be selected from E1, E2, E3, C, NSP-1, NSPO-2, NSP-3 or NSP-4. Togavirus antigens are preferably selected from E1, E2 or E3. Commercially available Rubella vaccines include a live cold-adapted virus, typically in combination with mumps and measles vaccines (MMR).

Flavivirus: Viral antigens may be derived from a Flavivirus, such as Tick-borne encephalitis (TBE), Dengue (types 1, 2, 3 or 4), Yellow Fever, Japanese encephalitis, West Nile encephalitis, St. Louis encephalitis, Russian spring-summer encephalitis, Powassan encephalitis. Flavivirus antigens may be selected from PrM, M, C, E, NS-1, NS-2a, NS2b, NS3, NS4a, NS4b, and NS5. Flavivirus antigens are preferably selected from PrM, M and E. Commercially available TBE vaccine include inactivated virus vaccines.

Pestivirus: Viral antigens may be derived from a Pestivirus, such as Bovine viral diarrhea (BVDV), Classical swine fever (CSFV) or Border disease (BDV).

Hepadnavirus: Viral antigens may be derived from a Hepadnavirus, such as Hepatitis B virus. Hepadnavirus antigens may be selected from surface antigens (L, M and S), core antigens (HBc, HBe). Commercially available HBV vaccines include subunit vaccines comprising the surface antigen S protein.

Hepatitis C virus: Viral antigens may be derived from a Hepatitis C virus (HCV). HCV antigens may be selected from one or more of E1, E2, E1/E2, NS345 polyprotein, NS345-core polyprotein, core, and/or peptides from the nonstructural regions (Houghton et al., Hepatology (1991) 14:381).

Rhabdovirus: Viral antigens may be derived from a Rhabdovirus, such as a Lyssavirus (Rabies virus) and Vesiculovirus (VSV). Rhabdovirus antigens may be selected from glycoprotein (G), nucleoprotein (N), large protein (L), nonstructural proteins (NS). Commercially available Rabies virus vaccine comprise killed virus grown on human diploid cells or fetal rhesus lung cells.

Caliciviridae; Viral antigens may be derived from Caliciviridae, such as Norwalk virus, and Norwalk-like Viruses, such as Hawaii Virus and Snow Mountain Virus.

Coronavirus: Viral antigens may be derived from a Coronavirus, SARS, Human respiratory Coronavirus, Avian infectious bronchitis (IBV), Mouse hepatitis virus (MHV), and Porcine transmissible gastroenteritis virus (TGEV). Coronavirus antigens may be selected from spike (S), envelope (E), matrix (M), nucleocapsid (N), and Hemagglutinin-esterase glycoprotein (HE). Preferably, the Coronavirus antigen is derived from a SARS virus. SARS viral antigens are described in WO 04/92360;

Retrovirus: Viral antigens may be derived from a Retrovirus, such as an Oncovirus, a Lentivirus or a Spumavirus. Oncovirus antigens may be derived from HTLV-1, HTLV-2 or HTLV-5. Lentivirus antigens may be derived from HIV-1 or HIV-2. Retrovirus antigens may be selected from gag, pol, env, tax, tat, rex, rev, nef, vif, vpu, and vpr. HIV antigens may be selected from gag (p24gag and p55gag), env (gp160 and gp41), pol, tat, nef, rev vpu, miniproteins, (preferably p55 gag and gp140v delete). HIV antigens may be derived from one or more of the following strains: HIVIIIb, HIVSF2, HIVLAV, HIVLAI, HIVMN, HIV-1CM235, HIV-1US4.

Reovirus: Viral antigens may be derived from a Reovirus, such as an Orthoreovirus, a Rotavirus, an Orbivirus, or a Coltivirus. Reovirus antigens may be selected from structural proteins $\lambda 1$, $\lambda 2$, $\lambda 3$, $\mu 1$, $\mu 2$, $\sigma 1$, $\sigma 2$, or $\sigma 3$, or nonstructural proteins $\sigma NS$, $\mu NS$, or $\sigma 1s$. Preferred Reovirus antigens may be derived from a Rotavirus. Rotavirus antigens may be selected from VP1, VP2, VP3, VP4 (or the cleaved product VP5 and VP8), NSP 1, VP6, NSP3, NSP2, VP7, NSP4, or NSP5. Preferred Rotavirus antigens include VP4 (or the cleaved product VP5 and VP8), and VP7.

Parvovirus: Viral antigens may be derived from a Parvovirus, such as Parvovirus B19. Parvovirus antigens may be selected from VP-1, VP-2, VP-3, NS-1 and NS-2. Preferably, the Parvovirus antigen is capsid protein VP-2.

Delta hepatitis virus (HDV): Viral antigens may be derived HDV, particularly $\delta$-antigen from HDV (see, e.g., U.S. Pat. No. 5,378,814).

Hepatitis E virus (HEV): Viral antigens may be derived from HEV.

Hepatitis G virus (HGV): Viral antigens may be derived from HGV.

Human Herpesvirus: Viral antigens may be derived from a Human Herpesvirus, such as Herpes Simplex Viruses (HSV), Varicella-zoster virus (VZV), Epstein-Barr virus (EBV), Cytomegalovirus (CMV), Human Herpesvirus 6 (HHV6), Human Herpesvirus 7 (HHV7), and Human Herpesvirus 8 (HHV8). Human Herpesvirus antigens may be selected from immediate early proteins ($\alpha$), early proteins ($\beta$), and late proteins ($\gamma$). HSV antigens may be derived from HSV-1 or HSV-2 strains. HSV antigens may be selected from glycoproteins gB, gC, gD and gH, fusion protein (gB), or immune escape proteins (gC, gE, or gI). VZV antigens may be selected from core, nucleocapsid, tegument, or envelope proteins. A live attenuated VZV vaccine is commercially available. EBV antigens may be selected from early antigen (EA) proteins, viral capsid antigen (VCA), and glycoproteins of the membrane antigen (MA). CMV antigens may be selected from capsid proteins, envelope glycoproteins (such as gB and gH), and tegument proteins Papovaviruses: Antigens may be derived from Papovaviruses, such as Papillomaviruses and Polyomaviruses. Papillomaviruses include HPV serotypes 1, 2, 4, 5, 6, 8, 11, 13, 16, 18, 31, 33, 35, 39, 41, 42, 47, 51, 57, 58, 63 and 65. Preferably, HPV antigens are derived from serotypes 6, 11, 16 or 18. HPV antigens may be selected from capsid proteins (L1) and (L2), or E1-E7, or fusions thereof. HPV antigens are preferably formulated into virus-like particles (VLPs). Polyomyavirus viruses include BK virus and JK virus. Polyomavirus antigens may be selected from VP1, VP2 or VP3.

Further provided are antigens, compositions, methods, and microbes included in Vaccines, 4th Edition (Plotkin and Orenstein ed. 2004); Medical Microbiology 4th Edition (Murray et al. ed. 2002); Virology, 3rd Edition (W. K. Joklik ed. 1988); Fundamental Virology, 2nd Edition (B. N. Fields and D. M. Knipe, eds. 1991), which are contemplated in conjunction with the compositions of the present invention.

C. Fungal Antigens

Fungal antigens for use in the invention may be derived from one or more of the fungi set forth below.

Fungal antigens may be derived from Dermatophytres, including: *Epidermophyton floccusum, Microsporum audouini, Microsporum canis, Microsporum distortum, Microsporum equinum, Microsporum gypsum, Microsporum nanum, Trichophyton concentricum, Trichophyton equinum, Trichophyton gallinae, Trichophyton gypseum, Trichophyton megnini, Trichophyton mentagrophytes, Trichophyton quinckeanum, Trichophyton rubrum, Trichophyton schoenleini, Trichophyton tonsurans, Trichophyton verrucosum, T. verrucosum* var. *album*, var. *discoides*, var. *ochraceum*, *Trichophyton violaceum*, and/or *Trichophyton faviforme*.

Fungal pathogens may be derived from *Aspergillus fumigatus, Aspergillus flavus, Aspergillus niger, Aspergillus nidulans, Aspergillus terreus, Aspergillus sydowi, Aspergillus flavatus, Aspergillus glaucus, Blastoschizomyces capitatus, Candida albicans, Candida enolase, Candida tropicalis, Candida glabrata, Candida krusei, Candida parapsilosis, Candida stellatoidea, Candida kusei, Candida parakwsei, Candida lusitaniae, Candida pseudotropicalis, Candida guilliermondi, Cladosporium carrionii, Coccidioides immitis, Blastomyces dermatidis, Cryptococcus neoformans, Geotrichum clavatum, Histoplasma capsulatum, Klebsiella pneumoniae, Paracoccidioides brasiliensis, Pneumocystis carinii, Pythiumn insidiosum, Pityrosporum ovale, Sacharomyces cerevisae, Saccharomyces boulardii, Saccharomyces pombe, Scedosporium apiosperum, Sporothrix schenckii, Trichosporon beigelii, Toxoplasma gondii, Penicillium marneffei, Malassezia* spp., *Fonsecaea* spp., *Wangiella* spp., *Sporothrix* spp., *Basidiobolus* spp., *Conidiobolus* spp., *Rhizopus* spp, *Mucor* spp, *Absidia* spp, *Mortierella* spp, *Cunninghamella* spp, *Saksenaea* spp., *Alternaria* spp, *Curvularia* spp,

*Helminthosporium* spp, *Fusarium* spp, *Aspergillus* spp, *Penicillium* spp, *Monolinia* spp, *Rhizoctonia* spp, *Paecilomyces* spp, *Pithomyces* spp, and *Cladosporium* spp.

Processes for producing a fungal antigens are well known in the art (see U.S. Pat. No. 6,333,164). In a preferred method a solubilized fraction extracted and separated from an insoluble fraction obtainable from fungal cells of which cell wall has been substantially removed or at least partially removed, characterized in that the process comprises the steps of: obtaining living fungal cells; obtaining fungal cells of which cell wall has been substantially removed or at least partially removed; bursting the fungal cells of which cell wall has been substantially removed or at least partially removed; obtaining an insoluble fraction; and extracting and separating a solubilized fraction from the insoluble fraction.

D. STD Antigens

The compositions of the invention may include one or more antigens derived from a sexually transmitted disease (STD). Such antigens may provide for prophylactic or therapy for STD's such as chlamydia, genital herpes, hepatits (such as HCV), genital warts, gonorrhoea, syphilis and/or chancroid (See, WO00/15255). Antigens may be derived from one or more viral or bacterial STD's. Viral STD antigens for use in the invention may be derived from, for example, HIV, herpes simplex virus (HSV-1 and HSV-2), human papillomavirus (HPV), and hepatitis (HCV). Bacterial STD antigens for use in the invention may be derived from, for example, *Neiserria gonorrhoeae, Chlamydia trachomatis, Treponema pallidum, Haemophilus ducreyi, E. coli*, and *Streptococcus agalactiae*. Examples of specific antigens derived from these pathogens are described above.

E. Respiratory Antigens

The compositions of the invention may include one or more antigens derived from a pathogen which causes respiratory disease. For example, respiratory antigens may be derived from a respiratory virus such as Orthomyxoviruses (influenza), Pneumovirus (RSV), Paramyxovirus (PIV), Morbillivirus (measles), Togavirus (Rubella), VZV, and Coronavirus (SARS). Respiratory antigens may be derived from a bacteria which causes respiratory disease, such as *Streptococcus pneumoniae, Pseudomonas aeruginosa, Bordetella pertussis, Mycobacterium tuberculosis, Mycoplasma pneumoniae, Chlamydia pneumoniae, Bacillus anthracis*, and *Moraxella catarrhalis*. Examples of specific antigens derived from these pathogens are described above.

F. Pediatric Vaccine Antigens

The compositions of the invention may include one or more antigens suitable for use in pediatric subjects. Pediatric subjects are typically less than about 3 years old, or less than about 2 years old, or less than about 1 years old. Pediatric antigens may be administered multiple times over the course of 6 months, 1, 2 or 3 years. Pediatric antigens may be derived from a virus which may target pediatric populations and/or a virus from which pediatric populations are susceptible to infection. Pediatric viral antigens include antigens derived from one or more of Orthomyxovirus (influenza), Pneumovirus (RSV), Paramyxovirus (PIV and Mumps), Morbillivirus (measles), Togavirus (Rubella), Enterovirus (polio), HBV, Coronavirus (SARS), and Varicella-zoster virus (VZV), Epstein Barr virus (EBV). Pediatric bacterial antigens include antigens derived from one or more of *Streptococcus pneumoniae, Neisseria meningitides, Streptococcus pyogenes* (Group A *Streptococcus*), *Moraxella catarrhalis, Bordetella pertussis, Staphylococcus aureus, Clostridium tetani* (Tetanus), *Cornynebacterium diphtheriae* (Diphtheria), *Haemophilus influenzae* B (Hib), *Pseudomonas aeruginosa, Streptococcus agalactiae* (Group B *Streptococcus*), and *E. coli*. Examples of specific antigens derived from these pathogens are described above.

G. Antigens Suitable for Use in Elderly or Immunocompromised Individuals

The compositions of the invention may include one or more antigens suitable for use in elderly or immunocompromised individuals. Such individuals may need to be vaccinated more frequently, with higher doses or with adjuvanted formulations to improve their immune response to the targeted antigens. Antigens which may be targeted for use in Elderly or Immunocompromised individuals include antigens derived from one or more of the following pathogens: *Neisseria meningitides, Streptococcus pneumoniae, Streptococcus pyogenes* (Group A *Streptococcus*), *Moraxella catarrhalis, Bordetella pertussis, Staphylococcus aureus, Staphylococcus epidermis, Clostridium tetani* (Tetanus), *Cornynebacterium diphtheriae* (Diphtheria), *Haemophilus influenzae* B (Hib), *Pseudomonas aeruginosa, Legionella pneumophila, Streptococcus agalactiae* (Group B *Streptococcus*), *Enterococcus faecalis, Helicobacter pylori, Clamydia pneumoniae, Orthomyxovirus* (influenza), Pneumovirus (RSV), Paramyxovirus (PIV and Mumps), Morbillivirus (measles), Togavirus (Rubella), Enterovirus (polio), HBV, Coronavirus (SARS), Varicella-zoster virus (VZV), Epstein Barr virus (EBV), Cytomegalovirus (CMV). Examples of specific antigens derived from these pathogens are described above.

H. Antigens Suitable for Use in Adolescent Vaccines

The compositions of the invention may include one or more antigens suitable for use in adolescent subjects. Adolescents may be in need of a boost of a previously administered pediatric antigen. Pediatric antigens which may be suitable for use in adolescents are described above. In addition, adolescents may be targeted to receive antigens derived from an STD pathogen in order to ensure protective or therapeutic immunity before the beginning of sexual activity. STD antigens which may be suitable for use in adolescents are described above.

I. Antigen Formulations

In other aspects of the invention, methods of producing microparticles having adsorbed antigens are provided. The methods comprise: (a) providing an emulsion by dispersing a mixture comprising (i) water, (ii) a detergent, (iii) an organic solvent, and (iv) a biodegradable polymer selected from the group consisting of a poly($\alpha$-hydroxy acid), a polyhydroxy butyric acid, a polycaprolactone, a polyorthoester, a polyanhydride, and a polycyanoacrylate. The polymer is typically present in the mixture at a concentration of about 1% to about 30% relative to the organic solvent, while the detergent is typically present in the mixture at a weight-to-weight detergent-to-polymer ratio of from about 0.00001:1 to about 0.1:1 (more typically about 0.0001:1 to about 0.1:1, about 0.001:1 to about 0.1:1, or about 0.005:1 to about 0.1:1); (b) removing the organic solvent from the emulsion; and (c) adsorbing an antigen on the surface of the microparticles. In certain embodiments, the biodegradable polymer is present at a concentration of about 3% to about 10% relative to the organic solvent.

Microparticles for use herein will be formed from materials that are sterilizable, non-toxic and biodegradable. Such materials include, without limitation, poly($\alpha$-hydroxy acid), polyhydroxybutyric acid, polycaprolactone, polyorthoester, polyanhydride, PACA, and polycyanoacrylate. Preferably, microparticles for use with the present invention are derived from a poly($\alpha$-hydroxy acid), in particular, from a poly(lactide) ("PLA") or a copolymer of D,L-lactide and glycolide or glycolic acid, such as a poly(D,L-lactide-co-glycolide) ("PLG" or "PLGA"), or a copolymer of D,L-lactide and caprolactone. The microparticles may be derived from any of various polymeric starting materials which have a variety of molecular weights and, in the case of the copolymers such as PLG, a variety of lactide:glycolide ratios, the selection of which will be largely a matter of choice, depending in part on the coadministered macromolecule. These parameters are discussed more fully below.

Further antigens may also include an outer membrane vesicle (OMV) preparation.

Additional formulation methods and antigens (especially tumor antigens) are provided in U.S. patent Ser. No. 09/581,772.

J. Antigen References

The following references include antigens useful in conjunction with the compositions of the present invention:
1 International patent application WO99/24578
2 International patent application WO99/36544.
3 International patent application WO99/57280.
4 International patent application WO00/22430.
5 Tettelin et al. (2000) Science 287:1809-1815.
6 International patent application WO96/29412.
7 Pizza et al. (2000) Science 287:1816-1820.
8 PCT WO 01/52885.
9 Bjune et al. (1991) Lancet 338(8775).
10 Fuskasawa et al. (1999) Vaccine 17:2951-2958.
11 Rosenqist et al. (1998) Dev. Biol. Strand 92:323-333.
12 Constantino et al. (1992) Vaccine 10:691-698.
13 Constantino et al. (1999) Vaccine 17:1251-1263.
14 Watson (2000) Pediatr Infect Dis J 19:331-332.
15 Rubin (20000) Pediatr Clin North Am 47:269-285,v.
16 Jedrzejas (2001) Microbiol Mol Biol Rev 65:187-207.
17 International patent application filed on 3 Jul. 2001 claiming priority from GB-0016363.4; WO 02/02606; PCT IB/01/00166.
18 Kalman et al. (1999) Nature Genetics 21:385-389.
19 Read et al. (2000) Nucleic Acids Res 28:1397-406.
20 Shirai et al. (2000) J. Infect. Dis 181 (Suppl 3):S524-S527.
21 International patent application WO99/27105.
22 International patent application WO00/27994.
23 International patent application WO00/37494.
24 International patent application WO99/28475.
25 Bell (2000) Pediatr Infect Dis J 19:1187-1188.
26 Iwarson (1995) APMIS 103:321-326.
27 Gerlich et al. (1990) Vaccine 8 Suppl:S63-68 & 79-80.
28 Hsu et al. (1999) Clin Liver Dis 3:901-915.
29 Gastofsson et al. (1996) N. Engl. J. Med. 334-:349-355.
30 Rappuoli et al. (1991) TIBTECH 9:232-238.
31 Vaccines (1988) eds. Plotkin & Mortimer. ISBN 0-7216-1946-0.
32 Del Guidice et al. (1998) Molecular Aspects of Medicine 19:1-70.
33 International patent application WO93/018150.
34 International patent application WO99/53310.
35 International patent application WO98/04702.
36 Ross et al. (2001) Vaccine 19:135-142.
37 Sutter et al. (2000) Pediatr Clin North Am 47:287-308.
38 Zimmerman & Spann (1999) Am Fan Physician 59:113-118, 125-126.
39 Dreensen (1997) Vaccine 15 Suppl" S2-6.
40 MMWR Morb Mortal Wkly rep 1998 January 16:47(1): 12, 9.
41 McMichael (2000) Vaccine 19 Suppl 1:S101-107.
42 Schuchat (1999) Lancer 353(9146):51-6.
43 GB patent applications 0026333.5, 0028727.6 & 0105640.7.
44 Dale (1999) Infect Disclin North Am 13:227-43, viii.
45 Ferretti et al. (2001) PNAS USA 98: 4658-4663.
46 Kuroda et al. (2001) Lancet 357(9264):1225-1240; see also pages 1218-1219.
47 Ramsay et al. (2001) Lancet 357(9251):195-196.
48 Lindberg (1999) Vaccine 17 Suppl 2:S28-36.
49 Buttery & Moxon (2000) J R Coil Physicians Long 34:163-168.
50 Ahmad & Chapnick (1999) Infect Dis Clin North Am 13:113-133, vii.
51 Goldblatt (1998) J. Med. Microbiol. 47:663-567.
52 European patent 0 477 508.
53 U.S. Pat. No. 5,306,492.
54 International patent application WO98/42721.
55 Conjugate Vaccines (eds. Cruse et al.) ISBN 3805549326, particularly vol. 10:48-114.
56 Hermanson (1996) Bioconjugate Techniques ISBN: 012323368 & 012342335X.
57 European patent application 0372501.
58 European patent application 0378881.
59 European patent application 0427347.
60 International patent application WO93/17712.
61 International patent application WO98/58668.
62 European patent application 0471177.
63 International patent application WO00/56360.
64 International patent application WO00/67161.

The contents of all of the above cited patents, patent applications and journal articles are incorporated by reference as if set forth fully herein.

Where a saccharide or carbohydrate antigen is used, it is preferably conjugated to a carrier protein in order to enhance immunogenicity. See Ramsay et al. (2001) Lancet 357(9251): 195-196; Lindberg (1999) Vaccine 17 Suppl 2:S28-36; Buttery & Moxon (2000) J R Coll Physicians Lond 34:163-168; Ahmad & Chapnick (1999) Infect Dis Clin North Am 13:113-133, vii; Goldblatt (1998) J. Med. Microbiol. 47:563-567; European patent 0 477 508; U.S. Pat. No. 5,306,492; WO98/42721; Conjugate Vaccines (eds. Cruse et al.) ISBN 3805549326, particularly vol. 10:48-114; Hermanson (1996) Bioconjugate Techniques ISBN: 0123423368 or 012342335X. Preferred carrier proteins are bacterial toxins or toxoids, such as diphtheria or tetanus toxoids. The CRM197 diphtheria toxoid is particularly preferred.

Other carrier polypeptides include the *N. meningitidis* outer membrane protein (EP-A-0372501), synthetic peptides (EP-A-0378881 and EP-A 0427347), heat shock proteins (WO 93/17712 and WO 94/03208), pertussis proteins (WO 98/58668 and EP A 0471177), protein D from *H. influenzae* (WO 00/56360), cytokines (WO 91/01146), lymphokines, hormones, growth factors, toxin A or B from *C. difficile* (WO 00/61761), iron-uptake proteins (WO 01/72337), etc. Where a mixture comprises capsular saccharide from both serigraphs A and C, it may be preferred that the ratio (w/w) of MenA saccharide:MenC saccharide is greater than 1 (e.g., 2:1, 3:1, 4:1, 5:1, 10:1 or higher). Different saccharides can be conjugated to the same or different type of carrier protein. Any suitable conjugation reaction can be used, with any suitable linker where necessary.

Toxic protein antigens may be detoxified where necessary e.g., detoxification of pertussis toxin by chemical and/or genetic means.

Pharmaceutically Acceptable Carriers

Compositions of the invention will typically, in addition to the components mentioned above, comprise one or more "pharmaceutically acceptable carriers." These include any carrier which does not itself induce the production of antibodies harmful to the individual receiving the composition. Suitable carriers typically are large, slowly metabolized macromolecules such as proteins, polysaccharides, polylactic acids, polyglycolic acids, polymeric amino acids, amino acid copolymers, and lipid aggregates (such as oil droplets or liposomes). Such carriers are well known to those of ordinary skill in the art. A composition may also contain a diluent, such as water, saline, glycerol, etc. Additionally, an auxiliary substance, such as a wetting or emulsifying agent, pH buffering substance, and the like, may be present. A thorough discussion of pharmaceutically acceptable components is available in Gennaro (2000) Remington: The Science and Practice of Pharmacy. 20th ed., ISBN: 0683306472.

Immunoregulatory Agents

Adjuvants

Vaccines of the invention may be administered in conjunction with other immunoregulatory agents. In particular, compositions will usually include an adjuvant. Adjuvants for use with the invention include, but are not limited to, one or more of the following set forth below:

A. Mineral Containing Compositions

Mineral containing compositions suitable for use as adjuvants in the invention include mineral salts, such as aluminum salts and calcium salts. The invention includes mineral salts such as hydroxides (e.g. oxyhydroxides), phosphates (e.g. hydroxyphosphates, orthophosphates), sulfates, etc. (e.g. see chapters 8 & 9 of Vaccine Design . . . (1995) eds. Powell & Newman. ISBN: 030644867X. Plenum.), or mixtures of different mineral compounds (e.g. a mixture of a phosphate and a hydroxide adjuvant, optionally with an excess of the phosphate), with the compounds taking any suitable form (e.g. gel, crystalline, amorphous, etc.), and with adsorption to the salt(s) being preferred. The mineral containing compositions may also be formulated as a particle of metal salt (WO00/23105).

Aluminum salts may be included in vaccines of the invention such that the dose of $Al^{3+}$ is between 0.2 and 1.0 mg per dose.

In one embodiment the aluminum based adjuvant for use in the present invention is alum (aluminum potassium sulfate ($AlK(SO_4)_2$)), or an alum derivative, such as that formed in-situ by mixing an antigen in phosphate buffer with alum, followed by titration and precipitation with a base such as ammonium hydroxide or sodium hydroxide.

Another aluminum-based adjuvant for use in vaccine formulations of the present invention is aluminum hydroxide adjuvant ($Al(OH)_3$) or crystalline aluminum oxyhydroxide (AlOOH), which is an excellent adsorbant, having a surface area of approximately 500 $m^2/g$. Alternatively, aluminum phosphate adjuvant ($AlPO_4$) or aluminum hydroxyphosphate, which contains phosphate groups in place of some or all of the hydroxyl groups of aluminum hydroxide adjuvant is provided. Preferred aluminum phosphate adjuvants provided herein are amorphous and soluble in acidic, basic and neutral media.

In another embodiment the adjuvant of the invention comprises both aluminum phosphate and aluminum hydroxide. In a more particular embodiment thereof, the adjuvant has a greater amount of aluminum phosphate than aluminum hydroxide, such as a ratio of 2:1, 3:1, 4:1, 5:1, 6:1, 7:1, 8:1, 9:1 or greater than 9:1, by weight aluminum phosphate to aluminum hydroxide. More particular still, aluminum salts in the vaccine are present at 0.4 to 1.0 mg per vaccine dose, or 0.4 to 0.8 mg per vaccine dose, or 0.5 to 0.7 mg per vaccine dose, or about 0.6 mg per vaccine dose.

Generally, the preferred aluminum-based adjuvant(s), or ratio of multiple aluminum-based adjuvants, such as aluminum phosphate to aluminum hydroxide is selected by optimization of electrostatic attraction between molecules such that the antigen carries an opposite charge as the adjuvant at the desired pH. For example, aluminum phosphate adjuvant (isoelectric point=4) adsorbs lysozyme, but not albumin at pH 7.4. Should albumin be the target, aluminum hydroxide adjuvant would be selected (iep 11.4). Alternatively, pretreatment of aluminum hydroxide with phosphate lowers its isoelectric point, making it a preferred adjuvant for more basic antigens.

B. Oil-Emulsions

Oil-emulsion compositions suitable for use as adjuvants in the invention include squalene-water emulsions, such as MF59 (5% Squalene, 0.5% TWEEN™ 80, and 0.5% Span 85, formulated into submicron particles using a microfluidizer). See WO90/14837. See also, Podda, Vaccine (2001) 19: 2673-2680; Frey et al., Vaccine (2003) 21:4234-4237. MF59 is used as the adjuvant in the FLUAD™ influenza virus trivalent subunit vaccine.

Particularly preferred adjuvants for use in the compositions are submicron oil-in-water emulsions. Preferred submicron oil-in-water emulsions for use herein are squalene/water emulsions optionally containing varying amounts of MTP-PE, such as a submicron oil-in-water emulsion containing 4-5% w/v squalene, 0.25-1.0% w/v TWEEN™ 80 (polyoxyethylenesorbitan monooleate), and/or 0.25-1.0% SPAN 85™ (sorbitan trioleate), and, optionally, N-acetylmuramyl-L-alanyl-D-isogluatminyl-L-alanine-2-(1'-2'-dipalmitoyl-sn-glycero-3-huydroxyphosphosphoryloxy)-ethylamine (MTP-PE), for example, the submicron oil-in-water emulsion known as "MF59" (International Publication No. WO90/14837; U.S. Pat. Nos. 6,299,884 and 6,451,325, and Ott et al., in Vaccine Design The Subunit and Adjuvant Approach (Powell, M. F. and Newman, M. J. eds.) Plenum Press, New York, 1995, pp. 277-296). MF59 contains 4-5% w/v Squalene (e.g. 4.3%), 0.25-0.5% w/v TWEEN™ 80, and 0.5% w/v SPAN 85™ and optionally contains various amounts of MTP-PE, formulated into submicron particles using a microfluidizer such as Model 110Y microfluidizer (Microfluidics, Newton, Mass.). For example, MTP-PE may be present in an amount of about 0-500 µg/dose, more preferably 0-250 µg/dose and most preferably, 0-100 µg/dose. As used herein, the term "MF59-0" refers to the above submicron oil-in-water emulsion lacking MTP-PE, while the term MF59-MTP denotes a formulation that contains MTP-PE. For instance, "MF59-100" contains 100 µg MTP-PE per dose, and so on. MF69, another submicron oil-in-water emulsion for use herein, contains 4.3% w/v squalene, 0.25% w/v TWEEN™ 80, and 0.75% w/v SPAN 85™ and optionally MTP-PE. Yet another submicron oil-in-water emulsion is MF75, also known as SAF, containing 10% squalene, 0.4% TWEEN™ 80, 5% pluronic-blocked polymer L121, and thr-MDP, also microfluidized into a submicron emulsion. MF75-MTP denotes an MF75 formulation that includes MTP, such as from 100-400 µg MTP-PE per dose.

Submicron oil-in-water emulsions, methods of making the same and immunostimulating agents, such as muramyl peptides, for use in the compositions, are described in detail in WO90/14837 and U.S. Pat. Nos. 6,299,884 and 6,451,325.

Complete Freund's adjuvant (CFA) and incomplete Freund's adjuvant (IFA) may also be used as adjuvants in the invention.

C. Saponin Formulations

Saponin formulations, may also be used as adjuvants in the invention. Saponins are a heterologous group of sterol glycosides and triterpenoid glycosides that are found in the bark, leaves, stems, roots and even flowers of a wide range of plant species. Saponins isolated from the bark of the Quillaia saponaria Molina tree have been widely studied as adjuvants. Saponins can also be commercially obtained from Smilax ornata (sarsaprilla), Gypsophilla paniculata (brides veil), and Saponaria officianalis (soap root). Saponin adjuvant formulations include purified formulations, such as QS21, as well as lipid formulations, such as ISCOMs.

Saponin compositions have been purified using High Performance Thin Layer Chromatography (HP-TLC) and Reversed Phase High Performance Liquid Chromatography (RP-HPLC). Specific purified fractions using these techniques have been identified, including QS7, QS17, QS18, QS21, QH-A, QH-B and QH-C. Preferably, the saponin is QS21. A method of production of QS21 is disclosed in U.S. Pat. No. 5,057,540. Saponin formulations may also comprise a sterol, such as cholesterol (see WO96/33739).

Combinations of saponins and cholesterols can be used to form unique particles called Immunostimulating Complexes (ISCOMs). ISCOMs typically also include a phospholipid such as phosphatidylethanolamine or phosphatidylcholine. Any known saponin can be used in ISCOMs. Preferably, the ISCOM includes one or more of Quil A, QHA and QHC. ISCOMs are further described in EP0109942, WO96/11711 and WO96/33739. Optionally, the ISCOMS may be devoid of (an) additional detergent(s). See WO00/07621.

A review of the development of saponin based adjuvants can be found in Barr, et al., Advanced Drug Delivery Reviews (1998) 32:247-271. See also Sjolander, et al., Advanced Drug Delivery Reviews (1998) 32:321-338.

D. Virosomes and Virus Like Particles (VLPs)

Virosomes and Virus Like Particles (VLPs) can also be used as adjuvants in the invention. These structures generally contain one or more proteins from a virus optionally combined or formulated with a phospholipid. They are generally non-pathogenic, non-replicating and generally do not contain any of the native viral genome. The viral proteins may be recombinantly produced or isolated from whole viruses. These viral proteins suitable for use in virosomes or VLPs include proteins derived from influenza virus (such as HA or NA), Hepatitis B virus (such as core or capsid proteins), Hepatitis E virus, measles virus, Sindbis virus, Rotavirus, Foot-and-Mouth Disease virus, Retrovirus, Norwalk virus, human Papilloma virus, HIV, RNA-phages, Qβ-phage (such as coat proteins), GA-phage, fr-phage, AP205 phage, and Ty (such as retrotransposon Ty protein p1). VLPs are discussed further in WO03/024480, WO03/024481, and Niikura et al., Virology (2002) 293:273-280; Lenz et al., Journal of Immunology (2001) 5246-5355; Pinto, et al., Journal of Infectious Diseases (2003) 188:327-338; and Gerber et al., Journal of Virology (2001) 75(10):4752-4760. Virosomes are discussed further in, for example, Gluck et al., Vaccine (2002) 20:B10-B16. Immunopotentiating reconstituted influenza virosomes (IRIV) are used as the subunit antigen delivery system in the intranasal trivalent INFLEXAL™ product {Mischler & Metcalfe (2002) Vaccine 20 Suppl 5:B17-23} and the INFLUVAC PLUS™ product.

E. Bacterial or Microbial Derivatives

Adjuvants suitable for use in the invention include bacterial or microbial derivatives such as:

(1) Non-Toxic Derivatives of Enterobacterial Lipopolysaccharide (LPS)

Such derivatives include Monophosphoryl lipid A (MPL) and 3-O-deacylated MPL (3dMPL). 3dMPL is a mixture of 3 De-O-acylated monophosphoryl lipid A with 4, 5 or 6 acylated chains. A preferred "small particle" form of 3 De-O-acylated monophosphoryl lipid A is disclosed in EP 0 689 454. Such "small particles" of 3dMPL are small enough to be sterile filtered through a 0.22 micron membrane (see EP 0 689 454). Other non-toxic LPS derivatives include monophosphoryl lipid A mimics, such as aminoalkyl glucosaminide phosphate derivatives e.g. RC 529. See Johnson et al. (1999) Bioorg Med Chem Lett 9:2273-2278.

(2) Lipid A Derivatives

Lipid A derivatives include derivatives of lipid A from Escherichia coli such as OM-174. OM-174 is described for example in Meraldi et al., Vaccine (2003) 21:2485-2491; and Pajak, et al., Vaccine (2003) 21:836-842.

(3) Immunostimulatory Oligonucleotides

Immunostimulatory oligonucleotides suitable for use as adjuvants in the invention include nucleotide sequences containing a CpG motif (a sequence containing an unmethylated cytosine followed by guanosine and linked by a phosphate bond). Bacterial double stranded RNA or oligonucleotides containing palindromic or poly(dG) sequences have also been shown to be immunostimulatory.

The CpGs can include nucleotide modifications/analogs such as phosphorothioate modifications and can be double-stranded or single-stranded. Optionally, the guanosine may be replaced with an analog such as 2'-deoxy-7-deazaguanosine. See Kandimalla, et al., Nucleic Acids Research (2003) 31(9): 2393-2400; WO02/26757 and WO99/62923 for examples of possible analog substitutions. The adjuvant effect of CpG oligonucleotides is further discussed in Krieg, Nature Medicine (2003) 9(7): 831-835; McCluskie, et al., FEMS Immunology and Medical Microbiology (2002) 32:179-185; WO98/40100; U.S. Pat. No. 6,207,646; U.S. Pat. No. 6,239,116 and U.S. Pat. No. 6,429,199.

The CpG sequence may be directed to TLR9, such as the motif GTCGTT or TTCGTT. See Kandimalla, et al., Biochemical Society Transactions (2003) 31 (part 3): 654-658. The CpG sequence may be specific for inducing a Th1 immune response, such as a CpG-A ODN, or it may be more specific for inducing a B cell response, such a CpG-B ODN. CpG-A and CpG-B ODNs are discussed in Blackwell, et al., J. Immunol. (2003) 170(8):4061-4068; Krieg, TRENDS in Immunology (2002) 23(2): 64-65 and WO01/95935. Preferably, the CpG is a CpG-A ODN.

Preferably, the CpG oligonucleotide is constructed so that the 5' end is accessible for receptor recognition. Optionally, two CpG oligonucleotide sequences may be attached at their 3' ends to form "immunomers". See, for example, Kandimalla, et al., BBRC (2003) 306:948-953; Kandimalla, et al., Biochemical Society Transactions (2003) 31 (part 3):664-658; Bhagat et al., BBRC (2003) 300:853-861 and WO03/035836.

(4) ADP-Ribosylating Toxins and Detoxified Derivatives Thereof

Bacterial ADP-ribosylating toxins and detoxified derivatives thereof may be used as adjuvants in the invention. Preferably, the protein is derived from E. coli (i.e., E. coli heat labile enterotoxin "LT), cholera ("CT"), or pertussis ("PT"). The use of detoxified ADP-ribosylating toxins as mucosal adjuvants is described in WO95/17211 and as parenteral adjuvants in WO98/42375. Preferably, the adjuvant is a detoxified LT mutant such as LT-K63, LT-R72, and LTR192G. The use of ADP-ribosylating toxins and detoxified derivatives thereof, particularly LT-K63 and LT-R72, as adjuvants can be found in the following references: Beignon, et al., Infection and Immunity (2002) 70(6):3012-3019; Pizza, et al., Vaccine (2001) 19:2534-2541; Pizza, et al., Int. J. Med. Microbiol. (2000) 290(4-5): 455-461; Scharton-Kersten et al., Infection and Immunity (2000) 68(9):5306-5313; Ryan et al., Infection and Immunity (1999) 67(12):6270-6280; Partidos et al., Immunol. Lett. (1999) 67(3):209-216; Peppoloni et al., Vaccines (2003) 2(2):285-293; and Pine et al., (2002) J. Control Release (2002) 85(1-3):263-270. Numerical reference for amino acid substitutions is preferably based on the alignments of the A and B subunits of ADP-ribosylating toxins set forth in Domenighini et al., Mol. Microbiol. (1995) 15(6):1165-1167.

F. Bioadhesives and Mucoadhesives

Bioadhesives and mucoadhesives may also be used as adjuvants in the invention. Suitable bioadhesives include esterified hyaluronic acid microspheres (Singh et al. (2001) J. Cont. Rele. 70:267-276) or mucoadhesives such as cross-linked derivatives of polyacrylic acid, polyvinyl alcohol, polyvinyl pyrollidone, polysaccharides and carboxymethylcellulose. Chitosan and derivatives thereof may also be used as adjuvants in the invention. See WO99/27960.

G. Microparticles

Microparticles may also be used as adjuvants in the invention. Microparticles (i.e. a particle of ~100 nm to ~150 μm in diameter, more preferably ~200 nm to ~30 μm in diameter, and most preferably ~500 nm to ~10 μm in diameter) formed from materials that are biodegradable and non toxic (e.g. a poly(α-hydroxy acid), a polyhydroxybutyric acid, a polyorthoester, a polyanhydride, a polycaprolactone, etc.), with poly(lactide co glycolide) are preferred, optionally treated to have a negatively-charged surface (e.g. with SDS) or a positively-charged surface (e.g. with a cationic detergent, such as CTAB).

H. Liposomes

Examples of liposome formulations suitable for use as adjuvants are described in U.S. Pat. No. 6,090,406, U.S. Pat. No. 5,916,588, and EP 0 626 169.

I. Polyoxyethylene Ether and Polyoxyethylene Ester Formulations

Adjuvants suitable for use in the invention include polyoxyethylene ethers and polyoxyethylene esters. WO99/52549. Such formulations further include polyoxyethylene sorbitan ester surfactants in combination with an octoxynol (WO01/21207) as well as polyoxyethylene alkyl ethers or ester surfactants in combination with at least one additional non-ionic surfactant such as an octoxynol (WO01/21152).

Preferred polyoxyethylene ethers are selected from the following group: polyoxyethylene-9-lauryl ether (laureth 9), polyoxyethylene-9-steoryl ether, polyoxytheylene-8-steoryl ether, polyoxyethylene-4-lauryl ether, polyoxyethylene-35-lauryl ether, and polyoxyethylene-23-lauryl ether.

J. Polyphosphazene (PCPP)

PCPP formulations are described, for example, in Andrianov et al., "Preparation of hydrogel microspheres by coacervation of aqueous polyphophazene solutions", Biomaterials (1998) 19(1-3):109-115 and Payne et al., "Protein Release from Polyphosphazene Matrices", Adv. Drug. Delivery Review (1998) 31(3):185-196.

K. Muramyl Peptides

Examples of muramyl peptides suitable for use as adjuvants in the invention include N-acetyl-muramyl-L-threonyl-D-isoglutamine (thr-MDP), N-acetyl-normuramyl-1-alanyl-d-isoglutamine (nor-MDP), and N acetylmuramyl-1-alanyl-d-isoglutaminyl-1-alanine-2-(1'-2'-dipalmitoyl-sn-glycero-3-hydroxyphosphoryloxy)-ethylamine MTP-PE).

L. Imidazoquinoline Compounds.

Examples of imidazoquinoline compounds suitable for use adjuvants in the invention include Imiquimod and its analogues, described further in Stanley, Clin Exp Dermatol (2002) 27(7):571-577; Jones, Curr Opin Investig Drugs (2003) 4(2):214-218; and U.S. Pat. Nos. 4,689,338, 5,389, 640, 5,268,376, 4,929,624, 5,266,575, 5,352,784, 5,494,916, 5,482,936, 5,346,905, 5,395,937, 5,238,944, and 5,525,612.

M. Thiosemicarbazone Compounds.

Examples of thiosemicarbazone compounds, as well as methods of formulating, manufacturing, and screening for compounds all suitable for use as adjuvants in the invention include those described in WO04/60308. The thiosemicarbazones are particularly effective in the stimulation of human peripheral blood mononuclear cells for the production of cytokines, such as TNF-α.

N. Tryptanthrin Compounds.

Examples of tryptanthrin compounds, as well as methods of formulating, manufacturing, and screening for compounds all suitable for use as adjuvants in the invention include those described in WO04/64759. The tryptanthrin compounds are particularly effective in the stimulation of human peripheral blood mononuclear cells for the production of cytokines, such as TNF-α.

The invention may also comprise combinations of aspects of one or more of the adjuvants identified above. For example, the following adjuvant compositions may be used in the invention:

(1) a saponin and an oil-in-water emulsion (WO99/11241);

(2) a saponin (e.g., QS21)+a non-toxic LPS derivative (e.g. 3dMPL) (see WO94/00153);

(3) a saponin (e.g., QS21)+a non-toxic LPS derivative (e.g. 3dMPL)+a cholesterol;

(4) a saponin (e.g., QS21)+3dMPL+IL 12 (optionally+a sterol) (WO98/57659);

(5) combinations of 3dMPL with, for example, QS21 and/or oil-in-water emulsions (See European patent applications 0835318, 0735898 and 0761231);

(6) SAF, containing 10% Squalane, 0.4% Tween 80, 5% pluronic-block polymer L121, and thr-MDP, either microfluidized into a submicron emulsion or vortexed to generate a larger particle size emulsion.

(7) RIBI™ adjuvant system (RAS), (Ribi Immunochem) containing 2% Squalene, 0.2% Tween 80, and one or more bacterial cell wall components from the group consisting of monophosphorylipid A (MPL), trehalose dimycolate (TDM), and cell wall skeleton (CWS), preferably MPL+CWS (DETOX™); and (8) one or more mineral salts (such as an aluminum salt)+a non-toxic derivative of LPS (such as 3dPML).

(9) one or more mineral salts (such as an aluminum salt)+ an immunostimulatory oligonucleotide (such as a nucleotide sequence including a CpG motif).

O. Human Immunomodulators

Human immunomodulators suitable for use as adjuvants in the invention include cytokines, such as interleukins (e.g. IL-1, IL-2, IL-4, IL-5, IL-6, IL-7, IL-12, etc.), interferons (e.g. interferon-γ), macrophage colony stimulating factor, and tumor necrosis factor.

Aluminum salts and MF59 are preferred adjuvants for use with injectable influenza vaccines. Bacterial toxins and bioadhesives are preferred adjuvants for use with mucosally-delivered vaccines, such as nasal vaccines.

The contents of all of the above cited patents, patent applications and journal articles are incorporated by reference as if set forth fully herein.

Therapeutic Methods

The invention provides the compositions described above for use in therapy. The invention provides the compositions described above for inducing or increasing an immune response to *S. pyogenes*. The invention provides methods for inducing or increasing an immune response to *S. pyogenes* using the compositions described above. The immune response is preferably protective and can include antibodies and/or cell-mediated immunity (including systemic and mucosal immunity). Immune responses include booster responses.

Teenagers and children, including toddles and infants, can receive a vaccine for prophylactic use; therapeutic vaccines typically are administered to teenagers or adults. A vaccine intended for children may also be administered to adults e.g., to assess safety, dosage, immunogenicity, etc.

Diseases caused by *Streptococcus pyogenes* which can be prevented or treated according to the invention include, but are not limited to, pharyngitis (such as streptococcal sore throat), scarlet fever, impetigo, erysipelas, cellulitis, septicemia, toxic shock syndrome, necrotizing fasciitis, and sequelae such as rheumatic fever and acute glomerulonephritis. The compositions may also be effective against other streptococcal bacteria, e.g., GBS.

Tests to Determine the Efficacy of the Immune Response

One way of assessing efficacy of therapeutic treatment involves monitoring GAS infection after administration of the composition of the invention. One way of assessing efficacy of prophylactic treatment involves monitoring immune responses against the mutant SLO proteins in the compositions of the invention after administration of the composition.

Another way of assessing the immunogenicity of the component proteins of the immunogenic compositions of the present invention is to express mutant SLO proteins recombinantly and to screen patient sera or mucosal secretions by immunoblot. A positive reaction between the protein and the patient serum indicates that the patient has previously mounted an immune response to the protein in question; i.e., the protein is an immunogen. This method may also be used to identify immunodominant proteins and/or epitopes.

Another way of checking efficacy of therapeutic treatment involves monitoring GAS infection after administration of the compositions of the invention. One way of checking efficacy of prophylactic treatment involves monitoring immune responses both systemically (such as monitoring the level of IgG1 and IgG2a production) and mucosally (such as monitoring the level of IgA production) against SLO after administration of the composition. Typically, serum specific antibody responses are determined post-immunization but pre-challenge whereas mucosal specific antibody body responses are determined post-immunization and post-challenge.

The vaccine compositions of the present invention can be evaluated in in vitro and in vivo animal models prior to host, e.g., human, administration. Particularly useful mouse models include those in which intraperitoneal immunization is followed by either intraperitoneal challenge or intranasal challenge.

The efficacy of immunogenic compositions of the invention can also be determined in vivo by immunizing animal models, (e.g., guinea pigs or mice) with the immunogenic compositions and ascertaining the level of protection obtained after challenge with GAS.

In vivo efficacy models include but are not limited to: (i) a murine infection model using human GAS serotypes; (ii) a murine disease model which is a murine model using a mouse-adapted GAS strain, such as the M23 strain which is particularly virulent in mice, and (iii) a primate model using human GAS isolates.

The immune response may be one or both of a TH1 immune response and a TH2 response. The immune response may be an improved or an enhanced or an altered immune response. The immune response may be one or both of a systemic and a mucosal immune response. Preferably the immune response is an enhanced system and/or mucosal response.

An enhanced systemic and/or mucosal immunity is reflected in an enhanced TH1 and/or TH2 immune response. Preferably, the enhanced immune response includes an increase in the production of IgG1 and/or IgG2a and/or IgA.

Preferably the mucosal immune response is a TH2 immune response. Preferably, the mucosal immune response includes an increase in the production of IgA.

Activated TH2 cells enhance antibody production and are therefore of value in responding to extracellular infections. Activated TH2 cells may secrete one or more of IL-4, IL-5, IL-6, and IL-10. A TH2 immune response may result in the production of IgG1, IgE, IgA and memory B cells for future protection.

A TH2 immune response may include one or more of an increase in one or more of the cytokines associated with a TH2 immune response (such as IL-4, IL-5, IL-6 and IL-10), or an increase in the production of IgG1, IgE, IgA and memory B cells. Preferably, the enhanced TH2 immune response will include an increase in IgG1 production.

A TH1 immune response may include one or more of an increase in CTLs, an increase in one or more of the cytokines associated with a TH1 immune response (such as IL-2, IFNγ, and TNFβ), an increase in activated macrophages, an increase in NK activity, or an increase in the production of IgG2a. Preferably, the enhanced TH1 immune response will include an increase in IgG2a production.

Immunogenic compositions of the invention, in particular, immunogenic composition comprising one or more mutant SLO proteins of the present invention may be used either alone or in combination with other GAS antigens optionally with an immunoregulatory agent capable of eliciting a Th1 and/or Th2 response.

The invention also comprises an immunogenic composition comprising one or more immunoregulatory agent, such as a mineral salt, such as an aluminium salt and an oligonucleotide containing a CpG motif Most preferably, the immunogenic composition includes both an aluminium salt and an oligonucleotide containing a CpG motif. Alternatively, the immunogenic composition includes an ADP ribosylating toxin, such as a detoxified ADP ribosylating toxin and an oligonucleotide containing a CpG motif. Preferably, one or more of the immunoregulatory agents include an adjuvant. The adjuvant may be selected from one or more of the group consisting of a TH1 adjuvant and TH2 adjuvant.

The compositions of the invention will preferably elicit both a cell mediated immune response as well as a humoral immune response in order to effectively address a GAS infection. This immune response will preferably induce long lasting (e.g., neutralizing) antibodies and a cell mediated immunity that can quickly respond upon exposure to one or more GAS antigens.

In one particularly preferred embodiment, the immunogenic composition comprises one or more mutant SLO protein(s) which elicit(s) a neutralizing antibody response and one or more mutant SLO protein(s) which elicit(s) a cell mediated immune response. In this way, the neutralizing antibody response prevents or inhibits an initial GAS infection while the cell-mediated immune response capable of eliciting an enhanced Th1 cellular response prevents further spreading of the GAS infection.

Compositions of the invention will generally be administered directly to a patient. The compositions of the present invention may be administered, either alone or as part of a composition, via a variety of different routes. Certain routes may be favored for certain compositions, as resulting in the generation of a more effective immune response, preferably a CMI response, or as being less likely to induce side effects, or as being easier for administration.

Delivery methods include parenteral injection (e.g., subcutaneous, intraperitoneal, intravenous, intramuscular, or interstitial injection) and rectal, oral (e.g., tablet, spray), vaginal, topical, transdermal (e.g., see WO 99/27961), transcutaneous (e.g., see WO02/074244 and WO02/064162), intranasal (e.g., see WO03/028760), ocular, aural, and pulmonary or other mucosal administration.

By way of example, the compositions of the present invention may be administered via a systemic route or a mucosal route or a transdermal route or it may be administered directly into a specific tissue. As used herein, the term "systemic administration" includes but is not limited to any parenteral routes of administration. In particular, parenteral administration includes but is not limited to subcutaneous, intraperitoneal, intravenous, intraarterial, intramuscular, or intrasternal injection, intravenous, intraarterial, or kidney dialytic infusion techniques. Preferably, the systemic, parenteral administration is intramuscular injection. As used herein, the term "mucosal administration" includes but is not limited to oral, intranasal, intravaginal, intrarectal, intratracheal, intestinal and ophthalmic administration.

Dosage treatment can be a single dose schedule or a multiple dose schedule. Multiple doses may be used in a primary immunization schedule and/or in a booster immunization schedule. In a multiple dose schedule the various doses may be given by the same or different routes e.g., a parenteral prime and mucosal boost, a mucosal prime and parenteral boost, etc.

The compositions of the invention may be prepared in various forms. For example, a composition can be prepared as an injectable, either as a liquid solution or a suspension. Solid forms suitable for solution in, or suspension in, liquid vehicles prior to injection can also be prepared (e.g., a lyophilized composition). A composition can be prepared for oral administration, such as a tablet or capsule, as a spray, or as a syrup (optionally flavored). A composition can be prepared for pulmonary administration, e.g., as an inhaler, using a fine powder or a spray. A composition can be prepared as a suppository or pessary. A composition can be prepared for nasal, aural or ocular administration e.g., as drops. A composition can be in kit form, designed such that a combined composition is reconstituted just prior to administration to a patient. Such kits may comprise one or more mutant SLO or other antigens in liquid form and one or more lyophilized antigens.

Immunogenic compositions used as vaccines comprise an immunologically effective amount of mutant SLO or other antigens (or nucleic acid molecules encoding the antigens), as well as any other components, as needed, such as antibiotics. An "immunologically effective amount" is an amount which, when administered to an individual, either in a single dose or as part of a series, increases a measurable immune response or prevents or reduces a clinical symptom.

The immunogenic compositions of the present invention may be administered in combination with an antibiotic treatment regime. In one embodiment, the antibiotic is administered prior to administration of the antigen of the invention or the composition comprising the one or more mutant SLO proteins of the invention.

In another embodiment, the antibiotic is administered subsequent to the administration of a mutant SLO protein of the invention. Examples of antibiotics suitable for use in the treatment of a GAS infection include but are not limited to penicillin or a derivative thereof or clindamycin, cephalosporins, glycopeptides (e.g., vancomycin), and cycloserine.

The amount of active agent in a composition varies, however, depending upon the health and physical condition of the individual to be treated, age, the taxonomic group of individual to be treated (e.g., non-human primate, primate, etc.), the capacity of the individual's immune system to synthesize antibodies, the degree of protection desired, the formulation of the vaccine, the treating doctor's assessment of the medical situation, and other relevant factors. The amount will fall in a relatively broad range which can be determined through routine trials.

Kits

The invention also provides kits comprising one or more containers of compositions of the invention. Compositions can be in liquid form or can be lyophilized, as can individual antigens. Suitable containers for the compositions include, for example, bottles, vials, syringes, and test tubes. Containers can be formed from a variety of materials, including glass or plastic. A container may have a sterile access port (for example, the container may be an intravenous solution bag or a vial having a stopper pierceable by a hypodermic injection needle).

The kit can further comprise a second container comprising a pharmaceutically-acceptable buffer, such as phosphate-buffered saline, Ringer's solution, or dextrose solution. It can also contain other materials useful to the end-user, including other buffers, diluents, filters, needles, and syringes. The kit can also comprise a second or third container with another active agent, for example an antibiotic.

The kit can also comprise a package insert containing written instructions for methods of inducing immunity against *S. pyogenes* or for treating *S. pyogenes* infections. The package insert can be an unapproved draft package insert or can be a package insert approved by the Food and Drug Administration (FDA) or other regulatory body.

All patents, patent applications, and references cited in this disclosure are expressly incorporated herein by reference. The above disclosure generally describes the present invention. A more complete understanding can be obtained by reference to the following specific examples, which are provided for purposes of illustration only and are not intended to limit the scope of the invention.

Example 1

Cloning of Wild-Type and Mutant SLO Proteins

Genes encoding wild-type and mutant SLO proteins were amplified by PCR using the primers from the SF370 genome shown in Table 1.

The PCR products were digested with NheI-XhoI and ligated with pet24b+ (Novagen) vector cut with the same enzymes. *E. coli* DH5α electrocompetent cells were transformed with the ligation reactions. LBPTK medium was added and, after incubation for 1 h at 37° C., with agitation at 250 rpm, bacteria were plated onto LBPTK plates containing 50 μg/ml kanamycin. Positive colonies were identified by colony PCR.

Plasmids from positive colonies were prepared from an overnight culture in LBPTK medium containing 50 µg/ml kanamycin and analyzed by DNA sequencing, which confirmed the expected insert gene under the T7 polymerase promoter. The final DNA and protein sequences of the cloned genes are shown in the sequence listing. See Table 2.

TABLE 1

| gene | primers | | |
|---|---|---|---|
| SLO wild-type tag-less | 25F NheI, | GTGCGT<u>GCTAGC</u>GAATCGAACAAACAAAACACTGC | (SEQ ID NO: 35) |
| | 25rev = | GCATTCGATC<u>CTCGAG</u>CTACTTATAAGTAATCGAACCATATG | (SEQ ID NO: 36) |
| SLO P427L tag-less | External primers: | | |
| | 25F NheI, | GTGCGT<u>GCTAGC</u>GAATCGAACAAACAAAACACTGC | (SEQ ID NO: 35) |
| | 25rev, | GCATTCGATC<u>CTCGAG</u>CTACTTATAAGTAATCGAACCATATG | (SEQ ID NO: 36) |
| | Internal primers: | | |
| | PL427_for, | GCTACCTTCAGTAGAAAAAACCTAGCTTATCCTATTTCATACACC | (SEQ ID NO: 37) |
| | PL427_rev, | GGTGTATGAAATAGGATAAGCTAGGTTTTTTCTACTGAAGGTAGC | (SEQ ID NO: 38) |
| SLO Wild Type His-tagged | 25F NheI, | GTGCGT<u>GCTAGC</u>GAATCGAACAAACAAAACACTGC | (SEQ ID NO: 35) |
| | 25revhis, | GCATTCGATC<u>CTCGAG</u>CTTATAAGTAATCGAACCATATGGG | (SEQ ID NO: 39) |
| SLO W535F His-tagged | External primers: | | |
| | 25F NheI, | GTGCGT<u>GCTAGC</u>GAATCGAACAAACAAAACACTGC | (SEQ ID NO: 35) |
| | 25revhis, | GCATTCGATC<u>CTCGAG</u>CTTATAAGTAATCGAACCATATGGG | (SEQ ID NO: 39) |
| | Internal primers: | | |
| | WF535_for, | GAGTGCACTGGCTTAGCTTTCGAATGGTGGCGAAAAGTGATC | (SEQ ID NO: 40) |
| | WF535_rev, | GATCACTTTTCGCCACCATTCGAAAGCTAAGCCAGTGCACTC | (SEQ ID NO: 41) |
| SLO W535F-D482N His-tagged | External primers: | | |
| | 25F NheI, | GTGCGT<u>GCTAGC</u>GAATCGAACAAACAAAACACTGC | (SEQ ID NO: 35) |
| | 25revhis, | GCATTCGATC<u>CTCGAG</u>CTTATAAGTAATCGAACCATATGGG | (SEQ ID NO: 39) |
| | Internal primers: | | |
| | WF535_for, | GAGTGCACTGGCTTAGCTTTCGAATGGTGGCGAAAAGTGATC | (SEQ ID NO: 40) |
| | WF535_rev, and | GATCACTTTTCGCCACCATTCGAAAGCTAAGCCAGTGCACTC | (SEQ ID NO: 41) |
| | DN482_for, | GTTGCTCAATATGAAATCCTTTGGAATGAAATCAATTATGATGACAAAGGAAAAG | (SEQ ID NO: 42) |
| | DN482_rev, | CTTTTCCTTTGTCATCATAATTGATTTCATTCCAAAGGATTTCATATTGAGCAAC | (SEQ ID NO: 43) |
| SLO C530G His-tagged | External primers: | | |
| | 25F NheI, | GTGCGT<u>GCTAGC</u>GAATCGAACAAACAAAACACTGC | (SEQ ID NO: 35) |
| | 25revhis, | GCATTCGATC<u>CTCGAG</u>CTTATAAGTAATCGAACCATATGGG | (SEQ ID NO: 39) |
| | Internal primers: | | |
| | CG530_for, | CCGTATCATGGCTAGAGAGGGCACTGGCTTAGCTTGGGAATG | (SEQ ID NO: 44) |
| | CG530_rev, | CATTCCCAAGCTAAGCCAGTGCCCTCTCTAGCCATGATACGG | (SEQ ID NO: 45) |
| SLO P427L His-tagged | External primers: | | |
| | 25F NheI, | GTGCGT<u>GCTAGC</u>GAATCGAACAAACAAAACACTGC | (SEQ ID NO: 35) |
| | 25 revhis, | GCATTCGATC<u>CTCGAG</u>CTTATAAGTAATCGAACCATATGGG | (SEQ ID NO: 39) |
| | Internal primers: | | |
| | PL427_for, | GCTACCTTCAGTAGAAAAAACCTAGCTTATCCTATTTCATACACC | (SEQ ID NO: 37) |
| | PL427_rev, | GGTGTATGAAATAGGATAAGCTAGGTTTTTTCTACTGAAGGTAGC | (SEQ ID NO: 38) |
| SLO P427L-W535F-C535G tag-less | External primers: | | |
| | 25_F, | GTGCGT<u>GCTAGC</u>GAATCGAACAAACAAAAC | (SEQ ID NO: 46) |
| | 25_stopR, | GCGT<u>CTCGAG</u>TCACTTATAAGTAATCGAACCATA | (SEQ ID NO: 47) |
| | Internal primers: | | |
| | W-C_for, | CCGTATCATGGCTAGAGAGGGCACTGGCTTAGCTTTCGAATG | (SEQ ID NO: 48) |
| | W-C_rev, | CATTCGAAAGCTAAGCCAGTGCCCTCTCTAGCCATGATACGG | (SEQ ID NO: 49) |
| SLO P427L-W535F tag-less | External primers: | | |
| | 25_F, | GTGCGT<u>GCTAGC</u>GAATCGAACAAACAAAAC | (SEQ ID NO: 46) |
| | 25_stopR, | GCGT<u>CTCGAG</u>TCACTTATAAGTAATCGAACCATA | (SEQ ID NO: 47) |
| | Internal primers: | | |
| | WF535_for, | GAGTGCACTGGCTTAGCTTTCGAATGGTGGCGAAAAGTGATC | (SEQ ID NO: 40) |
| | WF535_rev, | GATCACTTTTCGCCACCATTCGAAAGCTAAGCCAGTGCACTC | (SEQ ID NO: 41) |
| SLO P427L-C530G tag-less | External primers: | | |
| | 25_F, | GTGCGT<u>GCTAGC</u>GAATCGAACAAACAAAAC | (SEQ ID NO: 46) |
| | 25_stopR, | GCGT<u>CTCGAG</u>TCACTTATAAGTAATCGAACCATA | (SEQ ID NO: 47) |
| | Internal primers: | | |
| | CG530_for, | CCGTATCATGGCTAGAGAGGGCACTGGCTTAGCTTGGGAATG | (SEQ ID NO: 44) |
| | CG530_rev, | CATTCCCAAGCTAAGCCAGTGCCCTCTCTAGCCATGATACGG | (SEQ ID NO: 45) |
| SLO ΔA248 his-tagged | External primers: | | |
| | 25F NheI, | GTGCGT<u>GCTAGC</u>GAATCGAACAAACAAAACACTGC | (SEQ ID NO: 35) |
| | 25 revhis, | GCATTCGATC<u>CTCGAG</u>CTTATAAGTAATCGAACCATATGGG | (SEQ ID NO: 39) |
| | Internal primers: | | |
| | Δ248for, | CTGGTGGTAATACGCTTCCTAGAACACAATATACTGAATCAATGG | (SEQ ID NO: 50) |
| | Δ248rev, | CCATTGATTCAGTATATTGTGTTCTAGGAAGCGTATTACCACCAG | (SEQ ID NO: 51) |

TABLE 2

| | sequence identifier | | | |
|---|---|---|---|---|
| | amino acid | | nucleotide | |
| SLO gene | tag-less | His-tagged | tag-less | His-tagged |
| wild-type | 1-12 | 13 | 28 | 14 |
| P427L | 20 | 15 | 29 | 57 |
| C530G | 22 | 16 | 31 | 58 |
| W535F | 21 | 18 | 30 | 52 |
| ΔA248 | 23 | 17 | | 59 |
| W535F + D482N | 24 | 19 | | 53 |
| P427L + C530G | 26 | 54 | 33 | |
| P427L + W535F | 25 | 55 | 32 | |
| P427L + C530G + W535F | 27 | 56 | 34 | |

Figure 8A:
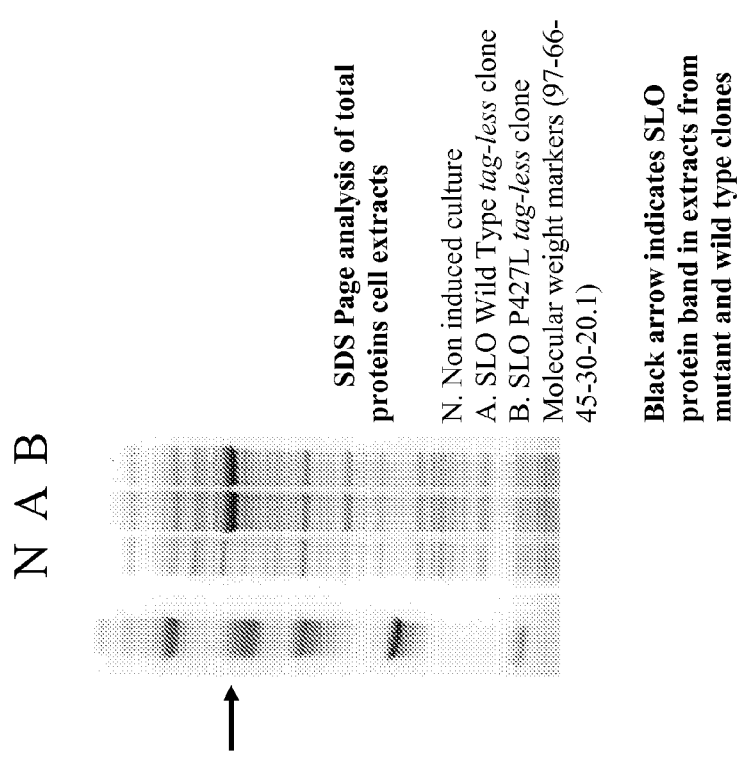
FIG. 8A, expression of SLO wild-type and P427L tag-less proteins.
Figure 8B:
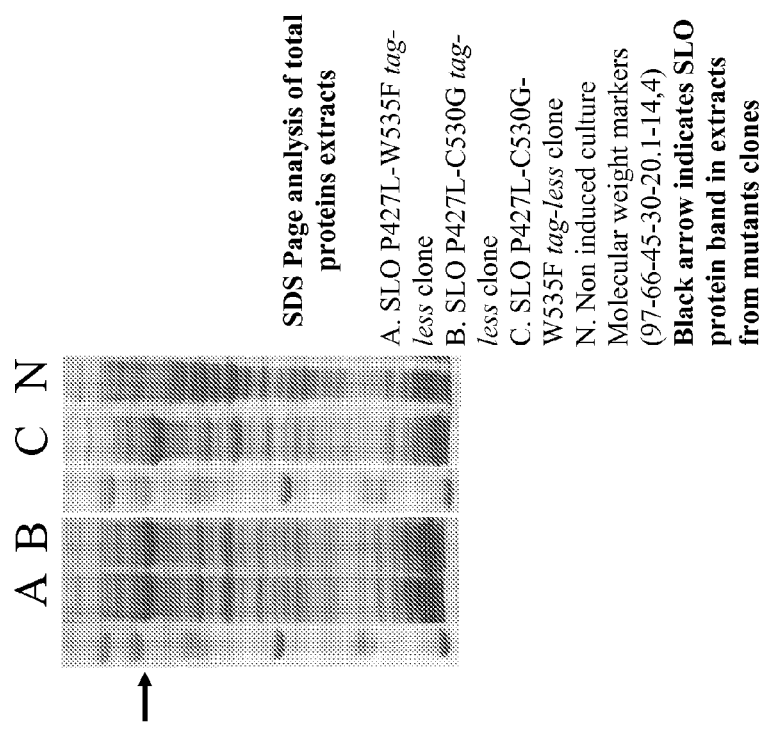
FIG. 8B, expression of SLO P427L+W535, P427L+C530G, and P427L+C530G+W535F tag-less proteins.

*E. coli* BL21(DE3) (Novagen) competent cells were transformed with the correct construct. LBPTK medium was added and, after incubation for 1 h at 37° C., with agitation at 250 rpm, bacteria were plated onto LBPTK plates containing 50 μg/ml kanamycin. BL21(DE3) pet24b+SLO wild-type tag-less cells were grown at 25° C. and induced with 1 mM IPTG. Clone expression was verified by SDS PAGE (tag-less, FIGS. 8A and 8B; His-tagged, FIG. 9).

Example 2

Purification of His-Tagged Proteins

Figure 9:
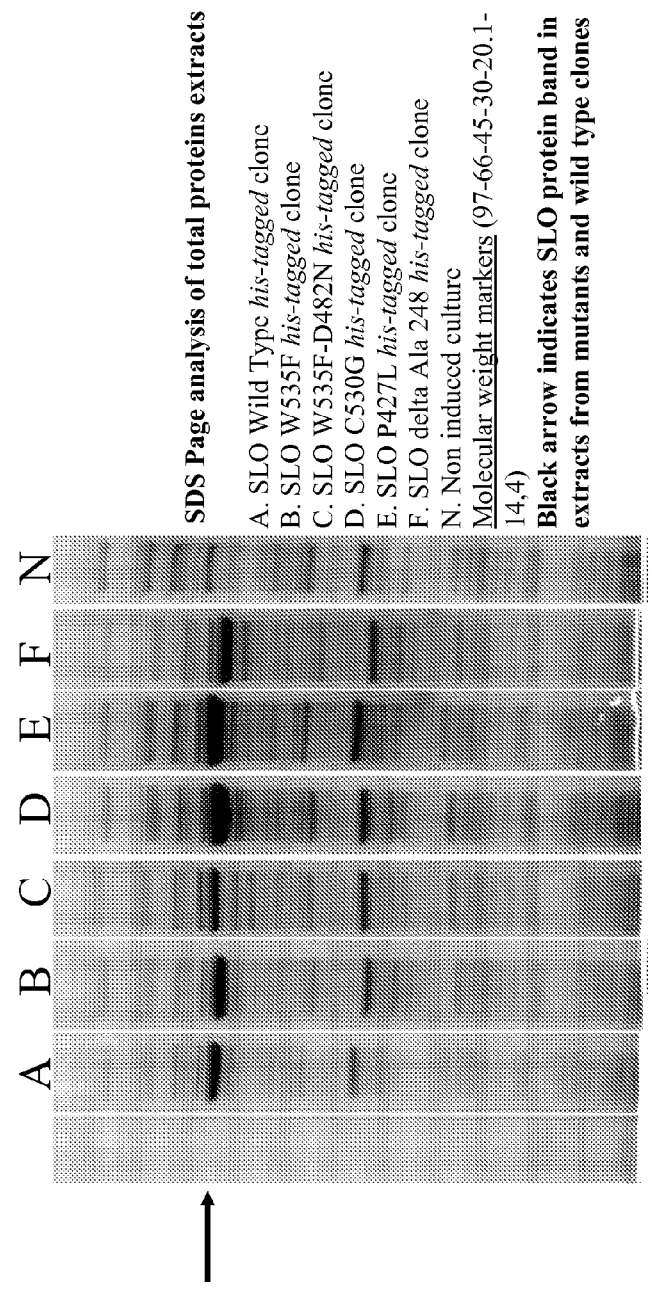
FIG. 9. Photomicrograph of SDS-PAGE analysis of total His-tagged proteins in cell extracts.

*E. coli* pellets were suspended in lysis buffer and mixed for 30-40 minutes at room temperature. Lysates were centrifuged at 30-40000×g for 20-25 minutes and supernatants were loaded onto wash buffer A equilibrated columns (Poly-Prep with 1 ml of Ni-Activated Chelating Sepharose Fast Flow resin). The loaded resin was washed three times with wash buffer A and three times with wash buffer B. Proteins were eluted with elution buffer in Eppendorf tubes containing 2 mM final of DTT. Total elution proteins are quantified with Bradford reagent and then analyzed by SDS-polyacrylamide gel electrophoresis (FIGS. 8 and 9).

Buffers lysis buffer:

- 10 ml B-PER™ (Bacterial-Protein Extraction Reagent, Pierce cat. 78266)
- $MgCl_2$ final concentration of 0.1 mM
- DNAsi I (Sigma cat. D-4263) 100 units
- lysozyme (Sigma cat. L-7651) final concentration of 1 mg/ml wash buffer A: 50 mM $NaH_2PO_4$, 300 mM NaCl, pH 8.0 wash buffer B: 20 mM imidazole, 50 mM $NaH_2PO_4$, 300 mM NaCl, pH 8.0 elution buffer: 250 mM imidazole, 50 mM $NaH_2PO_4$, 300 mM NaCl, pH 8.0

Example 3

Purification of Tag-Less Proteins

Lysate Preparation

About 80-110 g of bacterial culture pellet were suspended in 200-280 ml B-PER™ reagent (Pierce) supplemented with 6 tablets of COMPLETE® protease inhibitor, 10 ml 0.2M EDTA pH 7.5 (5 mM final concentration), 10 ml of a 100 mg/ml lysozyme solution, 8 ml of a 10000 K units/ml DNAse I solution and 1 ml of 50 mM $MgCl_2$ solution. Bacterial lysis was achieved by shaking the bacterial suspension for 60 minutes until a homogeneous suspension was obtained.

Following centrifugation for 60 minutes at 13000 rpm (25400×g), the supernatant was filtered using a 0.22 μm filter and is diluted with $H_2O$ until a 1.8-1.9 mS conductivity was obtained. The pH was adjusted to 8.0. Protein concentration was determined by the Bradford method.

Anionic Exchange Chromatography

The supernatant derived from the lysate treated as described above was loaded on an HP 50/10 Q Sepharose column (~200 ml), previously equilibrated with 30 mM TRIS, pH 8.0. The flow-through was collected. Fractions containing the GAS25 protein were pooled and dialyzed against 10 mM Na phosphate, pH 6.8. Protein concentration was determined by the Bradford method.

Buffer A: 30 mM TRIS, pH 8.0
Buffer B: 30 mM TRIS, 1M NaCl, pH 8.0
Equilibrium and Loading: 0% B

Gradient: 0-25% B in 5 CV−25% B 2 CV

Wash: 100% B 2 CV+3 CV
Flux: 20 ml/min

Fraction volume: 14 ml

Hydroxylapatite Chromatography

The previously obtained pool was loaded on a CHT20 column previously equilibrated with 10 mM Na-phosphate, pH 6.8. The flow through was collected.

Buffer A: 10 mM Na-phosphate, pH 6.8
Buffer B: 500 mM Na phosphate, pH 6.8
Wash: 8 CV
Wash: 30% B 6 CV
Gradient: 30-100% B (10 CV)
Wash: 100% B
Flux: 5 ml/min.

Fraction volume: 5 ml

Fraction aliquots were loaded on 12% Criterion gels under reducing and non-reducing conditions. Fractions containing GAS25 protein were pooled and protein concentration was determined by Bradford method.

Gel Filtration Chromatography

The collected pool was concentrated using an Amicon filter in order to get a volume <10 ml. The concentrated material was loaded on a HiLoad Superdex 200 26/60 equilibrated with at least 3-4 column volumes of PBS.

Buffer: PBS
Elution: Isocratic
Flux: 2.5 ml/min.
Fraction volume: 5 ml

Figure 11A:
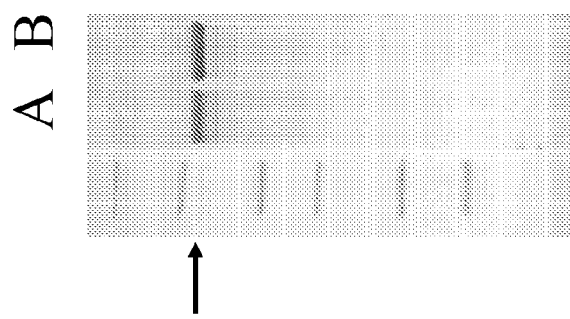
FIG. 11A, Lanes: A, SLO wild-type tag-less; B, SLO P427L tag-less; molecular weight markers (116-66.2-45-35-25-18.4-14.4); black arrow indicates SLO protein purified from mutants and wild-type clones.
Figure 11B:
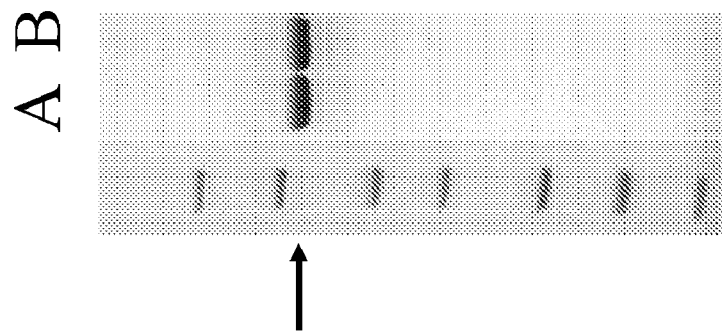
FIG. 11B, lane A, SLO Wild Type tag-less (3 µg), lane B, SLO P427L-W535F tag-less (3 µg); molecular weight markers (116-66.2-45-35-25-18.4-14.4); black arrow indicates SLO protein purified from mutants and wild-type clones.
Figure 12:
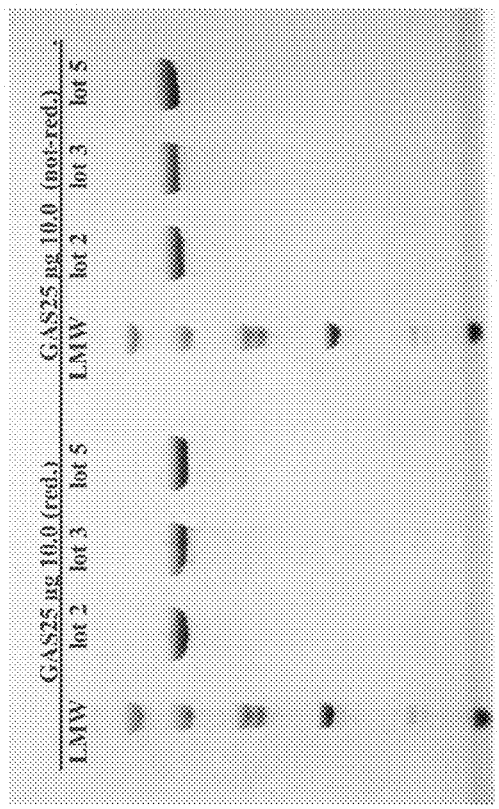
FIG. 12. Photomicrograph of SDS-PAGE analysis of purified tag-less SLO wild-type protein. Samples of different purification lots of wild-type SLO were analyzed under reducing and non-reducing conditions.
Figure 13:
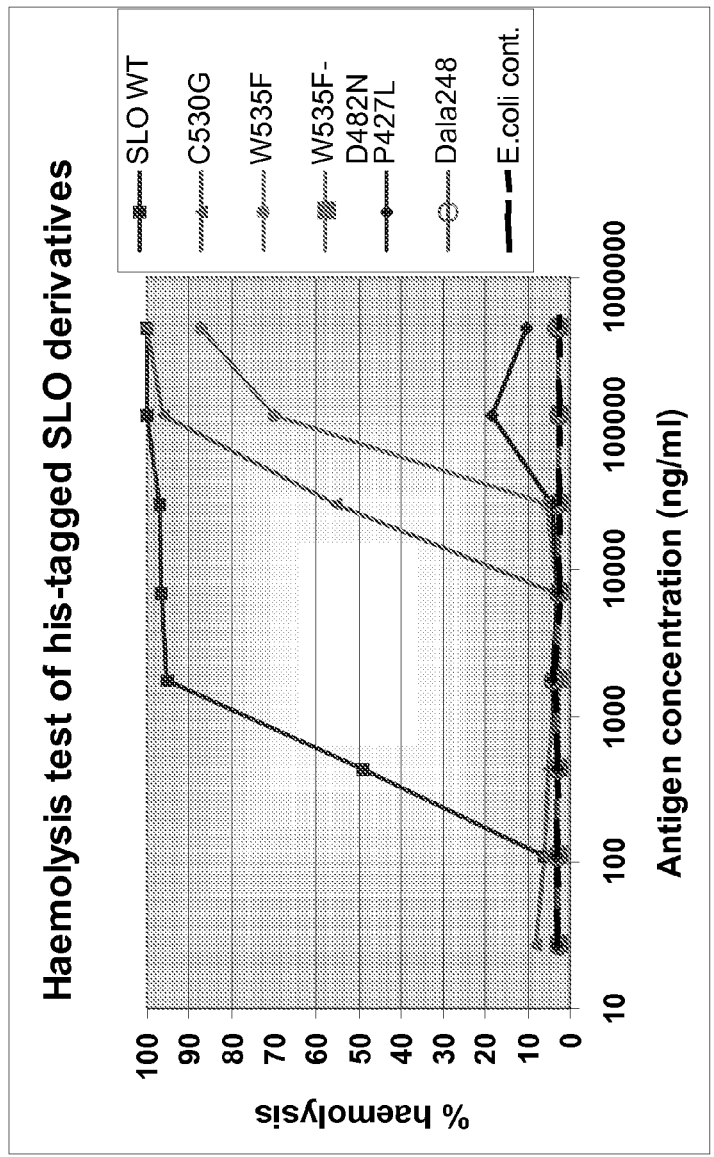
FIG. 13. Graph showing results of hemolysis tests of His-tagged SLO mutants.

Fractions containing GAS25 protein were pooled and protein concentration was determined by Bradford. An additional estimation of protein concentration was performed by UV measurement considering Abs 0.1% (=1 g/l) 1.119. Protein purity is analyzed by polyacrylamide gel electrophoresis (FIG. 11).

Example 4

Hemolytic Assays

Protocol for Quantitative Hemolytic Assay

Serial dilutions of toxin were prepared in 96-well plates with U-shaped bottoms using PBS+0.5% BSA. One ml of sheep blood was washed three times in PBS (with centrifugation at 3000×g), and blood cells were suspended in 5 ml of PBS. An equal volume of suspension was added to 50 μl of each toxin dilution and incubated at 37° C. for 30 min. Triton (2%) in water was used to give 100% hemolysis, and PBS+0.5% BSA was used as negative control. Plates were then centrifuged for 5 min at 1,000×g, and the supernatant was transferred carefully to 96-well flat-bottomed plates. The absorbance was read at 540 nm.

Comparison of *E. coli* Extracts Containing Wild-Type SLO and SLO Mutant P427L

Figure 2:
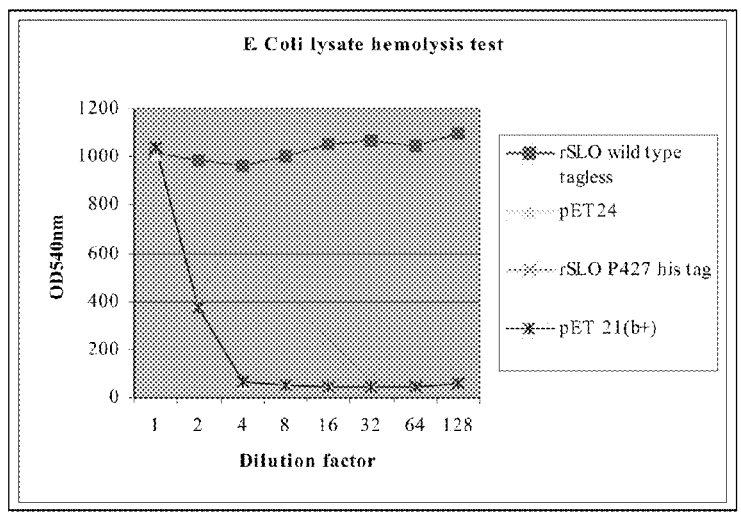
FIG. 2. Graph showing results of hemolytic assay using *E. coli* extracts containing wild-type SLO and SLO mutant P427L.
Figure 5:
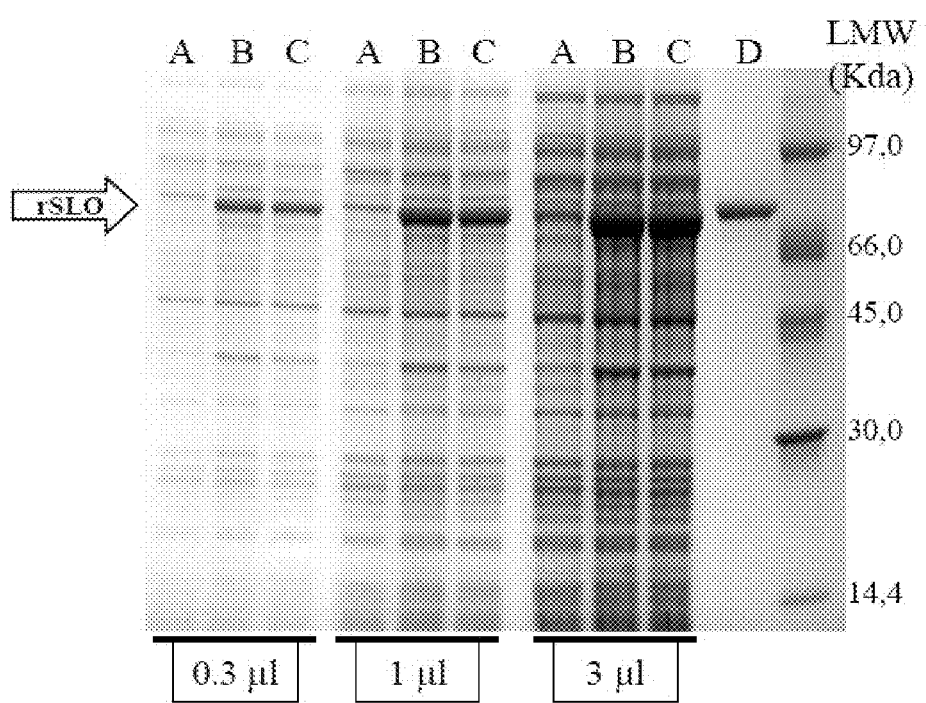
FIG. 5. Photomicrograph of SDS-polyacrylamide gel of *E. coli* lysate supernatants. Lane A, *E. coli* negative control; lane B, rSLO wild-type, without tag; lane C, rSLO P427L, without tag; and lane D, purified rSLO wild-type, without tag (5 mg).
Figure 6:
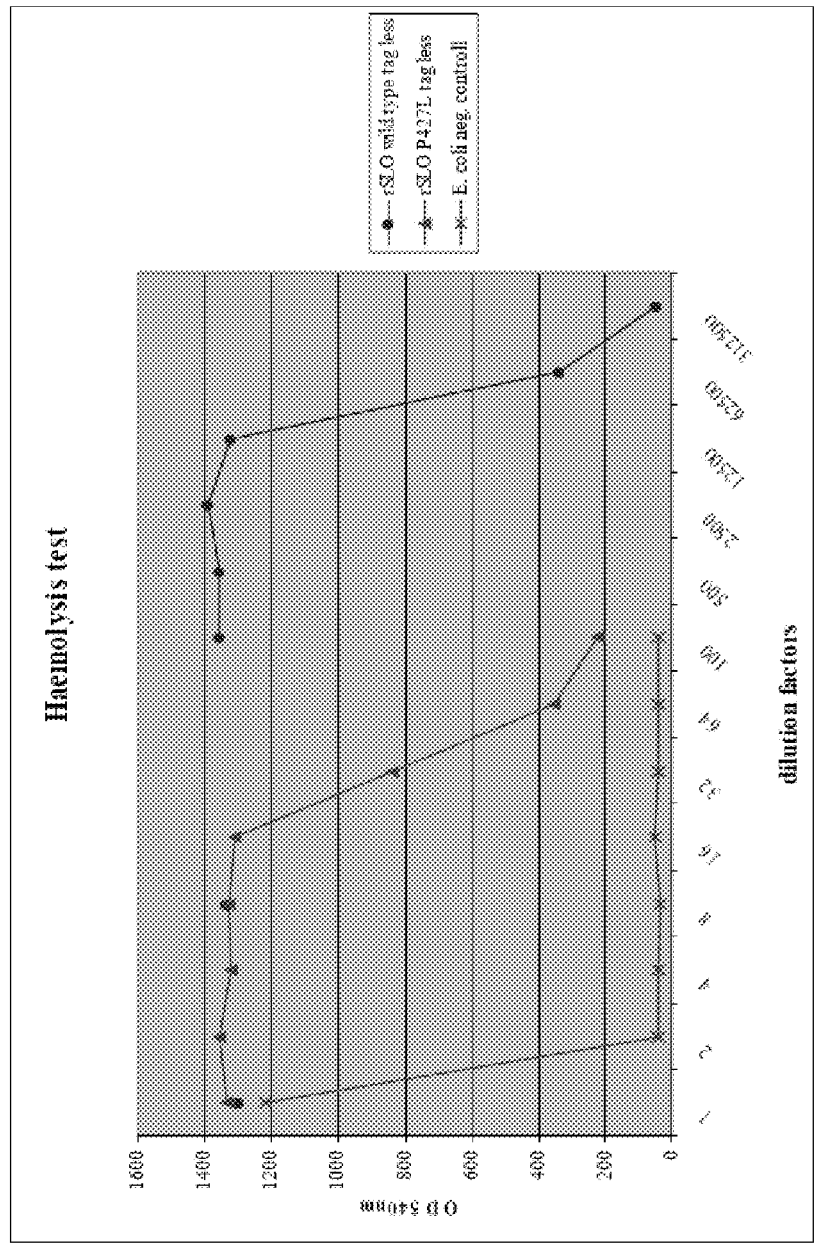
FIG. 6. Graph demonstrating that under the same conditions, SLO mutant P427L is 1000 times less hemolytic than wild-type SLO.
Figure 7:
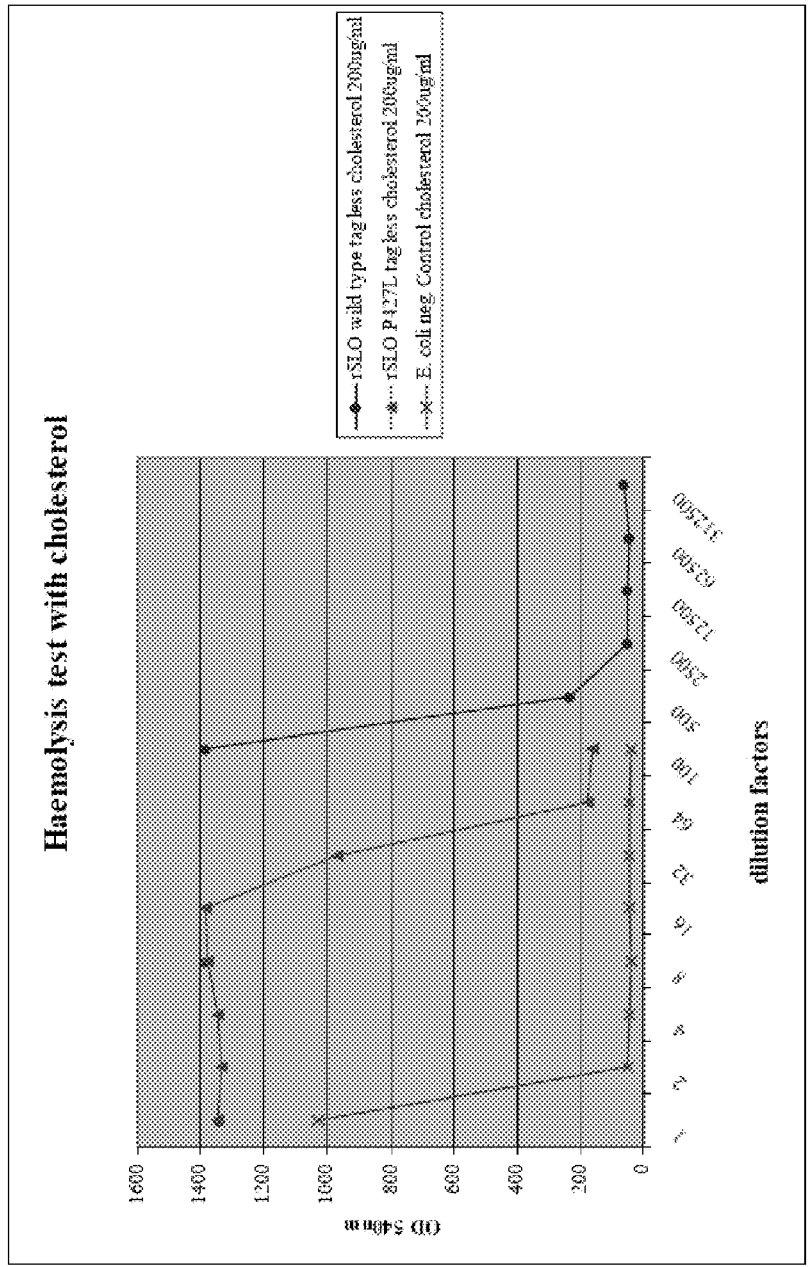
FIG. 7. Graph demonstrating effects of cholesterol on hemolysis by wild-type SLO and SLO mutant P427L.

The gene encoding SLO P427L was amplified using PCR from the SF370 M1 genome and cloned into the vector pET21b+, which allowed expression in *E. coli* BL21DE3 of the His-tagged protein. Soluble extracts of *E. coli* expressing similar amounts of the wild-type and mutated streptolysin O proteins (see FIG. 5) were used to perform a hemolytic assay to compare the cytolytic properties of the two antigens. The result of the assay is shown in FIG. 2, which demonstrates that the mutated protein is at least 100 times less toxic than wild-type.

Comparison of Purified Wild-Type SLO and SLO Mutant P427L

Figure 3:
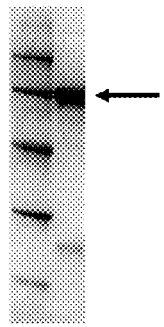
FIG. 3. Photomicrograph of SDS-polyacrylamide gel showing purified SLO mutant P427L.
Figure 4:
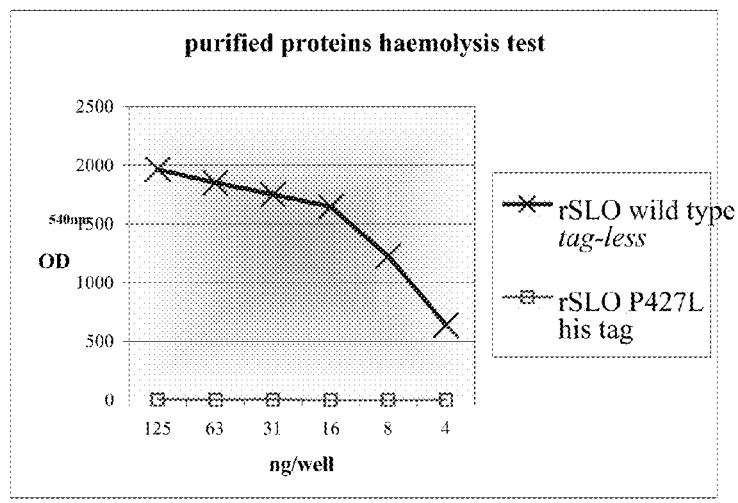
FIG. 4. Graph showing results of hemolytic assay using purified wild-type SLO and SLO mutant P427L.

The SLO P427L mutant was purified according to purification standard procedures for His-tagged recombinant proteins (FIG. 3). Different concentrations of the purified wt and mutated proteins were used to repeat the hemolytic assay, which confirmed the decreased cytolytic activity (FIG. 4).

Hemolytic Activity of *E. coli* Extracts Containing His-Tagged and Tag-Less Wild-Type SLO and SLO Mutant P427L We compared the hemolytic activity of *E. coli* lysates transformed with wild-type recombinant SLO (rSLO) without a His tag (BL21 DE3, Novagen No. 71382-pET24) and P427L mutant rSLO without a His tag (BL21 DE3, Novagen No. 71382-pET24). *E. coli* BL21 DE3 (Novagen, No. 71382) transformed with pET24 without insert was used as a negative control. The positive control was a hypotonic solution containing Triton 2% in water. The negative control was the protein dilution buffer (PBS containing 0.5% BSA, pH 7.4).

Hemolysis was determined by measuring absorbance at 540 nm ($A_{540nm}$) of the supernatants. The titer was calculated as the dilution with 50% of maximum $A_{540nm}$.

Results are shown in Tables 3 and 4 and in FIG. 6. These data demonstrate that, under the same conditions, mutant P427L is 1000 times less hemolytic than wild type SLO.

TABLE 3

| *E. coli* | CFU/ml |
|---|---|
| negative control | $3.9 \times 10^8$ |
| Wild-type rSLO (tag-less) | $1.2 \times 10^9$ |
| P427L rSLO (tag-less) | $1.03 \times 10^9$ |

TABLE 4

| | rSLO wild-type tag-less | rSLOP427L tag-less |
|---|---|---|
| titer (OD = 50% hemolysis) | 50,000 | 48 |
| titer Wt/P427L | 1042 | |

Comparison of Wild-Type SLO and Various SLO Mutants

Hemolytic activity of wild-type SLO was compared with hemolytic activity of several different SLO mutants. The results are shown in FIG. 13 and in Table 5, below. One hemolytic unit (HU) is defined as the amount of toxin required to obtained 50% of maximum lysis obtained treating the blood cells with 2% Triton.

TABLE 5

| Protein | HU/mg | HU/mg-SLO/mutants |
|---|---|---|
| rSLO WT | 22760 | 1 |
| C530G | 620 | 37 |
| W535F | 160 | 146 |
| W535F-D482N | <<20 | >>1000 |
| P427L | about 20 | about 1000 |
| Δala248 | <<20 | >>1000 |
| Neg. Control | <<20 | >>1000 |

Due to differences in protein purity, the hemolysis units/mg of mutants indicated in bold are overestimated; however, it is clear that (1) mutant W535F is less hemolytic than mutant C530G; (2) mutant P427L is about 1000 times less hemolytic than wild type and about 6-25 times less hemolytic than other two mutants W535F and C530G; and (3) mutant ΔA248 is certainly less hemolytic than wild type).

Effect of Cholesterol

Two-fivefold serial dilutions in PBS-BSA 0.5% of *E. coli* lysates or *E. coli* lysate with 200 mg/ml of cholesterol obtained after cells' growing at 30° C. and induction with 1 mM IPTG at 25° C. and $OD_{600nm}$ about 0.4-0.6, were assayed for their haemolytic activity. Fifty microliters of a 2% sheep erythrocyte solution in PBS were treated with an equal volume of protein preparations obtained by lysing bacteria, 3 hours after induction, with lysis buffer (B-PER solution-PIERCE-1 mM $MgCl_2$, 100K units/ml DNAse (Sigma) and lysozyme (Sigma) for 30-40 minutes. The insoluble fraction was then centrifuged (15 minutes, 21000×g, 4° C.), and the supernatant (*E. coli* lysate) was transferred to a new Eppendorf tube containing DTT at final concentration of 5 mM.

Under this condition, cholesterol did not inhibit either wild-type or mutant SLO until a 100-fold dilution factor was used; thus, there was no effect on the mutant-induced lysis. In contrast, wild-type-induced lysis was greatly reduced. Lysis induced by the negative control was not influenced by cholesterol, which suggests that cholesterol-induced inhibition is specific. See Table 6 and FIG. 7.

TABLE 6

| | rSLO wild-type tag-less | rSLO P427L tag-less |
|---|---|---|
| titer (OD = 50% hemolysis) | 400 | 40 |
| titre Wt/P427L | 10 | |

Example 5

Inhibition of Hemolysis

Protocol

Serial two-fold dilutions of sera from mice immunized with wild-type or mutant SLO proteins (without adjuvants or with Alum or MF59™ as adjuvants) were prepared in 96-well plates with U-shaped bottoms using PBS+0.5% BSA. Sera of mice immunized with PBS or with adjuvant alone, as appropriate, were used as negative controls. An equal volume of a 50-100 ng/ml (3.5-7 HU) toxin solution in PBS+0.5% BSA was added, and the plates were incubated at room temperature for 20 minutes under agitation (800 rpm). After incubation, 50 ml of this solution were transferred to a new 96-well plate, and an equal volume of a sheep red blood cell suspension (washed 3× in PBS) was added and incubated at 37° C. for 30 min. Plates were then centrifuged for 1 min at 1,000×g, the supernatant was carefully transferred to 96-well flat-bottomed plates, and the absorbance was read at 540 nm. In the results described below, inhibition titer is expressed as the sera dilution that reduced Triton-induced hemolysis by 50%.

Inhibition of SLO Hemolysis by Wild-Type SLO Antisera

Figure 14:
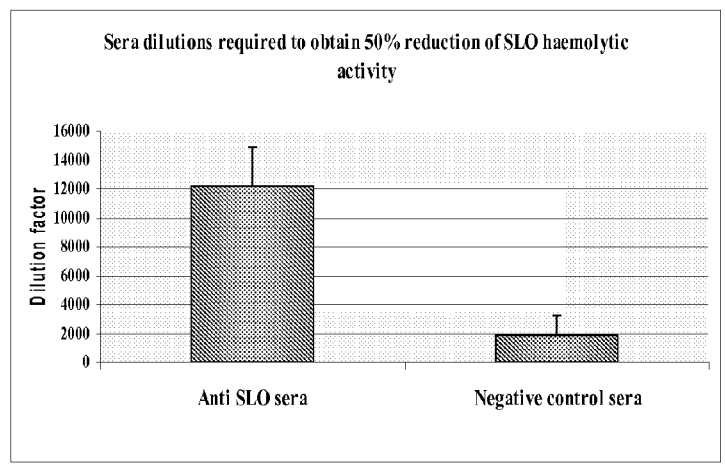
FIG. 14. Graph showing inhibition of SLO-induced hemolytic activity by anti-SLO antiserum.
Figure 15:
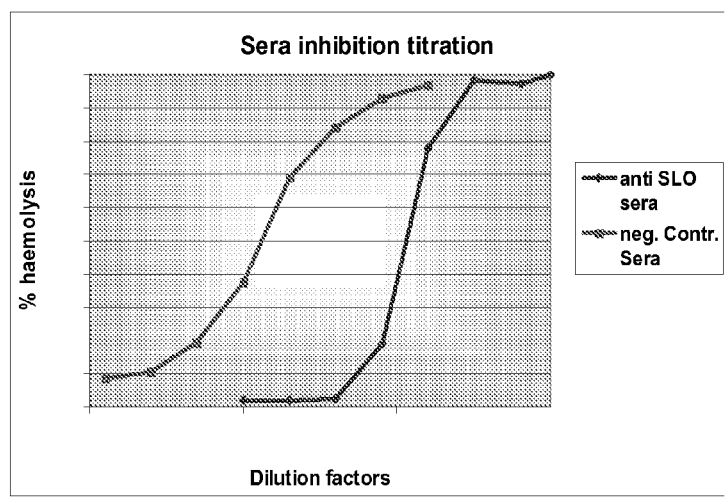
FIG. 15. Graph showing titration of anti-SLO antiserum inhibition of SLO hemolysis.
Figure 16:
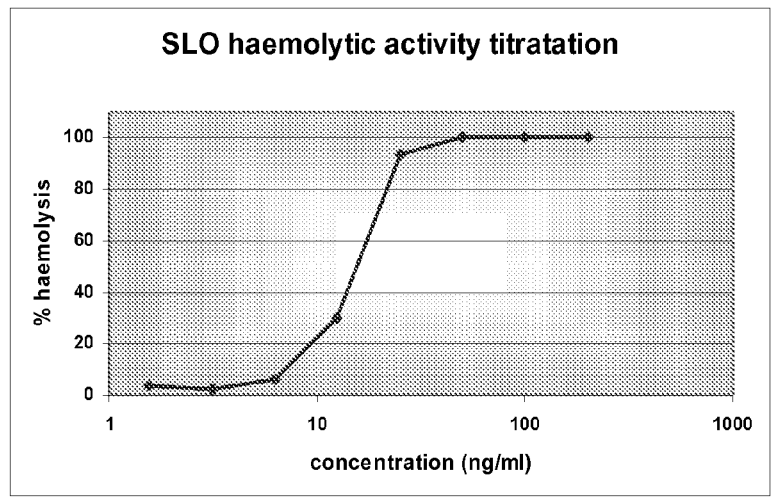
FIG. 16. Graph showing SLO hemolytic activity titration.

Inhibition of SLO hemolysis by anti-wild-type SLO antisera is shown in FIG. 14, FIG. 15, FIG. 16, and Tables 7-9. Anti-SLO sera titers are included between 1/7,000 and 1/14,000 (arithmetic mean, 1/12,167±2,714. Negative control sera (Freund's adjuvant) titers are included between 1/375 and 1/4,000 (arithmetic mean, 1/1,854±1,384).

TABLE 7

(shown graphically in FIG. 15).
arithmetic mean of tested sera - % hemolysis

| dilution factor/sera | anti-SLO sera | negative control sera |
|---|---|---|
| 125 | | 9 |
| 250 | | 10 |
| 500 | | 19 |
| 1,000 | 2 | 38 |
| 2,000 | 2 | 69 |
| 4,000 | 2 | 84 |
| 8,000 | 19 | 93 |
| 16,000 | 78 | 97 |
| 32,000 | 99 | |
| 64,000 | 97 | |
| 128,000 | 100 | |

TABLE 8

| anti-SLO sera (Freund's adjuvant) | | negative control sera (Freund's adjuvant) | |
|---|---|---|---|
| serum | 50% hemolysis inhib. | serum | 50% hemolysis inhib. |
| A | 14,000 | 1 | 4,000 |
| B | 7,000 | 2 | 1,500 |
| C | 12,000 | 3 | 375 |
| D | 12,000 | 4 | 3,000 |
| E | 14,000 | 5 | 1,500 |
| F | 14,000 | 6 | 750 |

TABLE 9

(shown graphically in FIG. 16)

| ng/ml SLO | % hemolysis |
|---|---|
| 1.6 | 4 |
| 3.1 | 3 |
| 6.3 | 6 |
| 12.5 | 30 |
| 25 | 94 |
| 50 | 100 |
| 100 | 100 |
| 200 | 100 |

Figure 17:
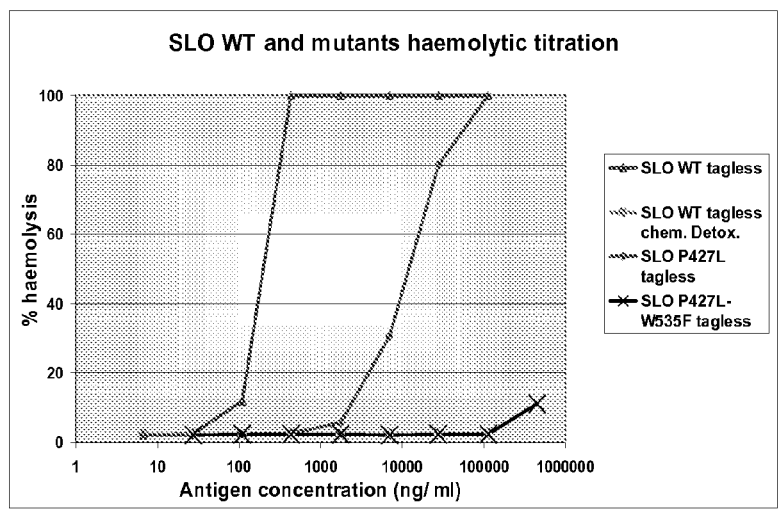
FIG. 17. Graph showing titration of hemolytic activity of wild-type SLO, chemically detoxified wild-type SLO, and SLO mutants (P427L; P427L+W535F).

Titration of Hemolytic Activity of Wild-Type SLO, Chemically Detoxified Wild-Type SLO and SLO Mutants Titration of hemolytic activity of wild-type SLO, chemically detoxified wild-type SLO, and SLO mutants (P427L; P427L+W535F) is shown in FIGS. 17-19 and in Table 10.

TABLE 10

Figure 18:
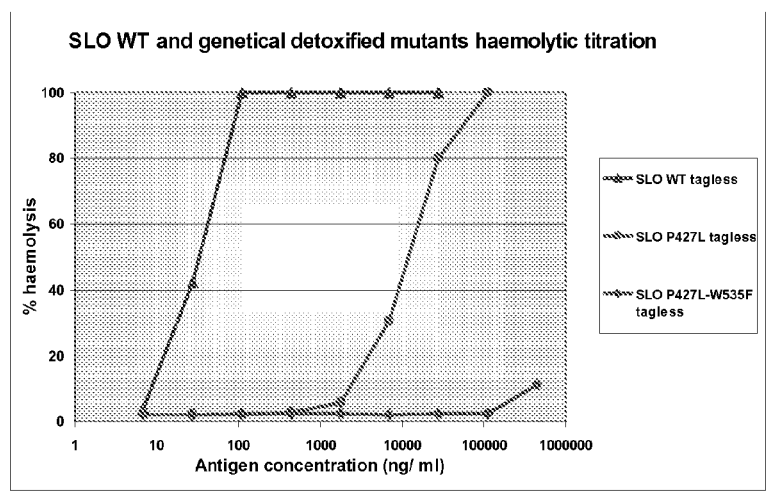
FIG. 18. Graph showing titration of hemolytic activity of wild-type SLO and SLO mutants (P427L; P427L+W535F).
Figure 19:
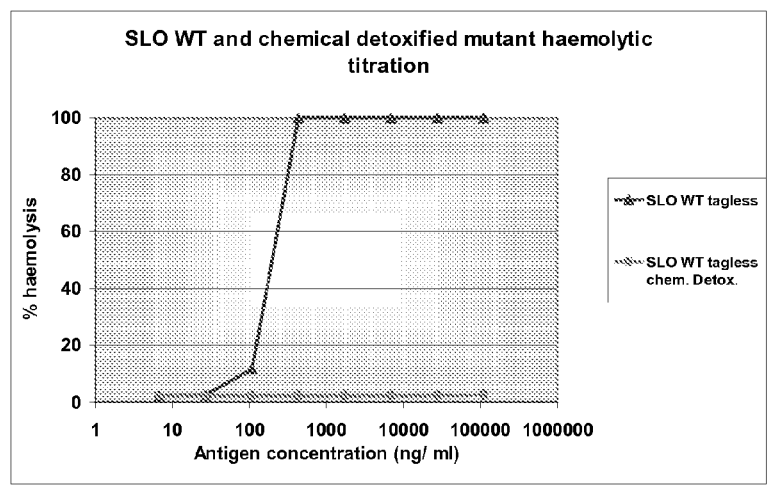
FIG. 19. Graph showing titration of hemolytic activity of wild-type SLO and chemically detoxified wild-type SLO.

(shown graphically in FIG. 18).

| protein | HU/mg | HU/mg-SLO/mutants |
|---|---|---|
| SLO wild-type tag-less | 728,307 | 1 |
| SLO P427L tag-less | 711 | 1,024 |
| SLO P427L + W535F tag-less | <22 (stim. 10) | >33.000 |
| SLO wild-type tag-less | 45,511 | |
| SLO wild-type tag-less, detoxified | <<89 | >>511 |

Inhibition of SLO Hemolysis by Antiserum Against Mutant SLO Proteins

Figure 20:
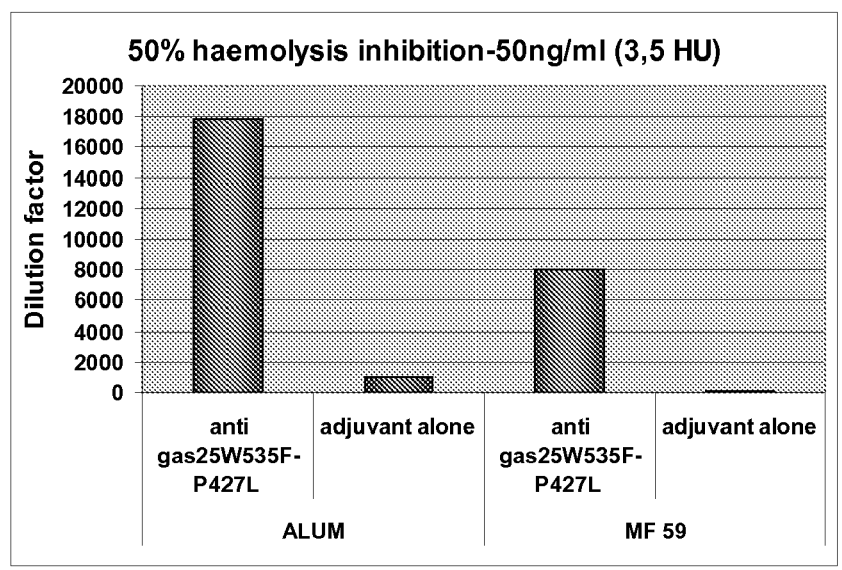
FIG. 20. Graph showing dilution of antiserum against SLO mutant P427L+W535F required to obtain 50% reduction of SLO hemolytic activity (50 ng/ml SLO).
Figure 21:
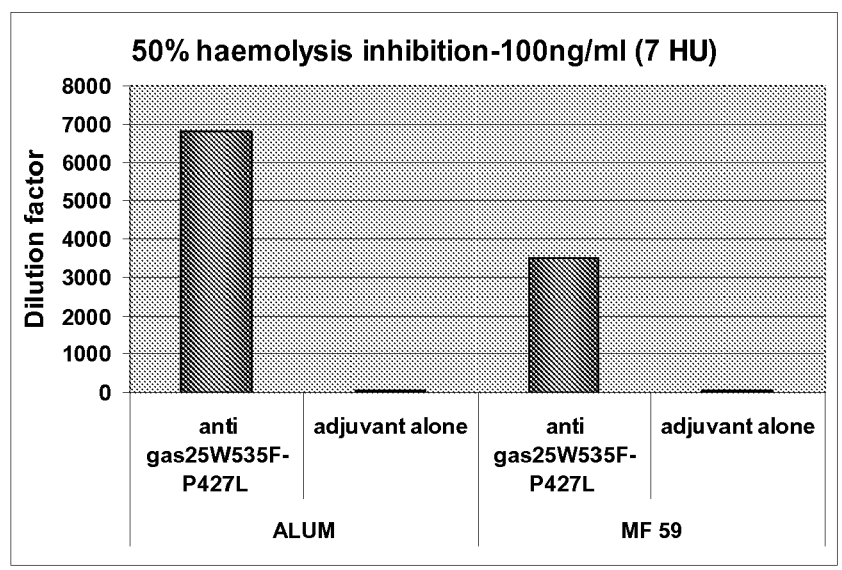
FIG. 21. Graph showing dilution of antiserum against SLO mutant P427L+W535F required to obtain 50% reduction of SLO hemolytic activity (100 ng/ml SLO).
Figure 22:
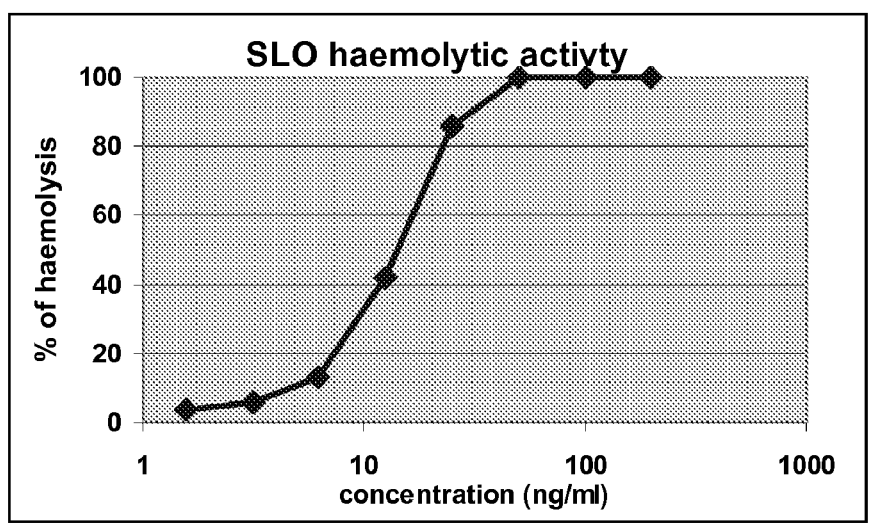
FIG. 22. Titration curve showing that hemolysis inhibition assays were performed with toxin concentrations which allow 100% haemolysis.
Figure 25:
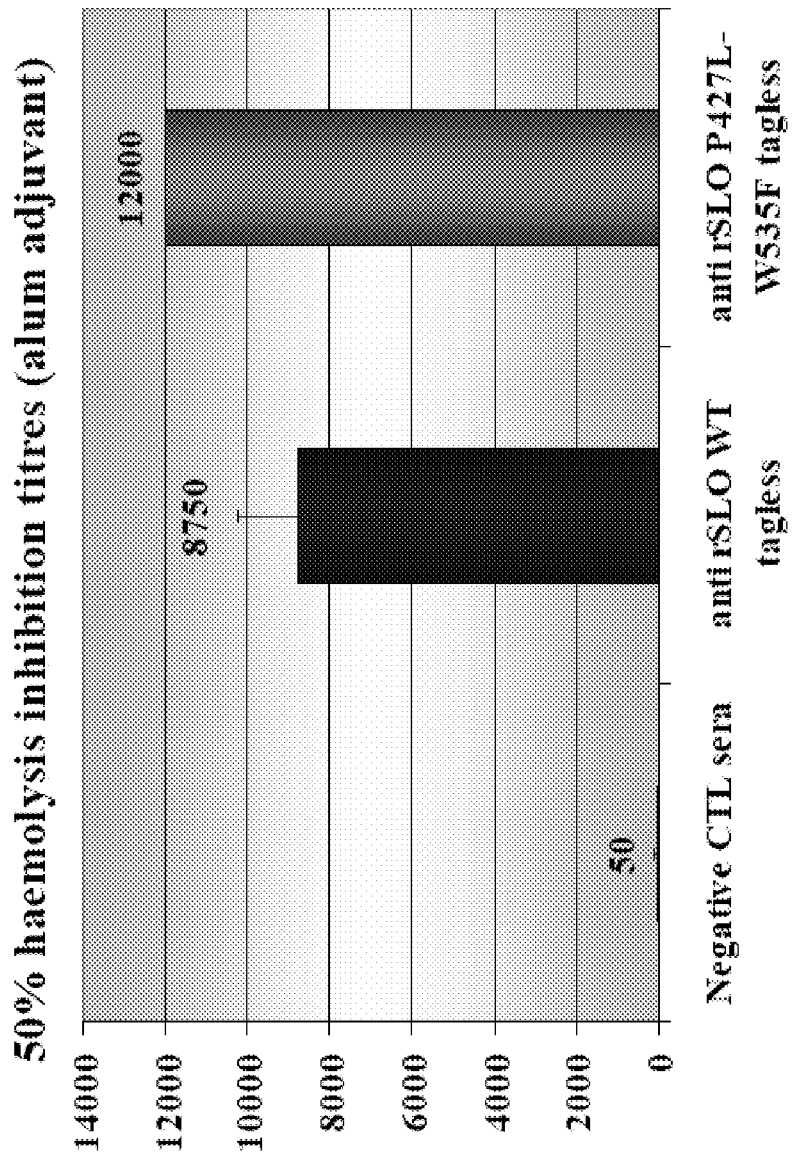
FIG. 25. Graph comparing reduction of SLO hemolytic activity by antiserum against wild-type SLO and antiserum against SLO mutant P427L+W535F.

Inhibition of SLO hemolysis by antisera against mutant SLO proteins is shown in FIGS. 20-22 and Tables 11-13. Using 50 ng/ml (3.5 HU) of toxin, the sera dilution required to obtain 50% reduction of SLO hemolytic activity for SLO mutant W535-P427L is 1/17,860 using Alum adjuvant and 1/7991 using MF59™ adjuvant. Negative control (adjuvant alone) titers are 1/1,000 (Alum) and 1/125 (MF59™).

TABLE 11

(shown graphically in FIG. 20).
50 ng/ml (3.5 HU) of wild-type SLO

| adjuvant | specific inhibition/non-specific inhibition |
|---|---|
| alum | 18 |
| MF ™ 59 | 64 |

TABLE 12

(shown graphically in FIG. 21) 100 ng/ml (37 HU) of wild-type SLO

| adjuvant | specific inhibition/non-specific inhibition |
|---|---|
| alum | >227 |
| MF ™ 59 | >117 |

TABLE 13

(shown graphically in FIG. 22)

| ng/ml SLO | % hemolysis |
|---|---|
| 1.6 | 3.5 |
| 3.1 | 5.8 |
| 6.3 | 13 |
| 12.5 | 42 |
| 25 | 86 |
| 50 | 100 |
| 100 | 100 |
| 200 | 100 |

A comparison of the sera dilutions required to obtain 50% reduction of SLO hemolytic activity for wild-type and for SLO mutant W535-P427L, both using Alum adjuvant, is shown in FIG. 25. Using 100 ng/ml (7 HU) of toxin, the serum dilution required to obtain 50% reduction of SLO hemolytic activity for SLO mutant W535-P427L is 1/12000, compared with a serum dilution of 1/8750+/−1500. The negative control (adjuvant alone) dilution is about 1/50.

Example 6

In Vivo Protection Experiments

The purified SLO P427L protein, together with Freund's adjuvant, was administered intraperitoneally to 40 mice. The mice were then challenged intranasally with the 3348 M1 GAS strain. Table 14 reports the data obtained in 3 separate experiments, showing that 100% protection was consistently achieved in all experiments.

TABLE 14

Infection survival rate of mice

| | % surviving mice | | |
|---|---|---|---|
| antigen | Experiment 1 | Experiment 2 | Experiment 3 |
| GAS25 Pro247Leu | 100 | 100 | 100 |
| E. coli contaminants (negative control) | 10 | 10 | 10 |
| homologous M1 protein (positive control) | 100 | 90 | 90 |

Groups of 10-20 mice were immunized with 20 µg of the recombinant protein at days 0, 21 and 35. Mice of negative control groups were immunized either with GST alone or with E. coli contaminants, depending on the version of the GAS recombinant protein used. Two weeks after the third immunization, blood samples were taken. A few days afterwards, immunized mice were challenged intranasally with $10^8$ cfu (50 µl) of the M1 3348 GAS strains. Mice survival was monitored for a 10-14 day period. Immune sera obtained from the different groups were tested for immunogenicity on the entire SLO recombinant protein (western blot analysis). The results are shown in Tables 15 and 16.

TABLE 15

| Protein | # mice | % survival | % negative control survival |
|---|---|---|---|
| GAS25_Pro247Leu His | 10 | 90 | 30 |
| GAS25_Pro247Leu His | 10 | 100 | 20 |
| GAS25_Pro247Leu His | 10 | 80 | 30 |
| GAS25_WT | 20 | 95 | 15 |
| GAS25_WT | 10 | 100 | 40 |

TABLE 16

| Protein | # mice | % survival | % negative control survival |
|---|---|---|---|
| rSLO WT his-tagged | 20 | 100 | 45 |
| C530G his-tagged | 20 | 100 | 45 |
| W535F his-tagged | 20 | 100 | 45 |
| W535F-D482N his-tagged | 20 | 100 | 45 |
| P427L his-tagged | 20 | 95 | 45 |
| Δala248 his-tagged | 20 | 100 | 45 |

Figure 26:
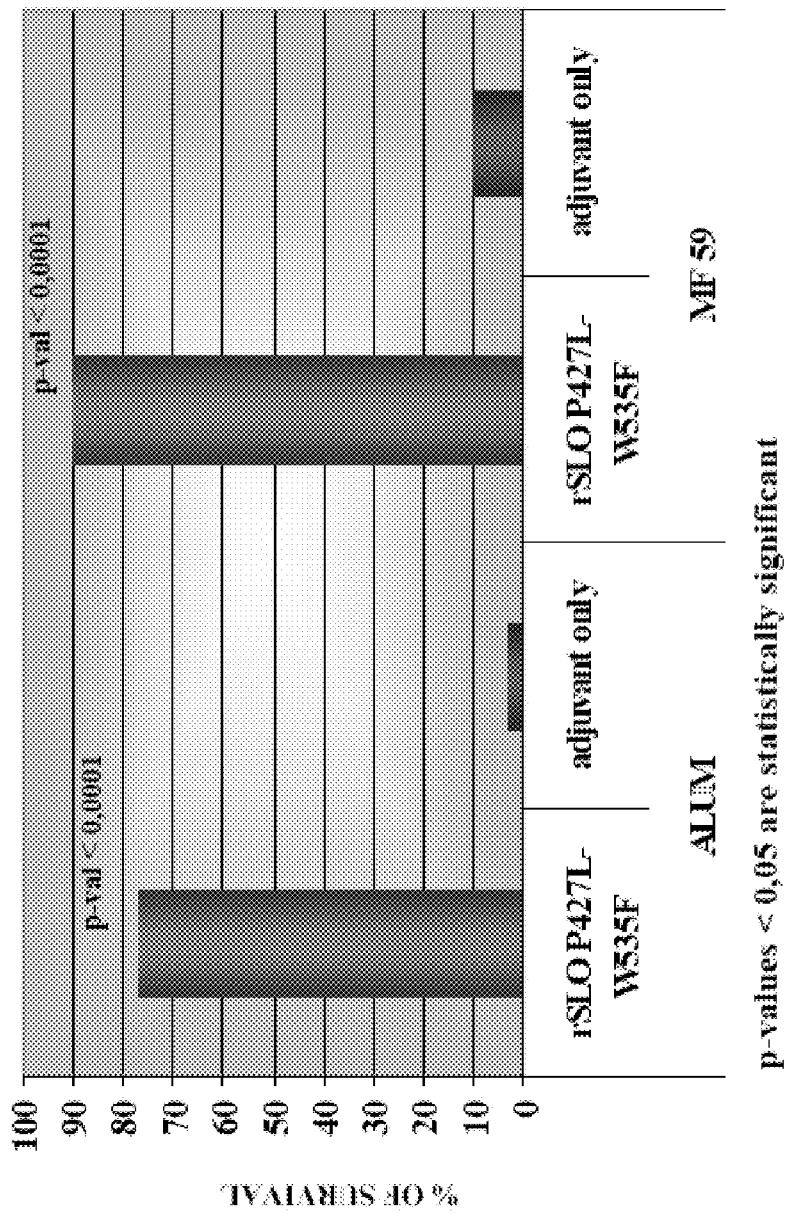
FIG. 26. Graph showing in vivo protective properties of recombinant SLO mutant P427L+W535F using either alum or MF59 as an adjuvant.

Protection Against Intranasal Challenge with GAS M1 Strain by SLO Mutant P427L-W535F Thirty mice were immunized intraperitoneally with the SLO mutant P427L-W535F, with either Alum or MF59 as adjuvants, and challenged intranasally with a GAS M1 strain. The results are shown in FIG. 26. Seventy-seven percent of the mice immunized with the SLO mutant P427L-W535F and Alum were protected against intranasal challenge with a GAS M1 strain, as compared with 3% of the negative control mice (immunized with adjuvant only). Ninety percent of the mice immunized with the SLO mutant P427L-W535F and MF59 were protected against intranasal challenge with a GAS M1 strain, as compared with 10% of the negative control mice (immunized with adjuvant only). These protection levels are comparable with those obtained by immunizing mice with wild-type SLO.

Example 7

Protocols

Intravenous injection of SLO. A solution of either wild-type or mutant SLO in PBS is diluted in a solution of PBS+2 mM DTT, then 100 µl is injected into the tail vein of a mouse. Mice are observed for 2-3 days. Injection of wild-type SLO typically results in death within a few minutes.

In vivo lethality inhibition assay. For lethality inhibition mediated by immune sera, 10 µg/mouse of wild-type SLO (a solution of 100 µg/ml in PBS, 2 mM DTT) are incubated for 20 minutes with rotation "end over end" at room temperature with either anti-SLO serum or control serum (obtained from mice immunized with adjuvant alone). After incubation, the samples are inoculated in the mice by intravenous injection into the tail vein. Mice are observed for 2-3 days.

The results for wild-type SLO and mutant SLO P427L-W535F are shown in Table 17.

TABLE 17

| wild-type SLO | | P427L-W535F | |
|---|---|---|---|
| µg/mouse | dead/treated | µg/mouse | dead/treated |
|  |  | 100 | 0/4 |
| 50 | 4/4 | 50 | 0/4 |
| 10 | 8/8 | 10 | 0/8 |
| 2 | 0/4 |  |  |
| 0.4 | 0/4 |  |  |
| 0.04 | 0/4 |  |  |

Acute in vivo acute toxicity was assessed using a dose of 10 µg/mouse of wild-type SLO as a positive control and injection of Freund's adjuvant alone as a negative control. Ten µg/mouse of wild-type SLO was incubated with either wild-type SLO antiserum or with control serum and inoculated into mice as described above. The results are shown in Table 18.

TABLE 18

| wild-type SLO (10 µg/mouse) | | |
|---|---|---|
| sera | serum dilution | dead/treated |
| none |  | 8/8 |
| wild-type SLO | 1/5 | 0/4 |
| wild-type SLO | 1/10 | 0/4 |
| wild-type SLO | 1/20 | 4/4 |
| wild-type SLO | 1/50 | 4/4 |
| wild-type SLO | 1/100 | 4/4 |
| negative control | 1/5 | 4/4 |

The results of another set of experiments performed as described above are shown in Tables 19 and 20. In vivo acute toxicity was assessed using either 5 or 10 µg/mouse of wild-type SLO. In particular, 10 µg/mouse of wild type SLO were preincubated either with sera from mice immunized with GAS25 P427L-W535F or only PBS (no serum). In addition, 5 µg/mouse of wild type SLO were preincubated either with sera from mice immunized with GAS25 P427L-W535F or sera from mice immunized with PBS plus adjuvant (Alum), as negative control serum.

The results demonstrate that lethal doses of wild-type SLO are neutralized by anti-SLO P427L-W535F sera but not by negative control sera at the same dilution.

TABLE 19

| wild-type SLO (10 µg/mouse) | | |
| --- | --- | --- |
| Sera | serum dilution | dead/treated |
| none | — | 4/4 |
| anti-SLO P427L-W535F, alum adjuvant | 1/5 | 0/4 |

TABLE 20

| wild-type SLO (5 µg/mouse) | | |
| --- | --- | --- |
| Sera | serum dilution | dead/treated |
| anti-SLO P427L-W535F, alum adjuvant | 1/5 | 0/4 |
| negative control (alum alone) | 1/5 | 4/4 |

Example 8

Immunization with SLO P427L-W535F Protects Mice Against Intravenous Injection of Wild-Type SLO Five-week old mice were immunized intraperitoneally three times (day 0, day 21, and day 35) with either wild-type SLO or with the SLO mutant P427L-W535F using alum as an adjuvant (20 µg protein in 2 mg/ml aluminium hydroxide). Mice immunized with adjuvant alone were used as a negative control. On day 55 mice were injected intravenously with different concentrations of a solution of wild-type SLO in PBS, 2 mM DTT and monitored for at least 72 hours. The results are shown in Table 21.

TABLE 21

| | Dose of wild-type tagless SLO injected into mouse tail vein | | | |
| --- | --- | --- | --- | --- |
| | 2.5 µg/mouse survival (no. of mice treated) | 5 µg/mouse survival (no. of mice treated) | 10 µg/mouse survival (no. of mice treated) | 20 µg/mouse survival (no. of mice treated) |
| adjuvant (alum) | 100% (4) | 0% (12) | not tested | not tested |
| wild-type SLO tagless | not tested | 100% (8) | 100% (4) | 100% (4) |
| SLO P427L-W535F tagless | not tested | 100% (8) | 100% (4) | 100% (4) |

Five µg/mouse of wild-type SLO is lethal for mice immunized with adjuvant alone; these mice died within a few minutes after SLO injection. However, even 20 µg/mouse of the same wild-type SLO preparation did not kill mice immunized with either wild-type SLO or with the P427L-W535F SLO mutant.

---

The invention claimed is:

1. A purified mutant streptolysin O (SLO) protein comprising an amino acid alteration to the amino acid sequence of wild-type SLO selected from the group consisting of:
   a. a substitution of leucine for proline at amino acid position 427;
   b. a substitution of phenylalanine for tryptophan at amino acid position 535;
   c. a substitution of glycine for cysteine at amino acid position 530; and
   e. a deletion of alanine at amino acid position 248, wherein the amino acid positions are numbered according to SEQ ID NO: 1.

2. The purified mutant SLO protein of claim 1 which comprises SEQ ID NO:20.

3. The purified mutant SLO protein of claim 1 which comprises SEQ ID NO:21.

4. The purified mutant SLO protein of claim 1 which comprises SEQ ID NO:22.

5. A vaccine composition comprising:
   (a) the mutant streptolysin 0 (SLO) protein of claim 2; and
   (b) a pharmaceutically acceptable carrier.

6. A method of treating infection by *Streptococcus pyogenes* comprising administering to an individual in need thereof an effective amount of a vaccine composition comprising:
   (a) the mutant streptolysin O (SLO) protein of claim 2; and
   (b) a pharmaceutically acceptable carrier.

7. A method of making a vaccine for the treatment of infection by *Streptococcus pyogenes* comprising combining:
   (a) the mutant streptolysin O (SLO) protein of claim 2; and
   (b) a pharmaceutically acceptable carrier.

* * * * *

SEQUENCE LISTING

<160> NUMBER OF SEQ ID NOS: 59

<210> SEQ ID NO 1
<211> LENGTH: 571
<212> TYPE: PRT
<213> ORGANISM: S. pyogenes

<400> SEQUENCE: 1

Met Ser Asn Lys Lys Thr Phe Lys Lys Tyr Ser Arg Val Ala Gly Leu
1               5                   10                  15

Leu Thr Ala Ala Leu Ile Ile Gly Asn Leu Val Thr Ala Asn Ala Glu
            20                  25                  30

Ser Asn Lys Gln Asn Thr Ala Ser Thr Glu Thr Thr Thr Thr Asn Glu
        35                  40                  45

Gln Pro Lys Pro Glu Ser Ser Glu Leu Thr Thr Glu Lys Ala Gly Gln
    50                  55                  60

Lys Thr Asp Asp Met Leu Asn Ser Asn Asp Met Ile Lys Leu Ala Pro
65                  70                  75                  80

Lys Glu Met Pro Leu Glu Ser Ala Glu Lys Glu Glu Lys Lys Ser Glu
                85                  90                  95

-continued

```
Asp Lys Lys Lys Ser Glu Glu Asp His Thr Glu Ile Asn Asp Lys
            100                 105                 110

Ile Tyr Ser Leu Asn Tyr Asn Glu Leu Glu Val Leu Ala Lys Asn Gly
        115                 120                 125

Glu Thr Ile Glu Asn Phe Val Pro Lys Glu Gly Val Lys Lys Ala Asp
    130                 135                 140

Lys Phe Ile Val Ile Glu Arg Lys Lys Asn Ile Asn Thr Thr Pro
145                 150                 155                 160

Val Asp Ile Ser Ile Ile Asp Ser Val Thr Asp Arg Thr Tyr Pro Ala
                165                 170                 175

Ala Leu Gln Leu Ala Asn Lys Gly Phe Thr Glu Asn Lys Pro Asp Ala
            180                 185                 190

Val Val Thr Lys Arg Asn Pro Gln Lys Ile His Ile Asp Leu Pro Gly
        195                 200                 205

Met Gly Asp Lys Ala Thr Val Glu Val Asn Asp Pro Thr Tyr Ala Asn
    210                 215                 220

Val Ser Thr Ala Ile Asp Asn Leu Val Asn Gln Trp His Asp Asn Tyr
225                 230                 235                 240

Ser Gly Gly Asn Thr Leu Pro Ala Arg Thr Gln Tyr Thr Glu Ser Met
                245                 250                 255

Val Tyr Ser Lys Ser Gln Ile Glu Ala Ala Leu Asn Val Asn Ser Lys
            260                 265                 270

Ile Leu Asp Gly Thr Leu Gly Ile Asp Phe Lys Ser Ile Ser Lys Gly
        275                 280                 285

Glu Lys Lys Val Met Ile Ala Ala Tyr Lys Gln Ile Phe Tyr Thr Val
    290                 295                 300

Ser Ala Asn Leu Pro Asn Asn Pro Ala Asp Val Phe Asp Lys Ser Val
305                 310                 315                 320

Thr Phe Lys Glu Leu Gln Arg Lys Gly Val Ser Asn Glu Ala Pro Pro
                325                 330                 335

Leu Phe Val Ser Asn Val Ala Tyr Gly Arg Thr Val Phe Val Lys Leu
            340                 345                 350

Glu Thr Ser Ser Lys Ser Asn Asp Val Glu Ala Ala Phe Ser Ala Ala
        355                 360                 365

Leu Lys Gly Thr Asp Val Lys Thr Asn Gly Lys Tyr Ser Asp Ile Leu
    370                 375                 380

Glu Asn Ser Ser Phe Thr Ala Val Val Leu Gly Gly Asp Ala Ala Glu
385                 390                 395                 400

His Asn Lys Val Val Thr Lys Asp Phe Asp Val Ile Arg Asn Val Ile
                405                 410                 415

Lys Asp Asn Ala Thr Phe Ser Arg Lys Asn Pro Ala Tyr Pro Ile Ser
            420                 425                 430

Tyr Thr Ser Val Phe Leu Lys Asn Asn Lys Ile Ala Gly Val Asn Asn
        435                 440                 445

Arg Thr Glu Tyr Val Glu Thr Thr Ser Thr Glu Tyr Thr Ser Gly Lys
    450                 455                 460

Ile Asn Leu Ser His Gln Gly Ala Tyr Val Ala Gln Tyr Glu Ile Leu
465                 470                 475                 480

Trp Asp Glu Ile Asn Tyr Asp Asp Lys Gly Lys Glu Val Ile Thr Lys
                485                 490                 495

Arg Arg Trp Asp Asn Asn Trp Tyr Ser Lys Thr Ser Pro Phe Ser Thr
            500                 505                 510

Val Ile Pro Leu Gly Ala Asn Ser Arg Asn Ile Arg Ile Met Ala Arg
        515                 520                 525
```

Glu Cys Thr Gly Leu Ala Trp Glu Trp Trp Arg Lys Val Ile Asp Glu
530                 535                 540

Arg Asp Val Lys Leu Ser Lys Glu Ile Asn Val Asn Ile Ser Gly Ser
545                 550                 555                 560

Thr Leu Ser Pro Tyr Gly Ser Ile Thr Tyr Lys
            565                 570

<210> SEQ ID NO 2
<211> LENGTH: 571
<212> TYPE: PRT
<213> ORGANISM: S. pyogenes

<400> SEQUENCE: 2

Met Ser Asn Lys Lys Thr Phe Lys Lys Tyr Ser Arg Val Ala Gly Leu
1               5                   10                  15

Leu Thr Ala Ala Leu Ile Ile Gly Asn Leu Val Thr Ala Asn Ala Glu
            20                  25                  30

Ser Asn Lys Gln Asn Thr Ala Ser Thr Glu Thr Thr Thr Thr Asn Glu
        35                  40                  45

Gln Pro Lys Pro Glu Ser Ser Glu Leu Thr Thr Glu Lys Ala Gly Gln
    50                  55                  60

Lys Met Asp Asp Met Leu Asn Ser Asn Asp Met Ile Lys Leu Ala Pro
65                  70                  75                  80

Lys Glu Met Pro Leu Glu Ser Ala Glu Lys Glu Lys Lys Ser Glu
                85                  90                  95

Asp Lys Lys Lys Ser Glu Glu Asp His Thr Glu Glu Ile Asn Asp Lys
                100                 105                 110

Ile Tyr Ser Leu Asn Tyr Asn Glu Leu Glu Val Leu Ala Lys Asn Gly
        115                 120                 125

Glu Thr Ile Glu Asn Phe Val Pro Lys Glu Gly Val Lys Lys Ala Asp
    130                 135                 140

Lys Phe Ile Val Ile Glu Arg Lys Lys Asn Ile Asn Thr Thr Pro
145                 150                 155                 160

Val Asp Ile Ser Ile Ile Asp Ser Val Thr Asp Arg Thr Tyr Pro Ala
                165                 170                 175

Ala Leu Gln Leu Ala Asn Lys Gly Phe Thr Glu Asn Lys Pro Asp Ala
            180                 185                 190

Val Val Thr Lys Arg Asn Pro Gln Lys Ile His Ile Asp Leu Pro Gly
        195                 200                 205

Met Gly Asp Lys Ala Thr Val Glu Val Asn Asp Pro Thr Tyr Ala Asn
    210                 215                 220

Val Ser Thr Ala Ile Asp Asn Leu Val Asn Gln Trp His Asp Asn Tyr
225                 230                 235                 240

Ser Gly Gly Asn Thr Leu Pro Ala Arg Thr Gln Tyr Thr Glu Ser Met
                245                 250                 255

Val Tyr Ser Lys Ser Gln Ile Glu Ala Ala Leu Asn Val Asn Ser Lys
            260                 265                 270

Ile Leu Asp Gly Thr Leu Gly Ile Asp Phe Lys Ser Ile Ser Lys Gly
        275                 280                 285

Glu Lys Lys Val Met Ile Ala Ala Tyr Lys Gln Ile Phe Tyr Thr Val
    290                 295                 300

Ser Ala Asn Leu Pro Asn Asn Pro Ala Asp Val Phe Asp Lys Ser Val
305                 310                 315                 320

Thr Phe Lys Glu Leu Gln Arg Lys Gly Val Ser Asn Glu Ala Pro Pro
                325                 330                 335

```
Leu Phe Val Ser Asn Val Ala Tyr Gly Arg Thr Val Phe Val Lys Leu
                340                 345                 350

Glu Thr Ser Ser Lys Ser Asn Asp Val Glu Ala Ala Phe Ser Ala Ala
                355                 360                 365

Leu Lys Gly Thr Asp Val Lys Thr Asn Gly Lys Tyr Ser Asp Ile Leu
        370                 375                 380

Glu Asn Ser Ser Phe Thr Ala Val Val Leu Gly Gly Asp Ala Ala Glu
385                 390                 395                 400

His Asn Lys Val Val Thr Lys Asp Phe Asp Val Ile Arg Asn Val Ile
                405                 410                 415

Lys Asp Asn Ala Thr Phe Ser Arg Lys Asn Pro Ala Tyr Pro Ile Ser
                420                 425                 430

Tyr Thr Ser Val Phe Leu Lys Asn Asn Lys Ile Ala Gly Val Asn Asn
                435                 440                 445

Arg Ser Glu Tyr Val Glu Thr Thr Ser Thr Glu Tyr Thr Ser Gly Lys
        450                 455                 460

Ile Asn Leu Ser His Gln Gly Ala Tyr Val Ala Gln Tyr Glu Ile Leu
465                 470                 475                 480

Trp Asp Glu Ile Asn Tyr Asp Asp Lys Gly Lys Glu Val Ile Thr Lys
                485                 490                 495

Arg Arg Trp Asp Asn Asn Trp Tyr Ser Lys Thr Ser Pro Phe Ser Thr
                500                 505                 510

Val Ile Pro Leu Gly Ala Asn Ser Arg Asn Ile Arg Ile Met Ala Arg
                515                 520                 525

Glu Cys Thr Gly Leu Ala Trp Glu Trp Trp Arg Lys Val Ile Asp Glu
                530                 535                 540

Arg Asp Val Lys Leu Ser Lys Glu Ile Asn Val Asn Ile Ser Gly Ser
545                 550                 555                 560

Thr Leu Ser Pro Tyr Gly Ser Ile Thr Tyr Lys
                565                 570

<210> SEQ ID NO 3
<211> LENGTH: 571
<212> TYPE: PRT
<213> ORGANISM: S. pyogenes

<400> SEQUENCE: 3

Met Ser Asn Lys Lys Thr Phe Lys Lys Tyr Ser Arg Val Ala Gly Leu
  1               5                  10                  15

Leu Thr Ala Ala Leu Ile Ile Gly Asn Leu Val Thr Ala Asn Ala Glu
                20                  25                  30

Ser Asn Lys Gln Asn Thr Ala Ser Thr Glu Thr Thr Thr Asn Glu
                35                  40                  45

Gln Pro Lys Pro Glu Ser Ser Glu Leu Thr Thr Glu Lys Ala Gly Gln
        50                  55                  60

Lys Met Asp Asp Met Leu Asn Ser Asn Asp Met Ile Lys Leu Ala Pro
65                  70                  75                  80

Lys Glu Met Pro Leu Glu Ser Ala Glu Lys Glu Lys Lys Ser Glu
                85                  90                  95

Asp Lys Lys Lys Ser Glu Glu Asp His Thr Glu Glu Ile Asn Asp Lys
                100                 105                 110

Ile Tyr Ser Leu Asn Tyr Asn Glu Leu Glu Val Leu Ala Lys Asn Gly
        115                 120                 125

Glu Thr Ile Glu Asn Phe Val Pro Lys Glu Gly Val Lys Lys Ala Asp
        130                 135                 140
```

```
Lys Phe Ile Val Ile Glu Arg Lys Lys Asn Ile Asn Thr Thr Pro
145                 150                 155                 160

Val Asp Ile Ser Ile Asp Ser Val Thr Asp Arg Thr Tyr Pro Ala
            165                 170                 175

Ala Leu Gln Leu Ala Asn Lys Gly Phe Thr Glu Asn Lys Pro Asp Ala
            180                 185                 190

Val Val Thr Lys Arg Asn Pro Gln Lys Ile His Ile Asp Leu Pro Gly
            195                 200                 205

Met Gly Asp Lys Ala Thr Val Glu Val Asn Asp Pro Thr Tyr Ala Asn
            210                 215                 220

Val Ser Thr Ala Ile Asp Asn Leu Val Asn Gln Trp His Asp Asn Tyr
225                 230                 235                 240

Ser Gly Gly Asn Thr Leu Pro Ala Arg Thr Gln Tyr Thr Glu Ser Met
                245                 250                 255

Val Tyr Ser Lys Ser Gln Ile Glu Ala Ala Leu Asn Val Asn Ser Lys
            260                 265                 270

Ile Leu Asp Gly Thr Leu Gly Ile Asp Phe Lys Ser Ile Ser Lys Gly
            275                 280                 285

Glu Lys Lys Val Met Ile Ala Ala Tyr Lys Gln Ile Phe Tyr Thr Val
290                 295                 300

Ser Ala Asn Leu Pro Asn Asn Pro Ala Asp Val Phe Asp Lys Ser Val
305                 310                 315                 320

Thr Phe Lys Glu Leu Gln Arg Lys Gly Val Ser Asn Glu Ala Pro Pro
            325                 330                 335

Leu Phe Val Ser Asn Val Ala Tyr Gly Arg Thr Val Phe Val Lys Leu
            340                 345                 350

Glu Thr Ser Ser Lys Ser Asn Asp Val Glu Ala Ala Phe Ser Ala Ala
            355                 360                 365

Leu Lys Gly Thr Asp Val Lys Thr Asn Gly Lys Tyr Ser Asp Ile Leu
            370                 375                 380

Glu Asn Ser Ser Phe Thr Ala Val Val Leu Gly Gly Asp Ala Ala Glu
385                 390                 395                 400

His Asn Lys Val Val Thr Lys Asp Phe Asp Val Ile Arg Asn Val Ile
                405                 410                 415

Lys Asp Asn Ala Thr Phe Ser Arg Lys Asn Pro Ala Tyr Pro Ile Ser
            420                 425                 430

Tyr Thr Ser Val Phe Leu Lys Asn Asn Lys Ile Ala Gly Val Asn Asn
            435                 440                 445

Arg Ser Glu Tyr Val Glu Thr Thr Ser Thr Tyr Thr Ser Gly Lys
450                 455                 460

Ile Asn Leu Ser His Gln Gly Ala Tyr Val Ala Gln Tyr Glu Ile Leu
465                 470                 475                 480

Trp Asp Glu Ile Asn Tyr Asp Asp Lys Gly Lys Glu Val Ile Thr Lys
                485                 490                 495

Arg Arg Trp Asp Asn Asn Trp Tyr Ser Lys Thr Ser Pro Phe Ser Thr
            500                 505                 510

Val Ile Pro Leu Gly Ala Asn Ser Arg Asn Ile Arg Ile Met Ala Arg
            515                 520                 525

Glu Cys Thr Gly Leu Ala Trp Glu Trp Trp Arg Lys Val Ile Asp Glu
530                 535                 540

Arg Asp Val Lys Leu Ser Lys Glu Ile Asn Val Asn Ile Ser Gly Ser
545                 550                 555                 560

Thr Leu Ser Pro Tyr Gly Ser Ile Thr Tyr Lys
                565                 570
```

<210> SEQ ID NO 4
<211> LENGTH: 571
<212> TYPE: PRT
<213> ORGANISM: S. pyogenes

<400> SEQUENCE: 4

```
Met Ser Asn Lys Lys Thr Phe Lys Lys Tyr Ser Arg Val Ala Gly Leu
 1               5                   10                  15

Leu Thr Ala Ala Leu Ile Ile Gly Asn Leu Val Thr Ala Asn Ala Glu
            20                  25                  30

Ser Asn Lys Gln Asn Thr Ala Ser Thr Glu Thr Thr Thr Asn Glu
            35                  40                  45

Gln Pro Lys Pro Glu Ser Ser Glu Leu Thr Thr Glu Lys Ala Gly Gln
 50                  55                  60

Lys Met Asp Asp Met Leu Asn Ser Asn Asp Met Ile Lys Leu Ala Pro
 65                  70                  75                  80

Lys Glu Met Pro Leu Glu Ser Ala Glu Lys Glu Lys Lys Ser Glu
                85                  90                  95

Asp Lys Lys Lys Ser Glu Glu Asp His Thr Glu Glu Ile Asn Asp Lys
                100                 105                 110

Ile Tyr Ser Leu Asn Tyr Asn Glu Leu Glu Val Leu Ala Lys Asn Gly
            115                 120                 125

Glu Thr Ile Glu Asn Phe Val Pro Lys Glu Gly Val Lys Lys Ala Asp
130                 135                 140

Lys Phe Ile Val Ile Glu Arg Lys Lys Asn Ile Asn Thr Thr Pro
145                 150                 155                 160

Val Asp Ile Ser Ile Ile Asp Ser Val Thr Asp Arg Thr Tyr Pro Ala
                165                 170                 175

Ala Leu Gln Leu Ala Asn Lys Gly Phe Thr Glu Asn Lys Pro Asp Ala
            180                 185                 190

Val Val Thr Lys Arg Asn Pro Gln Lys Ile His Ile Asp Leu Pro Gly
            195                 200                 205

Met Gly Asp Lys Ala Thr Val Glu Val Asn Asp Pro Thr Tyr Ala Asn
210                 215                 220

Val Ser Thr Ala Ile Asp Asn Leu Val Asn Gln Trp His Asp Asn Tyr
225                 230                 235                 240

Ser Gly Gly Asn Thr Leu Pro Ala Arg Thr Gln Tyr Thr Glu Ser Met
                245                 250                 255

Val Tyr Ser Lys Ser Gln Ile Glu Ala Ala Leu Asn Val Asn Ser Lys
            260                 265                 270

Ile Leu Asp Gly Thr Leu Gly Ile Asp Phe Lys Ser Ile Ser Lys Gly
            275                 280                 285

Glu Lys Lys Val Met Ile Ala Ala Tyr Lys Gln Ile Phe Tyr Thr Val
            290                 295                 300

Ser Ala Asn Leu Pro Asn Asn Pro Ala Asp Val Phe Asp Lys Ser Val
305                 310                 315                 320

Thr Phe Lys Glu Leu Gln Arg Lys Gly Val Ser Asn Glu Ala Pro Pro
                325                 330                 335

Leu Phe Val Ser Asn Val Ala Tyr Gly Arg Thr Val Phe Val Lys Leu
            340                 345                 350

Glu Thr Ser Ser Lys Ser Asn Asp Val Glu Ala Ala Phe Ser Ala Ala
            355                 360                 365

Leu Lys Gly Thr Asp Val Lys Thr Asn Gly Lys Tyr Ser Asp Ile Leu
370                 375                 380
```

-continued

```
Glu Asn Ser Ser Phe Thr Ala Val Val Leu Gly Gly Asp Ala Ala Glu
385                 390                 395                 400

His Asn Lys Val Val Thr Lys Asp Phe Asp Val Ile Arg Asn Val Ile
            405                 410                 415

Lys Asp Asn Ala Thr Phe Ser Arg Lys Asn Pro Ala Tyr Pro Ile Ser
        420                 425                 430

Tyr Thr Ser Val Phe Leu Lys Asn Asn Lys Ile Ala Gly Val Asn Asn
    435                 440                 445

Arg Ser Glu Tyr Val Glu Thr Thr Ser Thr Glu Tyr Thr Ser Gly Lys
450                 455                 460

Ile Asn Leu Ser His Gln Gly Ala Tyr Val Ala Gln Tyr Glu Ile Leu
465                 470                 475                 480

Trp Asp Glu Ile Asn Tyr Asp Asp Lys Gly Lys Glu Val Ile Thr Lys
            485                 490                 495

Arg Arg Trp Asp Asn Asn Trp Tyr Ser Lys Thr Ser Pro Phe Ser Thr
        500                 505                 510

Val Ile Pro Leu Gly Ala Asn Ser Arg Asn Ile Arg Ile Met Ala Arg
    515                 520                 525

Glu Cys Thr Gly Leu Ala Trp Glu Trp Trp Arg Lys Val Ile Asp Glu
530                 535                 540

Arg Asp Val Lys Leu Ser Lys Glu Ile Asn Val Asn Ile Ser Gly Ser
545                 550                 555                 560

Thr Leu Ser Pro Tyr Gly Ser Ile Thr Tyr Lys
            565                 570
```

<210> SEQ ID NO 5
<211> LENGTH: 571
<212> TYPE: PRT
<213> ORGANISM: S. pyogenes

<400> SEQUENCE: 5

```
Met Ser Asn Lys Lys Thr Phe Lys Tyr Ser Arg Val Ala Gly Leu
1               5                   10                  15

Leu Thr Ala Ala Leu Ile Ile Gly Asn Leu Val Thr Ala Asn Ala Glu
            20                  25                  30

Ser Asn Lys Gln Asn Thr Thr Ser Thr Glu Thr Thr Thr Asn Glu
        35                  40                  45

Gln Pro Lys Pro Glu Ser Ser Glu Leu Thr Ile Glu Lys Ala Gly Gln
    50                  55                  60

Lys Met Asp Asp Met Leu Asn Ser Asn Asp Met Ile Lys Leu Ala Pro
65                  70                  75                  80

Lys Glu Met Pro Leu Glu Ser Ala Glu Lys Glu Lys Lys Ser Glu
            85                  90                  95

Asp Lys Lys Lys Ser Glu Glu Asp His Thr Glu Glu Ile Asn Asp Lys
        100                 105                 110

Ile Tyr Ser Leu Asn Tyr Asn Glu Leu Glu Val Leu Ala Lys Asn Gly
    115                 120                 125

Glu Thr Ile Glu Asn Phe Val Pro Lys Glu Gly Val Lys Lys Ala Asp
130                 135                 140

Lys Phe Ile Val Ile Glu Arg Lys Lys Asn Ile Asn Thr Thr Pro
145                 150                 155                 160

Val Asp Ile Ser Ile Ile Asp Ser Val Thr Asp Met Thr Tyr Pro Ala
            165                 170                 175

Ala Leu Gln Leu Ala Asp Lys Gly Phe Thr Glu Asn Lys Pro Asp Ala
        180                 185                 190
```

```
Val Val Thr Lys Arg Asn Pro Gln Lys Ile His Ile Asp Leu Pro Gly
    195                 200                 205

Met Gly Asp Lys Ala Thr Val Glu Val Asn Asp Pro Thr Tyr Ala Asn
    210                 215                 220

Val Ser Thr Ala Ile Asp Asn Leu Val Asn Gln Trp His Asp Asn Tyr
225                 230                 235                 240

Ser Gly Gly Asn Thr Leu Pro Ala Arg Thr Gln Tyr Thr Glu Ser Met
                245                 250                 255

Val Tyr Ser Lys Ser Gln Ile Glu Ala Ala Leu Asn Val Asn Ser Lys
            260                 265                 270

Ile Leu Asp Gly Thr Leu Gly Ile Asp Phe Lys Ser Ile Ser Lys Gly
        275                 280                 285

Glu Lys Lys Val Met Ile Ala Ala Tyr Lys Gln Ile Phe Tyr Thr Val
    290                 295                 300

Ser Ala Asn Leu Pro Asn Asn Pro Ala Asp Val Phe Asp Lys Ser Val
305                 310                 315                 320

Thr Phe Lys Glu Leu Gln Arg Lys Gly Val Ser Asn Glu Ala Pro Pro
                325                 330                 335

Leu Phe Val Ser Asn Val Ala Tyr Gly Arg Thr Val Phe Val Lys Leu
            340                 345                 350

Glu Thr Ser Ser Lys Ser Asn Asp Val Glu Ala Ala Phe Ser Ala Ala
        355                 360                 365

Leu Lys Gly Thr Asp Val Lys Thr Asn Gly Lys Tyr Ser Asp Ile Leu
    370                 375                 380

Glu Asn Ser Ser Phe Thr Ala Val Val Leu Gly Gly Asp Ala Ala Glu
385                 390                 395                 400

His Asn Lys Val Val Thr Lys Asp Phe Asp Val Ile Arg Asn Val Ile
                405                 410                 415

Lys Asp Asn Ala Thr Phe Ser Arg Lys Asn Pro Ala Tyr Pro Ile Ser
            420                 425                 430

Tyr Thr Ser Val Phe Leu Lys Asn Asn Lys Ile Ala Gly Val Asn Asn
        435                 440                 445

Arg Thr Glu Tyr Val Glu Thr Thr Ser Thr Tyr Thr Ser Gly Lys
    450                 455                 460

Ile Asn Leu Ser His Arg Gly Ala Tyr Val Ala Gln Tyr Glu Ile Leu
465                 470                 475                 480

Trp Asp Glu Ile Asn Tyr Asp Asp Lys Gly Lys Glu Val Ile Thr Lys
                485                 490                 495

Arg Arg Trp Asp Asn Asn Trp Tyr Ser Lys Thr Ser Pro Phe Ser Thr
            500                 505                 510

Val Ile Pro Leu Gly Ala Asn Ser Arg Asn Ile Arg Ile Met Ala Arg
        515                 520                 525

Glu Cys Thr Gly Leu Ala Trp Glu Trp Trp Arg Lys Val Ile Asp Glu
    530                 535                 540

Arg Asp Val Lys Leu Ser Lys Glu Ile Asn Val Asn Ile Ser Gly Ser
545                 550                 555                 560

Thr Leu Ser Pro Tyr Gly Ser Ile Thr Tyr Lys
                565                 570

<210> SEQ ID NO 6
<211> LENGTH: 571
<212> TYPE: PRT
<213> ORGANISM: S. pyogenes
```

```
<400> SEQUENCE: 6

Met Ser Asn Lys Lys Thr Phe Lys Lys Tyr Ser Arg Val Ala Gly Leu
 1               5                   10                  15

Leu Thr Ala Ala Leu Ile Ile Gly Asn Leu Val Thr Ala Asn Ala Glu
             20                  25                  30

Ser Asn Lys Gln Asn Thr Ala Ser Thr Glu Thr Thr Thr Asn Glu
         35                  40                  45

Gln Pro Lys Pro Glu Ser Ser Glu Leu Thr Ile Glu Lys Ala Gly Gln
     50                  55                  60

Lys Met Asp Asp Met Leu Asn Ser Asn Asp Met Ile Lys Leu Ala Pro
65                  70                  75                  80

Lys Glu Met Pro Leu Glu Ser Ala Glu Lys Glu Lys Lys Ser Glu
                 85                  90                  95

Asp Lys Lys Lys Ser Glu Glu Asp His Thr Glu Glu Ile Asn Asp Lys
                100                 105                 110

Ile Tyr Ser Leu Asn Tyr Asn Glu Leu Glu Val Leu Ala Lys Asn Gly
             115                 120                 125

Glu Thr Ile Glu Asn Phe Val Pro Lys Glu Gly Val Lys Lys Ala Asp
     130                 135                 140

Lys Phe Ile Val Ile Glu Arg Lys Lys Lys Asn Ile Asn Thr Thr Pro
145                 150                 155                 160

Val Asp Ile Ser Ile Ile Asp Ser Val Thr Asp Met Thr Tyr Pro Ala
                 165                 170                 175

Ala Leu Gln Leu Ala Asp Lys Gly Phe Thr Glu Asn Lys Pro Asp Ala
             180                 185                 190

Val Val Thr Lys Arg Asn Pro Gln Lys Ile His Ile Asp Leu Pro Gly
     195                 200                 205

Met Gly Asp Lys Ala Thr Val Glu Val Asn Asp Pro Thr Tyr Ala Asn
210                 215                 220

Val Ser Thr Ala Ile Asp Asn Leu Val Asn Gln Trp His Asp Asn Tyr
225                 230                 235                 240

Ser Gly Gly Asn Thr Leu Pro Ala Arg Thr Gln Tyr Thr Glu Ser Met
                 245                 250                 255

Val Tyr Ser Lys Ser Gln Ile Glu Ala Ala Leu Asn Val Asn Ser Lys
             260                 265                 270

Ile Leu Asp Gly Thr Leu Gly Ile Asp Phe Lys Ser Ile Ser Lys Gly
     275                 280                 285

Glu Lys Lys Val Met Ile Ala Ala Tyr Lys Gln Ile Phe Tyr Thr Val
290                 295                 300

Ser Ala Asn Leu Pro Asn Asn Pro Ala Asp Val Phe Asp Lys Ser Val
305                 310                 315                 320

Thr Phe Lys Glu Leu Gln Arg Lys Gly Val Ser Asn Glu Ala Pro Pro
                 325                 330                 335

Leu Phe Val Ser Asn Val Ala Tyr Gly Arg Thr Val Phe Val Lys Leu
             340                 345                 350

Glu Thr Ser Ser Lys Ser Asn Asp Val Glu Ala Ala Phe Ser Ala Ala
     355                 360                 365

Leu Lys Gly Thr Asp Val Lys Thr Asn Gly Lys Tyr Ser Asp Ile Leu
370                 375                 380

Glu Asn Ser Ser Phe Thr Ala Val Val Leu Gly Gly Asp Ala Ala Glu
385                 390                 395                 400

His Asn Lys Val Val Thr Lys Asp Phe Asp Val Ile Arg Asn Val Ile
                 405                 410                 415
```

-continued

```
Lys Asp Asn Ala Thr Phe Ser Arg Lys Asn Pro Ala Tyr Pro Ile Ser
                420                 425                 430

Tyr Thr Ser Val Phe Leu Lys Asn Asn Lys Ile Ala Gly Val Asn Asn
            435                 440                 445

Arg Thr Glu Tyr Val Glu Thr Thr Ser Thr Tyr Thr Ser Gly Lys
        450                 455                 460

Ile Asn Leu Ser His Arg Gly Ala Tyr Val Ala Gln Tyr Glu Ile Leu
465             470                 475                 480

Trp Asp Glu Ile Asn Tyr Asp Lys Gly Lys Val Ile Thr Lys
                485                 490                 495

Arg Arg Trp Asp Asn Asn Trp Tyr Ser Lys Thr Ser Pro Phe Ser Thr
                500                 505                 510

Val Ile Pro Leu Gly Ala Asn Ser Arg Asn Ile Arg Ile Met Ala Arg
            515                 520                 525

Glu Cys Thr Gly Leu Ala Trp Glu Trp Trp Arg Lys Val Ile Asp Glu
        530                 535                 540

Arg Asp Val Lys Leu Ser Lys Glu Ile Asn Val Asn Ile Ser Gly Ser
545                 550                 555                 560

Thr Leu Ser Pro Tyr Gly Ser Ile Thr Tyr Lys
                565                 570

<210> SEQ ID NO 7
<211> LENGTH: 571
<212> TYPE: PRT
<213> ORGANISM: S. pyogenes

<400> SEQUENCE: 7

Met Ser Asn Lys Lys Thr Phe Lys Lys Tyr Ser Arg Val Ala Gly Leu
1               5                   10                  15

Leu Thr Val Ala Leu Ile Ile Gly Asn Leu Val Thr Ala Asn Ala Glu
            20                  25                  30

Ser Asn Lys Gln Asn Thr Ala Ser Thr Glu Thr Thr Thr Thr Asn Glu
        35                  40                  45

Gln Pro Lys Pro Glu Ser Ser Glu Leu Thr Ile Glu Lys Ala Gly Gln
    50                  55                  60

Lys Met Asp Asp Met Leu Asn Ser Asn Asp Met Ile Lys Leu Ala Pro
65                  70                  75                  80

Lys Glu Met Pro Leu Glu Ser Ala Glu Lys Glu Lys Lys Ser Glu
                85                  90                  95

Asp Lys Lys Lys Ser Glu Glu Asp His Thr Glu Glu Ile Asn Asp Lys
            100                 105                 110

Ile Tyr Ser Leu Asn Tyr Asn Glu Leu Glu Val Leu Ala Lys Asn Gly
        115                 120                 125

Glu Thr Ile Glu Asn Phe Val Pro Lys Glu Gly Val Lys Lys Ala Asp
    130                 135                 140

Lys Phe Ile Val Ile Glu Arg Lys Lys Asn Ile Asn Thr Thr Pro
145                 150                 155                 160

Val Asp Ile Ser Ile Ile Asp Ser Val Thr Asp Arg Thr Tyr Pro Ala
                165                 170                 175

Ala Leu Gln Leu Ala Asn Lys Gly Phe Thr Glu Asn Lys Pro Asp Ala
            180                 185                 190

Val Val Thr Lys Arg Asn Pro Gln Lys Ile His Ile Asp Leu Pro Gly
        195                 200                 205

Met Gly Asp Lys Ala Thr Val Glu Val Asn Asp Pro Thr Tyr Ala Asn
    210                 215                 220
```

```
Val Ser Thr Ala Ile Asp Asn Leu Val Asn Gln Trp His Asp Asn Tyr
225                 230                 235                 240

Ser Gly Gly Asn Thr Leu Pro Ala Arg Thr Gln Tyr Thr Glu Ser Met
            245                 250                 255

Val Tyr Ser Lys Ser Gln Ile Glu Ala Ala Leu Asn Val Asn Ser Lys
        260                 265                 270

Ile Leu Asp Gly Thr Leu Gly Ile Asp Phe Lys Ser Ile Ser Lys Gly
    275                 280                 285

Glu Lys Lys Val Met Ile Ala Ala Tyr Lys Gln Ile Phe Tyr Thr Val
290                 295                 300

Ser Ala Asn Leu Pro Asn Asn Pro Ala Asp Val Phe Lys Ser Val
305                 310                 315                 320

Thr Phe Lys Asp Leu Gln Arg Lys Gly Val Ser Asn Glu Ala Pro Pro
            325                 330                 335

Leu Phe Val Ser Asn Val Ala Tyr Gly Arg Thr Val Phe Val Lys Leu
        340                 345                 350

Glu Thr Ser Ser Lys Ser Asn Asp Val Glu Ala Ala Phe Ser Ala Ala
            355                 360                 365

Leu Lys Gly Thr Asp Val Lys Thr Asn Gly Lys Tyr Ser Asp Ile Leu
370                 375                 380

Glu Asn Ser Ser Phe Thr Ala Val Val Leu Gly Gly Asp Ala Ala Glu
385                 390                 395                 400

His Asn Lys Val Val Thr Lys Asp Phe Asp Val Ile Arg Asn Val Ile
            405                 410                 415

Lys Asp Asn Ala Thr Phe Ser Arg Lys Asn Pro Ala Tyr Pro Ile Ser
        420                 425                 430

Tyr Thr Ser Val Phe Leu Lys Asn Asn Lys Ile Ala Gly Val Asn Asn
            435                 440                 445

Arg Thr Glu Tyr Val Glu Thr Thr Ser Thr Glu Tyr Thr Ser Gly Lys
    450                 455                 460

Ile Asn Leu Ser His Gln Gly Ala Tyr Val Ala Gln Tyr Glu Ile Leu
465                 470                 475                 480

Trp Asp Glu Ile Asn Tyr Asp Asp Lys Gly Lys Glu Val Ile Thr Lys
            485                 490                 495

Arg Arg Trp Asp Asn Asn Trp Tyr Ser Lys Thr Ser Pro Phe Ser Thr
        500                 505                 510

Val Ile Pro Leu Gly Ala Asn Ser Arg Asn Ile Arg Ile Met Ala Arg
    515                 520                 525

Glu Cys Thr Gly Leu Ala Trp Glu Trp Trp Arg Lys Val Ile Asp Glu
530                 535                 540

Arg Asp Val Lys Leu Ser Lys Glu Ile Asn Val Asn Ile Ser Gly Ser
545                 550                 555                 560

Thr Leu Ser Pro Tyr Gly Ser Ile Thr Tyr Lys
            565                 570

<210> SEQ ID NO 8
<211> LENGTH: 571
<212> TYPE: PRT
<213> ORGANISM: S. pyogenes

<400> SEQUENCE: 8

Met Ser Asn Lys Lys Thr Phe Lys Lys Tyr Ser Arg Val Ala Gly Leu
1               5                   10                  15

Leu Thr Ala Ala Leu Ile Ile Gly Asn Leu Val Thr Ala Asn Ala Glu
            20                  25                  30
```

```
Ser Asn Lys Gln Asn Thr Ala Ser Thr Glu Thr Thr Thr Asn Glu
         35                  40                  45

Gln Pro Lys Pro Glu Ser Ser Glu Leu Thr Thr Glu Lys Ala Gly Gln
 50                  55                  60

Lys Thr Asp Asp Met Leu Asn Ser Asn Asp Met Ile Lys Leu Ala Pro
 65                  70                  75                  80

Lys Glu Met Pro Leu Glu Ser Ala Glu Lys Glu Lys Lys Ser Glu
                 85                  90                  95

Asp Lys Lys Lys Ser Glu Glu Asp His Thr Glu Glu Ile Asn Asp Lys
                100                 105                 110

Ile Tyr Ser Leu Asn Tyr Asn Glu Leu Glu Val Leu Ala Lys Asn Gly
             115                 120                 125

Glu Thr Ile Glu Asn Phe Val Pro Lys Glu Gly Val Lys Lys Ala Asp
    130                 135                 140

Lys Phe Ile Val Ile Glu Arg Lys Lys Asn Ile Asn Thr Thr Pro
145                 150                 155                 160

Val Asp Ile Ser Ile Asp Ser Val Thr Asp Arg Thr Tyr Pro Ala
                165                 170                 175

Ala Leu Gln Leu Ala Asn Lys Gly Phe Thr Glu Asn Lys Pro Asp Ala
                180                 185                 190

Val Val Thr Lys Arg Asn Pro Gln Lys Ile His Ile Asp Leu Pro Gly
            195                 200                 205

Met Gly Asp Lys Ala Thr Val Glu Val Asn Asp Pro Thr Tyr Ala Asn
    210                 215                 220

Val Ser Thr Ala Ile Asp Asn Leu Val Asn Gln Trp His Asp Asn Tyr
225                 230                 235                 240

Ser Gly Gly Asn Thr Leu Pro Ala Arg Thr Gln Tyr Thr Glu Ser Met
                245                 250                 255

Val Tyr Ser Lys Ser Gln Ile Glu Ala Ala Leu Asn Val Asn Ser Lys
            260                 265                 270

Ile Leu Asp Gly Thr Leu Gly Ile Asp Phe Lys Ser Ile Ser Lys Gly
            275                 280                 285

Glu Lys Lys Val Met Ile Ala Ala Tyr Lys Gln Ile Phe Tyr Thr Val
    290                 295                 300

Ser Ala Asn Leu Pro Asn Asn Pro Ala Asp Val Phe Asp Lys Ser Val
305                 310                 315                 320

Thr Phe Lys Glu Leu Gln Arg Lys Gly Val Ser Asn Glu Ala Pro Pro
                325                 330                 335

Leu Phe Val Ser Asn Val Ala Tyr Gly Arg Thr Val Phe Val Lys Leu
            340                 345                 350

Glu Thr Ser Ser Lys Ser Asn Asp Val Glu Ala Ala Phe Ser Ala Ala
        355                 360                 365

Leu Lys Gly Thr Asp Val Lys Thr Asn Gly Lys Tyr Ser Asp Ile Leu
    370                 375                 380

Glu Asn Ser Ser Phe Thr Ala Val Val Leu Gly Gly Asp Ala Ala Glu
385                 390                 395                 400

His Asn Lys Val Val Thr Lys Asp Phe Asp Val Ile Arg Asn Val Ile
                405                 410                 415

Lys Asp Asn Ala Thr Phe Ser Arg Lys Asn Pro Ala Tyr Pro Ile Ser
            420                 425                 430

Tyr Thr Ser Val Phe Leu Lys Asn Asn Lys Ile Ala Gly Val Asn Asn
        435                 440                 445

Arg Thr Glu Tyr Val Glu Thr Thr Ser Thr Glu Tyr Ser Gly Lys
    450                 455                 460
```

-continued

```
Ile Asn Leu Ser His Arg Gly Ala Tyr Val Ala Gln Tyr Glu Ile Leu
465                 470                 475                 480

Trp Asp Glu Ile Asn Tyr Asp Asp Lys Gly Lys Glu Val Ile Thr Lys
            485                 490                 495

Arg Arg Trp Asp Asn Asn Trp Tyr Ser Lys Thr Ser Pro Phe Ser Thr
        500                 505                 510

Val Ile Pro Leu Gly Ala Asn Ser Arg Asn Ile Arg Ile Met Ala Arg
    515                 520                 525

Glu Cys Thr Gly Leu Ala Trp Glu Trp Trp Arg Lys Val Ile Asp Glu
530                 535                 540

Arg Asp Val Lys Leu Ser Lys Glu Ile Asn Val Asn Ile Ser Gly Ser
545                 550                 555                 560

Thr Leu Ser Pro Tyr Gly Ser Ile Thr Tyr Lys
                565                 570
```

<210> SEQ ID NO 9
<211> LENGTH: 571
<212> TYPE: PRT
<213> ORGANISM: S. pyogenes

<400> SEQUENCE: 9

```
Met Ser Asn Lys Lys Thr Phe Lys Lys Tyr Ser Arg Val Ala Gly Leu
1               5                   10                  15

Leu Thr Ala Ala Leu Ile Ile Gly Asn Leu Val Thr Ala Asn Ala Glu
            20                  25                  30

Ser Asn Lys Gln Asn Thr Ala Ser Thr Glu Thr Thr Thr Thr Asn Glu
        35                  40                  45

Gln Pro Lys Pro Glu Ser Ser Glu Leu Thr Thr Glu Lys Ala Gly Gln
    50                  55                  60

Lys Thr Asp Asp Met Leu Asn Ser Asn Asp Met Ile Lys Leu Ala Pro
65                  70                  75                  80

Lys Glu Met Pro Leu Glu Ser Ala Glu Lys Glu Glu Lys Lys Ser Glu
                85                  90                  95

Asp Lys Lys Lys Ser Glu Glu Asp His Thr Glu Glu Ile Asn Asp Lys
            100                 105                 110

Ile Tyr Ser Leu Asn Tyr Asn Glu Leu Glu Val Leu Ala Lys Asn Gly
        115                 120                 125

Glu Thr Ile Glu Asn Phe Val Pro Lys Glu Gly Val Lys Lys Ala Asp
    130                 135                 140

Lys Phe Ile Val Ile Glu Arg Lys Lys Lys Asn Ile Asn Thr Thr Pro
145                 150                 155                 160

Val Asp Ile Ser Ile Ile Asp Ser Val Thr Asp Arg Thr Tyr Pro Ala
                165                 170                 175

Ala Leu Gln Leu Ala Asn Lys Gly Phe Thr Glu Asn Lys Pro Asp Ala
            180                 185                 190

Val Val Thr Lys Arg Asn Pro Gln Lys Ile His Ile Asp Leu Pro Gly
        195                 200                 205

Met Gly Asp Lys Ala Thr Val Glu Val Asn Asp Pro Thr Tyr Ala Asn
    210                 215                 220

Val Ser Thr Ala Ile Asp Asn Leu Val Asn Gln Trp His Asp Asn Tyr
225                 230                 235                 240

Ser Gly Gly Asn Thr Leu Pro Ala Arg Thr Gln Tyr Thr Glu Ser Met
                245                 250                 255

Val Tyr Ser Lys Ser Gln Ile Glu Ala Ala Leu Asn Val Asn Ser Lys
            260                 265                 270
```

-continued

```
Ile Leu Asp Gly Thr Leu Gly Ile Asp Phe Lys Ser Ile Ser Lys Gly
    275                 280                 285
Glu Lys Lys Val Met Ile Ala Ala Tyr Lys Gln Ile Phe Tyr Thr Val
290                 295                 300
Ser Ala Asn Leu Pro Asn Asn Pro Ala Asp Val Phe Asp Lys Ser Val
305                 310                 315                 320
Thr Phe Lys Asp Leu Gln Arg Lys Gly Val Ser Asn Glu Ala Pro Pro
                325                 330                 335
Leu Phe Val Ser Asn Val Ala Tyr Gly Arg Thr Val Phe Val Lys Leu
            340                 345                 350
Glu Thr Ser Ser Lys Ser Asn Asp Val Glu Ala Phe Ser Ala Ala
        355                 360                 365
Leu Lys Gly Thr Asp Val Lys Thr Asn Gly Lys Tyr Ser Asp Ile Leu
    370                 375                 380
Glu Asn Ser Ser Phe Thr Ala Val Val Leu Gly Gly Asp Ala Ala Glu
385                 390                 395                 400
His Asn Lys Val Val Thr Lys Asp Phe Asp Val Ile Arg Asn Val Ile
                405                 410                 415
Lys Asp Asn Ala Thr Phe Ser Arg Lys Asn Pro Ala Tyr Pro Ile Ser
            420                 425                 430
Tyr Thr Ser Val Phe Leu Lys Asn Asn Lys Ile Ala Gly Val Asn Asn
        435                 440                 445
Arg Thr Glu Tyr Val Glu Thr Thr Ser Thr Glu Tyr Thr Ser Gly Lys
    450                 455                 460
Ile Asn Leu Ser His Gln Gly Ala Tyr Val Ala Gln Tyr Glu Ile Leu
465                 470                 475                 480
Trp Asp Glu Ile Asn Tyr Asp Asp Lys Gly Lys Glu Val Ile Thr Lys
                485                 490                 495
Arg Arg Trp Asp Asn Asn Trp Tyr Ser Lys Thr Ser Pro Phe Ser Thr
            500                 505                 510
Val Ile Pro Leu Gly Ala Asn Ser Arg Asn Ile Arg Ile Met Ala Arg
        515                 520                 525
Glu Cys Thr Gly Leu Ala Trp Glu Trp Trp Arg Lys Val Ile Asp Glu
    530                 535                 540
Arg Asp Val Lys Leu Ser Lys Glu Ile Asn Val Asn Ile Ser Gly Ser
545                 550                 555                 560
Thr Leu Ser Pro Tyr Gly Ser Ile Thr Tyr Lys
                565                 570
```

<210> SEQ ID NO 10
<211> LENGTH: 571
<212> TYPE: PRT
<213> ORGANISM: S. pyogenes

<400> SEQUENCE: 10

```
Met Ser Asn Lys Lys Thr Phe Lys Lys Tyr Ser Arg Val Ala Gly Leu
1               5                   10                  15
Leu Thr Ala Ala Leu Ile Ile Gly Asn Leu Val Thr Ala Asn Ala Glu
            20                  25                  30
Ser Asn Lys Gln Asn Thr Ala Ser Thr Glu Thr Thr Thr Asn Glu
        35                  40                  45
Gln Pro Lys Pro Glu Ser Ser Glu Leu Thr Thr Glu Lys Ala Gly Gln
    50                  55                  60
Lys Thr Asp Asp Met Leu Asn Ser Asn Asp Met Ile Lys Leu Ala Pro
65                  70                  75                  80
```

```
Lys Glu Met Pro Leu Glu Ser Ala Glu Lys Glu Lys Ser Glu
             85                  90                  95

Asp Lys Lys Lys Ser Glu Glu Asp His Thr Glu Glu Ile Asn Asp Lys
            100                 105                 110

Ile Tyr Ser Leu Asn Tyr Asn Glu Leu Glu Val Leu Ala Lys Asn Gly
            115                 120                 125

Glu Thr Ile Glu Asn Phe Val Pro Lys Glu Gly Val Lys Lys Ala Asp
        130                 135                 140

Lys Phe Ile Val Ile Glu Arg Lys Lys Lys Asn Ile Asn Thr Thr Pro
145                 150                 155                 160

Val Asp Ile Ser Ile Ile Asp Ser Val Thr Asp Arg Thr Tyr Pro Ala
                165                 170                 175

Ala Leu Gln Leu Ala Asn Lys Gly Phe Thr Glu Asn Lys Pro Asp Ala
                180                 185                 190

Val Val Thr Lys Arg Asn Pro Gln Lys Ile His Ile Asp Leu Pro Gly
                195                 200                 205

Met Gly Asp Lys Ala Thr Val Glu Val Asn Asp Pro Thr Tyr Ala Asn
        210                 215                 220

Val Ser Thr Ala Ile Asp Asn Leu Val Asn Gln Trp His Asp Asn Tyr
225                 230                 235                 240

Ser Gly Gly Asn Thr Leu Pro Ala Arg Thr Gln Tyr Thr Glu Ser Met
                245                 250                 255

Val Tyr Ser Lys Ser Gln Ile Glu Ala Ala Leu Asn Val Asn Ser Lys
                260                 265                 270

Ile Leu Asp Gly Thr Leu Gly Ile Asp Phe Lys Ser Ile Ser Lys Gly
        275                 280                 285

Glu Lys Lys Val Met Ile Ala Ala Tyr Lys Gln Ile Phe Tyr Thr Val
        290                 295                 300

Ser Ala Asn Leu Pro Asn Asn Pro Ala Asp Val Phe Asp Lys Ser Val
305                 310                 315                 320

Thr Phe Lys Glu Leu Gln Arg Lys Gly Val Ser Asn Glu Ala Pro Pro
                325                 330                 335

Leu Phe Val Ser Asn Val Ala Tyr Gly Arg Thr Val Phe Val Lys Leu
                340                 345                 350

Glu Thr Ser Ser Lys Ser Asn Asp Val Glu Ala Ala Phe Ser Ala Ala
                355                 360                 365

Leu Lys Gly Thr Asp Val Lys Thr Asn Gly Lys Tyr Ser Asp Ile Leu
        370                 375                 380

Glu Asn Ser Ser Phe Thr Ala Val Val Leu Gly Gly Asp Ala Ala Glu
385                 390                 395                 400

His Asn Lys Val Val Thr Lys Asp Phe Asp Val Ile Arg Asn Val Ile
                405                 410                 415

Lys Asp Asn Ala Thr Phe Ser Arg Lys Asn Pro Ala Tyr Pro Ile Ser
                420                 425                 430

Tyr Thr Ser Val Phe Leu Lys Asn Asn Lys Ile Ala Gly Val Asn Asn
        435                 440                 445

Arg Thr Glu Tyr Val Glu Thr Thr Ser Thr Glu Tyr Thr Ser Gly Lys
        450                 455                 460

Ile Asn Leu Ser His Gln Gly Ala Tyr Val Ala Gln Tyr Glu Ile Leu
465                 470                 475                 480

Trp Asp Glu Ile Asn Tyr Asp Asp Lys Gly Lys Glu Val Ile Thr Lys
                485                 490                 495

Arg Arg Trp Asp Asn Asn Trp Tyr Ser Lys Thr Ser Pro Phe Ser Thr
                500                 505                 510
```

```
Val Ile Pro Leu Gly Ala Asn Ser Arg Asn Ile Arg Ile Met Ala Arg
        515                 520                 525

Glu Cys Thr Gly Leu Ala Trp Glu Trp Trp Arg Lys Val Ile Asp Glu
    530                 535                 540

Arg Asp Val Lys Leu Ser Lys Glu Ile Asn Val Asn Ile Ser Gly Ser
545                 550                 555                 560

Thr Leu Ser Pro Tyr Gly Ser Ile Thr Tyr Lys
                565                 570

<210> SEQ ID NO 11
<211> LENGTH: 571
<212> TYPE: PRT
<213> ORGANISM: S. pyogenes

<400> SEQUENCE: 11

Met Ser Asn Lys Lys Thr Phe Lys Lys Tyr Ser Arg Val Ala Gly Leu
  1               5                  10                  15

Leu Thr Ala Ala Leu Ile Ile Gly Asn Leu Val Thr Asn Ala Glu
             20                  25                  30

Ser Asn Lys Gln Asn Thr Ala Ser Thr Glu Thr Thr Thr Asn Glu
         35                  40                  45

Gln Pro Lys Pro Glu Ser Ser Glu Leu Thr Thr Glu Lys Ala Gly Gln
 50                  55                  60

Lys Thr Asp Asp Met Leu Asn Ser Asn Asp Met Ile Lys Leu Ala Pro
 65                  70                  75                  80

Lys Glu Met Pro Leu Glu Ser Ala Glu Lys Glu Lys Lys Ser Glu
                 85                  90                  95

Asp Lys Lys Lys Ser Glu Glu Asp His Thr Glu Glu Ile Asn Asp Lys
                100                 105                 110

Ile Tyr Ser Leu Asn Tyr Asn Glu Leu Glu Val Leu Ala Lys Asn Gly
            115                 120                 125

Glu Thr Ile Glu Asn Phe Val Pro Lys Glu Gly Val Leu Lys Ala Asp
        130                 135                 140

Lys Phe Ile Val Ile Glu Arg Lys Lys Lys Asn Ile Asn Thr Thr Pro
145                 150                 155                 160

Val Asp Ile Ser Ile Ile Asp Ser Val Thr Asp Arg Thr Tyr Pro Ala
                165                 170                 175

Ala Leu Gln Leu Ala Asn Lys Gly Phe Thr Glu Asn Lys Pro Asp Ala
            180                 185                 190

Val Val Thr Lys Arg Asn Pro Gln Lys Ile His Ile Asp Leu Pro Gly
        195                 200                 205

Met Gly Asp Lys Ala Thr Val Glu Val Asn Asp Pro Thr Tyr Ala Asn
    210                 215                 220

Val Ser Thr Ala Ile Asp Asn Leu Val Asn Gln Trp His Asp Asn Tyr
225                 230                 235                 240

Ser Gly Gly Asn Thr Leu Pro Ala Arg Thr Gln Tyr Thr Glu Ser Met
                245                 250                 255

Val Tyr Ser Lys Ser Gln Ile Glu Ala Ala Leu Asn Val Asn Ser Lys
            260                 265                 270

Ile Leu Asp Gly Thr Leu Gly Ile Asp Phe Lys Ser Ile Ser Lys Gly
        275                 280                 285

Glu Lys Lys Val Met Ile Ala Ala Tyr Lys Gln Ile Phe Tyr Thr Val
    290                 295                 300

Ser Ala Asn Leu Pro Asn Asn Pro Ala Asp Val Phe Asp Lys Ser Val
305                 310                 315                 320
```

```
Thr Phe Lys Glu Leu Gln Arg Lys Gly Val Ser Asn Glu Ala Pro Pro
            325                 330                 335
Leu Phe Val Ser Asn Val Ala Tyr Gly Arg Thr Val Phe Val Lys Leu
            340                 345                 350
Glu Thr Ser Ser Lys Ser Asn Asp Val Glu Ala Ala Phe Ser Ala Ala
            355                 360                 365
Leu Lys Gly Thr Asp Val Lys Thr Asn Gly Lys Tyr Ser Asp Ile Leu
            370                 375                 380
Glu Asn Ser Ser Phe Thr Ala Val Val Leu Gly Gly Asp Ala Ala Glu
385                 390                 395                 400
His Asn Lys Val Val Thr Lys Asp Phe Asp Val Ile Arg Asn Val Ile
            405                 410                 415
Lys Asp Asn Ala Thr Phe Ser Arg Lys Asn Pro Ala Tyr Pro Ile Ser
            420                 425                 430
Tyr Thr Ser Val Phe Leu Lys Asn Asn Lys Ile Ala Gly Val Asn Asn
            435                 440                 445
Arg Thr Glu Tyr Val Glu Thr Thr Ser Thr Glu Tyr Thr Ser Gly Lys
            450                 455                 460
Ile Asn Leu Ser His Gln Gly Ala Tyr Val Ala Gln Tyr Glu Ile Leu
465                 470                 475                 480
Trp Asp Glu Ile Asn Tyr Asp Asp Lys Gly Lys Glu Val Ile Thr Lys
            485                 490                 495
Arg Arg Trp Asp Asn Asn Trp Tyr Ser Lys Thr Ser Pro Phe Ser Thr
            500                 505                 510
Val Ile Pro Leu Gly Ala Asn Ser Arg Asn Ile Arg Ile Met Ala Arg
            515                 520                 525
Glu Cys Thr Gly Leu Ala Trp Glu Trp Trp Arg Lys Val Ile Asp Glu
            530                 535                 540
Arg Asp Val Lys Leu Ser Lys Glu Ile Asn Val Asn Ile Ser Gly Ser
545                 550                 555                 560
Thr Leu Ser Pro Tyr Gly Ser Ile Thr Tyr Lys
            565                 570

<210> SEQ ID NO 12
<211> LENGTH: 571
<212> TYPE: PRT
<213> ORGANISM: S. pyogenes

<400> SEQUENCE: 12

Met Ser Asn Lys Lys Thr Phe Lys Lys Tyr Ser Arg Val Ala Gly Leu
1               5                   10                  15
Leu Thr Ala Ala Leu Ile Ile Gly Asn Leu Val Thr Ala Asn Ala Glu
            20                  25                  30
Ser Asn Lys Gln Asn Thr Ala Ser Thr Glu Thr Thr Thr Thr Asn Glu
            35                  40                  45
Gln Pro Lys Pro Glu Ser Ser Glu Leu Thr Thr Glu Lys Ala Gly Gln
            50                  55                  60
Lys Thr Asp Asp Met Leu Asn Ser Asn Asp Met Ile Lys Leu Ala Pro
65                  70                  75                  80
Lys Glu Met Pro Leu Glu Ser Ala Glu Lys Glu Lys Lys Ser Glu
            85                  90                  95
Asp Lys Lys Lys Ser Glu Glu Asp His Thr Glu Glu Ile Asn Asp Lys
            100                 105                 110
Ile Tyr Ser Leu Asn Tyr Asn Glu Leu Glu Val Leu Ala Lys Asn Gly
            115                 120                 125
```

```
Glu Thr Ile Glu Asn Phe Ala Pro Lys Glu Val Lys Lys Ala Asp
    130                 135                 140
Lys Phe Ile Val Ile Glu Arg Lys Lys Lys Asn Ile Asn Thr Thr Pro
145                 150                 155                 160
Val Asp Ile Ser Ile Ile Asp Ser Val Thr Asp Arg Thr Tyr Pro Ala
                165                 170                 175
Ala Leu Gln Leu Ala Asn Lys Gly Phe Thr Glu Asn Lys Pro Asp Ala
                180                 185                 190
Val Val Thr Lys Arg Asn Pro Gln Lys Ile His Ile Asp Leu Pro Gly
            195                 200                 205
Met Gly Asp Lys Ala Thr Val Glu Val Asn Asp Pro Thr Tyr Ala Asn
    210                 215                 220
Val Ser Thr Ala Ile Asp Asn Leu Ile Asn Gln Trp His Asp Asn Tyr
225                 230                 235                 240
Ser Gly Gly Asn Thr Leu Pro Ala Arg Thr Gln Tyr Thr Glu Ser Met
                245                 250                 255
Val Tyr Ser Lys Ser Gln Ile Glu Ala Ala Leu Asn Val Asn Ser Lys
                260                 265                 270
Ile Leu Asp Gly Thr Leu Gly Ile Asp Phe Lys Ser Ile Ser Lys Gly
            275                 280                 285
Glu Lys Lys Val Met Ile Ala Ala Tyr Lys Gln Ile Phe Tyr Thr Val
    290                 295                 300
Ser Ala Asn Leu Pro Asn Asn Pro Ala Asp Val Phe Ala Lys Ser Val
305                 310                 315                 320
Thr Phe Lys Glu Leu Gln Arg Lys Gly Val Ser Asn Glu Ala Pro Pro
                325                 330                 335
Leu Phe Val Ser Asn Val Ala Tyr Gly Arg Thr Val Phe Val Lys Leu
                340                 345                 350
Glu Thr Ser Ser Lys Ser Asn Asp Val Glu Ala Ala Phe Ser Ala Ala
            355                 360                 365
Leu Lys Gly Thr Asp Val Lys Thr Asn Gly Lys Tyr Ser Asp Ile Leu
    370                 375                 380
Glu Asn Ser Ser Phe Thr Ala Val Val Leu Gly Gly Asp Ala Ala Glu
385                 390                 395                 400
His Asn Lys Val Val Thr Lys Asp Phe Asp Val Ile Arg Asn Val Ile
                405                 410                 415
Lys Asp Asn Ala Thr Phe Ser Arg Lys Asn Pro Ala Tyr Pro Ile Ser
                420                 425                 430
Tyr Thr Ser Val Phe Leu Lys Asn Asn Lys Ile Ala Gly Val Asn Asn
            435                 440                 445
Arg Thr Glu Tyr Val Glu Thr Thr Ser Thr Glu Tyr Thr Ser Gly Lys
    450                 455                 460
Ile Asn Leu Ser His Gln Gly Ala Tyr Val Ala Gln Tyr Glu Ile Leu
465                 470                 475                 480
Trp Asp Glu Ile Asn Tyr Asp Asp Lys Gly Lys Glu Val Ile Thr Lys
                485                 490                 495
Arg Arg Trp Asp Asn Asn Trp Tyr Ser Lys Thr Ser Pro Phe Ser Thr
                500                 505                 510
Val Ile Pro Leu Gly Ala Asn Ser Arg Asn Ile Arg Ile Met Ala Arg
            515                 520                 525
Glu Cys Thr Gly Leu Ala Trp Glu Trp Trp Arg Lys Val Ile Asp Glu
    530                 535                 540
```

Arg Asp Val Lys Leu Ser Lys Glu Ile Asn Val Asn Ile Ser Gly Ser
545                 550                 555                 560

Thr Leu Ser Pro Tyr Gly Ser Ile Thr Tyr Lys
                565                 570

<210> SEQ ID NO 13
<211> LENGTH: 551
<212> TYPE: PRT
<213> ORGANISM: S. pyogenes

<400> SEQUENCE: 13

Met Ala Ser Glu Ser Asn Lys Gln Asn Thr Ala Ser Thr Glu Thr Thr
1               5                   10                  15

Thr Thr Asn Glu Gln Pro Lys Pro Glu Ser Ser Glu Leu Thr Thr Glu
            20                  25                  30

Lys Ala Gly Gln Lys Thr Asp Met Leu Asn Ser Asn Asp Met Ile
        35                  40                  45

Lys Leu Ala Pro Lys Glu Met Pro Leu Glu Ser Ala Glu Lys Glu Glu
50                  55                  60

Lys Lys Ser Glu Asp Lys Lys Ser Glu Glu Asp His Thr Glu Glu
65                  70                  75                  80

Ile Asn Asp Lys Ile Tyr Ser Leu Asn Tyr Asn Glu Leu Glu Val Leu
                85                  90                  95

Ala Lys Asn Gly Glu Thr Ile Glu Asn Phe Val Pro Lys Glu Gly Val
            100                 105                 110

Lys Lys Ala Asp Lys Phe Ile Val Ile Glu Arg Lys Lys Lys Asn Ile
        115                 120                 125

Asn Thr Thr Pro Val Asp Ile Ser Ile Ile Asp Ser Val Thr Asp Arg
130                 135                 140

Thr Tyr Pro Ala Ala Leu Gln Leu Ala Asn Lys Gly Phe Thr Glu Asn
145                 150                 155                 160

Lys Pro Asp Ala Val Val Thr Lys Arg Asn Pro Gln Lys Ile His Ile
                165                 170                 175

Asp Leu Pro Gly Met Gly Asp Lys Ala Thr Val Glu Val Asn Asp Pro
            180                 185                 190

Thr Tyr Ala Asn Val Ser Thr Ala Ile Asp Asn Leu Val Asn Gln Trp
        195                 200                 205

His Asp Asn Tyr Ser Gly Gly Asn Thr Leu Pro Ala Arg Thr Gln Tyr
210                 215                 220

Thr Glu Ser Met Val Tyr Ser Lys Ser Gln Ile Glu Ala Ala Leu Asn
225                 230                 235                 240

Val Asn Ser Lys Ile Leu Asp Gly Thr Leu Gly Ile Asp Phe Lys Ser
                245                 250                 255

Ile Ser Lys Gly Glu Lys Lys Val Met Ile Ala Ala Tyr Lys Gln Ile
            260                 265                 270

Phe Tyr Thr Val Ser Ala Asn Leu Pro Asn Asn Pro Ala Asp Val Phe
        275                 280                 285

Asp Lys Ser Val Thr Phe Lys Glu Leu Gln Arg Lys Gly Val Ser Asn
290                 295                 300

Glu Ala Pro Pro Leu Phe Val Ser Asn Val Ala Tyr Gly Arg Thr Val
305                 310                 315                 320

Phe Val Lys Leu Glu Thr Ser Ser Lys Ser Asn Asp Val Glu Ala Ala
                325                 330                 335

Phe Ser Ala Ala Leu Lys Gly Thr Asp Val Lys Thr Asn Gly Lys Tyr
            340                 345                 350

-continued

```
Ser Asp Ile Leu Glu Asn Ser Ser Phe Thr Ala Val Val Leu Gly Gly
        355                 360                 365

Asp Ala Ala Glu His Asn Lys Val Val Thr Lys Asp Phe Asp Val Ile
    370                 375                 380

Arg Asn Val Ile Lys Asp Asn Ala Thr Phe Ser Arg Lys Asn Pro Ala
385                 390                 395                 400

Tyr Pro Ile Ser Tyr Thr Ser Val Phe Leu Lys Asn Asn Lys Ile Ala
                405                 410                 415

Gly Val Asn Asn Arg Thr Glu Tyr Val Glu Thr Ser Thr Glu Tyr
            420                 425                 430

Thr Ser Gly Lys Ile Asn Leu Ser His Gln Gly Ala Tyr Val Ala Gln
            435                 440                 445

Tyr Glu Ile Leu Trp Asp Glu Ile Asn Tyr Asp Asp Lys Gly Lys Glu
    450                 455                 460

Val Ile Thr Lys Arg Arg Trp Asp Asn Asn Trp Tyr Ser Lys Thr Ser
465                 470                 475                 480

Pro Phe Ser Thr Val Ile Pro Leu Gly Ala Asn Ser Arg Asn Ile Arg
                485                 490                 495

Ile Met Ala Arg Glu Cys Thr Gly Leu Ala Trp Glu Trp Trp Arg Lys
            500                 505                 510

Val Ile Asp Glu Arg Asp Val Lys Leu Ser Lys Glu Ile Asn Val Asn
            515                 520                 525

Ile Ser Gly Ser Thr Leu Ser Pro Tyr Gly Ser Ile Thr Tyr Lys Leu
530                 535                 540

Glu His His His His His His
545                 550

<210> SEQ ID NO 14
<211> LENGTH: 1656
<212> TYPE: DNA
<213> ORGANISM: S. pyogenes

<400> SEQUENCE: 14
atggctagcg aatcgaacaa acaaaacact gctagtacag aaaccacaac gacaaatgag      60
caaccaaagc cagaaagtag tgagctaact actgaaaaag caggtcagaa aacggatgat     120
atgcttaact ctaacgatat gattaagctt gctcccaaag aaatgccact agaatctgca     180 gaaaagaag aaaaaaagtc agaagacaaa aaaagagcg aagaagatca cactgaagaa      240
atcaatgaca gatttattc actaaattat aatgagcttg aagtacttgc taaaaatggt      300
gaaaccattg aaaatttttgt tcctaaagaa ggcgttaaga aagctgataa atttattgtc     360
attgaaagaa agaaaaaaaa tatcaacact caccagtcg atatttccat tattgactct      420
gtcactgata ggacctatcc agcagccctt cagctggcta ataaaggttt taccgaaaac     480
aaaccagacg cggtagtcac caagcgaaac ccacaaaaaa tccatattga tttaccaggt     540
atgggagaca agcaacggt tgaggtcaat gaccctacct atgccaatgt tcaacagct      600 attgataatc ttgttaacca atggcatgat aattattctg gtggtaatac gcttcctgcc     660
agaacacaat atactgaatc aatggtatat tctaagtcac agattgaagc agctctaaat     720
gttaatagca aaatcttaga tggtacttta ggcattgatt tcaagtcgat ttcaaaggt      780 gaaaagaagg tgatgattgc agcatacaag caaattttt acaccgtatc agcaaacctt      840
cctaataatc ctgcggatgt gtttgataaa tcggtgacct ttaaagagtt gcaacgaaaa      900
ggtgtcagca atgaagctcc gccactcttt gtgagtaacg tagcctatgg tcgaactgtt      960
tttgtcaaac tagaaacaag ttctaaaagt aatgatgttg aagcggcctt tagtgcagct     1020
```

-continued

```
ctaaaaggaa cagatgttaa aactaatgga aatattctg atatcttaga aaatagctca   1080
tttacagctg tcgttttagg aggagatgct gcagagcaca ataaggtagt cacaaaagac   1140
tttgatgtta ttagaaacgt tatcaaagac aatgctacct tcagtagaaa aacccagct   1200 tatcctattt catacaccag tgttttcctt aaaaataata aaattgcggg tgtcaataac   1260
agaactgaat acgttgaaac aacatctacc gagtacacta gtggaaaaat taacctgtct   1320
catcaaggcg cgtatgttgc tcaatatgaa atcctttggg atgaaatcaa ttatgatgac   1380
aaaggaaaag aagtgattac aaaacgacgt tgggacaaca actggtatag taagacatca   1440
ccatttagca cagttatccc actaggagct aattcacgaa atatccgtat catggctaga   1500
gagtgcactg gcttagcttg ggaatggtgg cgaaaagtga tcgacgaaag agatgtgaaa   1560
ctgtctaaag aaatcaatgt caatatctca ggatcaacct tgagcccata tggttcgatt   1620
acttataagc tcgagcacca ccaccaccac cactga                             1656
```

<210> SEQ ID NO 15
<211> LENGTH: 551
<212> TYPE: PRT
<213> ORGANISM: S. pyogenes

<400> SEQUENCE: 15

```
Met Ala Ser Glu Ser Asn Lys Gln Asn Thr Ala Ser Thr Glu Thr Thr
 1               5                  10                  15

Thr Thr Asn Glu Gln Pro Lys Pro Glu Ser Ser Glu Leu Thr Thr Glu
            20                  25                  30

Lys Ala Gly Gln Lys Thr Asp Asp Met Leu Asn Ser Asn Asp Met Ile
        35                  40                  45

Lys Leu Ala Pro Lys Glu Met Pro Leu Glu Ser Ala Glu Lys Glu Glu
    50                  55                  60

Lys Lys Ser Glu Asp Lys Lys Ser Glu Glu Asp His Thr Glu Glu
65                  70                  75                  80

Ile Asn Asp Lys Ile Tyr Ser Leu Asn Tyr Asn Glu Leu Glu Val Leu
                85                  90                  95

Ala Lys Asn Gly Glu Thr Ile Glu Asn Phe Val Pro Lys Glu Gly Val
            100                 105                 110

Lys Lys Ala Asp Lys Phe Ile Val Ile Glu Arg Lys Lys Lys Asn Ile
        115                 120                 125

Asn Thr Thr Pro Val Asp Ile Ser Ile Asp Ser Val Thr Asp Arg
    130                 135                 140

Thr Tyr Pro Ala Ala Leu Gln Leu Ala Asn Lys Gly Phe Thr Glu Asn
145                 150                 155                 160

Lys Pro Asp Ala Val Val Thr Lys Arg Asn Pro Gln Lys Ile His Ile
                165                 170                 175

Asp Leu Pro Gly Met Gly Asp Lys Ala Thr Val Glu Val Asn Asp Pro
            180                 185                 190

Thr Tyr Ala Asn Val Ser Thr Ala Ile Asp Asn Leu Val Asn Gln Trp
        195                 200                 205

His Asp Asn Tyr Ser Gly Gly Asn Thr Leu Pro Ala Arg Thr Gln Tyr
    210                 215                 220

Thr Glu Ser Met Val Tyr Ser Lys Ser Gln Ile Glu Ala Ala Leu Asn
225                 230                 235                 240

Val Asn Ser Lys Ile Leu Asp Gly Thr Leu Gly Ile Asp Phe Lys Ser
                245                 250                 255

Ile Ser Lys Gly Glu Lys Lys Val Met Ile Ala Ala Tyr Lys Gln Ile
            260                 265                 270
```

Phe Tyr Thr Val Ser Ala Asn Leu Pro Asn Asn Pro Ala Asp Val Phe
            275                 280                 285

Asp Lys Ser Val Thr Phe Lys Glu Leu Gln Arg Lys Gly Val Ser Asn
        290                 295                 300

Glu Ala Pro Pro Leu Phe Val Ser Asn Val Ala Tyr Gly Arg Thr Val
305                 310                 315                 320

Phe Val Lys Leu Glu Thr Ser Ser Lys Ser Asn Asp Val Glu Ala Ala
                325                 330                 335

Phe Ser Ala Ala Leu Lys Gly Thr Asp Val Lys Thr Asn Gly Lys Tyr
            340                 345                 350

Ser Asp Ile Leu Glu Asn Ser Ser Phe Thr Ala Val Val Leu Gly Gly
        355                 360                 365

Asp Ala Ala Glu His Asn Lys Val Val Thr Lys Asp Phe Asp Val Ile
370                 375                 380

Arg Asn Val Ile Lys Asp Asn Ala Thr Phe Ser Arg Lys Asn Leu Ala
385                 390                 395                 400

Tyr Pro Ile Ser Tyr Thr Ser Val Phe Leu Lys Asn Asn Lys Ile Ala
                405                 410                 415

Gly Val Asn Asn Arg Thr Glu Tyr Val Glu Thr Thr Ser Thr Glu Tyr
            420                 425                 430

Thr Ser Gly Lys Ile Asn Leu Ser His Gln Gly Ala Tyr Val Ala Gln
        435                 440                 445

Tyr Glu Ile Leu Trp Asp Glu Ile Asn Tyr Asp Lys Gly Lys Glu
            450                 455                 460

Val Ile Thr Lys Arg Arg Trp Asp Asn Asn Trp Tyr Ser Lys Thr Ser
465                 470                 475                 480

Pro Phe Ser Thr Val Ile Pro Leu Gly Ala Asn Ser Arg Asn Ile Arg
                485                 490                 495

Ile Met Ala Arg Glu Cys Thr Gly Leu Ala Trp Glu Trp Trp Arg Lys
            500                 505                 510

Val Ile Asp Glu Arg Asp Val Lys Leu Ser Lys Glu Ile Asn Val Asn
        515                 520                 525

Ile Ser Gly Ser Thr Leu Ser Pro Tyr Gly Ser Ile Thr Tyr Lys Leu
    530                 535                 540

Glu His His His His His His
545                 550

<210> SEQ ID NO 16
<211> LENGTH: 551
<212> TYPE: PRT
<213> ORGANISM: S. pyogenes

<400> SEQUENCE: 16

Met Ala Ser Glu Ser Asn Lys Gln Asn Thr Ala Ser Thr Glu Thr Thr
1               5                   10                  15

Thr Thr Asn Glu Gln Pro Lys Pro Glu Ser Ser Glu Leu Thr Thr Glu
            20                  25                  30

Lys Ala Gly Gln Lys Thr Asp Asp Met Leu Asn Ser Asn Asp Met Ile
        35                  40                  45

Lys Leu Ala Pro Lys Glu Met Pro Leu Glu Ser Ala Glu Lys Glu Glu
    50                  55                  60

Lys Lys Ser Glu Asp Lys Lys Ser Glu Glu Asp His Thr Glu Glu
65                  70                  75                  80

Ile Asn Asp Lys Ile Tyr Ser Leu Asn Tyr Asn Glu Leu Glu Val Leu
                85                  90                  95

```
Ala Lys Asn Gly Glu Thr Ile Glu Asn Phe Val Pro Lys Glu Gly Val
            100                 105                 110

Lys Lys Ala Asp Lys Phe Ile Val Ile Glu Arg Lys Lys Lys Asn Ile
            115                 120                 125

Asn Thr Thr Pro Val Asp Ile Ser Ile Ile Asp Ser Val Thr Asp Arg
130                 135                 140

Thr Tyr Pro Ala Ala Leu Gln Leu Ala Asn Lys Gly Phe Thr Glu Asn
145                 150                 155                 160

Lys Pro Asp Ala Val Val Thr Lys Arg Asn Pro Gln Lys Ile His Ile
                165                 170                 175

Asp Leu Pro Gly Met Gly Asp Lys Ala Thr Val Glu Val Asn Asp Pro
            180                 185                 190

Thr Tyr Ala Asn Val Ser Thr Ala Ile Asp Asn Leu Val Asn Gln Trp
            195                 200                 205

His Asp Asn Tyr Ser Gly Gly Asn Thr Leu Pro Ala Arg Thr Gln Tyr
            210                 215                 220

Thr Glu Ser Met Val Tyr Ser Lys Ser Gln Ile Glu Ala Ala Leu Asn
225                 230                 235                 240

Val Asn Ser Lys Ile Leu Asp Gly Thr Leu Gly Ile Asp Phe Lys Ser
                245                 250                 255

Ile Ser Lys Gly Glu Lys Lys Val Met Ile Ala Ala Tyr Lys Gln Ile
            260                 265                 270

Phe Tyr Thr Val Ser Ala Asn Leu Pro Asn Asn Pro Ala Asp Val Phe
            275                 280                 285

Asp Lys Ser Val Thr Phe Lys Glu Leu Gln Arg Lys Gly Val Ser Asn
            290                 295                 300

Glu Ala Pro Pro Leu Phe Val Ser Asn Val Ala Tyr Gly Arg Thr Val
305                 310                 315                 320

Phe Val Lys Leu Glu Thr Ser Ser Lys Ser Asn Asp Val Glu Ala Ala
                325                 330                 335

Phe Ser Ala Ala Leu Lys Gly Thr Asp Val Lys Thr Asn Gly Lys Tyr
            340                 345                 350

Ser Asp Ile Leu Glu Asn Ser Ser Phe Thr Ala Val Val Leu Gly Gly
            355                 360                 365

Asp Ala Ala Glu His Asn Lys Val Val Thr Lys Asp Phe Asp Val Ile
            370                 375                 380

Arg Asn Val Ile Lys Asp Asn Ala Thr Phe Ser Arg Lys Asn Pro Ala
385                 390                 395                 400

Tyr Pro Ile Ser Tyr Thr Ser Val Phe Leu Lys Asn Asn Lys Ile Ala
                405                 410                 415

Gly Val Asn Asn Arg Thr Glu Tyr Val Glu Thr Thr Ser Thr Glu Tyr
            420                 425                 430

Thr Ser Gly Lys Ile Asn Leu Ser His Gln Gly Ala Tyr Val Ala Gln
            435                 440                 445

Tyr Glu Ile Leu Trp Asp Glu Ile Asn Tyr Asp Asp Lys Gly Lys Glu
            450                 455                 460

Val Ile Thr Lys Arg Arg Trp Asp Asn Asn Trp Tyr Ser Lys Thr Ser
465                 470                 475                 480

Pro Phe Ser Thr Val Ile Pro Leu Gly Ala Asn Ser Arg Asn Ile Arg
                485                 490                 495

Ile Met Ala Arg Glu Gly Thr Gly Leu Ala Trp Glu Trp Trp Arg Lys
            500                 505                 510

Val Ile Asp Glu Arg Asp Val Lys Leu Ser Lys Glu Ile Asn Val Asn
            515                 520                 525
```

```
Ile Ser Gly Ser Thr Leu Ser Pro Tyr Gly Ser Ile Thr Tyr Lys Leu
        530                 535                 540

Glu His His His His His
545                 550
```

<210> SEQ ID NO 17
<211> LENGTH: 550
<212> TYPE: PRT
<213> ORGANISM: S. pyogenes

<400> SEQUENCE: 17

```
Met Ala Ser Glu Ser Asn Lys Gln Asn Thr Ala Ser Thr Glu Thr Thr
  1               5                  10                  15

Thr Thr Asn Glu Gln Pro Lys Pro Glu Ser Ser Glu Leu Thr Thr Glu
             20                  25                  30

Lys Ala Gly Gln Lys Thr Asp Met Leu Asn Ser Asn Asp Met Ile
         35                  40                  45

Lys Leu Ala Pro Lys Glu Met Pro Leu Glu Ser Ala Lys Glu Glu
 50                  55                  60

Lys Lys Ser Glu Asp Lys Lys Ser Glu Glu Asp His Thr Glu Glu
 65                  70                  75                  80

Ile Asn Asp Lys Ile Tyr Ser Leu Asn Tyr Asn Glu Leu Glu Val Leu
                 85                  90                  95

Ala Lys Asn Gly Glu Thr Ile Glu Asn Phe Val Pro Lys Glu Gly Val
            100                 105                 110

Lys Lys Ala Asp Lys Phe Ile Val Ile Glu Arg Lys Lys Lys Asn Ile
        115                 120                 125

Asn Thr Thr Pro Val Asp Ile Ser Ile Asp Ser Val Thr Asp Arg
130                 135                 140

Thr Tyr Pro Ala Ala Leu Gln Leu Ala Asn Lys Gly Phe Thr Glu Asn
145                 150                 155                 160

Lys Pro Asp Ala Val Val Thr Lys Arg Asn Pro Gln Lys Ile His Ile
                165                 170                 175

Asp Leu Pro Gly Met Gly Asp Lys Ala Thr Val Glu Val Asn Asp Pro
            180                 185                 190

Thr Tyr Ala Asn Val Ser Thr Ala Ile Asp Asn Leu Val Asn Gln Trp
        195                 200                 205

His Asp Asn Tyr Ser Gly Gly Asn Thr Leu Pro Arg Thr Gln Tyr Thr
    210                 215                 220

Glu Ser Met Val Tyr Ser Lys Ser Gln Ile Glu Ala Ala Leu Asn Val
225                 230                 235                 240

Asn Ser Lys Ile Leu Asp Gly Thr Leu Gly Ile Asp Phe Lys Ser Ile
                245                 250                 255

Ser Lys Gly Glu Lys Lys Val Met Ile Ala Ala Tyr Lys Gln Ile Phe
            260                 265                 270

Tyr Thr Val Ser Ala Asn Leu Pro Asn Asn Pro Ala Asp Val Phe Asp
        275                 280                 285

Lys Ser Val Thr Phe Lys Glu Leu Gln Arg Lys Gly Val Ser Asn Glu
    290                 295                 300

Ala Pro Pro Leu Phe Val Ser Asn Val Ala Tyr Gly Arg Thr Val Phe
305                 310                 315                 320

Val Lys Leu Glu Thr Ser Ser Lys Ser Asn Asp Val Glu Ala Ala Phe
                325                 330                 335

Ser Ala Ala Leu Lys Gly Thr Asp Val Lys Thr Asn Gly Lys Tyr Ser
            340                 345                 350
```

-continued

Asp Ile Leu Glu Asn Ser Ser Phe Thr Ala Val Val Leu Gly Gly Asp
            355                 360                 365

Ala Ala Glu His Asn Lys Val Val Thr Lys Asp Phe Asp Val Ile Arg
    370                 375                 380

Asn Val Ile Lys Asp Asn Ala Thr Phe Ser Arg Lys Asn Pro Ala Tyr
385                 390                 395                 400

Pro Ile Ser Tyr Thr Ser Val Phe Leu Lys Asn Asn Lys Ile Ala Gly
                405                 410                 415

Val Asn Asn Arg Thr Glu Tyr Val Glu Thr Thr Ser Thr Glu Tyr Thr
            420                 425                 430

Ser Gly Lys Ile Asn Leu Ser His Gln Gly Ala Tyr Val Ala Gln Tyr
        435                 440                 445

Glu Ile Leu Trp Asp Glu Ile Asn Tyr Asp Asp Lys Gly Lys Glu Val
    450                 455                 460

Ile Thr Lys Arg Arg Trp Asp Asn Asn Trp Tyr Ser Lys Thr Ser Pro
465                 470                 475                 480

Phe Ser Thr Val Ile Pro Leu Gly Ala Asn Ser Arg Asn Ile Arg Ile
                485                 490                 495

Met Ala Arg Glu Cys Thr Gly Leu Ala Trp Glu Trp Trp Arg Lys Val
            500                 505                 510

Ile Asp Glu Arg Asp Val Lys Leu Ser Lys Glu Ile Asn Val Asn Ile
    515                 520                 525

Ser Gly Ser Thr Leu Ser Pro Tyr Gly Ser Ile Thr Tyr Lys Leu Glu
530                 535                 540

His His His His His His
545                 550

<210> SEQ ID NO 18
<211> LENGTH: 551
<212> TYPE: PRT
<213> ORGANISM: S. pyogenes

<400> SEQUENCE: 18

Met Ala Ser Glu Ser Asn Lys Gln Asn Thr Ala Ser Thr Glu Thr Thr
1               5                   10                  15

Thr Thr Asn Glu Gln Pro Lys Pro Glu Ser Ser Glu Leu Thr Thr Glu
            20                  25                  30

Lys Ala Gly Gln Lys Thr Asp Asp Met Leu Asn Ser Asn Asp Met Ile
        35                  40                  45

Lys Leu Ala Pro Lys Glu Met Pro Leu Glu Ser Ala Glu Lys Glu Glu
    50                  55                  60

Lys Lys Ser Glu Asp Lys Lys Ser Glu Glu Asp His Thr Glu Glu
65                  70                  75                  80

Ile Asn Asp Lys Ile Tyr Ser Leu Asn Tyr Asn Glu Leu Glu Val Leu
                85                  90                  95

Ala Lys Asn Gly Glu Thr Ile Glu Asn Phe Val Pro Lys Glu Gly Val
            100                 105                 110

Lys Lys Ala Asp Lys Phe Ile Val Ile Glu Arg Lys Lys Lys Asn Ile
        115                 120                 125

Asn Thr Thr Pro Val Asp Ile Ser Ile Ile Asp Ser Val Thr Asp Arg
    130                 135                 140

Thr Tyr Pro Ala Ala Leu Gln Leu Ala Asn Lys Gly Phe Thr Glu Asn
145                 150                 155                 160

Lys Pro Asp Ala Val Val Thr Lys Arg Asn Pro Gln Lys Ile His Ile
                165                 170                 175

```
Asp Leu Pro Gly Met Gly Asp Lys Ala Thr Val Glu Val Asn Asp Pro
            180                 185                 190

Thr Tyr Ala Asn Val Ser Thr Ala Ile Asp Asn Leu Val Asn Gln Trp
        195                 200                 205

His Asp Asn Tyr Ser Gly Gly Asn Thr Leu Pro Ala Arg Thr Gln Tyr
    210                 215                 220

Thr Glu Ser Met Val Tyr Ser Lys Ser Gln Ile Glu Ala Ala Leu Asn
225                 230                 235                 240

Val Asn Ser Lys Ile Leu Asp Gly Thr Leu Gly Ile Asp Phe Lys Ser
                245                 250                 255

Ile Ser Lys Gly Glu Lys Lys Val Met Ile Ala Ala Tyr Lys Gln Ile
                260                 265                 270

Phe Tyr Thr Val Ser Ala Asn Leu Pro Asn Asn Pro Ala Asp Val Phe
        275                 280                 285

Asp Lys Ser Val Thr Phe Lys Glu Leu Gln Arg Lys Gly Val Ser Asn
    290                 295                 300

Glu Ala Pro Pro Leu Phe Val Ser Asn Val Ala Tyr Gly Arg Thr Val
305                 310                 315                 320

Phe Val Lys Leu Glu Thr Ser Ser Lys Ser Asn Asp Val Glu Ala Ala
                325                 330                 335

Phe Ser Ala Ala Leu Lys Gly Thr Asp Val Lys Thr Asn Gly Lys Tyr
            340                 345                 350

Ser Asp Ile Leu Glu Asn Ser Ser Phe Thr Ala Val Val Leu Gly Gly
        355                 360                 365

Asp Ala Ala Glu His Asn Lys Val Val Thr Lys Asp Phe Asp Val Ile
    370                 375                 380

Arg Asn Val Ile Lys Asp Asn Ala Thr Phe Ser Arg Lys Asn Pro Ala
385                 390                 395                 400

Tyr Pro Ile Ser Tyr Thr Ser Val Phe Leu Lys Asn Asn Lys Ile Ala
                405                 410                 415

Gly Val Asn Asn Arg Thr Glu Tyr Val Glu Thr Thr Ser Thr Glu Tyr
            420                 425                 430

Thr Ser Gly Lys Ile Asn Leu Ser His Gln Gly Ala Tyr Val Ala Gln
        435                 440                 445

Tyr Glu Ile Leu Trp Asp Glu Ile Asn Tyr Asp Asp Lys Gly Lys Glu
    450                 455                 460

Val Ile Thr Lys Arg Arg Trp Asp Asn Asn Trp Tyr Ser Lys Thr Ser
465                 470                 475                 480

Pro Phe Ser Thr Val Ile Pro Leu Gly Ala Asn Ser Arg Asn Ile Arg
                485                 490                 495

Ile Met Ala Arg Glu Cys Thr Gly Leu Ala Phe Glu Trp Trp Arg Lys
            500                 505                 510

Val Ile Asp Glu Arg Asp Val Lys Leu Ser Lys Glu Ile Asn Val Asn
        515                 520                 525

Ile Ser Gly Ser Thr Leu Ser Pro Tyr Gly Ser Ile Thr Tyr Lys Leu
    530                 535                 540

Glu His His His His His His
545                 550

<210> SEQ ID NO 19
<211> LENGTH: 551
<212> TYPE: PRT
<213> ORGANISM: S. pyogenes
```

<400> SEQUENCE: 19

```
Met Ala Ser Glu Ser Asn Lys Gln Asn Thr Ala Ser Thr Glu Thr Thr
 1               5                  10                  15

Thr Thr Asn Glu Gln Pro Lys Pro Glu Ser Ser Glu Leu Thr Thr Glu
             20                  25                  30

Lys Ala Gly Gln Lys Thr Asp Asp Met Leu Asn Ser Asn Asp Met Ile
         35                  40                  45

Lys Leu Ala Pro Lys Glu Met Pro Leu Glu Ser Ala Glu Lys Glu Glu
 50                  55                  60

Lys Lys Ser Glu Asp Lys Lys Ser Glu Glu Asp His Thr Glu Glu
 65                  70                  75                  80

Ile Asn Asp Lys Ile Tyr Ser Leu Asn Tyr Asn Glu Leu Glu Val Leu
                 85                  90                  95

Ala Lys Asn Gly Glu Thr Ile Glu Asn Phe Val Pro Lys Glu Gly Val
            100                 105                 110

Lys Lys Ala Asp Lys Phe Ile Val Ile Glu Arg Lys Lys Lys Asn Ile
        115                 120                 125

Asn Thr Thr Pro Val Asp Ile Ser Ile Ile Asp Ser Val Thr Asp Arg
    130                 135                 140

Thr Tyr Pro Ala Ala Leu Gln Leu Ala Asn Lys Gly Phe Thr Glu Asn
145                 150                 155                 160

Lys Pro Asp Ala Val Val Thr Lys Arg Asn Pro Gln Lys Ile His Ile
                165                 170                 175

Asp Leu Pro Gly Met Gly Asp Lys Ala Thr Val Glu Val Asn Asp Pro
            180                 185                 190

Thr Tyr Ala Asn Val Ser Thr Ala Ile Asp Asn Leu Val Asn Gln Trp
        195                 200                 205

His Asp Asn Tyr Ser Gly Gly Asn Thr Leu Pro Ala Arg Thr Gln Tyr
    210                 215                 220

Thr Glu Ser Met Val Tyr Ser Lys Ser Gln Ile Glu Ala Ala Leu Asn
225                 230                 235                 240

Val Asn Ser Lys Ile Leu Asp Gly Thr Leu Gly Ile Asp Phe Lys Ser
                245                 250                 255

Ile Ser Lys Gly Glu Lys Lys Val Met Ile Ala Ala Tyr Lys Gln Ile
            260                 265                 270

Phe Tyr Thr Val Ser Ala Asn Leu Pro Asn Asn Pro Ala Asp Val Phe
        275                 280                 285

Asp Lys Ser Val Thr Phe Lys Glu Leu Gln Arg Lys Gly Val Ser Asn
    290                 295                 300

Glu Ala Pro Pro Leu Phe Val Ser Asn Val Ala Tyr Gly Arg Thr Val
305                 310                 315                 320

Phe Val Lys Leu Glu Thr Ser Ser Lys Ser Asn Asp Val Glu Ala Ala
                325                 330                 335

Phe Ser Ala Ala Leu Lys Gly Thr Asp Val Lys Thr Asn Gly Lys Tyr
            340                 345                 350

Ser Asp Ile Leu Glu Asn Ser Ser Phe Thr Ala Val Val Leu Gly Gly
        355                 360                 365

Asp Ala Ala Glu His Asn Lys Val Val Thr Lys Asp Phe Asp Val Ile
    370                 375                 380

Arg Asn Val Ile Lys Asp Asn Ala Thr Phe Ser Arg Lys Asn Pro Ala
385                 390                 395                 400

Tyr Pro Ile Ser Tyr Thr Ser Val Phe Leu Lys Asn Asn Lys Ile Ala
                405                 410                 415
```

-continued

Gly Val Asn Asn Arg Thr Glu Tyr Val Glu Thr Thr Ser Thr Glu Tyr
                420                 425                 430

Thr Ser Gly Lys Ile Asn Leu Ser His Gln Gly Ala Tyr Val Ala Gln
            435                 440                 445

Tyr Glu Ile Leu Trp Asn Glu Ile Asn Tyr Asp Asp Lys Gly Lys Glu
        450                 455                 460

Val Ile Thr Lys Arg Arg Trp Asp Asn Asn Trp Tyr Ser Lys Thr Ser
465                 470                 475                 480

Pro Phe Ser Thr Val Ile Pro Leu Gly Ala Asn Ser Arg Asn Ile Arg
                485                 490                 495

Ile Met Ala Arg Glu Cys Thr Gly Leu Ala Phe Glu Trp Trp Arg Lys
            500                 505                 510

Val Ile Asp Glu Arg Asp Val Lys Leu Ser Lys Glu Ile Asn Val Asn
        515                 520                 525

Ile Ser Gly Ser Thr Leu Ser Pro Tyr Gly Ser Ile Thr Tyr Lys Leu
530                 535                 540

Glu His His His His His His
545                 550

<210> SEQ ID NO 20
<211> LENGTH: 543
<212> TYPE: PRT
<213> ORGANISM: S. pyogenes

<400> SEQUENCE: 20

Met Ala Ser Glu Ser Asn Lys Gln Asn Thr Ala Ser Thr Glu Thr Thr
 1               5                   10                  15

Thr Thr Asn Glu Gln Pro Lys Pro Glu Ser Ser Glu Leu Thr Thr Glu
            20                  25                  30

Lys Ala Gly Gln Lys Thr Asp Asp Met Leu Asn Ser Asn Asp Met Ile
        35                  40                  45

Lys Leu Ala Pro Lys Glu Met Pro Leu Glu Ser Ala Lys Glu Glu
    50                  55                  60

Lys Lys Ser Glu Asp Lys Lys Ser Glu Glu Asp His Thr Glu Glu
65                  70                  75                  80

Ile Asn Asp Lys Ile Tyr Ser Leu Asn Tyr Asn Glu Leu Glu Val Leu
                85                  90                  95

Ala Lys Asn Gly Glu Thr Ile Glu Asn Phe Val Pro Lys Glu Gly Val
            100                 105                 110

Lys Lys Ala Asp Lys Phe Ile Val Ile Glu Arg Lys Lys Lys Asn Ile
        115                 120                 125

Asn Thr Thr Pro Val Asp Ile Ser Ile Ile Asp Ser Val Thr Asp Arg
    130                 135                 140

Thr Tyr Pro Ala Ala Leu Gln Leu Ala Asn Lys Gly Phe Thr Glu Asn
145                 150                 155                 160

Lys Pro Asp Ala Val Val Thr Lys Arg Asn Pro Gln Lys Ile His Ile
                165                 170                 175

Asp Leu Pro Gly Met Gly Asp Lys Ala Thr Val Glu Val Asn Asp Pro
            180                 185                 190

Thr Tyr Ala Asn Val Ser Thr Ala Ile Asp Asn Leu Val Asn Gln Trp
        195                 200                 205

His Asp Asn Tyr Ser Gly Gly Asn Thr Leu Pro Ala Arg Thr Gln Tyr
    210                 215                 220

Thr Glu Ser Met Val Tyr Ser Lys Ser Gln Ile Glu Ala Ala Leu Asn
225                 230                 235                 240

```
Val Asn Ser Lys Ile Leu Asp Gly Thr Leu Gly Ile Asp Phe Lys Ser
                245                 250                 255

Ile Ser Lys Gly Glu Lys Lys Val Met Ile Ala Ala Tyr Lys Gln Ile
            260                 265                 270

Phe Tyr Thr Val Ser Ala Asn Leu Pro Asn Asn Pro Ala Asp Val Phe
            275                 280                 285

Asp Lys Ser Val Thr Phe Lys Glu Leu Gln Arg Lys Gly Val Ser Asn
    290                 295                 300

Glu Ala Pro Pro Leu Phe Val Ser Asn Val Ala Tyr Gly Arg Thr Val
305                 310                 315                 320

Phe Val Lys Leu Glu Thr Ser Ser Lys Ser Asn Asp Val Glu Ala Ala
                325                 330                 335

Phe Ser Ala Ala Leu Lys Gly Thr Asp Val Lys Thr Asn Gly Lys Tyr
            340                 345                 350

Ser Asp Ile Leu Glu Asn Ser Ser Phe Thr Ala Val Val Leu Gly Gly
            355                 360                 365

Asp Ala Ala Glu His Asn Lys Val Val Thr Lys Asp Phe Asp Val Ile
    370                 375                 380

Arg Asn Val Ile Lys Asp Asn Ala Thr Phe Ser Arg Lys Asn Leu Ala
385                 390                 395                 400

Tyr Pro Ile Ser Tyr Thr Ser Val Phe Leu Lys Asn Asn Lys Ile Ala
                405                 410                 415

Gly Val Asn Asn Arg Thr Glu Tyr Val Glu Thr Thr Ser Thr Glu Tyr
            420                 425                 430

Thr Ser Gly Lys Ile Asn Leu Ser His Gln Gly Ala Tyr Val Ala Gln
            435                 440                 445

Tyr Glu Ile Leu Trp Asp Glu Ile Asn Tyr Asp Asp Lys Gly Lys Glu
    450                 455                 460

Val Ile Thr Lys Arg Arg Trp Asp Asn Asn Trp Tyr Ser Lys Thr Ser
465                 470                 475                 480

Pro Phe Ser Thr Val Ile Pro Leu Gly Ala Asn Ser Arg Asn Ile Arg
                485                 490                 495

Ile Met Ala Arg Glu Cys Thr Gly Leu Ala Trp Glu Trp Trp Arg Lys
            500                 505                 510

Val Ile Asp Glu Arg Asp Val Lys Leu Ser Lys Glu Ile Asn Val Asn
            515                 520                 525

Ile Ser Gly Ser Thr Leu Ser Pro Tyr Gly Ser Ile Thr Tyr Lys
    530                 535                 540

<210> SEQ ID NO 21
<211> LENGTH: 571
<212> TYPE: PRT
<213> ORGANISM: S. pyogenes

<400> SEQUENCE: 21

Met Ser Asn Lys Lys Thr Phe Lys Lys Tyr Ser Arg Val Ala Gly Leu
1               5                   10                  15

Leu Thr Ala Ala Leu Ile Ile Gly Asn Leu Val Thr Ala Asn Ala Glu
            20                  25                  30

Ser Asn Lys Gln Asn Thr Ala Ser Thr Glu Thr Thr Thr Asn Glu
            35                  40                  45

Gln Pro Lys Pro Glu Ser Ser Glu Leu Thr Thr Glu Lys Ala Gly Gln
    50                  55                  60

Lys Thr Asp Asp Met Leu Asn Ser Asn Asp Met Ile Lys Leu Ala Pro
65                  70                  75                  80
```

```
Lys Glu Met Pro Leu Glu Ser Ala Glu Lys Glu Lys Lys Ser Glu
                85                  90                  95
Asp Lys Lys Lys Ser Glu Glu Asp His Thr Glu Ile Asn Asp Lys
            100                 105                 110
Ile Tyr Ser Leu Asn Tyr Asn Glu Leu Glu Val Leu Ala Lys Asn Gly
        115                 120                 125
Glu Thr Ile Glu Asn Phe Val Pro Lys Glu Gly Val Lys Lys Ala Asp
    130                 135                 140
Lys Phe Ile Val Ile Glu Arg Lys Lys Lys Asn Ile Asn Thr Thr Pro
145                 150                 155                 160
Val Asp Ile Ser Ile Ile Asp Ser Val Thr Asp Arg Thr Tyr Pro Ala
                165                 170                 175
Ala Leu Gln Leu Ala Asn Lys Gly Phe Thr Glu Asn Lys Pro Asp Ala
            180                 185                 190
Val Val Thr Lys Arg Asn Pro Gln Lys Ile His Ile Asp Leu Pro Gly
        195                 200                 205
Met Gly Asp Lys Ala Thr Val Glu Val Asn Asp Pro Thr Tyr Ala Asn
    210                 215                 220
Val Ser Thr Ala Ile Asp Asn Leu Val Asn Gln Trp His Asp Asn Tyr
225                 230                 235                 240
Ser Gly Gly Asn Thr Leu Pro Ala Arg Thr Gln Tyr Thr Glu Ser Met
                245                 250                 255
Val Tyr Ser Lys Ser Gln Ile Glu Ala Ala Leu Asn Val Asn Ser Lys
            260                 265                 270
Ile Leu Asp Gly Thr Leu Gly Ile Asp Phe Lys Ser Ile Ser Lys Gly
        275                 280                 285
Glu Lys Lys Val Met Ile Ala Ala Tyr Lys Gln Ile Phe Tyr Thr Val
    290                 295                 300
Ser Ala Asn Leu Pro Asn Asn Pro Ala Asp Val Phe Asp Lys Ser Val
305                 310                 315                 320
Thr Phe Lys Glu Leu Gln Arg Lys Gly Val Ser Asn Glu Ala Pro Pro
                325                 330                 335
Leu Phe Val Ser Asn Val Ala Tyr Gly Arg Thr Val Phe Val Lys Leu
            340                 345                 350
Glu Thr Ser Ser Lys Ser Asn Asp Val Glu Ala Ala Phe Ser Ala Ala
    355                 360                 365
Leu Lys Gly Thr Asp Val Lys Thr Asn Gly Lys Tyr Ser Asp Ile Leu
370                 375                 380
Glu Asn Ser Ser Phe Thr Ala Val Val Leu Gly Gly Asp Ala Ala Glu
385                 390                 395                 400
His Asn Lys Val Val Thr Lys Asp Phe Asp Val Ile Arg Asn Val Ile
            405                 410                 415
Lys Asp Asn Ala Thr Phe Ser Arg Lys Asn Pro Ala Tyr Pro Ile Ser
        420                 425                 430
Tyr Thr Ser Val Phe Leu Lys Asn Asn Lys Ile Ala Gly Val Asn Asn
    435                 440                 445
Arg Thr Glu Tyr Val Glu Thr Thr Ser Thr Glu Tyr Thr Ser Gly Lys
450                 455                 460
Ile Asn Leu Ser His Gln Gly Ala Tyr Val Ala Gln Tyr Glu Ile Leu
465                 470                 475                 480
Trp Asp Glu Ile Asn Tyr Asp Asp Lys Gly Lys Glu Val Ile Thr Lys
                485                 490                 495
Arg Arg Trp Asp Asn Asn Trp Tyr Ser Lys Thr Ser Pro Phe Ser Thr
            500                 505                 510
```

```
Val Ile Pro Leu Gly Ala Asn Ser Arg Asn Ile Arg Ile Met Ala Arg
            515                 520                 525

Glu Cys Thr Gly Leu Ala Phe Glu Trp Trp Arg Lys Val Ile Asp Glu
        530                 535                 540

Arg Asp Val Lys Leu Ser Lys Glu Ile Asn Val Asn Ile Ser Gly Ser
545                 550                 555                 560

Thr Leu Ser Pro Tyr Gly Ser Ile Thr Tyr Lys
                565                 570

<210> SEQ ID NO 22
<211> LENGTH: 571
<212> TYPE: PRT
<213> ORGANISM: S. pyogenes

<400> SEQUENCE: 22

Met Ser Asn Lys Lys Thr Phe Lys Lys Tyr Ser Arg Val Ala Gly Leu
1               5                   10                  15

Leu Thr Ala Ala Leu Ile Ile Gly Asn Leu Val Thr Ala Asn Ala Glu
            20                  25                  30

Ser Asn Lys Gln Asn Thr Ala Ser Thr Glu Thr Thr Thr Thr Asn Glu
        35                  40                  45

Gln Pro Lys Pro Glu Ser Ser Glu Leu Thr Thr Glu Lys Ala Gly Gln
    50                  55                  60

Lys Thr Asp Asp Met Leu Asn Ser Asn Asp Met Ile Lys Leu Ala Pro
65                  70                  75                  80

Lys Glu Met Pro Leu Glu Ser Ala Glu Lys Glu Lys Lys Ser Glu
            85                  90                  95

Asp Lys Lys Lys Ser Glu Glu Asp His Thr Glu Glu Ile Asn Asp Lys
            100                 105                 110

Ile Tyr Ser Leu Asn Tyr Asn Glu Leu Glu Val Leu Ala Lys Asn Gly
            115                 120                 125

Glu Thr Ile Glu Asn Phe Val Pro Lys Glu Gly Val Lys Lys Ala Asp
        130                 135                 140

Lys Phe Ile Val Ile Glu Arg Lys Lys Asn Ile Asn Thr Thr Pro
145                 150                 155                 160

Val Asp Ile Ser Ile Ile Asp Ser Val Thr Asp Arg Thr Tyr Pro Ala
                165                 170                 175

Ala Leu Gln Leu Ala Asn Lys Gly Phe Thr Glu Asn Lys Pro Asp Ala
            180                 185                 190

Val Val Thr Lys Arg Asn Pro Gln Lys Ile His Ile Asp Leu Pro Gly
        195                 200                 205

Met Gly Asp Lys Ala Thr Val Glu Val Asn Asp Pro Thr Tyr Ala Asn
    210                 215                 220

Val Ser Thr Ala Ile Asp Asn Leu Val Asn Gln Trp His Asp Asn Tyr
225                 230                 235                 240

Ser Gly Gly Asn Thr Leu Pro Ala Arg Thr Gln Tyr Thr Glu Ser Met
            245                 250                 255

Val Tyr Ser Lys Ser Gln Ile Glu Ala Ala Leu Asn Val Asn Ser Lys
        260                 265                 270

Ile Leu Asp Gly Thr Leu Gly Ile Asp Phe Lys Ser Ile Ser Lys Gly
    275                 280                 285

Glu Lys Lys Val Met Ile Ala Ala Tyr Lys Gln Ile Phe Tyr Thr Val
        290                 295                 300

Ser Ala Asn Leu Pro Asn Asn Pro Ala Asp Val Phe Asp Lys Ser Val
305                 310                 315                 320
```

```
Thr Phe Lys Glu Leu Gln Arg Lys Gly Val Ser Asn Glu Ala Pro Pro
            325                 330                 335

Leu Phe Val Ser Asn Val Ala Tyr Gly Arg Thr Val Phe Val Lys Leu
            340                 345                 350

Glu Thr Ser Ser Lys Ser Asn Asp Val Glu Ala Ala Phe Ser Ala Ala
            355                 360                 365

Leu Lys Gly Thr Asp Val Lys Thr Asn Gly Lys Tyr Ser Asp Ile Leu
            370                 375                 380

Glu Asn Ser Ser Phe Thr Ala Val Val Leu Gly Gly Asp Ala Ala Glu
385                 390                 395                 400

His Asn Lys Val Val Thr Lys Asp Phe Asp Val Ile Arg Asn Val Ile
            405                 410                 415

Lys Asp Asn Ala Thr Phe Ser Arg Lys Asn Pro Ala Tyr Pro Ile Ser
            420                 425                 430

Tyr Thr Ser Val Phe Leu Lys Asn Asn Lys Ile Ala Gly Val Asn Asn
            435                 440                 445

Arg Thr Glu Tyr Val Glu Thr Thr Ser Thr Glu Tyr Thr Ser Gly Lys
            450                 455                 460

Ile Asn Leu Ser His Gln Gly Ala Tyr Val Ala Gln Tyr Glu Ile Leu
465                 470                 475                 480

Trp Asp Glu Ile Asn Tyr Asp Asp Lys Gly Lys Glu Val Ile Thr Lys
            485                 490                 495

Arg Arg Trp Asp Asn Asn Trp Tyr Ser Lys Thr Ser Pro Phe Ser Thr
            500                 505                 510

Val Ile Pro Leu Gly Ala Asn Ser Arg Asn Ile Arg Ile Met Ala Arg
            515                 520                 525

Glu Gly Thr Gly Leu Ala Trp Glu Trp Trp Arg Lys Val Ile Asp Glu
            530                 535                 540

Arg Asp Val Lys Leu Ser Lys Glu Ile Asn Val Asn Ile Ser Gly Ser
545                 550                 555                 560

Thr Leu Ser Pro Tyr Gly Ser Ile Thr Tyr Lys
            565                 570

<210> SEQ ID NO 23
<211> LENGTH: 570
<212> TYPE: PRT
<213> ORGANISM: S. pyogenes

<400> SEQUENCE: 23

Met Ser Asn Lys Lys Thr Phe Lys Lys Tyr Ser Arg Val Ala Gly Leu
1               5                   10                  15

Leu Thr Ala Ala Leu Ile Ile Gly Asn Leu Val Thr Ala Asn Ala Glu
            20                  25                  30

Ser Asn Lys Gln Asn Thr Ala Ser Thr Glu Thr Thr Thr Asn Glu
            35                  40                  45

Gln Pro Lys Pro Glu Ser Ser Glu Leu Thr Thr Glu Lys Ala Gly Gln
            50                  55                  60

Lys Thr Asp Asp Met Leu Asn Ser Asn Asp Met Ile Lys Leu Ala Pro
65                  70                  75                  80

Lys Glu Met Pro Leu Glu Ser Ala Glu Lys Glu Lys Lys Ser Glu
            85                  90                  95

Asp Lys Lys Lys Ser Glu Glu Asp His Thr Glu Glu Ile Asn Asp Lys
            100                 105                 110

Ile Tyr Ser Leu Asn Tyr Asn Glu Leu Glu Val Leu Ala Lys Asn Gly
            115                 120                 125
```

-continued

```
Glu Thr Ile Glu Asn Phe Val Pro Lys Glu Gly Val Lys Lys Ala Asp
    130                 135                 140

Lys Phe Ile Val Ile Glu Arg Lys Lys Lys Asn Ile Asn Thr Thr Pro
145                 150                 155                 160

Val Asp Ile Ser Ile Ile Asp Ser Val Thr Asp Arg Thr Tyr Pro Ala
                165                 170                 175

Ala Leu Gln Leu Ala Asn Lys Gly Phe Thr Glu Asn Lys Pro Asp Ala
                180                 185                 190

Val Val Thr Lys Arg Asn Pro Gln Lys Ile His Ile Asp Leu Pro Gly
            195                 200                 205

Met Gly Asp Lys Ala Thr Val Glu Val Asn Asp Pro Tyr Ala Asn
    210                 215                 220

Val Ser Thr Ala Ile Asp Asn Leu Val Asn Gln Trp His Asp Asn Tyr
225                 230                 235                 240

Ser Gly Gly Asn Thr Leu Pro Arg Thr Gln Tyr Thr Glu Ser Met Val
                245                 250                 255

Tyr Ser Lys Ser Gln Ile Glu Ala Ala Leu Asn Val Asn Ser Lys Ile
                260                 265                 270

Leu Asp Gly Thr Leu Gly Ile Asp Phe Lys Ser Ile Ser Lys Gly Glu
            275                 280                 285

Lys Lys Val Met Ile Ala Ala Tyr Lys Gln Ile Phe Tyr Thr Val Ser
    290                 295                 300

Ala Asn Leu Pro Asn Asn Pro Ala Asp Val Phe Asp Lys Ser Val Thr
305                 310                 315                 320

Phe Lys Glu Leu Gln Arg Lys Gly Val Ser Asn Glu Ala Pro Pro Leu
                325                 330                 335

Phe Val Ser Asn Val Ala Tyr Gly Arg Thr Val Phe Val Lys Leu Glu
                340                 345                 350

Thr Ser Ser Lys Ser Asn Asp Val Glu Ala Ala Phe Ser Ala Ala Leu
            355                 360                 365

Lys Gly Thr Asp Val Lys Thr Asn Gly Lys Tyr Ser Asp Ile Leu Glu
    370                 375                 380

Asn Ser Ser Phe Thr Ala Val Leu Gly Gly Asp Ala Ala Glu His
385                 390                 395                 400

Asn Lys Val Val Thr Lys Asp Phe Asp Val Ile Arg Asn Val Ile Lys
                405                 410                 415

Asp Asn Ala Thr Phe Ser Arg Lys Asn Pro Ala Tyr Pro Ile Ser Tyr
                420                 425                 430

Thr Ser Val Phe Leu Lys Asn Asn Lys Ile Ala Gly Val Asn Asn Arg
            435                 440                 445

Thr Glu Tyr Val Glu Thr Thr Ser Thr Glu Tyr Thr Ser Gly Lys Ile
    450                 455                 460

Asn Leu Ser His Gln Gly Ala Tyr Val Ala Gln Tyr Glu Ile Leu Trp
465                 470                 475                 480

Asp Glu Ile Asn Tyr Asp Asp Lys Gly Lys Glu Val Ile Thr Lys Arg
                485                 490                 495

Arg Trp Asp Asn Asn Trp Tyr Ser Lys Thr Ser Pro Phe Ser Thr Val
                500                 505                 510

Ile Pro Leu Gly Ala Asn Ser Arg Asn Ile Arg Ile Met Ala Arg Glu
            515                 520                 525

Cys Thr Gly Leu Ala Trp Glu Trp Trp Arg Lys Val Ile Asp Glu Arg
    530                 535                 540
```

```
Asp Val Lys Leu Ser Lys Glu Ile Asn Val Asn Ile Ser Gly Ser Thr
545                 550                 555                 560

Leu Ser Pro Tyr Gly Ser Ile Thr Tyr Lys
            565                 570

<210> SEQ ID NO 24
<211> LENGTH: 571
<212> TYPE: PRT
<213> ORGANISM: S. pyogenes

<400> SEQUENCE: 24

Met Ser Asn Lys Lys Thr Phe Lys Lys Tyr Ser Arg Val Ala Gly Leu
  1               5                  10                  15

Leu Thr Ala Ala Leu Ile Ile Gly Asn Leu Val Thr Ala Asn Ala Glu
             20                  25                  30

Ser Asn Lys Gln Asn Thr Ala Ser Thr Glu Thr Thr Thr Asn Glu
             35                  40                  45

Gln Pro Lys Pro Glu Ser Ser Glu Leu Thr Thr Glu Lys Ala Gly Gln
 50                  55                  60

Lys Thr Asp Asp Met Leu Asn Ser Asn Asp Met Ile Lys Leu Ala Pro
 65                  70                  75                  80

Lys Glu Met Pro Leu Glu Ser Ala Glu Lys Glu Lys Lys Ser Glu
                 85                  90                  95

Asp Lys Lys Lys Ser Glu Glu Asp His Thr Glu Glu Ile Asn Asp Lys
                100                 105                 110

Ile Tyr Ser Leu Asn Tyr Asn Glu Leu Glu Val Leu Ala Lys Asn Gly
            115                 120                 125

Glu Thr Ile Glu Asn Phe Val Pro Lys Glu Gly Val Lys Lys Ala Asp
130                 135                 140

Lys Phe Ile Val Ile Glu Arg Lys Lys Lys Asn Ile Asn Thr Thr Pro
145                 150                 155                 160

Val Asp Ile Ser Ile Ile Asp Ser Val Thr Asp Arg Thr Tyr Pro Ala
                165                 170                 175

Ala Leu Gln Leu Ala Asn Lys Gly Phe Thr Glu Asn Lys Pro Asp Ala
            180                 185                 190

Val Val Thr Lys Arg Asn Pro Gln Lys Ile His Ile Asp Leu Pro Gly
            195                 200                 205

Met Gly Asp Lys Ala Thr Val Glu Val Asn Asp Pro Thr Tyr Ala Asn
210                 215                 220

Val Ser Thr Ala Ile Asp Asn Leu Val Asn Gln Trp His Asp Asn Tyr
225                 230                 235                 240

Ser Gly Gly Asn Thr Leu Pro Ala Arg Thr Gln Tyr Thr Glu Ser Met
                245                 250                 255

Val Tyr Ser Lys Ser Gln Ile Glu Ala Ala Leu Asn Val Asn Ser Lys
            260                 265                 270

Ile Leu Asp Gly Thr Leu Gly Ile Asp Phe Lys Ser Ile Ser Lys Gly
            275                 280                 285

Glu Lys Lys Val Met Ile Ala Ala Tyr Lys Gln Ile Phe Tyr Thr Val
290                 295                 300

Ser Ala Asn Leu Pro Asn Asn Pro Ala Asp Val Phe Asp Lys Ser Val
305                 310                 315                 320

Thr Phe Lys Glu Leu Gln Arg Lys Gly Val Ser Asn Glu Ala Pro Pro
                325                 330                 335

Leu Phe Val Ser Asn Val Ala Tyr Gly Arg Thr Val Phe Val Lys Leu
                340                 345                 350
```

```
Glu Thr Ser Ser Lys Ser Asn Asp Val Glu Ala Ala Phe Ser Ala Ala
        355                 360                 365
Leu Lys Gly Thr Asp Val Lys Thr Asn Gly Lys Tyr Ser Asp Ile Leu
370                 375                 380
Glu Asn Ser Ser Phe Thr Ala Val Val Leu Gly Gly Asp Ala Ala Glu
385                 390                 395                 400
His Asn Lys Val Val Thr Lys Asp Phe Asp Val Ile Arg Asn Val Ile
                405                 410                 415
Lys Asp Asn Ala Thr Phe Ser Arg Lys Asn Pro Ala Tyr Pro Ile Ser
                420                 425                 430
Tyr Thr Ser Val Phe Leu Lys Asn Asn Lys Ile Ala Gly Val Asn Asn
        435                 440                 445
Arg Thr Glu Tyr Val Glu Thr Thr Ser Thr Glu Tyr Thr Ser Gly Lys
450                 455                 460
Ile Asn Leu Ser His Gln Gly Ala Tyr Val Ala Gln Tyr Glu Ile Leu
465                 470                 475                 480
Trp Asn Glu Ile Asn Tyr Asp Asp Lys Gly Lys Glu Val Ile Thr Lys
                485                 490                 495
Arg Arg Trp Asp Asn Asn Trp Tyr Ser Lys Thr Ser Pro Phe Ser Thr
                500                 505                 510
Val Ile Pro Leu Gly Ala Asn Ser Arg Asn Ile Arg Ile Met Ala Arg
        515                 520                 525
Glu Cys Thr Gly Leu Ala Phe Glu Trp Trp Arg Lys Val Ile Asp Glu
530                 535                 540
Arg Asp Val Lys Leu Ser Lys Glu Ile Asn Val Asn Ile Ser Gly Ser
545                 550                 555                 560
Thr Leu Ser Pro Tyr Gly Ser Ile Thr Tyr Lys
                565                 570

<210> SEQ ID NO 25
<211> LENGTH: 543
<212> TYPE: PRT
<213> ORGANISM: S. pyogenes

<400> SEQUENCE: 25

Met Ala Ser Glu Ser Asn Lys Gln Asn Thr Ala Ser Thr Glu Thr Thr
1               5                   10                  15
Thr Thr Asn Glu Gln Pro Lys Pro Glu Ser Ser Glu Leu Thr Thr Glu
                20                  25                  30
Lys Ala Gly Gln Lys Thr Asp Asp Met Leu Asn Ser Asn Asp Met Ile
            35                  40                  45
Lys Leu Ala Pro Lys Glu Met Pro Leu Glu Ser Ala Glu Lys Glu Glu
        50                  55                  60
Lys Lys Ser Glu Asp Lys Lys Ser Glu Glu Asp His Thr Glu Glu
65                  70                  75                  80
Ile Asn Asp Lys Ile Tyr Ser Leu Asn Tyr Asn Glu Leu Glu Val Leu
                85                  90                  95
Ala Lys Asn Gly Glu Thr Ile Glu Asn Phe Val Pro Lys Glu Gly Val
            100                 105                 110
Lys Lys Ala Asp Lys Phe Ile Val Ile Glu Arg Lys Lys Lys Asn Ile
        115                 120                 125
Asn Thr Thr Pro Val Asp Ile Ser Ile Ile Asp Ser Val Thr Asp Arg
    130                 135                 140
Thr Tyr Pro Ala Ala Leu Gln Leu Ala Asn Lys Gly Phe Thr Glu Asn
145                 150                 155                 160
```

```
Lys Pro Asp Ala Val Thr Lys Arg Asn Pro Gln Lys Ile His Ile
                165                 170                 175

Asp Leu Pro Gly Met Gly Asp Lys Ala Thr Val Glu Val Asn Asp Pro
            180                 185                 190

Thr Tyr Ala Asn Val Ser Thr Ala Ile Asp Asn Leu Val Asn Gln Trp
        195                 200                 205

His Asp Asn Tyr Ser Gly Gly Asn Thr Leu Pro Ala Arg Thr Gln Tyr
    210                 215                 220

Thr Glu Ser Met Val Tyr Ser Lys Ser Gln Ile Glu Ala Ala Leu Asn
225                 230                 235                 240

Val Asn Ser Lys Ile Leu Asp Gly Thr Leu Gly Ile Asp Phe Lys Ser
                245                 250                 255

Ile Ser Lys Gly Glu Lys Lys Val Met Ile Ala Ala Tyr Lys Gln Ile
            260                 265                 270

Phe Tyr Thr Val Ser Ala Asn Leu Pro Asn Asn Pro Ala Asp Val Phe
        275                 280                 285

Asp Lys Ser Val Thr Phe Lys Glu Leu Gln Arg Lys Gly Val Ser Asn
    290                 295                 300

Glu Ala Pro Pro Leu Phe Val Ser Asn Val Ala Tyr Gly Arg Thr Val
305                 310                 315                 320

Phe Val Lys Leu Glu Thr Ser Ser Lys Ser Asn Asp Val Glu Ala Ala
                325                 330                 335

Phe Ser Ala Ala Leu Lys Gly Thr Asp Val Lys Thr Asn Gly Lys Tyr
            340                 345                 350

Ser Asp Ile Leu Glu Asn Ser Ser Phe Thr Ala Val Val Leu Gly Gly
        355                 360                 365

Asp Ala Ala Glu His Asn Lys Val Val Thr Lys Asp Phe Asp Val Ile
    370                 375                 380

Arg Asn Val Ile Lys Asp Asn Ala Thr Phe Ser Arg Lys Asn Leu Ala
385                 390                 395                 400

Tyr Pro Ile Ser Tyr Thr Ser Val Phe Leu Lys Asn Asn Lys Ile Ala
                405                 410                 415

Gly Val Asn Asn Arg Thr Glu Tyr Val Glu Thr Thr Ser Thr Glu Tyr
            420                 425                 430

Thr Ser Gly Lys Ile Asn Leu Ser His Gln Gly Ala Tyr Val Ala Gln
        435                 440                 445

Tyr Glu Ile Leu Trp Asp Glu Ile Asn Tyr Asp Asp Lys Gly Lys Glu
    450                 455                 460

Val Ile Thr Lys Arg Arg Trp Asp Asn Asn Trp Tyr Ser Lys Thr Ser
465                 470                 475                 480

Pro Phe Ser Thr Val Ile Pro Leu Gly Ala Asn Ser Arg Asn Ile Arg
                485                 490                 495

Ile Met Ala Arg Glu Cys Thr Gly Leu Ala Phe Glu Trp Trp Arg Lys
            500                 505                 510

Val Ile Asp Glu Arg Asp Val Lys Leu Ser Lys Glu Ile Asn Val Asn
    515                 520                 525

Ile Ser Gly Ser Thr Leu Ser Pro Tyr Gly Ser Ile Thr Tyr Lys
530                 535                 540

<210> SEQ ID NO 26
<211> LENGTH: 543
<212> TYPE: PRT
<213> ORGANISM: S. pyogenes
```

<400> SEQUENCE: 26

```
Met Ala Ser Glu Ser Asn Lys Gln Asn Thr Ala Ser Thr Glu Thr Thr
1               5                   10                  15

Thr Thr Asn Glu Gln Pro Lys Pro Glu Ser Ser Glu Leu Thr Thr Glu
            20                  25                  30

Lys Ala Gly Gln Lys Thr Asp Asp Met Leu Asn Ser Asn Asp Met Ile
        35                  40                  45

Lys Leu Ala Pro Lys Glu Met Pro Leu Glu Ser Ala Glu Lys Glu Glu
    50                  55                  60

Lys Lys Ser Glu Asp Lys Lys Ser Glu Glu Asp His Thr Glu Glu
65                  70                  75                  80

Ile Asn Asp Lys Ile Tyr Ser Leu Asn Tyr Asn Glu Leu Glu Val Leu
                85                  90                  95

Ala Lys Asn Gly Glu Thr Ile Glu Asn Phe Val Pro Lys Glu Gly Val
            100                 105                 110

Lys Lys Ala Asp Lys Phe Ile Val Ile Glu Arg Lys Lys Lys Asn Ile
        115                 120                 125

Asn Thr Thr Pro Val Asp Ile Ser Ile Ile Asp Ser Val Thr Asp Arg
130                 135                 140

Thr Tyr Pro Ala Ala Leu Gln Leu Ala Asn Lys Gly Phe Thr Glu Asn
145                 150                 155                 160

Lys Pro Asp Ala Val Val Thr Lys Arg Asn Pro Gln Lys Ile His Ile
                165                 170                 175

Asp Leu Pro Gly Met Gly Asp Lys Ala Thr Val Glu Val Asn Asp Pro
            180                 185                 190

Thr Tyr Ala Asn Val Ser Thr Ala Ile Asp Asn Leu Val Asn Gln Trp
        195                 200                 205

His Asp Asn Tyr Ser Gly Gly Asn Thr Leu Pro Ala Arg Thr Gln Tyr
    210                 215                 220

Thr Glu Ser Met Val Tyr Ser Lys Ser Gln Ile Glu Ala Ala Leu Asn
225                 230                 235                 240

Val Asn Ser Lys Ile Leu Asp Gly Thr Leu Gly Ile Asp Phe Lys Ser
                245                 250                 255

Ile Ser Lys Gly Glu Lys Lys Val Met Ile Ala Ala Tyr Lys Gln Ile
            260                 265                 270

Phe Tyr Thr Val Ser Ala Asn Leu Pro Asn Asn Pro Ala Asp Val Phe
        275                 280                 285

Asp Lys Ser Val Thr Phe Lys Glu Leu Gln Arg Lys Gly Val Ser Asn
    290                 295                 300

Glu Ala Pro Pro Leu Phe Val Ser Asn Val Ala Tyr Gly Arg Thr Val
305                 310                 315                 320

Phe Val Lys Leu Glu Thr Ser Ser Lys Ser Asn Asp Val Glu Ala Ala
                325                 330                 335

Phe Ser Ala Ala Leu Lys Gly Thr Asp Val Lys Thr Asn Gly Lys Tyr
            340                 345                 350

Ser Asp Ile Leu Glu Asn Ser Ser Phe Thr Ala Val Val Leu Gly Gly
        355                 360                 365

Asp Ala Ala Glu His Asn Lys Val Val Thr Lys Asp Phe Asp Val Ile
    370                 375                 380

Arg Asn Val Ile Lys Asp Asn Ala Thr Phe Ser Arg Lys Asn Leu Ala
385                 390                 395                 400

Tyr Pro Ile Ser Tyr Thr Ser Val Phe Leu Lys Asn Asn Lys Ile Ala
                405                 410                 415
```

```
Gly Val Asn Asn Arg Thr Glu Tyr Val Glu Thr Thr Ser Thr Glu Tyr
            420                 425                 430

Thr Ser Gly Lys Ile Asn Leu Ser His Gln Gly Ala Tyr Val Ala Gln
        435                 440                 445

Tyr Glu Ile Leu Trp Asp Glu Ile Asn Tyr Asp Asp Lys Gly Lys Glu
    450                 455                 460

Val Ile Thr Lys Arg Arg Trp Asp Asn Asn Trp Tyr Ser Lys Thr Ser
465                 470                 475                 480

Pro Phe Ser Thr Val Ile Pro Leu Gly Ala Asn Ser Arg Asn Ile Arg
                485                 490                 495

Ile Met Ala Arg Glu Gly Thr Gly Leu Ala Trp Glu Trp Arg Lys
                500                 505                 510

Val Ile Asp Glu Arg Asp Val Lys Leu Ser Lys Glu Ile Asn Val Asn
                515                 520                 525

Ile Ser Gly Ser Thr Leu Ser Pro Tyr Gly Ser Ile Thr Tyr Lys
        530                 535                 540

<210> SEQ ID NO 27
<211> LENGTH: 543
<212> TYPE: PRT
<213> ORGANISM: S. pyogenes

<400> SEQUENCE: 27

Met Ala Ser Glu Ser Asn Lys Gln Asn Thr Ala Ser Thr Glu Thr Thr
 1               5                  10                  15

Thr Thr Asn Glu Gln Pro Lys Pro Glu Ser Ser Glu Leu Thr Thr Glu
                20                  25                  30

Lys Ala Gly Gln Lys Thr Asp Asp Met Leu Asn Ser Asn Asp Met Ile
            35                  40                  45

Lys Leu Ala Pro Lys Glu Met Pro Leu Glu Ser Ala Glu Lys Glu Glu
     50                  55                  60

Lys Lys Ser Glu Asp Lys Lys Ser Glu Glu Asp His Thr Glu Glu
65                  70                  75                  80

Ile Asn Asp Lys Ile Tyr Ser Leu Asn Tyr Asn Glu Leu Glu Val Leu
                85                  90                  95

Ala Lys Asn Gly Glu Thr Ile Glu Asn Phe Val Pro Lys Glu Gly Val
            100                 105                 110

Lys Lys Ala Asp Lys Phe Ile Val Ile Glu Arg Lys Lys Asn Ile
        115                 120                 125

Asn Thr Thr Pro Val Asp Ile Ser Ile Ile Asp Ser Val Thr Asp Arg
        130                 135                 140

Thr Tyr Pro Ala Ala Leu Gln Leu Ala Asn Lys Gly Phe Thr Glu Asn
145                 150                 155                 160

Lys Pro Asp Ala Val Val Thr Lys Arg Asn Pro Gln Lys Ile His Ile
                165                 170                 175

Asp Leu Pro Gly Met Gly Asp Lys Ala Thr Val Glu Val Asn Asp Pro
                180                 185                 190

Thr Tyr Ala Asn Val Ser Thr Ala Ile Asp Asn Leu Val Asn Gln Trp
            195                 200                 205

His Asp Asn Tyr Ser Gly Gly Asn Thr Leu Pro Ala Arg Thr Gln Tyr
        210                 215                 220

Thr Glu Ser Met Val Tyr Ser Lys Ser Gln Ile Glu Ala Ala Leu Asn
225                 230                 235                 240

Val Asn Ser Lys Ile Leu Asp Gly Thr Leu Gly Ile Asp Phe Lys Ser
                245                 250                 255
```

```
Ile Ser Lys Gly Glu Lys Lys Val Met Ile Ala Ala Tyr Lys Gln Ile
            260                 265                 270

Phe Tyr Thr Val Ser Ala Asn Leu Pro Asn Asn Pro Ala Asp Val Phe
                275                 280                 285

Asp Lys Ser Val Thr Phe Lys Glu Leu Gln Arg Lys Gly Val Ser Asn
        290                 295                 300

Glu Ala Pro Pro Leu Phe Val Ser Asn Val Ala Tyr Gly Arg Thr Val
305                 310                 315                 320

Phe Val Lys Leu Glu Thr Ser Ser Lys Ser Asn Asp Val Glu Ala Ala
                325                 330                 335

Phe Ser Ala Ala Leu Lys Gly Thr Asp Val Lys Thr Asn Gly Lys Tyr
                340                 345                 350

Ser Asp Ile Leu Glu Asn Ser Ser Phe Thr Ala Val Val Leu Gly Gly
            355                 360                 365

Asp Ala Ala Glu His Asn Lys Val Val Thr Lys Asp Phe Asp Val Ile
        370                 375                 380

Arg Asn Val Ile Lys Asp Asn Ala Thr Phe Ser Arg Lys Asn Leu Ala
385                 390                 395                 400

Tyr Pro Ile Ser Tyr Thr Ser Val Phe Leu Lys Asn Asn Lys Ile Ala
                405                 410                 415

Gly Val Asn Asn Arg Thr Glu Tyr Val Glu Thr Thr Ser Thr Glu Tyr
            420                 425                 430

Thr Ser Gly Lys Ile Asn Leu Ser His Gln Gly Ala Tyr Val Ala Gln
        435                 440                 445

Tyr Glu Ile Leu Trp Asp Glu Ile Asn Tyr Asp Lys Gly Lys Glu
            450                 455                 460

Val Ile Thr Lys Arg Arg Trp Asp Asn Asn Trp Tyr Ser Lys Thr Ser
465                 470                 475                 480

Pro Phe Ser Thr Val Ile Pro Leu Gly Ala Asn Ser Arg Asn Ile Arg
                485                 490                 495

Ile Met Ala Arg Glu Gly Thr Gly Leu Ala Phe Glu Trp Trp Arg Lys
            500                 505                 510

Val Ile Asp Glu Arg Asp Val Lys Leu Ser Lys Glu Ile Asn Val Asn
        515                 520                 525

Ile Ser Gly Ser Thr Leu Ser Pro Tyr Gly Ser Ile Thr Tyr Lys
        530                 535                 540

<210> SEQ ID NO 28
<211> LENGTH: 1632
<212> TYPE: DNA
<213> ORGANISM: S. pyogenes

<400> SEQUENCE: 28
atggctagcg aatcgaacaa acaaaacact gctagtacag aaaccacaac gacaaatgag      60
caaccaaagc cagaaagtag tgagctaact actgaaaaag caggtcagaa aacggatgat     120
atgcttaact ctaacgatat gattaagctt gctcccaaag aaatgccact agaatctgca     180
gaaaaagaag aaaaaaagtc agaagacaaa aaaagagcg aagaagatca cactgaagaa     240
atcaatgaca gatttattc actaaattat aatgagcttg aagtacttgc taaaaatggt     300
gaaaccattg aaaattttgt tcctaaagaa ggcgttaaga agctgataa atttattgtc     360 attgaaagaa agaaaaaaaa tatcaacact acaccagtcg atatttccat tattgactct     420
gtcactgata ggacctatcc agcagccctt cagctggcta taaaggttt taccgaaaac     480 aaaccagacg cggtagtcac caagcgaaac ccacaaaaaa tccatattga tttaccaggt     540
```

| | |
|---|---|
| atgggagaca aagcaacggt tgaggtcaat gaccctacct atgccaatgt tcaacagct | 600 |
| attgataatc ttgttaacca atggcatgat aattattctg gtggtaatac gcttcctgcc | 660 |
| agaacacaat atactgaatc aatggtatat tctaagtcac agattgaggc agctctaaat | 720 |
| gttaatagca aaatcttaga tggtacttta ggcattgatt tcaagtcgat ttcaaaaggt | 780 |
| gaaaagaagg tgatgattgc agcatacaag caaatttttt acaccgtatc agcaaacctt | 840 |
| cctaataatc ctgcggatgt gtttgataaa tcggtgacct ttaaagagtt gcaacgaaaa | 900 |
| ggtgtcagca atgaagctcc gccactcttt gtgagtaacg tagcctatgg tcgaactgtt | 960 |
| tttgtcaaac tagaaacaag ttctaaaagt aatgatgttg aagcggcctt tagtgcagct | 1020 |
| ctaaaaggaa cagatgttaa aactaatgga aaatattctg atatcttaga aaatagctca | 1080 |
| tttacagctg tcgttttagg aggagatgct gcagagcaca ataaggtagt cacaaaagac | 1140 |
| tttgatgtta ttagaaacgt tatcaaagac aatgctacct tcagtagaaa aaacctagct | 1200 |
| tatcctattt catacaccag tgttttcctt aaaaataata aaattgcggg tgtcaataac | 1260 |
| agaactgaat acgttgaaac aacatctacc gagtacacta gtggaaaaat taacctgtct | 1320 |
| catcaaggcg cgtatgttgc tcaatatgaa atcctttggg atgaaatcaa ttatgatgac | 1380 |
| aaaggaaaag aagtgattac aaaacgacgt tgggacaaca actggtatag taagacatca | 1440 |
| ccatttagca cagttatccc actaggagct aattcacgaa atatccgtat catggctaga | 1500 |
| gagtgcactg gcttagcttg gaatggtgg cgaaaagtga tcgacgaaag agatgtgaaa | 1560 |
| ctgtctaaag aaatcaatgt caatatctca ggatcaacct tgagcccata tggttcgatt | 1620 |
| acttataagt ag | 1632 |

<210> SEQ ID NO 29
<211> LENGTH: 1632
<212> TYPE: DNA
<213> ORGANISM: S. pyogenes

<400> SEQUENCE: 29

| | |
|---|---|
| atggctagcg aatcgaacaa acaaaacact gctagtacag aaaccacaac gacaaatgag | 60 |
| caaccaaagc cagaaagtag tgagctaact actgaaaaag caggtcagaa aacggatgat | 120 |
| atgcttaact ctaacgatat gattaagctt gctcccaaag aaatgccact agaatctgca | 180 |
| gaaaagaag aaaaaaagtc agaagacaaa aaaagagcg aagaagatca cactgaagaa | 240 |
| atcaatgaca gatttattc actaaattat aatgagcttg aagtacttgc taaaaatggt | 300 |
| gaaaccattg aaattttgt tcctaaagaa ggcgttaaga agctgataa atttattgtc | 360 |
| attgaaagaa agaaaaaaaa tatcaacact acaccagtcg atatttccat tattgactct | 420 |
| gtcactgata ggacctatcc agcagccctt cagctggcta taaaggtt taccgaaaac | 480 |
| aaaccagacg cggtagtcac caagcgaaac ccacaaaaaa tccatattga tttaccaggt | 540 |
| atgggagaca aagcaacggt tgaggtcaat gaccctacct atgccaatgt tcaacagct | 600 |
| attgataatc ttgttaacca atggcatgat aattattctg gtggtaatac gcttcctgcc | 660 |
| agaacacaat atactgaatc aatggtatat tctaagtcac agattgaggc agctctaaat | 720 |
| gttaatagca aaatcttaga tggtacttta ggcattgatt tcaagtcgat ttcaaaaggt | 780 |
| gaaaagaagg tgatgattgc agcatacaag caaatttttt acaccgtatc agcaaacctt | 840 |
| cctaataatc ctgcggatgt gtttgataaa tcggtgacct ttaaagagtt gcaacgaaaa | 900 |
| ggtgtcagca atgaagctcc gccactcttt gtgagtaacg tagcctatgg tcgaactgtt | 960 |
| tttgtcaaac tagaaacaag ttctaaaagt aatgatgttg aagcggcctt tagtgcagct | 1020 |

-continued

```
ctaaaaggaa cagatgttaa aactaatgga aaatattctg atatcttaga aaatagctca    1080
tttacagctg tcgttttagg aggagatgct gcagagcaca ataaggtagt cacaaaagac    1140
tttgatgtta ttagaaacgt tatcaaagac aatgctacct tcagtagaaa aaacctagct    1200
tatcctattt catacaccag tgttttcctt aaaaataata aaattgcggg tgtcaataac    1260
agaactgaat acgttgaaac aacatctacc gagtacacta gtggaaaaat taacctgtct    1320
catcaaggcg cgtatgttgc tcaatatgaa atcctttggg atgaaatcaa ttatgatgac    1380
aaaggaaaag aagtgattac aaaacgacgt tgggacaaca actggtatag taagacatca    1440
ccatttagca cagttatccc actaggagct aattcacgaa atatccgtat catggctaga    1500
gagggcactg gcttagcttt cgaatggtgg cgaaaagtga tcgacgaaag agatgtgaaa    1560
ctgtctaaag aaatcaatgt caatatctca ggatcaacct tgagcccata tggttcgatt    1620
acttataagt ga                                                       1632
```

<210> SEQ ID NO 30
<211> LENGTH: 1632
<212> TYPE: DNA
<213> ORGANISM: S. pyogenes

<400> SEQUENCE: 30

```
atggctagcg aatcgaacaa acaaaacact gctagtacag aaaccacaac gacaaatgag     60
caaccaaagc cagaaagtag tgagctaact actgaaaaag caggtcagaa aacggatgat    120
atgcttaact ctaacgatat gattaagctt gctcccaaag aaatgccact agaatctgca    180
gaaaaagaag aaaaaaagtc agaagacaaa aaaagagcg aagaagatca cactgaagaa    240
atcaatgaca gatttattc actaaattat aatgagcttg aagtacttgc taaaaatggt    300
gaaaccattg aaaattttgt tcctaaagaa ggcgttaaga aagctgataa atttattgtc    360
attgaaagaa agaaaaaaaa tatcaacact acaccagtcg atatttccat tattgactct    420
gtcactgata ggacctatcc agcagccctt cagctggcta ataaggtttt taccgaaaac    480
aaaccagacg cggtagtcac caagcgaaac ccacaaaaaa tccatattga tttaccaggt    540
atgggagaca agcaacggt tgaggtcaat gaccctacct atgccaatgt ttcaacagct    600
attgataatc ttgttaacca atggcatgat aattattctg gtggtaatac gcttcctgcc    660
agaacacaat atactgaatc aatggtatat tctaagtcac agattgaggc agctctaaat    720
gttaatagca aaatcttaga tggtactttc ggcattgatt tcaagtcgat ttcaaaaggt    780
gaaaagaagg tgatgattgc agcatacaag caaattttt acaccgtatc agcaaacctt    840
cctaataatc ctgcggatgt gtttgataaa tcggtgacct taaagagtt gcaacgaaaa    900 ggtgtcagca atgaagctcc gccactcttt gtgagtaacg tagcctatgg tcgaactgtt    960
tttgtcaaac tagaaacaag ttctaaaagt aatgatgttg aagcggcctt tagtgcagct   1020
ctaaaaggaa cagatgttaa aactaatgga aaatattctg atatcttaga aaatagctca   1080
tttacagctg tcgttttagg aggagatgct gcagagcaca ataaggtagt cacaaaagac   1140
tttgatgtta ttagaaacgt tatcaaagac aatgctacct tcagtagaaa aaacctagct   1200
tatcctattt catacaccag tgttttcctt aaaaataata aaattgcggg tgtcaataac   1260
agaactgaat acgttgaaac aacatctacc gagtacacta gtggaaaaat taacctgtct   1320
catcaaggcg cgtatgttgc tcaatatgaa atcctttggg atgaaatcaa ttatgatgac   1380
aaaggaaaag aagtgattac aaaacgacgt tgggacaaca actggtatag taagacatca   1440
ccatttagca cagttatccc actaggagct aattcacgaa atatccgtat catggctaga   1500
```

-continued

```
gagggcactg gcttagcttt cgaatggtgg cgaaaagtga tcgacgaaag agatgtgaaa    1560
ctgtctaaag aaatcaatgt caatatctca ggatcaacct tgagcccata tggttcgatt    1620
acttataagt ga                                                        1632

<210> SEQ ID NO 31
<211> LENGTH: 1632
<212> TYPE: DNA
<213> ORGANISM: S. pyogenes

<400> SEQUENCE: 31
atggctagcg aatcgaacaa acaaaacact gctagtacag aaaccacaac gacaaatgag      60
caaccaaagc cagaaagtag tgagctaact actgaaaaag caggtcagaa acggatgat     120 atgcttaact ctaacgatat gattaagctt gctcccaaag aaatgccact agaatctgca    180 gaaaagaag aaaaaaagtc agaagacaaa aaaagagcg aagaagatca cactgaagaa     240
atcaatgaca agatttattc actaaattat aatgagcttg aagtacttgc taaaaatggt    300
gaaaccattg aaaattttgt tcctaaagaa ggcgttaaga agctgataa atttattgtc    360 attgaaagaa agaaaaaaaa tatcaacact acaccagtcg atatttccat tattgactct    420
gtcactgata ggacctatcc agcagccctt cagctggcta taaaggtttt taccgaaaac    480
aaaccagacg cggtagtcac caagcgaaac ccacaaaaaa tccatattga tttaccaggt    540
atgggagaca agcaacggt tgaggtcaat gaccctacct atgccaatgt ttcaacagct    600
attgataatc ttgttaacca atggcatgat aattattctg gtggtaatac gcttcctgcc    660
agaacacaat atactgaatc aatggtatat tctaagtcac agattgaggc agctctaaat    720
gttaatagca aaatcttaga tggtacttta ggcattgatt tcaagtcgat ttcaaaaggt    780
gaaaagaagg tgatgattgc agcatacaag caaatttttt acaccgtatc agcaaacctt    840
cctaataatc ctgcggatgt gtttgataaa tcggtgacct ttaaagagtt gcaacgaaaa    900
ggtgtcagca atgaagctcc gccactcttt gtgagtaacg tagcctatgg tcgaactgtt    960
tttgtcaaac tagaaacaag ttctaaaagt aatgatgttg aagcggcctt tagtgcagct   1020
ctaaaaggaa cagatgttaa aactaatgga aaatattctg atatcttaga aaatagctca   1080
tttacagctg tcgttttagg aggagatgct gcagagcaca taaggtagt cacaaaagac   1140 tttgatgtta ttagaaacgt tatcaaagac aatgctacct tcagtagaaa aaacctagct   1200
tatcctattt catacaccag tgttttcctt aaaaataata aaattgcggg tgtcaataac   1260
agaactgaat acgttgaaac aacatctacc gagtacacta gtggaaaaat taacctgtct   1320
catcaaggcg cgtatgttgc tcaatatgaa atcctttggg atgaaatcaa ttatgatgac   1380
aaaggaaaag aagtgattac aaaacgacgt tgggacaaca actggtatag taagacatca   1440
ccatttagca cagttatccc actaggagct aattcacgaa atatccgtat catggctaga   1500
gagtgcactg gcttagcttt cgaatggtgg cgaaaagtga tcgacgaaag agatgtgaaa   1560
ctgtctaaag aaatcaatgt caatatctca ggatcaacct tgagcccata tggttcgatt   1620
acttataagt ag                                                       1632

<210> SEQ ID NO 32
<211> LENGTH: 1632
<212> TYPE: DNA
<213> ORGANISM: S. pyogenes
```

<400> SEQUENCE: 32

```
atggctagcg aatcgaacaa acaaaacact gctagtacag aaaccacaac gacaaatgag    60
caaccaaagc cagaaagtag tgagctaact actgaaaaag caggtcagaa acggatgat   120
atgcttaact ctaacgatat gattaagctt gctcccaaag aaatgccact agaatctgca   180
gaaaagaag aaaaaaagtc agaagacaaa aaaagagcg aagaagatca cactgaagaa    240
atcaatgaca agatttattc actaaattat aatgagcttg aagtacttgc taaaaatggt   300
gaaccattg aaaattttgt tcctaaagaa ggcgttaaga agctgataa atttattgtc    360
attgaaagaa agaaaaaaaa tatcaacact acaccagtcg atatttccat tattgactct   420
gtcactgata ggacctatcc agcagccctt cagctggcta taaaggtttt taccgaaaac   480
aaaccagacg cggtagtcac caagcgaaac ccacaaaaaa tccatattga tttaccaggt   540
atgggagaca agcaacggt tgaggtcaat gaccctacct atgccaatgt ttcaacagct   600
attgataatc ttgttaacca atggcatgat aattattctg gtggtaatac gcttcctgcc   660
agaacacaat atactgaatc aatggtatat tctaagtcac agattgaggc agctctaaat   720
gttaatagca aaatcttaga tggtacttta ggcattgatt tcaagtcgat ttcaaaggt    780
gaaaagaagg tgatgattgc agcatacaag caaatttttt acaccgtatc agcaaacctt   840
cctaataatc ctgcggatgt gttttgataaa tcggtgacct ttaaagagtt gcaacgaaaa   900
ggtgtcagca atgaagctcc gccactcttt gtgagtaacg tagcctatgg tcgaactgtt   960
tttgtcaaac tagaaacaag ttctaaaagt aatgatgttg aagcggcctt tagtgcagct  1020
ctaaaggaa cagatgttaa aactaatgga aaatattctg atatcttaga aaatagctca  1080
tttacagctg tcgttttagg aggagatgct gcagagcaca taaggtagt cacaaaagac  1140
tttgatgtta ttagaaacgt tatcaaagac aatgctacct tcagtagaaa aaacctagct  1200
tatcctatt catacaccag tgttttcctt aaaaataata aaattgcggg tgtcaataac  1260
agaactgaat acgttgaaac aacatctacc gagtacacta gtggaaaaat taacctgtct  1320
catcaaggcg cgtatgttgc tcaatatgaa atcctttggg atgaaatcaa ttatgatgac  1380
aaaggaaaag aagtgattac aaaacgacgt tgggacaaca actggtatag taagacatca  1440
ccatttagca cagttatccc actaggagct aattcacgaa atatccgtat catggctaga  1500
gagggcactg gcttagcttg ggaatggtgg cgaaaagtga tcgacgaaag agatgtgaaa  1560
ctgtctaaag aaatcaatgt caatatctca ggatcaacct tgagcccata tggttcgatt  1620
acttataagt ag                                                    1632
```

<210> SEQ ID NO 33
<211> LENGTH: 1632
<212> TYPE: DNA
<213> ORGANISM: S. pyogenes

<400> SEQUENCE: 33

```
atggctagcg aatcgaacaa acaaaacact gctagtacag aaaccacaac gacaaatgag    60
caaccaaagc cagaaagtag tgagctaact actgaaaaag caggtcagaa acggatgat   120
atgcttaact ctaacgatat gattaagctt gctcccaaag aaatgccact agaatctgca   180
gaaaagaag aaaaaaagtc agaagacaaa aaaagagcg aagaagatca cactgaagaa    240
atcaatgaca agatttattc actaaattat aatgagcttg aagtacttgc taaaaatggt   300
gaaccattg aaaattttgt tcctaaagaa ggcgttaaga agctgataa atttattgtc    360
attgaaagaa agaaaaaaaa tatcaacact acaccagtcg atatttccat tattgactct   420
```

-continued

```
gtcactgata ggacctatcc agcagccctt cagctggcta ataaaggttt taccgaaaac      480
aaaccagacg cggtagtcac caagcgaaac ccacaaaaaa tccatattga tttaccaggt      540
atgggagaca aagcaacggt tgaggtcaat gaccctacct atgccaatgt ttcaacagct      600
attgataatc ttgttaacca atggcatgat aattattctg gtggtaatac gcttcctgcc      660
agaacacaat atactgaatc aatggtatat tctaagtcac agattgaggc agctctaaat      720
gttaatagca aaatcttaga tggtacttta ggcattgatt tcaagtcgat ttcaaaaggt      780 gaaagaagg tgatgattgc agcatacaag caaattttt acaccgtatc agcaaacctt       840
cctaataatc ctgcggatgt gtttgataaa tcggtgacct ttaaagagtt gcaacgaaaa      900
ggtgtcagca atgaagctcc gccactcttt gtgagtaacg tagcctatgg tcgaactgtt      960
tttgtcaaac tagaaacaag ttctaaaagt aatgatgttg aagcggcctt tagtgcagct     1020
ctaaaaggaa cagatgttaa aactaatgga aaatattctg atatcttaga aaatagctca     1080
tttacagctg tcgttttagg aggagatgct gcagagcaca ataaggtagt cacaaaagac     1140
tttgatgtta ttagaaacgt tatcaaagac aatgctacct tcagtagaaa aaacctagct     1200 tatcctatt catacaccag tgttttcctt aaaaataata aaattgcggg tgtcaataac      1260
agaactgaat acgttgaaac aacatctacc gagtacacta gtggaaaaat taacctgtct     1320
catcaaggcg cgtatgttgc tcaatatgaa atcctttggg atgaaatcaa ttatgatgac     1380
aaaggaaaag aagtgattac aaaacgacgt tgggacaaca actggtatag taagacatca     1440
ccatttagca cagttatccc actaggagct aattcacgaa atatccgtat catggctaga     1500
gagggcactg gcttagcttt cgaatggtgg cgaaaagtga tcgacgaaag agatgtgaaa     1560
ctgtctaaag aaatcaatgt caatatctca ggatcaacct tgagcccata tggttcgatt     1620
acttataagt ga                                                          1632

<210> SEQ ID NO 34
<211> LENGTH: 35
<212> TYPE: DNA
<213> ORGANISM: S. pyogenes

<400> SEQUENCE: 34
gtgcgtgcta gcgaatcgaa caaacaaaac actgc                                 35

<210> SEQ ID NO 35
<211> LENGTH: 42
<212> TYPE: DNA
<213> ORGANISM: S. pyogenes

<400> SEQUENCE: 35
gcattcgatc ctcgagctac ttataagtaa tcgaaccata tg                         42

<210> SEQ ID NO 36
<211> LENGTH: 45
<212> TYPE: DNA
<213> ORGANISM: S. pyogenes

<400> SEQUENCE: 36
gctaccttca gtagaaaaaa cctagcttat cctatttcat acacc                      45

<210> SEQ ID NO 37
<211> LENGTH: 45
<212> TYPE: DNA
<213> ORGANISM: S. pyogenes
```

```
<400> SEQUENCE: 37
ggtgtatgaa ataggataag ctaggttttt tctactgaag gtagc              45

<210> SEQ ID NO 38
<211> LENGTH: 41
<212> TYPE: DNA
<213> ORGANISM: S. pyogenes

<400> SEQUENCE: 38
gcattcgatc ctcgagctta taagtaatcg aaccatatgg g                  41

<210> SEQ ID NO 39
<211> LENGTH: 42
<212> TYPE: DNA
<213> ORGANISM: S. pyogenes

<400> SEQUENCE: 39
gagtgcactg gcttagcttt cgaatggtgg cgaaaagtga tc                 42

<210> SEQ ID NO 40
<211> LENGTH: 42
<212> TYPE: DNA
<213> ORGANISM: S. pyogenes

<400> SEQUENCE: 40
gatcactttt cgccaccatt cgaaagctaa gccagtgcac tc                 42

<210> SEQ ID NO 41
<211> LENGTH: 55
<212> TYPE: DNA
<213> ORGANISM: S. pyogenes

<400> SEQUENCE: 41
gttgctcaat atgaaatcct ttggaatgaa atcaattatg atgacaaagg aaaag   55

<210> SEQ ID NO 42
<211> LENGTH: 55
<212> TYPE: DNA
<213> ORGANISM: S. pyogenes

<400> SEQUENCE: 42
cttttccttt gtcatcataa ttgatttcat tccaaaggat ttcatattga gcaac   55

<210> SEQ ID NO 43
<211> LENGTH: 42
<212> TYPE: DNA
<213> ORGANISM: S. pyogenes

<400> SEQUENCE: 43
ccgtatcatg gctagagagg gcactggctt agcttgggaa tg                 42

<210> SEQ ID NO 44
<211> LENGTH: 42
<212> TYPE: DNA
<213> ORGANISM: S. pyogenes

<400> SEQUENCE: 44
cattcccaag ctaagccagt gccctctcta gccatgatac gg                 42

<210> SEQ ID NO 45
<211> LENGTH: 30
<212> TYPE: DNA
<213> ORGANISM: S. pyogenes
```

<400> SEQUENCE: 45
gtgcgtgcta gcgaatcgaa caaacaaaac                                30

<210> SEQ ID NO 46
<211> LENGTH: 34
<212> TYPE: DNA
<213> ORGANISM: S. pyogenes

<400> SEQUENCE: 46
gcgtctcgag tcacttataa gtaatcgaac cata                           34

<210> SEQ ID NO 47
<211> LENGTH: 42
<212> TYPE: DNA
<213> ORGANISM: S. pyogenes

<400> SEQUENCE: 47
ccgtatcatg gctagagagg gcactggctt agctttcgaa tg                  42

<210> SEQ ID NO 48
<211> LENGTH: 42
<212> TYPE: DNA
<213> ORGANISM: S. pyogenes

<400> SEQUENCE: 48
cattcgaaag ctaagccagt gccctctcta gccatgatac gg                  42

<210> SEQ ID NO 49
<211> LENGTH: 45
<212> TYPE: DNA
<213> ORGANISM: S. pyogenes

<400> SEQUENCE: 49
ctggtggtaa tacgcttcct agaacacaat atactgaatc aatgg               45

<210> SEQ ID NO 50
<211> LENGTH: 45
<212> TYPE: DNA
<213> ORGANISM: S. pyogenes

<400> SEQUENCE: 50
ccattgattc agtatattgt gttctaggaa gcgtattacc accag               45

<210> SEQ ID NO 51
<211> LENGTH: 1656
<212> TYPE: DNA
<213> ORGANISM: S. pyogenes

<400> SEQUENCE: 51
atggctagcg aatcgaacaa acaaaacact gctagtacag aaaccacaac gacaaatgag    60
caaccaaagc cagaaagtag tgagctaact actgaaaaag caggtcagaa aacggatgat   120
atgcttaact ctaacgatat gattaagctt gctcccaaag aaatgccact agaatctgca   180 gaaaagaag aaaaaagtc agaagacaaa aaaagagcg aagaagatca cactgaagaa    240
atcaatgaca gatttattc actaaattat aatgagcttg aagtacttgc taaaaatggt   300
gaaaccattg aaaattttgt tcctaaagaa ggcgttaaga agctgataaa atttattgtc   360
attgaaagaa agaaaaaaaa tatcaacact acaccagtcg atatttccat tattgactct   420
gtcactgata ggacctatcc agcagccctt cagctgctaa taaaggtttt taccgaaaac   480
aaaccagacg cggtagtcac caagcgaaac ccacaaaaaa tccatattga tttaccaggt   540

```
atgggagaca aagcaacggt tgaggtcaat gaccctacct atgccaatgt tcaacagct    600 attgataatc ttgttaacca atggcatgat aattattctg gtggtaatac gcttcctgcc    660
agaacacaat atactgaatc aatggtatat tctaagtcac agattgaagc agctctaaat    720
gttaatagca aatcttaga tggtacttta ggcattgatt tcaagtcgat ttcaaaaggt    780
gaaaagaagg tgatgattgc agcatacaag caaatttttt acaccgtatc agcaaacctt    840
cctaataatc ctgcggatgt gtttgataaa tcggtgacct ttaaagagtt gcaacgaaaa    900
ggtgtcagca atgaagctcc gccactcttt gtgagtaacg tagcctatgg tcgaactgtt    960
tttgtcaaac tagaaacaag ttctaaaagt aatgatgttg aagcggcctt tagtgcagct   1020
ctaaaaggaa cagatgttaa aactaatgga aaatattctg atatcttaga aaatagctca   1080
tttacagctg tcgttttagg aggagatgct gcagagcaca ataaggtagt cacaaaagac   1140
tttgatgtta ttagaaacgt tatcaaagac aatgctacct tcagtagaaa aaacccagct   1200
tatcctattt catacaccag tgttttcctt aaaaataata aaattgcggg tgtcaataac   1260
agaactgaat acgttgaaac aacatctacc gagtacacta gtggaaaaat taacctgtct   1320
catcaaggcg cgtatgttgc tcaatatgaa atcctttggg atgaaatcaa ttatgatgac   1380
aaaggaaaag aagtgattac aaaacgacgt tgggacaaca actggtatag taagacatca   1440
ccatttagca cagttatccc actaggagct aattcacgaa atatccgtat catggctaga   1500
gagtgcactg gcttagcttt cgaatggtgg cgaaaagtga tcgacgaaag agatgtgaaa   1560
ctgtctaaag aaatcaatgt caatatctca ggatcaacct tgagcccata tggttcgatt   1620
acttataagc tcgagcacca ccaccaccac cactga                             1656

<210> SEQ ID NO 52
<211> LENGTH: 1656
<212> TYPE: DNA
<213> ORGANISM: S. pyogenes

<400> SEQUENCE: 52
atggctagcg aatcgaacaa acaaaacact gctagtacag aaaccacaac gacaaatgag     60
caaccaaagc cagaaagtag tgagctaact actgaaaaag caggtcagaa aacggatgat    120
atgcttaact ctaacgatat gattaagctt gctcccaaag aaatgccact agaatctgca    180 gaaaagaag aaaaaagtc agaagacaaa aaaagagcg aagaagatca cactgaagaa    240
atcaatgaca agatttattc actaaattat aatgagcttg aagtacttgc taaaaatggt    300
gaaaccattg aaaattttgt tcctaaagaa ggcgttaaga agctgataa atttattgtc    360 attgaaagaa agaaaaaaaa tatcaacact acaccagtcg atatttccat tattgactct    420
gtcactgata ggacctatcc agcagccctt cagctggcta ataaggtttt taccgaaaac    480
aaaccagacg cggtagtcac caagcgaaac ccacaaaaaa tccatattga tttaccaggt    540
atgggagaca aagcaacggt tgaggtcaat gaccctacct atgccaatgt tcaacagct    600 attgataatc ttgttaacca atggcatgat aattattctg gtggtaatac gcttcctgcc    660
agaacacaat atactgaatc aatggtatat tctaagtcac agattgaagc agctctaaat    720
gttaatagca aatcttaga tggtacttta ggcattgatt tcaagtcgat ttcaaaaggt    780
gaaaagaagg tgatgattgc agcatacaag caaatttttt acaccgtatc agcaaacctt    840
cctaataatc ctgcggatgt gtttgataaa tcggtgacct ttaaagagtt gcaacgaaaa    900
ggtgtcagca atgaagctcc gccactcttt gtgagtaacg tagcctatgg tcgaactgtt    960
tttgtcaaac tagaaacaag ttctaaaagt aatgatgttg aagcggcctt tagtgcagct   1020
```

```
ctaaaaggaa cagatgttaa aactaatgga aatattctg atatcttaga aaatagctca    1080
tttacagctg tcgttttagg aggagatgct gcagagcaca ataaggtagt cacaaaagac    1140
tttgatgtta ttagaaacgt tatcaaagac aatgctacct tcagtagaaa aaacccagct    1200
tatcctattt catacaccag tgttttcctt aaaaataata aaattgcggg tgtcaataac    1260
agaactgaat acgttgaaac aacatctacc gagtacacta gtggaaaaat taacctgtct    1320
catcaaggcg cgtatgttgc tcaatatgaa atcctttgga atgaaatcaa ttatgatgac    1380
aaaggaaaag aagtgattac aaaacgacgt tgggacaaca actggtatag taagacatca    1440
ccatttagca cagttatccc actaggagct aattcacgaa atatccgtat catggctaga    1500
gagtgcactg gcttagcttt cgaatggtgg cgaaaagtga tcgacgaaag agatgtgaaa    1560
ctgtctaaag aaatcaatgt caatatctca ggatcaacct tgagcccata tggttcgatt    1620
acttataagc tcgagcacca ccaccaccac cactga                              1656
```

<210> SEQ ID NO 53
<211> LENGTH: 551
<212> TYPE: PRT
<213> ORGANISM: S. pyogenes

<400> SEQUENCE: 53

```
Met Ala Ser Glu Ser Asn Lys Gln Asn Thr Ala Ser Thr Glu Thr Thr
 1               5                  10                  15

Thr Thr Asn Glu Gln Pro Lys Pro Glu Ser Ser Glu Leu Thr Thr Glu
            20                  25                  30

Lys Ala Gly Gln Lys Thr Asp Asp Met Leu Asn Ser Asn Asp Met Ile
        35                  40                  45

Lys Leu Ala Pro Lys Glu Met Pro Leu Glu Ser Ala Glu Lys Glu Glu
    50                  55                  60

Lys Lys Ser Glu Asp Lys Lys Ser Glu Glu Asp His Thr Glu Glu
65                  70                  75                  80

Ile Asn Asp Lys Ile Tyr Ser Leu Asn Tyr Asn Glu Leu Glu Val Leu
                85                  90                  95

Ala Lys Asn Gly Glu Thr Ile Glu Asn Phe Val Pro Lys Glu Gly Val
            100                 105                 110

Lys Lys Ala Asp Lys Phe Ile Val Ile Glu Arg Lys Lys Lys Asn Ile
        115                 120                 125

Asn Thr Thr Pro Val Asp Ile Ser Ile Ile Asp Ser Val Thr Asp Arg
    130                 135                 140

Thr Tyr Pro Ala Ala Leu Gln Leu Ala Asn Lys Gly Phe Thr Glu Asn
145                 150                 155                 160

Lys Pro Asp Ala Val Val Thr Lys Arg Asn Pro Gln Lys Ile His Ile
                165                 170                 175

Asp Leu Pro Gly Met Gly Asp Lys Ala Thr Val Glu Val Asn Asp Pro
            180                 185                 190

Thr Tyr Ala Asn Val Ser Thr Ala Ile Asp Asn Leu Val Asn Gln Trp
        195                 200                 205

His Asp Asn Tyr Ser Gly Gly Asn Thr Leu Pro Ala Arg Thr Gln Tyr
    210                 215                 220

Thr Glu Ser Met Val Tyr Ser Lys Ser Gln Ile Glu Ala Ala Leu Asn
225                 230                 235                 240

Val Asn Ser Lys Ile Leu Asp Gly Thr Leu Gly Ile Asp Phe Lys Ser
                245                 250                 255

Ile Ser Lys Gly Glu Lys Lys Val Met Ile Ala Ala Tyr Lys Gln Ile
            260                 265                 270
```

```
Phe Tyr Thr Val Ser Ala Asn Leu Pro Asn Asn Pro Ala Asp Val Phe
            275                 280                 285

Asp Lys Ser Val Thr Phe Lys Glu Leu Gln Arg Lys Gly Val Ser Asn
        290                 295                 300

Glu Ala Pro Pro Leu Phe Val Ser Asn Val Ala Tyr Gly Arg Thr Val
305                 310                 315                 320

Phe Val Lys Leu Glu Thr Ser Ser Lys Ser Asn Asp Val Glu Ala Ala
                325                 330                 335

Phe Ser Ala Ala Leu Lys Gly Thr Asp Val Lys Thr Asn Gly Lys Tyr
            340                 345                 350

Ser Asp Ile Leu Glu Asn Ser Ser Phe Thr Ala Val Val Leu Gly Gly
        355                 360                 365

Asp Ala Ala Glu His Asn Lys Val Val Thr Lys Asp Phe Asp Val Ile
370                 375                 380

Arg Asn Val Ile Lys Asp Asn Ala Thr Phe Ser Arg Lys Asn Leu Ala
385                 390                 395                 400

Tyr Pro Ile Ser Tyr Thr Ser Val Phe Leu Lys Asn Asn Lys Ile Ala
                405                 410                 415

Gly Val Asn Asn Arg Thr Glu Tyr Val Glu Thr Thr Ser Thr Glu Tyr
            420                 425                 430

Thr Ser Gly Lys Ile Asn Leu Ser His Gln Gly Ala Tyr Val Ala Gln
        435                 440                 445

Tyr Glu Ile Leu Trp Asp Glu Ile Asn Tyr Asp Asp Lys Gly Lys Glu
    450                 455                 460

Val Ile Thr Lys Arg Arg Trp Asp Asn Trp Tyr Ser Lys Thr Ser
465                 470                 475                 480

Pro Phe Ser Thr Val Ile Pro Leu Gly Ala Asn Ser Arg Asn Ile Arg
                485                 490                 495

Ile Met Ala Arg Glu Gly Thr Gly Leu Ala Trp Glu Trp Trp Arg Lys
            500                 505                 510

Val Ile Asp Glu Arg Asp Val Lys Leu Ser Lys Glu Ile Asn Val Asn
        515                 520                 525

Ile Ser Gly Ser Thr Leu Ser Pro Tyr Gly Ser Ile Thr Tyr Lys Leu
    530                 535                 540

Glu His His His His His His
545                 550

<210> SEQ ID NO 54
<211> LENGTH: 551
<212> TYPE: PRT
<213> ORGANISM: S. pyogenes

<400> SEQUENCE: 54

Met Ala Ser Glu Ser Asn Lys Gln Asn Thr Ala Ser Thr Glu Thr Thr
1               5                   10                  15

Thr Thr Asn Glu Gln Pro Lys Pro Glu Ser Ser Glu Leu Thr Thr Glu
            20                  25                  30

Lys Ala Gly Gln Lys Thr Asp Asp Met Leu Asn Ser Asn Asp Met Ile
        35                  40                  45

Lys Leu Ala Pro Lys Glu Met Pro Leu Glu Ser Ala Lys Glu Glu
    50                  55                  60

Lys Lys Ser Glu Asp Lys Lys Ser Glu Glu Asp His Thr Glu Glu
65                  70                  75                  80

Ile Asn Asp Lys Ile Tyr Ser Leu Asn Tyr Asn Glu Leu Glu Val Leu
                85                  90                  95
```

-continued

```
Ala Lys Asn Gly Glu Thr Ile Glu Asn Phe Val Pro Lys Glu Gly Val
        100                 105                 110

Lys Lys Ala Asp Lys Phe Ile Val Ile Glu Arg Lys Lys Lys Asn Ile
        115                 120                 125

Asn Thr Thr Pro Val Asp Ile Ser Ile Ile Asp Ser Val Thr Asp Arg
130                 135                 140

Thr Tyr Pro Ala Ala Leu Gln Leu Ala Asn Lys Gly Phe Thr Glu Asn
145                 150                 155                 160

Lys Pro Asp Ala Val Val Thr Lys Arg Asn Pro Gln Lys Ile His Ile
                165                 170                 175

Asp Leu Pro Gly Met Gly Asp Lys Ala Thr Val Glu Val Asn Asp Pro
                180                 185                 190

Thr Tyr Ala Asn Val Ser Thr Ala Ile Asp Asn Leu Val Asn Gln Trp
                195                 200                 205

His Asp Asn Tyr Ser Gly Gly Asn Thr Leu Pro Ala Arg Thr Gln Tyr
                210                 215                 220

Thr Glu Ser Met Val Tyr Ser Lys Ser Gln Ile Glu Ala Ala Leu Asn
225                 230                 235                 240

Val Asn Ser Lys Ile Leu Asp Gly Thr Leu Gly Ile Asp Phe Lys Ser
                245                 250                 255

Ile Ser Lys Gly Glu Lys Lys Val Met Ile Ala Ala Tyr Lys Gln Ile
                260                 265                 270

Phe Tyr Thr Val Ser Ala Asn Leu Pro Asn Asn Pro Ala Asp Val Phe
                275                 280                 285

Asp Lys Ser Val Thr Phe Lys Glu Leu Gln Arg Lys Gly Val Ser Asn
                290                 295                 300

Glu Ala Pro Pro Leu Phe Val Ser Asn Val Ala Tyr Gly Arg Thr Val
305                 310                 315                 320

Phe Val Lys Leu Glu Thr Ser Ser Lys Ser Asn Asp Val Glu Ala Ala
                325                 330                 335

Phe Ser Ala Ala Leu Lys Gly Thr Asp Val Lys Thr Asn Gly Lys Tyr
                340                 345                 350

Ser Asp Ile Leu Glu Asn Ser Ser Phe Thr Ala Val Val Leu Gly Gly
                355                 360                 365

Asp Ala Ala Glu His Asn Lys Val Val Thr Lys Asp Phe Asp Val Ile
                370                 375                 380

Arg Asn Val Ile Lys Asp Asn Ala Thr Phe Ser Arg Lys Asn Leu Ala
385                 390                 395                 400

Tyr Pro Ile Ser Tyr Thr Ser Val Phe Leu Lys Asn Asn Lys Ile Ala
                405                 410                 415

Gly Val Asn Asn Arg Thr Glu Tyr Val Glu Thr Thr Ser Thr Glu Tyr
                420                 425                 430

Thr Ser Gly Lys Ile Asn Leu Ser His Gln Gly Ala Tyr Val Ala Gln
                435                 440                 445

Tyr Glu Ile Leu Trp Asp Glu Ile Asn Tyr Asp Asp Lys Gly Lys Glu
                450                 455                 460

Val Ile Thr Lys Arg Arg Trp Asp Asn Asn Trp Tyr Ser Lys Thr Ser
465                 470                 475                 480

Pro Phe Ser Thr Val Ile Pro Leu Gly Ala Asn Ser Arg Asn Ile Arg
                485                 490                 495

Ile Met Ala Arg Glu Cys Thr Gly Leu Ala Phe Glu Trp Trp Arg Lys
                500                 505                 510

Val Ile Asp Glu Arg Asp Val Lys Leu Ser Lys Glu Ile Asn Val Asn
                515                 520                 525
```

-continued

Ile Ser Gly Ser Thr Leu Ser Pro Tyr Gly Ser Ile Thr Tyr Lys Leu
530                 535                 540

Glu His His His His His
545                 550

<210> SEQ ID NO 55
<211> LENGTH: 551
<212> TYPE: PRT
<213> ORGANISM: S. pyogenes

<400> SEQUENCE: 55

Met Ala Ser Glu Ser Asn Lys Gln Asn Thr Ala Ser Thr Glu Thr Thr
1               5                   10                  15

Thr Thr Asn Glu Gln Pro Lys Pro Glu Ser Ser Glu Leu Thr Thr Glu
            20                  25                  30

Lys Ala Gly Gln Lys Thr Asp Met Leu Asn Ser Asn Asp Met Ile
        35                  40                  45

Lys Leu Ala Pro Lys Glu Met Pro Leu Glu Ser Ala Lys Glu Glu
50                  55                  60

Lys Lys Ser Glu Asp Lys Lys Ser Glu Glu Asp His Thr Glu Glu
65                  70                  75                  80

Ile Asn Asp Lys Ile Tyr Ser Leu Asn Tyr Asn Glu Leu Glu Val Leu
                85                  90                  95

Ala Lys Asn Gly Glu Thr Ile Glu Asn Phe Val Pro Lys Glu Gly Val
            100                 105                 110

Lys Lys Ala Asp Lys Phe Ile Val Ile Glu Arg Lys Lys Lys Asn Ile
        115                 120                 125

Asn Thr Thr Pro Val Asp Ile Ser Ile Ile Asp Ser Val Thr Asp Arg
130                 135                 140

Thr Tyr Pro Ala Ala Leu Gln Leu Ala Asn Lys Gly Phe Thr Glu Asn
145                 150                 155                 160

Lys Pro Asp Ala Val Val Thr Lys Arg Asn Pro Gln Lys Ile His Ile
                165                 170                 175

Asp Leu Pro Gly Met Gly Asp Lys Ala Thr Val Glu Val Asn Asp Pro
            180                 185                 190

Thr Tyr Ala Asn Val Ser Thr Ala Ile Asp Asn Leu Val Asn Gln Trp
        195                 200                 205

His Asp Asn Tyr Ser Gly Gly Asn Thr Leu Pro Ala Arg Thr Gln Tyr
210                 215                 220

Thr Glu Ser Met Val Tyr Ser Lys Ser Gln Ile Glu Ala Ala Leu Asn
225                 230                 235                 240

Val Asn Ser Lys Ile Leu Asp Gly Thr Leu Gly Ile Asp Phe Lys Ser
                245                 250                 255

Ile Ser Lys Gly Glu Lys Lys Val Met Ile Ala Ala Tyr Lys Gln Ile
            260                 265                 270

Phe Tyr Thr Val Ser Ala Asn Leu Pro Asn Asn Pro Ala Asp Val Phe
        275                 280                 285

Asp Lys Ser Val Thr Phe Lys Glu Leu Gln Arg Lys Gly Val Ser Asn
290                 295                 300

Glu Ala Pro Pro Leu Phe Val Ser Asn Val Ala Tyr Gly Arg Thr Val
305                 310                 315                 320

Phe Val Lys Leu Glu Thr Ser Ser Lys Ser Asn Asp Val Glu Ala Ala
                325                 330                 335

Phe Ser Ala Ala Leu Lys Gly Thr Asp Val Lys Thr Asn Gly Lys Tyr
            340                 345                 350

```
Ser Asp Ile Leu Glu Asn Ser Ser Phe Thr Ala Val Val Leu Gly Gly
        355                 360                 365

Asp Ala Ala Glu His Asn Lys Val Val Thr Lys Asp Phe Asp Val Ile
    370                 375                 380

Arg Asn Val Ile Lys Asp Asn Ala Thr Phe Ser Arg Lys Asn Leu Ala
385                 390                 395                 400

Tyr Pro Ile Ser Tyr Thr Ser Val Phe Leu Lys Asn Asn Lys Ile Ala
                405                 410                 415

Gly Val Asn Asn Arg Thr Glu Tyr Val Glu Thr Ser Thr Glu Tyr
            420                 425                 430

Thr Ser Gly Lys Ile Asn Leu Ser His Gln Gly Ala Tyr Val Ala Gln
        435                 440                 445

Tyr Glu Ile Leu Trp Asp Glu Ile Asn Tyr Asp Asp Lys Gly Lys Glu
    450                 455                 460

Val Ile Thr Lys Arg Arg Trp Asp Asn Asn Trp Tyr Ser Lys Thr Ser
465                 470                 475                 480

Pro Phe Ser Thr Val Ile Pro Leu Gly Ala Asn Ser Arg Asn Ile Arg
                485                 490                 495

Ile Met Ala Arg Glu Gly Thr Gly Leu Ala Phe Glu Trp Trp Arg Lys
            500                 505                 510

Val Ile Asp Glu Arg Asp Val Lys Leu Ser Lys Glu Ile Asn Val Asn
    515                 520                 525

Ile Ser Gly Ser Thr Leu Ser Pro Tyr Gly Ser Ile Thr Tyr Lys Leu
530                 535                 540

Glu His His His His His His
545                 550

<210> SEQ ID NO 56
<211> LENGTH: 1656
<212> TYPE: DNA
<213> ORGANISM: S. pyogenes

<400> SEQUENCE: 56
atggctagcg aatcgaacaa acaaaacact gctagtacag aaaccacaac gacaaatgag      60
caaccaaagc cagaaagtag tgagctaact actgaaaaag caggtcagaa aacggatgat     120
atgcttaact ctaacgatat gattaagctt gctcccaaag aaatgccact agaatctgca     180 gaaaagaag aaaaaaagtc agaagacaaa aaaagagcg aagaagatca cactgaagaa       240
atcaatgaca gatttattc actaaattat aatgagcttg aagtacttgc taaaaatggt      300
gaaaccattg aaaattttgt tcctaaagaa ggcgttaaga agctgataa atttattgtc      360 attgaaagaa agaaaaaaaa tatcaacact caccagtcg atatttccat tattgactct      420
gtcactgata ggacctatcc agcagccctt cagctggcta taaaggtttt accgaaaac     480 aaaccagacg cggtagtcac caagcgaaac ccacaaaaaa tccatattga tttaccaggt     540
atgggagaca agcaacggt tgaggtcaat gaccctacct atgccaatgt ttcaacagct     600
attgataatc ttgttaacca atggcatgat aattattctg gtggtaatac gcttcctgcc     660
agaacacaat atactgaatc aatggtatat tctaagtcac agattgaggc agctctaaat     720
gttaatagca aaatcttaga tggtactta ggcattgatt tcaagtcgat tcaaaaggt      780 gaaaagaagg tgatgattgc agcatacaag caaattttt acaccgtatc agcaaacctt     840
cctaataatc ctgcggatgt gtttgataaa tcggtgacct ttaaagagtt gcaacgaaaa     900
ggtgtcagca atgaagctcc gccactcttt gtgagtaacg tagcctatgg tcgaactgtt     960
tttgtcaaac tagaaacaag ttctaaaagt aatgatgttg aagcggcctt tagtgcagct    1020
```

```
ctaaaaggaa cagatgttaa aactaatgga aaatattctg atatcttaga aaatagctca    1080
tttacagctg tcgttttagg aggagatgct gcagagcaca ataaggtagt cacaaaagac    1140
tttgatgtta ttagaaacgt tatcaaagac aatgctacct tcagtagaaa aaacctagct    1200
tatcctattt catacaccag tgttttcctt aaaaataata aaattgcggg tgtcaataac    1260
agaactgaat acgttgaaac aacatctacc gagtacacta gtggaaaaat taacctgtct    1320
catcaaggcg cgtatgttgc tcaatatgaa atcctttggg atgaaatcaa ttatgatgac    1380
aaaggaaaag aagtgattac aaaacgacgt tgggacaaca actggtatag taagacatca    1440
ccatttagca cagttatccc actaggagct aattcacgaa atatccgtat catggctaga    1500
gagtgcactg gcttagcttg ggaatggtgg cgaaaagtga tcgacgaaag agatgtgaaa    1560
ctgtctaaag aaatcaatgt caatatctca ggatcaacct tgagcccata tggttcgatt    1620
acttataagc tcgagcacca ccaccaccac cactga                             1656
```

<210> SEQ ID NO 57
<211> LENGTH: 1656
<212> TYPE: DNA
<213> ORGANISM: S. pyogenes

<400> SEQUENCE: 57

```
atggctagcg aatcgaacaa acaaaacact gctagtacag aaaccacaac gacaaatgag     60
caaccaaagc cagaaagtag tgagctaact actgaaaaag caggtcagaa aacgacgatgat  120 atgcttaact ctaacgatat gattaagctt gctcccaaag aaatgccact agaatctgca    180
gaaaaagaag aaaaaaagtc agaagacaaa aaaagagcg aagaagatca cactgaagaa     240
atcaatgaca agatttattc actaaattat aatgagcttg aagtacttgc taaaaatggt    300 gaaccattg aaaattttgt tcctaaagaa ggcgttaaga agctgataa atttattgtc      360 attgaaagaa agaaaaaaaa tatcaacact acaccagtcg atatttccat tattgactct    420
gtcactgata ggacctatcc agcagccctt cagctggcta ataaaggttt taccgaaaac    480
aaaccagacg cggtagtcac caagcgaaac ccacaaaaaa tccatattga tttaccaggt    540
atgggagaca aagcaacggt tgaggtcaat gaccctacct atgccaatgt ttcaacagct    600
attgataatc ttgttaacca atggcatgat aattattctg gtggtaatac gcttcctgcc    660
agaacacaat atactgaatc aatggtatat tctaagtcac agattgaagc agctctaaat    720
gttaatagca aaatcttaga tggtactta ggcattgatt tcaagtcgat ttcaaaaggt    780
gaaaagaagg tgatgattgc agcatacaag caatttttttt acaccgtatc agcaaacctt   840
cctaataatc ctgcggatgt gtttgataaa tcggtgacct taaagagtt gcaacgaaaa    900 ggtgtcagca atgaagctcc gccactcttt gtgagtaacg tagcctatgg tcgaactgtt    960
tttgtcaaac tagaaacaag ttctaaagt aatgatgttg aagcggcctt tagtgcagct  1020
ctaaaaggaa cagatgttaa aactaatgga aaatattctg atatcttaga aaatagctca   1080
tttacagctg tcgttttagg aggagatgct gcagagcaca ataaggtagt cacaaaagac   1140
tttgatgtta ttagaaacgt tatcaaagac aatgctacct tcagtagaaa aaacccagct   1200
tatcctattt catacaccag tgttttcctt aaaaataata aaattgcggg tgtcaataac   1260
agaactgaat acgttgaaac aacatctacc gagtacacta gtggaaaaat taacctgtct   1320
catcaaggcg cgtatgttgc tcaatatgaa atcctttggg atgaaatcaa ttatgatgac   1380
aaaggaaaag aagtgattac aaaacgacgt tgggacaaca actggtatag taagacatca   1440
```

```
ccatttagca cagttatccc actaggagct aattcacgaa atatccgtat catggctaga    1500
gagggcactg gcttagcttg ggaatggtgg cgaaaagtga tcgacgaaag agatgtgaaa    1560
ctgtctaaag aaatcaatgt caatatctca ggatcaacct tgagcccata tggttcgatt    1620
acttataagc tcgagcacca ccaccaccac cactga                             1656
```

<210> SEQ ID NO 58
<211> LENGTH: 1653
<212> TYPE: DNA
<213> ORGANISM: S. pyogenes

<400> SEQUENCE: 58

```
atggctagcg aatcgaacaa acaaaacact gctagtacag aaaccacaac gacaaatgag     60
caaccaaagc cagaaagtag tgagctaact actgaaaaag caggtcagaa aacggatgat    120
atgcttaact ctaacgatat gattaagctt gctcccaaag aaatgccact agaatctgca    180
gaaaaagaag aaaaaaagtc agaagacaaa aaaaagagcg aagaagatca cactgaagaa    240
atcaatgaca agatttattc actaaattat aatgagcttg aagtacttgc taaaaatggt    300
gaaaccattg aaaattttgt tcctaaagaa ggcgttaaga agctgataaa atttattgtc    360
attgaaagaa agaaaaaaaa tatcaacact acaccagtcg atatttccat tattgactct    420
gtcactgata ggacctatcc agcagcccct cagctggcta taaaggttt taccgaaaac    480 aaaccagacg cggtagtcac caagcgaaac ccacaaaaaa tccatattga tttaccaggt    540
atgggagaca agcaacggt tgaggtcaat gaccctacct atgccaatgt ttcaacagct    600
attgataatc ttgttaacca atggcatgat aattattctg gtggtaatac gcttcctaga    660
acacaatata ctgaatcaat ggtatattct aagtcacaga ttgaagcagc tctaaatgtt    720
aatagcaaaa tcttagatgg tactttaggc attgatttca gtcgatttc aaaaggtgaa    780 aagaaggtga tgattgcagc atacaagcaa attttttaca ccgtatcagc aaaccttcct    840
aataatcctg cggatgtgtt tgataaatcg gtgacccttta aagagttgca acgaaaaggt    900
gtcagcaatg aagctccgcc actctttgtg agtaacgtag cctatggtcg aactgttttt    960
gtcaaactag aaacaagttc taaaagtaat gatgttgaag cggcctttag tgcagctcta   1020
aaaggaacag atgttaaaac taatggaaaa tattctgata tcttagaaaa tagctcattt   1080
acagctgtcg ttttaggagg agatgctgca gagcacaata aggtagtcac aaaagacttt   1140
gatgttatta gaaacgttat caaagacaat gctaccttca gtagaaaaaa cccagcttat   1200
cctatttcat acaccagtgt tttccttaaa aataataaaa ttgcgggtgt caataacaga   1260
actgaatacg ttgaaacaac atctaccgag tacactagtg gaaaaattaa cctgtctcat   1320
caaggcgcgt atgttgctca atatgaaatc ctttgggatg aaatcaatta tgatgacaaa   1380
ggaaaagaag tgattacaaa acgacgttgg gacaacaact ggtatagtaa gacatcacca   1440
tttagcacag ttatcccact aggagctaat tcacgaaata tccgtatcat ggctagagag   1500
tgcactggct tagcttggga atggtggcga aaagtgatcg acgaaagaga tgtgaaactg   1560
tctaaagaaa tcaatgtcaa tatctcagga tcaaccttga gcccatatgg ttcgattact   1620
tataagctcg agcaccacca ccaccaccac tga                                1653
```

<210> SEQ ID NO 59
<211> LENGTH: 1653
<212> TYPE: DNA
<213> ORGANISM: S. pyogenes

```
<400> SEQUENCE: 59
atggctagcg aatcgaacaa acaaaacact gctagtacag aaaccacaac gacaaatgag      60
caaccaaagc cagaaagtag tgagctaact actgaaaaag caggtcagaa aacggatgat     120
atgcttaact ctaacgatat gattaagctt gctcccaaag aaatgccact agaatctgca     180
gaaaaagaag aaaaaaagtc agaagacaaa aaaaagagcg aagaagatca cactgaagaa     240
atcaatgaca agatttattc actaaattat aatgagcttg aagtacttgc taaaaatggt     300
gaaaccattg aaaattttgt tcctaaagaa ggcgttaaga aagctgataa atttattgtc     360
attgaaagaa agaaaaaaaa tatcaacact acaccagtcg atatttccat tattgactct     420
gtcactgata ggacctatcc agcagccctt cagctggcta ataaaggttt taccgaaaac     480
aaaccagacg cggtagtcac caagcgaaac ccacaaaaaa tccatattga tttaccaggt     540
atgggagaca aagcaacggt tgaggtcaat gaccctacct atgccaatgt ttcaacagct     600
attgataatc ttgttaacca atggcatgat aattattctg gtggtaatac gcttcctaga     660
acacaatata ctgaatcaat ggtatattct aagtcacaga ttgaagcagc tctaaatgtt     720
aatagcaaaa tcttagatgg tactttaggc attgatttca agtcgatttc aaaaggtgaa     780
aagaaggtga tgattgcagc atacaagcaa attttttaca ccgtatcagc aaaccttcct     840
aataatcctg cggatgtgtt tgataaatcg gtgaccttta aagagttgca acgaaaaggt     900
gtcagcaatg aagctccgcc actctttgtg agtaacgtag cctatggtcg aactgttttt     960
gtcaaactag aaacaagttc taaaagtaat gatgttgaag cggcctttag tgcagctcta    1020
aaaggaacag atgttaaaac taatggaaaa tattctgata tcttagaaaa tagctcattt    1080
acagctgtcg ttttaggagg agatgctgca gagcacaata aggtagtcac aaaagacttt    1140
gatgttatta gaaacgttat caaagacaat gctaccttca gtagaaaaaa cccagcttat    1200
cctatttcat acaccagtgt tttccttaaa aataataaaa ttgcgggtgt caataacaga    1260
actgaatacg ttgaaacaac atctaccgag tacactagtg gaaaaattaa cctgtctcat    1320
caaggcgcgt atgttgctca atatgaaatc ctttgggatg aaatcaatta tgatgacaaa    1380
ggaaaagaag tgattacaaa acgacgttgg gacaacaact ggtatagtaa gacatcacca    1440
tttagcacag ttatcccact aggagctaat tcacgaaata tccgtatcat ggctagagag    1500
tgcactggct tagcttggga atggtggcga aaagtgatcg acgaaagaga tgtgaaactg    1560
tctaaagaaa tcaatgtcaa tatctcagga tcaaccttga gcccatatgg ttcgattact    1620
tataagctcg agcaccacca ccaccaccac tga                                  1653
```